US012492254B2

(12) United States Patent
Davila et al.

(10) Patent No.: US 12,492,254 B2
(45) **Date of Patent: *Dec. 9, 2025**

(54) CD83-BINDING CHIMERIC ANTIGEN RECEPTORS

(71) Applicant: H. Lee Moffitt Cancer Center and Research Institute, Inc., Tampa, FL (US)

(72) Inventors: Marco Davila, Tampa, FL (US); Brian Betts, Minneapolis, MN (US)

(73) Assignee: H. Lee Moffitt Cancer Center and Research Intitute. Inc., Tampa, FL (US)

( * ) Notice: Subject to any disclaimer, the term of this patent is extended or adjusted under 35 U.S.C. 154(b) by 1312 days.

This patent is subject to a terminal disclaimer.

(21) Appl. No.: 16/969,056

(22) PCT Filed: Feb. 22, 2019

(86) PCT No.: PCT/US2019/019065

§ 371 (c)(1),
(2) Date: Aug. 11, 2020

(87) PCT Pub. No.: WO2019/165156

PCT Pub. Date: Aug. 29, 2019

(65) Prior Publication Data

US 2021/0032336 A1 Feb. 4, 2021

Related U.S. Application Data

(60) Provisional application No. 62/677,783, filed on May 30, 2018, provisional application No. 62/634,435, filed on Feb. 23, 2018.

(51) Int. Cl.

| | |
|---|---|
| ***C07K 16/00*** | (2006.01) |
| ***A61K 40/11*** | (2025.01) |
| ***A61K 40/19*** | (2025.01) |
| ***A61K 40/24*** | (2025.01) |
| ***A61K 40/31*** | (2025.01) |
| ***A61K 40/42*** | (2025.01) |
| ***A61P 37/06*** | (2006.01) |
| ***C07K 16/28*** | (2006.01) |
| ***C12N 5/0783*** | (2010.01) |
| *A61K 39/00* | (2006.01) |

(52) U.S. Cl.

CPC .......... *C07K 16/2803* (2013.01); *A61K 40/11* (2025.01); *A61K 40/19* (2025.01); *A61K 40/24* (2025.01); *A61K 40/31* (2025.01); *A61K 40/421* (2025.01); *A61P 37/06* (2018.01); *C12N 5/0636* (2013.01); *A61K 2039/505* (2013.01); *A61K 2239/38* (2023.05); *A61K 2239/48* (2023.05); *C07K 2317/622* (2013.01); *C07K 2319/02* (2013.01); *C07K 2319/03* (2013.01)

(58) Field of Classification Search

CPC .......... C07K 16/2803; C07K 2317/622; C07K 2319/02; C07K 2319/03; A61P 37/06; A61K 35/17; A61K 2039/505

See application file for complete search history.

(56) References Cited

U.S. PATENT DOCUMENTS

| | | | |
|---|---|---|---|
| 2010/0249380 | A1 | 9/2010 | Garcia-Martinez et al. |
| 2014/0286950 | A1 | 9/2014 | Diehl et al. |
| 2015/0376277 | A1 | 12/2015 | Seldon et al. |
| 2017/0014453 | A1 | 1/2017 | Strober et al. |
| 2017/0258835 | A1 | 9/2017 | Zhao et al. |
| 2017/0335006 | A1 | 11/2017 | Casey et al. |
| 2017/0355756 | A1 | 12/2017 | Julien et al. |
| 2018/0170964 | A1 | 6/2018 | Donini et al. |
| 2018/0187149 | A1 | 7/2018 | Ma et al. |
| 2019/0022199 | A1 | 1/2019 | Riley et al. |
| 2019/0352409 | A1 | 11/2019 | Onhuoha et al. |
| 2020/0108098 | A1 | 4/2020 | Davila et al. |
| 2020/0230221 | A1 | 7/2020 | Irvine et al. |
| 2020/0277396 | A1 | 9/2020 | Hart et al. |
| 2020/0281973 | A1 | 9/2020 | Dranoff |
| 2023/0051885 | A1 | 2/2023 | Davila |

(Continued)

FOREIGN PATENT DOCUMENTS

| | | | |
|---|---|---|---|
| CN | 103906766 | A | 7/2014 |
| JP | 2013-150592 | A | 8/2013 |

(Continued)

OTHER PUBLICATIONS

Ju, X. et al. The Analysis of CD83 Expression on Human Immune Cells Identifies a Unique CD83+-Activated T Cell Population. J Immunol Dec. 15, 2016; 197 (12): 4613-4625 (Year: 2016).*

(Continued)

*Primary Examiner* — Peter J Reddig
*Assistant Examiner* — Estella M. Gustilo
(74) *Attorney, Agent, or Firm* — Pabst Patent Group LLP

(57) ABSTRACT

Disclosed are compositions and methods for preventing graft versus host disease (GVHD) in subjects receiving donor cells. In particular, chimeric antigen receptor (CAR) polypeptides are disclosed that can be used with adoptive cell transfer suppress alloreactive donor cells. Also disclosed are immune effector cells, such as T cells or Natural Killer (NK) cells, that are engineered to express these CARs. Therefore, also disclosed are methods of suppressing alloreactive donor cells in a subject receiving transplant donor cells that involves adoptive transfer of the disclosed immune effector cells engineered to express the disclosed CARs.

15 Claims, 26 Drawing Sheets

Specification includes a Sequence Listing.

(56) References Cited

U.S. PATENT DOCUMENTS

| | | | |
|---|---|---|---|
| 2024/0248307 A1 | 7/2024 | Takeda | |
| 2025/0052748 A1 | 2/2025 | Betts et al. | |

FOREIGN PATENT DOCUMENTS

| | | | |
|---|---|---|---|
| JP | 2016-5072521 A | 3/2016 | |
| WO | WO 2004/048552 A2 | 6/2004 | |
| WO | 2008068048 A2 | 6/2008 | |
| WO | WO 2013/006505 A1 | 1/2013 | |
| WO | 2016164731 A3 | 11/2016 | |
| WO | 2016210293 A1 | 12/2016 | |
| WO | WO 2016/201300 A1 | 12/2016 | |
| WO | WO2017149515 A1 * | 9/2017 | ........... C12N 5/0636 |
| WO | 2019099639 A1 | 5/2019 | |
| WO | WO 2019/136335 A1 | 7/2019 | |
| WO | 2019165156 A1 | 8/2019 | |
| WO | WO 2019/157158 A2 | 8/2019 | |
| WO | 2020109953 A1 | 6/2020 | |
| WO | WO 2021/034689 A1 | 2/2021 | |
| WO | WO 2021/150970 A1 | 7/2021 | |

OTHER PUBLICATIONS

Zhang C et al. Engineering CAR-T cells. Biomark Res. Jun. 24, 2017;5:22 (Year: 2017).*

International Search Report issued for PCT/US2019/019065, mailed May 3, 2019.

Radford et al., CD11c+ blood dendritic cells induce antigen-specific cytotoxic T lymphocytes with similar efficiency compared to monocyte-derived dendritic cells despite higher levels of MHC class I expression. J Immunother. Nov.-Dec. 2006;29(6):596-605.

Davila et al., Bispecific CAR-T Cells that Recognize CD83 and IL-6Rα to Prevent Graft-versus-Host Disease (GVHD) and Protect "Off the Shelf" Allogeneic CAR-T cells from Rejection. Moffitt Cancer Center. Jan. 1, 2020. 1 page. Accessible at moffitt.org/media/12197/20ma003-bispecific-anti-cd83-anti-il6-car-t-tom.pdf.

Fesnak et al., Engineered T cells: the promise and challenges of cancer immunotherapy. Nat Rev Cancer. Aug. 23, 2016; 16(9):566-81.

Imai e tal., Chimeric receptors with 4-1BB signaling capacity provoke potent cytotoxicity against acute lymphoblastic leukemia. Leukemia. Apr. 2004;18(4):676-84.

Jiang et al., IL-6 trans-signaling promotes the expansion and anti-tumor activity of CAR T cells. Leukemia. May 2021;35(5):1380-1391. Epub Nov. 9, 2020.

Larson et al.,Recent advances and discoveries in the mechanisms and functions of CAR T cells. Nat Rev Cancer. Mar. 2021;21(3):145-161. Epub Jan. 22, 2021.

Lee et al., Current concepts in the diagnosis and management of cytokine release syndrome. Blood. Jul. 10, 2014;124(2):188-95. Epub May 29, 2014. Erratum in: Blood. Aug. 20, 2015;126(8):1048. Dosage error in article text. Erratum in: Blood. Sep. 15, 2016;128(11):1533.

Li et al., IL6 trans-signaling robustly promotes the expansion and antitumor activity of CAR T cells. Proceedings of the American Association for Cancer Research Annual Meeting 2019; Mar. 29-Apr. 3, 2019; Atlanta, GA. Philadelphia (PA): AACR; Cancer Res 2019;79(13 Suppl):Abstract 1427. 1 page.

Maher et al., Human T-lymphocyte cytotoxicity and proliferation directed by a single chimeric TCRzeta /CD28 receptor. Nat Biotechnol. Jan. 2002;20(1):70-5.

Mishra et al., Preclinical development of CD126 CAR-T cells with broad antitumor activity. Blood Cancer J. Jan. 4, 2021;11(1):3(1-10).

Mohanty et al., CAR T cell therapy: A new era for cancer treatment (Review). Oncol Rep. Dec. 2019;42(6):2183-2195. Epub Sep. 24, 2019.

Morgan et al., Case report of a serious adverse event following the administration of T cells transduced with a chimeric antigen receptor recognizing ERBB2. Mol Ther. Apr. 2010;18(4):843-51. Epub Feb. 23, 2010.

Narni-Mancinelli et al., The 'T-cell-ness' of NK cells: unexpected similarities between NK cells and T cells. Int Immunol. Jul. 2011;23(7):427-31. Epub Jun. 10, 2011.

Porter et al., Chimeric antigen receptor-modified T cells in chronic lymphoid leukemia. N Engl J Med. Aug. 25, 2011;365(8):725-33. Epub Aug. 10, 2011. Erratum in: N Engl J Med. Mar. 10, 2016;374(10):998.

Rosenberg et al., Use of tumor-infiltrating lymphocytes and interleukin-2 in the immunotherapy of patients with metastatic melanoma. A preliminary report. N Engl J Med. Dec. 22, 1988;319(25):1676-80.

Shrestha et al., Human CD83-targeted chimeric antigen receptor T cells prevent and treat graft-versus-host disease. J Clin Invest. Sep. 1, 2020;130(9):4652-4662.

Tan et al., Chimeric antigen receptor-T cells with cytokine neutralizing capacity. Blood Adv. Apr. 9, 2020;4(7):1419-31.

Tanaka et al., Interleukin-6 Inhibition in Inflammatory Diseases: Results Achieved and Tasks to Accomplish. J Scleroderma Relat Disord. Jan. 1, 2017;2(2 Suppl):S20-S28.

Tvedt et al., Interleukin-6 in Allogeneic Stem Cell Transplantation: Its Possible Importance for Immunoregulation and As a Therapeutic Target. Front Immunol. Jun. 8, 2017;8:667(1-15).

Wang et al., Targeting CD83 for the treatment of graft-versus-host disease. Exp Ther Med. Jun. 2013;5(6):1545-1550. Epub Apr. 2, 2013.

Woof et al., Human antibody-Fc receptor interactions illuminated by crystal structures. Nat Rev Immunol. Feb. 2004;4(2):89-99.

Adler, CD83 Targeting Chimeric Antigen Receptor Expressing T cell (CAR-T) to prevent GVHD. Moffitt.org. Oct. 1, 2018. 1 page.

MacDonald et al., Alloantigen-specific regulatory T cells generated with a chimeric antigen receptor. J Clin Invest. Apr. 1, 2016;126(4):1413-24. Epub Mar. 21, 2016.

Shrestha et al., Human CD83 Targeted Chimeric Antigen Receptor T Cell for the Prevention of Graft versus Host Disease and Treatment of Myeloid Leukemia. Blood. Nov. 13, 2019;134(Supplement_1):196.

Wilson et al., Antibody to the dendritic cell surface activation antigen CD83 prevents acute graft-versus-host disease. J Exp Med. Feb. 16, 2009;206(2):387-98. Epub Jan. 26, 2009. Erratum in: J Exp Med. May 11, 2009;206(5):1203.

Office Action issued by Korean Patent Office, KR App. 10-2020-7027148, mailed Jun. 19, 2024.

Office Action issued by Chinese Patent Office, CN App. 201980027877.0, mailed Jun. 27, 2024.

Arjomandnejad, et al., "CAR-T Regulatory (CAR-Treg) Cells: Engineering and Applications", Biomedicines, vol. 10, No. 2; 287, Jan. 26, 2022, 21 pages.

Chen, et al., "Enhancement and Destruction of Antibody Function by Somatic Mutation: Unequal Occurrence is Controlled by V Gene Combinatorial Associations.", The EMBO Journal, vol. 14, No. 12, 1995, pp. 2784-2794.

Edwards, et al., "The Remarkable Flexibility of the Human Antibody Repertoire; Isolation of Over One Thousand Different Antibodies to a Single Protein, BLyS", Journal of Molecular Biology, vol. 334, No. 1, Nov. 14, 2003, pp. 103-118.

Jones, et al., "A Method for Rapid, Ligation-Independent Reformatting of Recombinant Monoclonal Antibodies", Journal of Immunological Methods, vol. 354, No. 1-2 2010, pp. 85-90.

Koenig, et al., "Mutational Landscape of Antibody Variable Domains Reveals a Switch Modulating the Interdomain Conformational Dynamics and Antigen Binding", Proceedings of the National Academt of Sciences, vol. 114, No. 4, Jan. 5, 2017, pp. E486-495.

Kussie, et al., "A Single Engineered Amino Acid Substitution Changes Antibody Fine Specificity", The Journal of Immunology, vol. 152, No. 1, Jan. 1, 1994, pp. 146-152.

Li, et al., "CD83: Activation Marker for Antigen Presenting Cells and Its Therapeutic Potential", Frontiers in Immunology, vol. 10, Jun. 7, 2019, 9 pages.

Seldon, et al., "Immunosuppresive Human Anti-Cd83 Monoclonal Antibody Depletion of Activated Dendritic Cells in Transplantation", Leukemia, vol. 30, No. 3, Mar. 2016, pp. 692-700.

(56) References Cited

OTHER PUBLICATIONS

Vignali, et al., "How Regulatory T Cells Work", Nature Reviews Immunology, vol. 8, 2008, pp. 523-532.

* cited by examiner

SEQUENCE LISTING

```
<160> NUMBER OF SEQ ID NOS: 71

<210> SEQ ID NO 1
<211> LENGTH: 12
```

<212> TYPE: PRT
<213> ORGANISM: Artificial Sequence
<220> FEATURE:
<223> OTHER INFORMATION: Synthetic Construct

<400> SEQUENCE: 1

Gly Phe Ser Ile Thr Thr Gly Gly Tyr Trp Trp Thr
1 5 10

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Gly Tyr Ile Phe Ser Ser Gly Asn Thr Asn Tyr Asn Pro Ser Ile Lys
1 5 10 15

Ser

<210> SEQ ID NO 3
<211> LENGTH: 12
<212> TYPE: PRT
<213> ORGANISM: Artificial Sequence
<220> FEATURE:
<223> OTHER INFORMATION: Synthetic Construct

<400> SEQUENCE: 3

Cys Ala Arg Ala Tyr Gly Lys Leu Gly Phe Asp Tyr
1 5 10

<210> SEQ ID NO 4
<211> LENGTH: 12
<212> TYPE: PRT
<213> ORGANISM: Artificial Sequence
<220> FEATURE:
<223> OTHER INFORMATION: Synthetic Construct

<400> SEQUENCE: 4

Thr Leu Ser Ser Gln His Ser Thr Tyr Thr Ile Gly
1 5 10

<210> SEQ ID NO 5
<211> LENGTH: 11
<212> TYPE: PRT
<213> ORGANISM: Artificial Sequence
<220> FEATURE:
<223> OTHER INFORMATION: Synthetic Construct

<400> SEQUENCE: 5

Val Asn Ser Asp Gly Ser His Ser Lys Gly Asp
1 5 10

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gly Ser Ser Asp Ser Ser Gly Tyr Val
1 5

<210> SEQ ID NO 7

<211> LENGTH: 5
<212> TYPE: PRT
<213> ORGANISM: Artificial Sequence
<220> FEATURE:
<223> OTHER INFORMATION: Synthetic Construct

<400> SEQUENCE: 7

Ser Asp Gly Ile Ser
1 5

<210> SEQ ID NO 8
<211> LENGTH: 16
<212> TYPE: PRT
<213> ORGANISM: Artificial Sequence
<220> FEATURE:
<223> OTHER INFORMATION: Synthetic Construct

<400> SEQUENCE: 8

Ile Ile Ser Ser Gly Gly Asn Thr Tyr Tyr Ala Ser Trp Ala Lys Gly
1 5 10 15

<210> SEQ ID NO 9
<211> LENGTH: 8
<212> TYPE: PRT
<213> ORGANISM: Artificial Sequence
<220> FEATURE:
<223> OTHER INFORMATION: Synthetic Construct

<400> SEQUENCE: 9

Val Val Gly Gly Thr Tyr Ser Ile
1 5

<210> SEQ ID NO 10
<211> LENGTH: 13
<212> TYPE: PRT
<213> ORGANISM: Artificial Sequence
<220> FEATURE:
<223> OTHER INFORMATION: Synthetic Construct

<400> SEQUENCE: 10

Gln Ser Ser Gln Ser Val Tyr Asn Asn Asp Phe Leu Ser
1 5 10

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct

<400> SEQUENCE: 11

Tyr Ala Ser Thr Leu Ala Ser
1 5

<210> SEQ ID NO 12
<211> LENGTH: 13
<212> TYPE: PRT
<213> ORGANISM: Artificial Sequence
<220> FEATURE:
<223> OTHER INFORMATION: Synthetic Construct

<400> SEQUENCE: 12

Thr Gly Thr Tyr Gly Asn Ser Ala Trp Tyr Glu Asp Ala
1 5 10

<210> SEQ ID NO 13
<211> LENGTH: 5

<212> TYPE: PRT
<213> ORGANISM: Artificial Sequence
<220> FEATURE:
<223> OTHER INFORMATION: Synthetic Construct

<400> SEQUENCE: 13

Ser Asn Ala Met Ile
1 5

<210> SEQ ID NO 14
<211> LENGTH: 16
<212> TYPE: PRT
<213> ORGANISM: Artificial Sequence
<220> FEATURE:
<223> OTHER INFORMATION: Synthetic Construct

<400> SEQUENCE: 14

Ala Met Asp Ser Asn Ser Arg Thr Tyr Tyr Ala Thr Trp Ala Lys Gly
1 5 10 15

<210> SEQ ID NO 15
<211> LENGTH: 11
<212> TYPE: PRT
<213> ORGANISM: Artificial Sequence
<220> FEATURE:
<223> OTHER INFORMATION: Synthetic Construct

<400> SEQUENCE: 15

Gly Asp Gly Gly Ser Ser Asp Tyr Thr Glu Met
1 5 10

<210> SEQ ID NO 16
<211> LENGTH: 13
<212> TYPE: PRT
<213> ORGANISM: Artificial Sequence
<220> FEATURE:
<223> OTHER INFORMATION: Synthetic Construct

<400> SEQUENCE: 16

Gln Ser Ser Gln Ser Val Tyr Gly Asn Asn Glu Leu Ser
1 5 10

<210> SEQ ID NO 17
<211> LENGTH: 7
<212> TYPE: PRT
<213> ORGANISM: Artificial Sequence
<220> FEATURE:
<223> OTHER INFORMATION: Synthetic Construct

<400> SEQUENCE: 17

Gln Ala Ser Ser Leu Ala Ser
1 5

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct

<400> SEQUENCE: 18

Leu Gly Glu Tyr Ser Ile Ser Ala Asp Asn His
1 5 10

<210> SEQ ID NO 19
<211> LENGTH: 120
<212> TYPE: PRT

<213> ORGANISM: Artificial Sequence
<220> FEATURE:
<223> OTHER INFORMATION: Synthetic Construct

<400> SEQUENCE: 19

```
Gln Val Gln Leu Lys Glu Ser Gly Pro Gly Leu Val Lys Pro Ser Gln
1               5                   10                  15

Ser Leu Ser Leu Thr Cys Ser Val Thr Gly Phe Ser Ile Thr Thr Gly
            20                  25                  30

Gly Tyr Trp Trp Thr Trp Ile Arg Gln Phe Pro Gly Gln Lys Leu Glu
        35                  40                  45

Trp Met Gly Tyr Ile Phe Ser Ser Gly Asn Thr Asn Tyr Asn Pro Ser
    50                  55                  60

Ile Lys Ser Arg Ile Ser Ile Thr Arg Asp Thr Ser Lys Asn Gln Phe
65                  70                  75                  80

Phe Leu Gln Leu Asn Ser Val Thr Thr Glu Gly Asp Thr Ala Arg Tyr
                85                  90                  95

Tyr Cys Ala Arg Ala Tyr Gly Lys Leu Gly Phe Asp Tyr Trp Gly Gln
            100                 105                 110

Gly Thr Leu Val Thr Val Ser Ser
        115                 120
```

<210> SEQ ID NO 20
<211> LENGTH: 111
<212> TYPE: PRT
<213> ORGANISM: Artificial Sequence
<220> FEATURE:
<223> OTHER INFORMATION: Synthetic Construct

<400> SEQUENCE: 20

```
Gln Pro Val Leu Thr Gln Ser Pro Ser Ala Ser Ala Ser Leu Gly Asn
1               5                   10                  15

Ser Val Lys Ile Thr Cys Thr Leu Ser Ser Gln His Ser Thr Tyr Thr
            20                  25                  30

Ile Gly Trp Tyr Gln Gln His Pro Asp Lys Ala Pro Lys Tyr Val Met
        35                  40                  45

Tyr Val Asn Ser Asp Gly Ser His Ser Lys Gly Asp Gly Ile Pro Asp
    50                  55                  60

Arg Phe Ser Gly Ser Ser Ser Gly Ala His Arg Tyr Leu Ser Ile Ser
65                  70                  75                  80

Asn Ile Gln Pro Glu Asp Glu Ala Asp Tyr Phe Cys Gly Ser Ser Asp
                85                  90                  95

Ser Ser Gly Tyr Val Phe Gly Ser Gly Thr Gln Leu Thr Val Leu
            100                 105                 110
```

<210> SEQ ID NO 21
<211> LENGTH: 454
<212> TYPE: PRT
<213> ORGANISM: Artificial Sequence
<220> FEATURE:
<223> OTHER INFORMATION: Synthetic Construct

<400> SEQUENCE: 21

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45
```

```
Asn Asn Ala Ile Asn Trp Val Arg Gln Ala Pro Gly Lys Gly Leu Glu
    50                  55                  60

Trp Ile Gly Tyr Ile Trp Ser Gly Gly Leu Thr Tyr Tyr Ala Asn Trp
65                  70                  75                  80

Ala Glu Gly Arg Phe Thr Ile Ser Lys Thr Ser Thr Thr Val Asp Leu
                85                  90                  95

Lys Met Thr Ser Pro Thr Ile Glu Asp Thr Ala Thr Tyr Phe Cys Ala
            100                 105                 110

Arg Gly Ile Asn Asn Ser Ala Leu Trp Gly Pro Gly Thr Leu Val Thr
        115                 120                 125

Val Ser Ser Gly Gln Pro Lys Ala Pro Ser Val Phe Pro Leu Ala Pro
    130                 135                 140

Cys Cys Gly Asp Thr Pro Ser Ser Thr Val Thr Leu Gly Cys Leu Val
145                 150                 155                 160

Lys Gly Tyr Leu Pro Glu Pro Val Thr Val Thr Trp Asn Ser Gly Thr
                165                 170                 175

Leu Thr Asn Gly Val Arg Thr Phe Pro Ser Val Arg Gln Ser Ser Gly
            180                 185                 190

Leu Tyr Ser Leu Ser Ser Val Val Ser Val Thr Ser Ser Ser Gln Pro
        195                 200                 205

Val Thr Cys Asn Val Ala His Pro Ala Thr Asn Thr Lys Val Asp Lys
    210                 215                 220

Thr Val Ala Pro Ser Thr Cys Ser Lys Pro Thr Cys Pro Pro Pro Glu
225                 230                 235                 240

Leu Leu Gly Gly Pro Ser Val Phe Ile Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Asp Asp Pro Glu Val Gln Phe Thr Trp Tyr Ile Asn Asn
        275                 280                 285

Glu Gln Val Arg Thr Ala Arg Pro Pro Leu Arg Glu Gln Gln Phe Asn
    290                 295                 300

Ser Thr Ile Arg Val Val Ser Thr Leu Pro Ile Ala His Gln Asp Trp
305                 310                 315                 320

Leu Arg Gly Lys Glu Phe Lys Cys Lys Val His Asn Lys Ala Leu Pro
                325                 330                 335

Ala Pro Ile Glu Lys Thr Ile Ser Lys Ala Arg Gly Gln Pro Leu Glu
            340                 345                 350

Pro Lys Val Tyr Thr Met Gly Pro Pro Arg Glu Glu Leu Ser Ser Arg
        355                 360                 365

Ser Val Ser Leu Thr Cys Met Ile Asn Gly Phe Tyr Pro Ser Asp Ile
    370                 375                 380

Ser Val Glu Trp Glu Lys Asn Gly Lys Ala Glu Asp Asn Tyr Lys Thr
385                 390                 395                 400

Thr Pro Ala Val Leu Asp Ser Asp Gly Ser Tyr Phe Leu Tyr Asn Lys
                405                 410                 415

Leu Ser Val Pro Thr Ser Glu Trp Gln Arg Gly Asp Val Phe Thr Cys
            420                 425                 430

Ser Val Met His Glu Ala Leu His Asn His Tyr Thr Gln Lys Ser Ile
        435                 440                 445

Ser Arg Ser Pro Gly Lys
    450
```

<210> SEQ ID NO 22
<211> LENGTH: 239
<212> TYPE: PRT
<213> ORGANISM: Artificial Sequence
<220> FEATURE:
<223> OTHER INFORMATION: Synthetic Construct

<400> SEQUENCE: 22

```
Met Asp Met Arg Ala Pro Thr Gln Leu Leu Gly Leu Leu Leu Leu Trp
1               5                   10                  15

Leu Pro Gly Ala Arg Cys Ala Asp Val Val Met Thr Gln Thr Pro Ala
            20                  25                  30

Ser Val Ser Ala Ala Val Gly Gly Thr Val Thr Ile Asn Cys Gln Ala
        35                  40                  45

Ser Glu Ser Ile Ser Asn Tyr Leu Ser Trp Tyr Gln Gln Lys Pro Gly
    50                  55                  60

Gln Pro Pro Lys Leu Leu Ile Tyr Arg Thr Ser Thr Leu Ala Ser Gly
65                  70                  75                  80

Val Ser Ser Arg Phe Lys Gly Ser Gly Ser Gly Thr Glu Tyr Thr Leu
                85                  90                  95

Thr Ile Ser Gly Val Gln Cys Asp Asp Val Ala Thr Tyr Tyr Cys Gln
            100                 105                 110

Cys Thr Ser Gly Gly Lys Phe Ile Ser Asp Gly Ala Ala Phe Gly Gly
        115                 120                 125

Gly Thr Glu Val Val Val Lys Gly Asp Pro Val Ala Pro Thr Val Leu
    130                 135                 140

Leu Phe Pro Pro Ser Ser Asp Glu Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Ser Arg Lys Asn Cys
225                 230                 235
```

<210> SEQ ID NO 23
<211> LENGTH: 452
<212> TYPE: PRT
<213> ORGANISM: Artificial Sequence
<220> FEATURE:
<223> OTHER INFORMATION: Synthetic Construct

<400> SEQUENCE: 23

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Thr Ile Ser
        35                  40                  45

Asp Tyr Asp Leu Ser Trp Val Arg Gln Ala Pro Gly Glu Gly Leu Lys
    50                  55                  60

Tyr Ile Gly Phe Ile Ala Ile Asp Gly Asn Pro Tyr Tyr Ala Thr Trp
65                  70                  75                  80
```

```
Ala Lys Gly Arg Phe Thr Ile Ser Lys Thr Ser Thr Thr Val Asp Leu
                85                  90                  95

Lys Ile Thr Ala Pro Thr Thr Glu Asp Thr Ala Thr Tyr Phe Cys Ala
            100                 105                 110

Arg Gly Ala Gly Asp Leu Trp Gly Pro Gly Thr Leu Val Thr Val Ser
        115                 120                 125

Ser Gly Gln Pro Lys Ala Pro Ser Val Phe Pro Leu Ala Pro Cys Cys
    130                 135                 140

Gly Asp Thr Pro Ser Ser Thr Val Thr Leu Gly Cys Leu Val Lys Gly
145                 150                 155                 160

Tyr Leu Pro Glu Pro Val Thr Val Thr Trp Asn Ser Gly Thr Leu Thr
                165                 170                 175

Asn Gly Val Arg Thr Phe Pro Ser Val Arg Gln Ser Ser Gly Leu Tyr
            180                 185                 190

Ser Leu Ser Ser Val Val Ser Val Thr Ser Ser Ser Gln Pro Val Thr
        195                 200                 205

Cys Asn Val Ala His Pro Ala Thr Asn Thr Lys Val Asp Lys Thr Val
    210                 215                 220

Ala Pro Ser Thr Cys Ser Lys Pro Thr Cys Pro Pro Pro Glu Leu Leu
225                 230                 235                 240

Gly Gly Pro Ser Val Phe Ile Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Asp Asp Pro Glu Val Gln Phe Thr Trp Tyr Ile Asn Asn Glu Gln
        275                 280                 285

Val Arg Thr Ala Arg Pro Pro Leu Arg Glu Gln Gln Phe Asn Ser Thr
    290                 295                 300

Ile Arg Val Val Ser Thr Leu Pro Ile Ala His Gln Asp Trp Leu Arg
305                 310                 315                 320

Gly Lys Glu Phe Lys Cys Lys Val His Asn Lys Ala Leu Pro Ala Pro
                325                 330                 335

Ile Glu Lys Thr Ile Ser Lys Ala Arg Gly Gln Pro Leu Glu Pro Lys
            340                 345                 350

Val Tyr Thr Met Gly Pro Pro Arg Glu Glu Leu Ser Ser Arg Ser Val
        355                 360                 365

Ser Leu Thr Cys Met Ile Asn Gly Phe Tyr Pro Ser Asp Ile Ser Val
    370                 375                 380

Glu Trp Glu Lys Asn Gly Lys Ala Glu Asp Asn Tyr Lys Thr Thr Pro
385                 390                 395                 400

Ala Val Leu Asp Ser Asp Gly Ser Tyr Phe Leu Tyr Asn Lys Leu Ser
                405                 410                 415

Val Pro Thr Ser Glu Trp Gln Arg Gly Asp Val Phe Thr Cys Ser Val
            420                 425                 430

Met His Glu Ala Leu His Asn His Tyr Thr Gln Lys Ser Ile Ser Arg
        435                 440                 445

Ser Pro Gly Lys
    450
```

<210> SEQ ID NO 24
<211> LENGTH: 238
<212> TYPE: PRT
<213> ORGANISM: Artificial Sequence
<220> FEATURE:

<223> OTHER INFORMATION: Synthetic Construct

<400> SEQUENCE: 24

Met Asp Thr Arg Glu Pro Thr Gln Leu Leu Gly Leu Leu Leu Leu Trp
1 5 10 15

Leu Pro Gly Ala Arg Cys Ala Asp Val Val Met Thr Gln Thr Pro Ala
20 25 30

Ser Val Ser Ala Ala Val Gly Gly Thr Val Thr Ile Asn Cys Gln Ser
35 40 45

Ser Lys Asn Val Tyr Asn Asn Asn Trp Leu Ser Trp Phe Gln Gln Lys
50 55 60

Pro Gly Gln Pro Pro Lys Leu Leu Ile Tyr Tyr Ala Ser Thr Leu Ala
65 70 75 80

Ser Gly Val Pro Ser Arg Phe Arg Gly Ser Gly Ser Gly Thr Gln Phe
85 90 95

Thr Leu Thr Ile Ser Asp Val Gln Cys Asp Asp Ala Ala Thr Tyr Tyr
100 105 110

Cys Ala Gly Asp Tyr Ser Ser Ser Ser Asp Asn Gly Phe Gly Gly Gly
115 120 125

Thr Glu Val Val Val Lys Gly Asp Pro Val Ala Pro Thr Val Leu Leu
130 135 140

Phe Pro Pro Ser Ser Asp Glu Val Ala Thr Gly Thr Val Thr Ile Val
145 150 155 160

Cys Val Ala Asn Lys Tyr Phe Pro Asp Val Thr Val Thr Trp Glu Val
165 170 175

Asp Gly Thr Thr Gln Thr Thr Gly Ile Glu Asn Ser Lys Thr Pro Gln
180 185 190

Asn Ser Ala Asp Cys Thr Tyr Asn Leu Ser Ser Thr Leu Thr Leu Thr
195 200 205

Ser Thr Gln Tyr Asn Ser His Lys Glu Tyr Thr Cys Lys Val Thr Gln
210 215 220

Gly Thr Thr Ser Val Val Gln Ser Phe Ser Arg Lys Asn Cys
225 230 235

<210> SEQ ID NO 25
<211> LENGTH: 454
<212> TYPE: PRT
<213> ORGANISM: Artificial Sequence
<220> FEATURE:
<223> OTHER INFORMATION: Synthetic Construct

<400> SEQUENCE: 25

Met Glu Thr Gly Leu Arg Trp Leu Leu Leu Val Ala Val Leu Lys Gly
1 5 10 15

Val His Cys Gln Ser Val Glu Glu Ser Gly Gly Arg Leu Val Thr Pro
20 25 30

Gly Thr Pro Leu Thr Leu Thr Cys Thr Ala Ser Gly Phe Ser Arg Ser
35 40 45

Ser Tyr Asp Met Ser Trp Val Arg Gln Ala Pro Gly Lys Gly Leu Glu
50 55 60

Trp Val Gly Val Ile Ser Thr Ala Tyr Asn Ser His Tyr Ala Ser Trp
65 70 75 80

Ala Lys Gly Arg Phe Thr Ile Ser Arg Thr Ser Thr Thr Val Asp Leu
85 90 95

Lys Met Thr Ser Leu Thr Thr Glu Asp Thr Ala Thr Tyr Phe Cys Ala
100 105 110

```
Arg Gly Gly Ser Trp Leu Asp Leu Trp Gly Gln Gly Thr Leu Val Thr
        115                 120                 125

Val Ser Ser Gly Gln Pro Lys Ala Pro Ser Val Phe Pro Leu Ala Pro
    130                 135                 140

Cys Cys Gly Asp Thr Pro Ser Ser Thr Val Thr Leu Gly Cys Leu Val
145                 150                 155                 160

Lys Gly Tyr Leu Pro Glu Pro Val Thr Val Thr Trp Asn Ser Gly Thr
                165                 170                 175

Leu Thr Asn Gly Val Arg Thr Phe Pro Ser Val Arg Gln Ser Ser Gly
            180                 185                 190

Leu Tyr Ser Leu Ser Ser Val Val Ser Val Thr Ser Ser Ser Gln Pro
        195                 200                 205

Val Thr Cys Asn Val Ala His Pro Ala Thr Asn Thr Lys Val Asp Lys
    210                 215                 220

Thr Val Ala Pro Ser Thr Cys Ser Lys Pro Thr Cys Pro Pro Pro Glu
225                 230                 235                 240

Leu Leu Gly Gly Pro Ser Val Phe Ile Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Asp Asp Pro Glu Val Gln Phe Thr Trp Tyr Ile Asn Asn
        275                 280                 285

Glu Gln Val Arg Thr Ala Arg Pro Pro Leu Arg Glu Gln Gln Phe Asn
    290                 295                 300

Ser Thr Ile Arg Val Val Ser Thr Leu Pro Ile Ala His Gln Asp Trp
305                 310                 315                 320

Leu Arg Gly Lys Glu Phe Lys Cys Lys Val His Asn Lys Ala Leu Pro
                325                 330                 335

Ala Pro Ile Glu Lys Thr Ile Ser Lys Ala Arg Gly Gln Pro Leu Glu
            340                 345                 350

Pro Lys Val Tyr Thr Met Gly Pro Pro Arg Glu Glu Leu Ser Ser Arg
        355                 360                 365

Ser Val Ser Leu Thr Cys Met Ile Asn Gly Phe Tyr Pro Ser Asp Ile
    370                 375                 380

Ser Val Glu Trp Glu Lys Asn Gly Lys Ala Glu Asp Asn Tyr Lys Thr
385                 390                 395                 400

Thr Pro Ala Val Leu Asp Ser Asp Gly Ser Tyr Phe Leu Tyr Asn Lys
                405                 410                 415

Leu Ser Val Pro Thr Ser Glu Trp Gln Arg Gly Asp Val Phe Thr Cys
            420                 425                 430

Ser Val Met His Glu Ala Leu His Asn His Tyr Thr Gln Lys Ser Ile
        435                 440                 445

Ser Arg Ser Pro Gly Lys
    450
```

<210> SEQ ID NO 26
<211> LENGTH: 239
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 26

Met Asp Xaa Arg Ala Pro Thr Gln Leu Leu Gly Leu Leu Leu Leu Trp
1 5 10 15

Leu Pro Gly Ala Arg Cys Ala Leu Val Met Thr Gln Thr Pro Ala Ser
20 25 30

Val Ser Ala Ala Val Gly Gly Thr Val Thr Ile Asn Cys Gln Ser Ser
35 40 45

Gln Ser Val Tyr Asp Asn Asp Glu Leu Ser Trp Tyr Gln Gln Lys Pro
50 55 60

Gly Gln Pro Pro Lys Leu Leu Ile Tyr Ala Leu Ala Ser Lys Leu Ala
65 70 75 80

Ser Gly Val Pro Ser Arg Phe Lys Gly Ser Gly Ser Gly Thr Gln Phe
85 90 95

Ala Leu Thr Ile Ser Gly Val Gln Cys Asp Asp Ala Ala Thr Tyr Tyr
100 105 110

Cys Gln Ala Thr His Tyr Ser Ser Asp Trp Tyr Leu Thr Phe Gly Gly
115 120 125

Gly Thr Glu Val Val Val Lys Gly Phe Pro Val Ala Pro Thr Val Leu
130 135 140

Leu Phe Pro Pro Ser Ser Asp Glu Val Ala Thr Gly Thr Val Thr Ile
145 150 155 160

Val Cys Val Ala Asn Lys Tyr Phe Pro Asp Val Thr Val Thr Trp Glu
165 170 175

Val Asp Gly Thr Thr Gln Thr Thr Gly Thr Glu Asn Ser Lys Thr Pro
180 185 190

Gln Asn Ser Ala Asp Cys Thr Tyr Asn Leu Ser Ser Thr Leu Thr Leu
195 200 205

Thr Ser Thr Gln Tyr Asn Ser His Lys Glu Tyr Thr Cys Lys Val Thr
210 215 220

Gln Gly Thr Thr Ser Val Val Gln Ser Phe Ser Arg Lys Asn Cys
225 230 235

<210> SEQ ID NO 27
<211> LENGTH: 456
<212> TYPE: PRT
<213> ORGANISM: Artificial Sequence
<220> FEATURE:
<223> OTHER INFORMATION: Synthetic Construct

<400> SEQUENCE: 27

Met Glu Thr Gly Leu Arg Trp Leu Leu Leu Val Ala Val Leu Lys Gly
1 5 10 15

Val Gln Cys Gln Ser Val Glu Glu Ser Gly Gly Arg Leu Val Thr Pro
20 25 30

Gly Thr Pro Leu Thr Leu Thr Cys Thr Val Ser Gly Phe Ser Leu Ser
35 40 45

Ser Tyr Asp Met Thr Trp Val Arg Gln Ala Pro Gly Lys Gly Leu Glu
50 55 60

Trp Ile Gly Ile Ile Tyr Ala Ser Gly Thr Thr Tyr Tyr Ala Asn Trp
65 70 75 80

Ala Lys Gly Arg Phe Thr Ile Ser Lys Thr Ser Thr Thr Val Asp Leu
85 90 95

Lys Val Thr Ser Pro Thr Ile Gly Asp Thr Ala Thr Tyr Phe Cys Ala
100 105 110

Arg Glu Gly Ala Gly Val Ser Met Thr Leu Trp Gly Pro Gly Thr Leu

```
        115                 120                 125

Val Thr Val Ser Ser Gly Gln Pro Lys Ala Pro Ser Val Phe Pro Leu
    130                 135                 140

Ala Pro Cys Cys Gly Asp Thr Pro Ser Ser Thr Val Thr Leu Gly Cys
145                 150                 155                 160

Leu Val Lys Gly Tyr Leu Pro Glu Pro Val Thr Val Thr Trp Asn Ser
                165                 170                 175

Gly Thr Leu Thr Asn Gly Val Arg Thr Phe Pro Ser Val Arg Gln Ser
            180                 185                 190

Ser Gly Leu Tyr Ser Leu Ser Ser Val Val Ser Val Thr Ser Ser Ser
        195                 200                 205

Gln Pro Val Thr Cys Asn Val Ala His Pro Ala Thr Asn Thr Lys Val
    210                 215                 220

Asp Lys Thr Val Ala Pro Ser Thr Cys Ser Lys Pro Thr Cys Pro Pro
225                 230                 235                 240

Pro Glu Leu Leu Gly Gly Pro Ser Val Phe Ile Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Gln Asp Asp Pro Glu Val Gln Phe Thr Trp Tyr Ile
        275                 280                 285

Asn Asn Glu Gln Val Arg Thr Ala Arg Pro Pro Leu Arg Glu Gln Gln
    290                 295                 300

Phe Asn Ser Thr Ile Arg Val Val Ser Thr Leu Pro Ile Ala His Gln
305                 310                 315                 320

Asp Trp Leu Arg Gly Lys Glu Phe Lys Cys Lys Val His Asn Lys Ala
                325                 330                 335

Leu Pro Ala Pro Ile Glu Lys Thr Ile Ser Lys Ala Arg Gly Gln Pro
            340                 345                 350

Leu Glu Pro Lys Val Tyr Thr Met Gly Pro Pro Arg Glu Glu Leu Ser
        355                 360                 365

Ser Arg Ser Val Ser Leu Thr Cys Met Ile Asn Gly Phe Tyr Pro Ser
    370                 375                 380

Asp Ile Ser Val Glu Trp Glu Lys Asn Gly Lys Ala Glu Asp Asn Tyr
385                 390                 395                 400

Lys Thr Thr Pro Ala Val Leu Asp Ser Asp Gly Ser Tyr Phe Leu Tyr
                405                 410                 415

Asn Lys Leu Ser Val Pro Thr Ser Glu Trp Gln Arg Gly Asp Val Phe
            420                 425                 430

Thr Cys Ser Val Met His Glu Ala Leu His Asn His Tyr Thr Gln Lys
        435                 440                 445

Ser Ile Ser Arg Ser Pro Gly Lys
    450                 455


<210> SEQ ID NO 28
<211> LENGTH: 236
<212> TYPE: PRT
<213> ORGANISM: Artificial Sequence
<220> FEATURE:
<223> OTHER INFORMATION: Synthetic Construct

<400> SEQUENCE: 28

Met Asp Met Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
```

```
            20                  25                  30

Val Glu Val Ala Val Gly Gly Thr Val Thr Ile Lys Cys Gln Ala Ser
        35                  40                  45

Gln Ser Ile Ser Thr Tyr Leu Asp Trp Tyr Gln Gln Lys Pro Gly Gln
    50                  55                  60

Pro Pro Lys Leu Leu Ile Tyr Asp Ala Ser Asp Leu Ala Ser Gly Val
65                  70                  75                  80

Pro Ser Arg Phe Lys Gly Ser Gly Ser Gly Thr Gln Phe Thr Leu Thr
                85                  90                  95

Ile Ser Asp Leu Glu Cys Ala Asp Ala Ala Thr Tyr Tyr Cys Gln Gln
            100                 105                 110

Gly Tyr Thr His Ser Asn Val Asp Asn Val Phe Gly Gly Gly Thr Glu
        115                 120                 125

Val Val Val Lys Gly Asp Pro Val Ala Pro Thr Val Leu Leu Phe Pro
    130                 135                 140

Pro Ser Ser Asp Glu Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
    210                 215                 220

Thr Ser Val Val Gln Ser Phe Ser Arg Lys Asn Cys
225                 230                 235


<210> SEQ ID NO 29
<211> LENGTH: 459
<212> TYPE: PRT
<213> ORGANISM: Artificial Sequence
<220> FEATURE:
<223> OTHER INFORMATION: Synthetic Construct

<400> SEQUENCE: 29

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Ser Pro
            20                  25                  30

Gly Thr Pro Leu Thr Leu Thr Cys Thr Ala Ser Gly Phe Ser Leu Ser
        35                  40                  45

Ser Tyr Asp Met Ser Trp Val Arg Gln Ala Pro Gly Lys Gly Leu Glu
    50                  55                  60

Tyr Ile Gly Ile Ile Ser Ser Ser Gly Ser Thr Tyr Tyr Ala Ser Trp
65                  70                  75                  80

Ala Lys Gly Arg Phe Thr Ile Ser Lys Thr Ser Thr Thr Val Asp Leu
                85                  90                  95

Glu Val Thr Ser Leu Thr Thr Glu Asp Thr Ala Thr Tyr Phe Cys Ser
            100                 105                 110

Arg Glu His Ala Gly Tyr Ser Gly Asp Thr Gly His Leu Trp Gly Pro
        115                 120                 125

Gly Thr Leu Val Thr Val Ser Ser Gly Gln Pro Lys Ala Pro Ser Val
    130                 135                 140

Phe Pro Leu Ala Pro Cys Cys Gly Asp Thr Pro Ser Ser Thr Val Thr
```

```
145                 150                 155                 160

Leu Gly Cys Leu Val Lys Gly Tyr Leu Pro Glu Pro Val Thr Val Thr
                165                 170                 175

Trp Asn Ser Gly Thr Leu Thr Asn Gly Val Arg Thr Phe Pro Ser Val
            180                 185                 190

Arg Gln Ser Ser Gly Leu Tyr Ser Leu Ser Ser Val Val Ser Val Thr
        195                 200                 205

Ser Ser Ser Gln Pro Val Thr Cys Asn Val Ala His Pro Ala Thr Asn
    210                 215                 220

Thr Lys Val Asp Lys Thr Val Ala Pro Ser Thr Cys Ser Lys Pro Thr
225                 230                 235                 240

Cys Pro Pro Pro Glu Leu Leu Gly Gly Pro Ser Val Gly Ile Gly Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Asp Asp Pro Glu Val Gln Phe Thr
        275                 280                 285

Trp Tyr Ile Asn Asn Glu Gln Val Arg Thr Ala Arg Pro Pro Leu Arg
    290                 295                 300

Glu Gln Gln Phe Asn Ser Thr Ile Arg Val Val Ser Thr Leu Pro Ile
305                 310                 315                 320

Ala His Gln Asp Trp Leu Arg Gly Lys Glu Phe Lys Cys Lys Val His
                325                 330                 335

Asn Lys Ala Leu Pro Ala Pro Ile Glu Lys Thr Ile Ser Lys Ala Arg
            340                 345                 350

Gly Gln Pro Leu Glu Pro Lys Val Tyr Thr Met Gly Pro Pro Arg Glu
        355                 360                 365

Glu Leu Ser Ser Arg Ser Val Ser Leu Thr Cys Met Ile Asn Gly Phe
    370                 375                 380

Tyr Pro Ser Asp Ile Ser Val Glu Trp Glu Lys Asn Gly Lys Ala Glu
385                 390                 395                 400

Asp Asn Tyr Lys Thr Thr Pro Ala Val Leu Asp Ser Asp Gly Ser Tyr
                405                 410                 415

Phe Leu Tyr Asn Lys Leu Ser Val Pro Thr Ser Glu Trp Gln Arg Gly
            420                 425                 430

Asp Val Phe Thr Cys Ser Val Met His Glu Ala Leu His Asn His Tyr
        435                 440                 445

Thr Gln Lys Ser Ile Ser Arg Ser Pro Gly Lys
    450                 455


<210> SEQ ID NO 30
<211> LENGTH: 236
<212> TYPE: PRT
<213> ORGANISM: Artificial Sequence
<220> FEATURE:
<223> OTHER INFORMATION: Synthetic Construct

<400> SEQUENCE: 30

Met Asp Met Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Ala Ile Lys Cys Gln Ala Ser
        35                  40                  45

Gln Ser Val Ser Ser Tyr Leu Ala Trp Tyr Gln Gln Lys Pro Gly Gln
```

```
    50                  55                  60

Pro Pro Lys Pro Leu Ile Tyr Glu Ala Ser Met Leu Ala Ala Gly Val
65                  70                  75                  80

Ser Ser Arg Phe Lys Gly Ser Gly Ser Gly Thr Asp Phe Thr Leu Thr
                85                  90                  95

Ile Ser Asp Leu Glu Cys Asp Asp Ala Ala Thr Tyr Tyr Cys Gln Gln
            100                 105                 110

Gly Tyr Ser Ile Ser Asp Ile Asp Asn Ala Phe Gly Gly Gly Thr Glu
        115                 120                 125

Val Val Val Lys Gly Asp Pro Val Ala Pro Thr Val Leu Leu Phe Pro
    130                 135                 140

Pro Ser Ser Asp Glu Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
    210                 215                 220

Thr Ser Val Val Gln Ser Phe Ser Arg Lys Asn Cys
225                 230                 235


<210> SEQ ID NO 31
<211> LENGTH: 455
<212> TYPE: PRT
<213> ORGANISM: Artificial Sequence
<220> FEATURE:
<223> OTHER INFORMATION: Synthetic Construct

<400> SEQUENCE: 31

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Ser Asp Gly Ile Ser Trp Val Arg Gln Ala Pro Gly Lys Gly Leu Glu
    50                  55                  60

Trp Ile Gly Ile Ile Ser Ser Gly Gly Asn Thr Tyr Tyr Ala Ser Trp
65                  70                  75                  80

Ala Lys Gly Arg Phe Thr Ile Ser Arg Thr Ser Thr Thr Val Asp Leu
                85                  90                  95

Lys Met Thr Ser Leu Thr Thr Glu Asp Thr Ala Thr Tyr Phe Cys Ala
            100                 105                 110

Arg Val Val Gly Gly Thr Tyr Ser Ile Trp Gly Gln Gly Thr Leu Val
        115                 120                 125

Thr Val Ser Ser Ala Ser Thr Lys Gly Pro Ser Val Tyr Pro Leu Ala
    130                 135                 140

Pro Gly Ser Ala Ala Gln Thr Asn Ser Met Val Thr Leu Gly Cys Leu
145                 150                 155                 160

Val Lys Gly Tyr Phe Pro Glu Pro Val Thr Val Thr Trp Asn Ser Gly
                165                 170                 175

Ser Leu Ser Ser Gly Val His Thr Phe Pro Ala Val Leu Gln Ser Asp
```

```
            180                 185                 190

Leu Tyr Thr Leu Ser Ser Ser Val Thr Val Pro Ser Ser Thr Trp Pro
        195                 200                 205

Ser Glu Thr Val Thr Cys Asn Val Ala His Pro Ala Ser Ser Thr Lys
    210                 215                 220

Val Asp Lys Lys Ile Val Pro Arg Asp Cys Gly Cys Lys Pro Cys Ile
225                 230                 235                 240

Cys Thr Val Pro Glu Val Ser Ser Val Phe Ile Phe Pro Pro Lys Pro
                245                 250                 255

Asp Val Leu Thr Ile Thr Leu Thr Pro Lys Val Thr Cys Val Val Val
            260                 265                 270

Asp Ile Ser Lys Asp Asp Pro Glu Val Gln Phe Ser Trp Phe Val Asp
        275                 280                 285

Asp Val Glu Val His Thr Ala Gln Thr Gln Pro Arg Glu Glu Gln Phe
    290                 295                 300

Asn Ser Thr Phe Arg Ser Val Ser Glu Leu Pro Ile Met His Gln Asp
305                 310                 315                 320

Trp Leu Asn Gly Lys Glu Phe Lys Cys Arg Val Asn Ser Ala Ala Phe
                325                 330                 335

Pro Ala Pro Ile Glu Lys Thr Ile Ser Lys Thr Lys Gly Arg Pro Lys
            340                 345                 350

Ala Pro Gln Val Tyr Thr Ile Pro Pro Pro Lys Glu Gln Met Ala Lys
        355                 360                 365

Asp Lys Val Ser Leu Thr Cys Met Ile Thr Asp Phe Phe Pro Glu Asp
    370                 375                 380

Ile Thr Val Glu Trp Gln Trp Asn Gly Gln Pro Ala Glu Asn Tyr Lys
385                 390                 395                 400

Asn Thr Gln Pro Ile Met Asp Thr Asp Gly Ser Tyr Phe Val Tyr Ser
                405                 410                 415

Lys Leu Asn Val Gln Lys Ser Asn Trp Glu Ala Gly Asn Thr Phe Thr
            420                 425                 430

Cys Ser Val Leu His Glu Gly Leu His Asn His His Thr Glu Lys Ser
        435                 440                 445

Leu Ser His Ser Pro Gly Lys
    450                 455


<210> SEQ ID NO 32
<211> LENGTH: 240
<212> TYPE: PRT
<213> ORGANISM: Artificial Sequence
<220> FEATURE:
<223> OTHER INFORMATION: Synthetic Construct

<400> SEQUENCE: 32

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Pro
            20                  25                  30

Val Ser Ala Pro Val Gly Gly Thr Val Thr Ile Asn Cys Gln Ser Ser
        35                  40                  45

Gln Ser Val Tyr Asn Asn Asp Phe Leu Ser Trp Tyr Gln Gln Lys Pro
    50                  55                  60

Gly Gln Pro Pro Lys Leu Leu Ile Tyr Tyr Ala Ser Thr Leu Ala Ser
65                  70                  75                  80

Gly Val Pro Ser Arg Phe Lys Gly Ser Gly Ser Gly Thr Gln Phe Thr
```

```
                85                  90                  95

Leu Thr Ile Ser Asp Leu Glu Cys Asp Asp Ala Ala Thr Tyr Tyr Cys
            100                 105                 110

Thr Gly Thr Tyr Gly Asn Ser Ala Trp Tyr Glu Asp Ala Phe Gly Gly
        115                 120                 125

Gly Thr Glu Val Val Val Lys Arg Thr Pro Val Ala Pro Thr Val Leu
    130                 135                 140

Leu Phe Pro Pro Ser Ser Ala Glu Leu Ala Thr Gly Thr Ala Thr Ile
145                 150                 155                 160

Val Cys Val Ala Asn Lys Tyr Phe Pro Asp Gly Thr Val Thr Trp Lys
                165                 170                 175

Val Asp Gly Ile Thr Gln Ser Ser Gly Ile Asn Asn Ser Arg Thr Pro
            180                 185                 190

Gln Asn Ser Ala Asp Cys Thr Tyr Asn Leu Ser Ser Thr Leu Thr Leu
        195                 200                 205

Ser Ser Asp Glu Tyr Asn Ser His Asp Glu Tyr Thr Cys Gln Val Ala
    210                 215                 220

Gln Asp Ser Gly Ser Pro Val Val Gln Ser Phe Ser Arg Lys Ser Cys
225                 230                 235                 240


<210> SEQ ID NO 33
<211> LENGTH: 460
<212> TYPE: PRT
<213> ORGANISM: Artificial Sequence
<220> FEATURE:
<223> OTHER INFORMATION: Synthetic Construct

<400> SEQUENCE: 33

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Ser Asn Ala Met Ile Trp Val Arg Gln Ala Pro Arg Glu Gly Leu Glu
    50                  55                  60

Trp Ile Gly Ala Met Asp Ser Asn Ser Arg Thr Tyr Tyr Ala Thr Trp
65                  70                  75                  80

Ala Lys Gly Arg Phe Thr Ile Ser Arg Thr Ser Ser Ile Thr Val Asp
                85                  90                  95

Leu Lys Ile Thr Ser Pro Thr Thr Glu Asp Thr Ala Thr Tyr Phe Cys
            100                 105                 110

Ala Arg Gly Asp Gly Gly Ser Ser Asp Tyr Thr Glu Met Trp Gly Pro
        115                 120                 125

Gly Thr Leu Val Thr Val Ser Ser Ala Ser Thr Lys Gly Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205

Ser Thr Trp Pro Ser Glu Thr Val Thr Cys Asn Val Ala His Pro Ala
```

```
    210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Pro Glu Val Gln Phe
        275                 280                 285

Ser Trp Phe Val Asp Asp Val Glu Val His Thr Ala Gln Thr Gln Pro
    290                 295                 300

Arg Glu Glu Gln Phe Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
            340                 345                 350

Lys Gly Arg Pro Lys Ala Pro Gln Val Tyr Thr Ile Pro Pro Pro Lys
        355                 360                 365

Glu Gln Met Ala Lys Asp Lys Val Ser Leu Thr Cys Met Ile Thr Asp
    370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
                405                 410                 415

Tyr Phe Val Tyr Ser Lys Leu Asn Val Gln Lys Ser Asn Trp Glu Ala
            420                 425                 430

Gly Asn Thr Phe Thr Cys Ser Val Leu His Glu Gly Leu His Asn His
        435                 440                 445

His Thr Glu Lys Ser Leu Ser His Ser Pro Gly Lys
    450                 455                 460


<210> SEQ ID NO 34
<211> LENGTH: 239
<212> TYPE: PRT
<213> ORGANISM: Artificial Sequence
<220> FEATURE:
<223> OTHER INFORMATION: Synthetic Construct

<400> SEQUENCE: 34

Met Asp Thr Arg Ala Pro Thr Gln Leu Leu Gly Leu Leu Leu Leu Trp
1               5                   10                  15

Leu Pro Gly Ala Thr Phe Ala Gln Ala Val Val Thr Gln Thr Thr Ser
            20                  25                  30

Pro Val Ser Ala Pro Val Gly Gly Thr Val Thr Ile Asn Cys Gln Ser
        35                  40                  45

Ser Gln Ser Val Tyr Gly Asn Asn Glu Leu Ser Trp Tyr Gln Gln Lys
    50                  55                  60

Pro Gly Gln Pro Pro Lys Leu Leu Ile Tyr Gln Ala Ser Ser Leu Ala
65                  70                  75                  80

Ser Gly Val Pro Ser Arg Phe Lys Gly Ser Gly Ser Gly Thr Gln Phe
                85                  90                  95

Thr Leu Thr Ile Ser Asp Leu Glu Cys Asp Asp Ala Ala Thr Tyr Tyr
            100                 105                 110

Cys Leu Gly Glu Tyr Ser Ile Ser Ala Asp Asn His Phe Gly Gly Gly
```

```
        115                 120                 125

Thr Glu Val Val Val Lys Arg Thr Pro Val Ala Pro Thr Val Leu Leu
    130                 135                 140

Phe Pro Pro Ser Ser Ala Glu Leu Ala Thr Gly Thr Ala Thr Ile Val
145                 150                 155                 160

Cys Val Ala Asn Lys Tyr Phe Pro Asp Gly Thr Val Thr Trp Lys Val
                165                 170                 175

Asp Gly Ile Thr Gln Ser Ser Gly Ile Asn Asn Ser Arg Thr Pro Gln
            180                 185                 190

Asn Ser Ala Asp Cys Thr Tyr Asn Leu Ser Ser Thr Leu Thr Leu Ser
        195                 200                 205

Ser Asp Glu Tyr Asn Ser His Asp Glu Tyr Thr Cys Gln Val Ala Gln
    210                 215                 220

Asp Ser Gly Ser Pro Val Val Gln Ser Phe Ser Arg Lys Ser Cys
225                 230                 235


<210> SEQ ID NO 35
<211> LENGTH: 221
<212> TYPE: PRT
<213> ORGANISM: Artificial Sequence
<220> FEATURE:
<223> OTHER INFORMATION: Synthetic Construct

<400> SEQUENCE: 35

Gln Val Gln Leu Val Gln Ser Gly Gly Ala Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Ala Val Ser Tyr Asp Gly Ser Asn Lys Tyr Tyr Ala Asp Phe Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Arg Gly Gly Leu Asp Ile Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Ala Ala Ala
    210                 215                 220


<210> SEQ ID NO 36
<211> LENGTH: 110
<212> TYPE: PRT
```

<213> ORGANISM: Artificial Sequence
<220> FEATURE:
<223> OTHER INFORMATION: Synthetic Construct

<400> SEQUENCE: 36

```
Leu Thr Gln Pro Pro Pro Ala Ser Gly Thr Pro Gly Gln Gln Arg Val
1               5                   10                  15

Thr Ile Ser Cys Ser Gly Ser Ser Ser Asn Ile Gly Ser Asn Thr Val
            20                  25                  30

Asn Trp Tyr Gln Gln Leu Pro Gly Thr Ala Pro Lys Leu Leu Ile Tyr
        35                  40                  45

Tyr Gly Asn Asp Gln Arg Pro Ser Gly Val Pro Asp Arg Phe Ser Ala
    50                  55                  60

Ser Lys Ser Gly Thr Ser Ala Ser Leu Ala Ile Ser Gly Leu Gln Ser
65                  70                  75                  80

Glu Asp Glu Ala His Tyr Tyr Cys Ala Ala Trp Asp Gly Ser Leu Asn
                85                  90                  95

Gly Gly Val Ile Phe Gly Gly Gly Thr Lys Val Thr Leu Gly
            100                 105                 110
```

<210> SEQ ID NO 37
<211> LENGTH: 109
<212> TYPE: PRT
<213> ORGANISM: Artificial Sequence
<220> FEATURE:
<223> OTHER INFORMATION: Synthetic Construct

<400> SEQUENCE: 37

```
Val Thr Gln Pro Pro Ser Ala Ser Gly Thr Pro Gly Gln Arg Val Thr
1               5                   10                  15

Ile Ser Cys Ser Gly Ser Ser Ser Asn Ile Gly Thr Asn Pro Val Asn
            20                  25                  30

Trp Tyr Gln Gln Leu Pro Gly Thr Ala Pro Lys Leu Leu Ile Tyr Thr
        35                  40                  45

Thr Asp Gln Arg Pro Ser Gly Val Pro Asp Arg Phe Ser Gly Ser Lys
    50                  55                  60

Ser Gly Thr Ser Ala Ser Leu Ala Ile Ser Gly Leu Gln Ser Glu Asp
65                  70                  75                  80

Glu Ala Asp Tyr Tyr Cys Ala Ala Trp Asp Asp Ser Leu Ser Gly Leu
                85                  90                  95

Tyr Val Phe Gly Thr Gly Thr Lys Val Thr Val Leu Gly
            100                 105
```

<210> SEQ ID NO 38
<211> LENGTH: 109
<212> TYPE: PRT
<213> ORGANISM: Artificial Sequence
<220> FEATURE:
<223> OTHER INFORMATION: Synthetic Construct

<400> SEQUENCE: 38

```
Met Thr His Thr Pro Leu Ser Leu Ser Val Thr Pro Gly Gln Pro Ala
1               5                   10                  15

Ser Ile Ser Cys Lys Ser Ser Gln Ser Leu Leu His Ser Asp Gly Lys
            20                  25                  30

Thr Tyr Leu Tyr Trp Tyr Leu Gln Arg Pro Gly Gln Ser Pro Gln Pro
        35                  40                  45

Leu Ile Tyr Glu Val Ser Asn Arg Phe Ser Gly Val Pro Asp Arg Phe
    50                  55                  60
```

Ser Gly Ser Gly Ser Gly Thr Asp Phe Thr Leu Lys Ile Ser Arg Val
65 70 75 80

Gln Ala Glu Asp Val Gly Val Tyr Tyr Cys Met Gln Ser Leu Gln Leu
85 90 95

Trp Thr Phe Gly Gln Gly Thr Lys Val Glu Ile Lys Arg
100 105

<210> SEQ ID NO 39
<211> LENGTH: 110
<212> TYPE: PRT
<213> ORGANISM: Artificial Sequence
<220> FEATURE:
<223> OTHER INFORMATION: Synthetic Construct

<400> SEQUENCE: 39

Met Thr Gln Ser Pro Leu Ser Leu Pro Val Thr Leu Gly Gln Pro Ala
1 5 10 15

Ser Ile Ser Cys Arg Ser Ser Gln Ser Leu Ile His Ser Asp Gly Asn
20 25 30

Thr Tyr Leu Asp Trp Phe Gln Gln Arg Pro Gly Gln Ser Pro Arg Arg
35 40 45

Leu Ile Tyr Lys Val Ser Asn Arg Asp Ser Gly Val Pro Asp Arg Phe
50 55 60

Ser Gly Ser Gly Ser Gly Thr Asp Phe Thr Leu Arg Ile Ser Arg Val
65 70 75 80

Glu Ala Glu Asp Ile Gly Val Tyr Tyr Cys Met Gln Ala Thr His Trp
85 90 95

Pro Arg Thr Phe Gly Gln Gly Thr Lys Val Glu Ile Lys Arg
100 105 110

<210> SEQ ID NO 40
<211> LENGTH: 110
<212> TYPE: PRT
<213> ORGANISM: Artificial Sequence
<220> FEATURE:
<223> OTHER INFORMATION: Synthetic Construct

<400> SEQUENCE: 40

Met Thr Gln Ser Pro Leu Ser Leu Pro Val Thr Leu Gly Gln Pro Ala
1 5 10 15

Ser Ile Ser Cys Arg Ser Ser Gln Ser Leu Val Asp Ser Ala Gly Asn
20 25 30

Thr Phe Leu His Trp Phe His Gln Arg Pro Gly Gln Ser Pro Arg Arg
35 40 45

Leu Ile Tyr Lys Val Ser Asn Arg Asp Ser Gly Val Pro Asp Arg Phe
50 55 60

Ser Gly Ser Gly Ser Gly Thr Asp Phe Thr Leu Lys Ile Ser Arg Val
65 70 75 80

Glu Ala Glu Asp Val Gly Val Tyr Tyr Cys Met Gln Gly Thr His Trp
85 90 95

Pro Arg Thr Phe Gly Gln Gly Thr Lys Val Glu Ile Lys Arg
100 105 110

<210> SEQ ID NO 41
<211> LENGTH: 110
<212> TYPE: PRT
<213> ORGANISM: Artificial Sequence
<220> FEATURE:
<223> OTHER INFORMATION: Synthetic Construct

<400> SEQUENCE: 41

Leu Thr Gln Ser Pro Leu Ser Leu Pro Val Thr Leu Gly Gln Pro Ala
1 5 10 15

Ser Ile Ser Cys Lys Ser Ser Gln Ser Leu Val Asp Ser Asp Gly Asn
20 25 30

Thr Tyr Leu Asn Trp Phe Gln Gln Arg Pro Gly Gln Ser Pro Arg Arg
35 40 45

Leu Ile Tyr Lys Val Ser Asn Arg Asp Ser Gly Val Pro Asp Arg Phe
50 55 60

Ser Gly Ser Gly Ser Gly Thr Asp Phe Thr Leu Lys Ile Ser Arg Val
65 70 75 80

Glu Ala Glu Asp Val Gly Val Tyr Tyr Cys Met Gln Gly Thr His Trp
85 90 95

Pro Arg Thr Phe Gly Gln Gly Thr Lys Val Glu Ile Lys Arg
100 105 110

<210> SEQ ID NO 42
<211> LENGTH: 110
<212> TYPE: PRT
<213> ORGANISM: Artificial Sequence
<220> FEATURE:
<223> OTHER INFORMATION: Synthetic Construct

<400> SEQUENCE: 42

Met Thr Gln Ser Pro Leu Ser Leu Pro Val Thr Leu Gly Gln Pro Ala
1 5 10 15

Ser Ile Ser Cys Arg Ser Ser Gln Ser Leu Val His Ser Asp Gly Asn
20 25 30

Met Tyr Leu Asn Trp Phe Gln Gln Arg Pro Gly Gln Ser Pro Arg Arg
35 40 45

Leu Ile Tyr Lys Val Ser Asn Arg Asp Ser Gly Val Pro Asp Arg Phe
50 55 60

Ser Gly Ser Gly Ser Gly Thr Asp Phe Thr Leu Lys Ile Ser Arg Val
65 70 75 80

Glu Ala Glu Asp Val Gly Val Tyr Tyr Cys Met Gln Ala Thr Gln Pro
85 90 95

Thr Trp Thr Phe Gly Gln Gly Thr Lys Leu Glu Ile Lys Arg
100 105 110

<210> SEQ ID NO 43
<211> LENGTH: 92
<212> TYPE: PRT
<213> ORGANISM: Artificial Sequence
<220> FEATURE:
<223> OTHER INFORMATION: Synthetic Construct

<400> SEQUENCE: 43

Met Thr Gln Ser Pro Ser Ser Leu Ser Ala Ser Val Gly Asp Arg Val
1 5 10 15

Thr Ile Thr Cys Gln Ala Ser Gln Asp Ile Ser Asn Tyr Leu Asn Trp
20 25 30

Tyr Gln Gln Lys Pro Gly Lys Ala Pro Lys Leu Leu Ile Tyr Asp Ala
35 40 45

Ser Asn Leu Glu Thr Gly Val Pro Ser Arg Phe Ser Gly Ser Gly Ser
50 55 60

Gly Thr Asp Phe Thr Phe Thr Ile Ser Ser Ala Thr Tyr Tyr Cys Gln
65 70 75 80

Gln Thr Tyr Gln Gly Thr Lys Leu Glu Ile Lys Arg
85 90

<210> SEQ ID NO 44
<211> LENGTH: 105
<212> TYPE: PRT
<213> ORGANISM: Artificial Sequence
<220> FEATURE:
<223> OTHER INFORMATION: Synthetic Construct

<400> SEQUENCE: 44

Met Thr Gln Ser Pro Ser Ser Leu Ser Ala Ser Val Gly His Pro Val
1 5 10 15

Thr Ile Thr Cys Arg Ala Ser Gln Ser Leu Ile Ser Tyr Leu Asn Trp
20 25 30

Tyr His Gln Lys Pro Gly Lys Ala Pro Lys Leu Leu Ile Tyr Ala Ala
35 40 45

Ser Ile Leu Gln Ser Gly Val Pro Ser Arg Phe Ser Gly Ser Gly Ser
50 55 60

Gly Thr Asp Phe Thr Leu Thr Ile Ser Ser Leu Gln Pro Glu Asn Phe
65 70 75 80

Ala Ser Tyr Tyr Cys Gln His Thr Asp Ser Phe Pro Arg Thr Phe Gly
85 90 95

His Gly Thr Lys Val Glu Ile Lys Arg
100 105

<210> SEQ ID NO 45
<211> LENGTH: 108
<212> TYPE: PRT
<213> ORGANISM: Artificial Sequence
<220> FEATURE:
<223> OTHER INFORMATION: Synthetic Construct

<400> SEQUENCE: 45

Leu Thr Gln Pro Pro Ser Ala Ser Gly Thr Pro Gly Gln Gly Val Thr
1 5 10 15

Ile Ser Cys Arg Gly Ser Thr Ser Asn Ile Gly Asn Asn Val Val Asn
20 25 30

Trp Tyr Gln His Val Pro Gly Ser Ala Pro Lys Leu Leu Ile Trp Ser
35 40 45

Asn Ile Gln Arg Pro Ser Gly Ile Pro Asp Arg Phe Ser Gly Ser Lys
50 55 60

Ser Gly Thr Ser Ala Ser Leu Ala Ile Ser Gly Leu Gln Ser Glu Asp
65 70 75 80

Gln Ala Val Tyr Tyr Cys Ala Val Trp Asp Asp Gly Leu Ala Gly Trp
85 90 95

Val Phe Gly Gly Gly Thr Thr Val Thr Val Leu Ser
100 105

<210> SEQ ID NO 46
<211> LENGTH: 105
<212> TYPE: PRT
<213> ORGANISM: Artificial Sequence
<220> FEATURE:
<223> OTHER INFORMATION: Synthetic Construct

<400> SEQUENCE: 46

Met Thr Gln Ala Pro Val Val Ser Val Ala Leu Glu Gln Thr Val Arg
1 5 10 15

```
Ile Thr Cys Gln Gly Asp Ser Leu Ala Ile Tyr Tyr Asp Phe Trp Tyr
            20                  25                  30

Gln His Lys Pro Gly Gln Ala Pro Val Leu Val Ile Tyr Gly Lys Asn
        35                  40                  45

Asn Arg Pro Ser Gly Ile Pro His Arg Phe Ser Gly Ser Ser Ser Asn
    50                  55                  60

Thr Asp Ser Leu Thr Ile Thr Gly Ala Gln Ala Glu Asp Glu Ala Asp
65                  70                  75                  80

Tyr Tyr Cys Asn Ser Arg Asp Ser Ser Gly Asn His Trp Val Phe Gly
                85                  90                  95

Gly Gly Thr Asn Leu Thr Val Leu Gly
            100                 105


<210> SEQ ID NO 47
<211> LENGTH: 111
<212> TYPE: PRT
<213> ORGANISM: Artificial Sequence
<220> FEATURE:
<223> OTHER INFORMATION: Synthetic Construct

<400> SEQUENCE: 47

Leu Thr Gln Ser Pro Leu Ser Leu Pro Val Thr Leu Gly Gln Pro Ala
1               5                   10                  15

Ser Ile Ser Cys Lys Ser Asn Gln Ser Leu Val His Ser Asp Gly Asn
            20                  25                  30

Thr Tyr Leu Asn Trp Phe Gln Gln Arg Pro Gly Gln Ser Pro Arg Arg
        35                  40                  45

Leu Ile Tyr Lys Val Ser Asn Arg Asp Ser Gly Val Pro Asp Arg Phe
    50                  55                  60

Ser Gly Ser Gly Ser Gly Thr Asp Phe Thr Leu Lys Ile Asn Arg Val
65                  70                  75                  80

Glu Ala Glu Asp Val Gly Val Tyr Tyr Cys Met Gln Gly Thr Gln Trp
                85                  90                  95

Pro Arg Thr Phe Gly Gly Gln Gly Thr Lys Leu Asp Ile Lys Arg
            100                 105                 110


<210> SEQ ID NO 48
<211> LENGTH: 119
<212> TYPE: PRT
<213> ORGANISM: Artificial Sequence
<220> FEATURE:
<223> OTHER INFORMATION: Synthetic Construct

<400> SEQUENCE: 48

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Thr Thr Gly
            20                  25                  30

Gly Tyr Trp Trp Thr Trp Ile Arg Gln Pro Pro Gly Lys Gly Leu Glu
        35                  40                  45

Trp Ile Gly Tyr Ile Phe Ser Ser Gly Asn Thr Asn Tyr Asn Pro Ser
    50                  55                  60

Ile Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Tyr Gly Lys Leu Gly Phe Asp Tyr Trp Gly Gln Gly
            100                 105                 110
```

Thr Leu Val Thr Val Ser Ser
115

<210> SEQ ID NO 49
<211> LENGTH: 119
<212> TYPE: PRT
<213> ORGANISM: Artificial Sequence
<220> FEATURE:
<223> OTHER INFORMATION: Synthetic Construct

<400> SEQUENCE: 49

Gln Val Gln Leu Gln Glu Ser Gly Pro Gly Leu Val Lys Pro Ser Gln
1 5 10 15

Thr Leu Ser Leu Thr Cys Thr Val Ser Gly Phe Ser Ile Thr Thr Gly
20 25 30

Gly Tyr Trp Trp Thr Trp Ile Arg Gln His Pro Gly Lys Gly Leu Glu
35 40 45

Trp Ile Gly Tyr Ile Phe Ser Ser Gly Asn Thr Asn Tyr Asn Pro Ser
50 55 60

Ile Lys Ser Leu Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Ala Tyr Gly Lys Leu Gly Phe Asp Tyr Trp Gly Gln Gly
100 105 110

Thr Leu Val Thr Val Ser Ser
115

<210> SEQ ID NO 50
<211> LENGTH: 119
<212> TYPE: PRT
<213> ORGANISM: Artificial Sequence
<220> FEATURE:
<223> OTHER INFORMATION: Synthetic Construct

<400> SEQUENCE: 50

Gln Val Gln Leu Gln Glu Ser Gly Pro Gly Leu Val Lys Pro Ser Gln
1 5 10 15

Thr Leu Ser Leu Thr Cys Thr Val Ser Gly Phe Ser Ile Thr Thr Gly
20 25 30

Gly Tyr Trp Trp Thr Trp Ile Arg Gln Pro Pro Gly Lys Gly Leu Glu
35 40 45

Trp Ile Gly Tyr Ile Phe Ser Ser Gly Asn Thr Asn Tyr Asn Pro Ser
50 55 60

Ile Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Ala Tyr Gly Lys Leu Gly Phe Asp Tyr Trp Gly Gln Gly
100 105 110

Thr Leu Val Thr Val Ser Ser
115

<210> SEQ ID NO 51
<211> LENGTH: 119
<212> TYPE: PRT
<213> ORGANISM: Artificial Sequence
<220> FEATURE:
<223> OTHER INFORMATION: Synthetic Construct

<400> SEQUENCE: 51

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Thr Thr Gly
            20                  25                  30

Gly Tyr Trp Trp Thr Trp Ile Arg Gln Pro Pro Gly Lys Gly Leu Glu
        35                  40                  45

Trp Ile Gly Tyr Ile Phe Ser Ser Gly Asn Thr Asn Tyr Asn Pro Ser
    50                  55                  60

Ile Lys Ser Arg Val Thr Ile Ser Arg Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Tyr Gly Lys Leu Gly Phe Asp Tyr Trp Gly Gln Gly
            100                 105                 110

Thr Leu Val Thr Val Ser Ser
        115

<210> SEQ ID NO 52
<211> LENGTH: 119
<212> TYPE: PRT
<213> ORGANISM: Artificial Sequence
<220> FEATURE:
<223> OTHER INFORMATION: Synthetic Construct

<400> SEQUENCE: 52

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Thr Thr Gly
            20                  25                  30

Gly Tyr Trp Trp Thr Trp Ile Arg Gln Pro Pro Gly Lys Gly Leu Glu
        35                  40                  45

Trp Ile Gly Tyr Ile Phe Ser Ser Gly Asn Thr Asn Tyr Asn Pro Ser
    50                  55                  60

Ile Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Arg Tyr Tyr
                85                  90                  95

Cys Ala Arg Ala Tyr Gly Lys Leu Gly Phe Asp Tyr Trp Gly Gln Gly
            100                 105                 110

Thr Leu Val Thr Val Ser Ser
        115

<210> SEQ ID NO 53
<211> LENGTH: 120
<212> TYPE: PRT
<213> ORGANISM: Artificial Sequence
<220> FEATURE:
<223> OTHER INFORMATION: Synthetic Construct

<400> SEQUENCE: 53

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Thr Thr Gly
            20                  25                  30

Gly Tyr Trp Trp Thr Trp Ile Arg Gln Pro Pro Gly Lys Gly Leu Glu
        35                  40                  45

```
Trp Ile Gly Tyr Ile Phe Ser Ser Gly Asn Thr Asn Tyr Asn Pro Ser
    50                  55                  60

Ile Lys Ser Arg Ile Ser Ile Thr Arg Asp Thr Ser Lys Asn Gln Phe
65                  70                  75                  80

Phe Leu Gln Leu Asn Ser Val Thr Thr Glu Gly Asp Thr Ala Arg Tyr
                85                  90                  95

Tyr Cys Ala Arg Ala Tyr Gly Lys Leu Gly Phe Asp Tyr Trp Gly Gln
            100                 105                 110

Gly Thr Leu Val Thr Val Ser Ser
        115                 120


<210> SEQ ID NO 54
<211> LENGTH: 111
<212> TYPE: PRT
<213> ORGANISM: Artificial Sequence
<220> FEATURE:
<223> OTHER INFORMATION: Synthetic Construct

<400> SEQUENCE: 54

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Gly Trp His Gln Gln Gln Pro Glu Lys Gly Pro Arg Tyr Leu Met
        35                  40                  45

Lys Val Asn Ser Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Ser Ser Asp
                85                  90                  95

Ser Ser Gly Tyr Val Phe Gly Ser Gly Thr Lys Val Thr Val Leu
            100                 105                 110


<210> SEQ ID NO 55
<211> LENGTH: 111
<212> TYPE: PRT
<213> ORGANISM: Artificial Sequence
<220> FEATURE:
<223> OTHER INFORMATION: Synthetic Construct

<400> SEQUENCE: 55

Leu Pro Val Leu Thr Gln Pro Pro Ser Ala Ser Ala Leu Leu Gly Ala
1               5                   10                  15

Ser Ile Lys Leu Thr Cys Thr Leu Ser Ser Gln His Ser Thr Tyr Thr
            20                  25                  30

Ile Gly Trp Tyr Gln Gln Arg Pro Gly Arg Ser Pro Gln Tyr Ile Met
        35                  40                  45

Lys Val Asn Ser Asp Gly Ser His Ser Lys Gly Asp Gly Ile Pro Asp
    50                  55                  60

Arg Phe Met Gly Ser Ser Ser Gly Ala Asp Arg Tyr Leu Thr Phe Ser
65                  70                  75                  80

Asn Leu Gln Ser Asp Asp Glu Ala Glu Tyr His Cys Gly Ser Ser Asp
                85                  90                  95

Ser Ser Gly Tyr Val Phe Gly Ser Gly Thr Lys Val Thr Val Leu
            100                 105                 110
```

<210> SEQ ID NO 56
<211> LENGTH: 15
<212> TYPE: PRT
<213> ORGANISM: Artificial Sequence
<220> FEATURE:
<223> OTHER INFORMATION: Synthetic Construct

<400> SEQUENCE: 56

Gly Gly Gly Gly Ser Gly Gly Gly Gly Ser Gly Gly Gly Gly Ser
1 5 10 15

<210> SEQ ID NO 57
<211> LENGTH: 247
<212> TYPE: PRT
<213> ORGANISM: Artificial Sequence
<220> FEATURE:
<223> OTHER INFORMATION: Synthetic Construct

<400> SEQUENCE: 57

Gln Pro Val Leu Thr Gln Ser Pro Ser Ala Ser Ala Ser Leu Gly Asn
1 5 10 15

Ser Val Lys Ile Thr Cys Thr Leu Ser Ser Gln His Ser Thr Tyr Thr
20 25 30

Ile Gly Trp Tyr Gln Gln His Pro Asp Lys Ala Pro Lys Tyr Val Met
35 40 45

Tyr Val Asn Ser Asp Gly Ser His Ser Lys Gly Asp Gly Ile Pro Asp
50 55 60

Arg Phe Ser Gly Ser Ser Ser Gly Ala His Arg Tyr Leu Ser Ile Ser
65 70 75 80

Asn Ile Gln Pro Glu Asp Glu Ala Asp Tyr Phe Cys Gly Ser Ser Asp
85 90 95

Ser Ser Gly Tyr Val Phe Gly Ser Gly Thr Gln Leu Thr Val Leu Arg
100 105 110

Ala Ala Ala Ser Ser Gly Gly Gly Gly Ser Gly Gly Gly Gly Ser Gly
115 120 125

Gly Gly Gly Ser Gln Pro Val Leu Thr Gln Ser Pro Ser Ala Ser Ala
130 135 140

Ser Leu Gly Asn Ser Val Lys Ile Thr Cys Thr Leu Ser Ser Gln His
145 150 155 160

Ser Thr Tyr Thr Ile Gly Trp Tyr Gln Gln His Pro Asp Lys Ala Pro
165 170 175

Lys Tyr Val Met Tyr Val Asn Ser Asp Gly Ser His Ser Lys Gly Asp
180 185 190

Gly Ile Pro Asp Arg Phe Ser Gly Ser Ser Ser Gly Ala His Arg Tyr
195 200 205

Leu Ser Ile Ser Asn Ile Gln Pro Glu Asp Glu Ala Asp Tyr Phe Cys
210 215 220

Gly Ser Ser Asp Ser Ser Gly Tyr Val Phe Gly Ser Gly Thr Gln Leu
225 230 235 240

Thr Val Leu Arg Ala Ala Ala
245

<210> SEQ ID NO 58
<211> LENGTH: 253
<212> TYPE: PRT
<213> ORGANISM: Artificial Sequence
<220> FEATURE:
<223> OTHER INFORMATION: Synthetic Construct

<400> SEQUENCE: 58

Gln Val Gln Leu Lys Glu Ser Gly Pro Gly Leu Val Lys Pro Ser Gln
1 5 10 15

Ser Leu Ser Leu Thr Cys Ser Val Thr Gly Phe Ser Ile Thr Thr Gly
20 25 30

Gly Tyr Trp Trp Thr Trp Ile Arg Gln Phe Pro Gly Gln Lys Leu Glu
35 40 45

Trp Met Gly Tyr Ile Phe Ser Ser Gly Asn Thr Asn Tyr Asn Pro Ser
50 55 60

Ile Lys Ser Arg Ile Ser Ile Thr Arg Asp Thr Ser Lys Asn Gln Phe
65 70 75 80

Phe Leu Gln Leu Asn Ser Val Thr Thr Glu Gly Asp Thr Ala Arg Tyr
85 90 95

Tyr Cys Ala Arg Ala Tyr Gly Lys Leu Gly Phe Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Gln Val Gln Leu Lys Glu Ser Gly Pro
130 135 140

Gly Leu Val Lys Pro Ser Gln Ser Leu Ser Leu Thr Cys Ser Val Thr
145 150 155 160

Gly Phe Ser Ile Thr Thr Gly Gly Tyr Trp Trp Thr Trp Ile Arg Gln
165 170 175

Phe Pro Gly Gln Lys Leu Glu Trp Met Gly Tyr Ile Phe Ser Ser Gly
180 185 190

Asn Thr Asn Tyr Asn Pro Ser Ile Lys Ser Arg Ile Ser Ile Thr Arg
195 200 205

Asp Thr Ser Lys Asn Gln Phe Phe Leu Gln Leu Asn Ser Val Thr Thr
210 215 220

Glu Gly Asp Thr Ala Arg Tyr Tyr Cys Ala Arg Ala Tyr Gly Lys Leu
225 230 235 240

Gly Phe Asp Tyr Trp Gly Gln Gly Thr Leu Val Thr Val
245 250

<210> SEQ ID NO 59
<211> LENGTH: 245
<212> TYPE: PRT
<213> ORGANISM: Artificial Sequence
<220> FEATURE:
<223> OTHER INFORMATION: Synthetic Construct

<400> SEQUENCE: 59

Gln Val Gln Leu Gln Glu Ser Gly Pro Gly Leu Val Lys Pro Ser Glu
1 5 10 15

Thr Leu Ser Leu Thr Cys Thr Val Ser Gly Phe Ser Ile Thr Thr Gly
20 25 30

Gly Tyr Trp Trp Thr Trp Ile Arg Gln Pro Pro Gly Lys Gly Leu Glu
35 40 45

Trp Ile Gly Tyr Ile Phe Ser Ser Gly Asn Thr Asn Tyr Asn Pro Ser
50 55 60

Ile Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Ala Tyr Gly Lys Leu Gly Phe Asp Tyr Trp Gly Gln Gly
100 105 110

```
Thr Leu Val Thr Val Ser Ser Gly Gly Gly Gly Ser Gly Gly Gly Gly
        115                 120                 125

Ser Gly Gly Gly Gly Ser Gln Leu Val Leu Thr Gln Ser Pro Ser Ala
    130                 135                 140

Ser Ala Ser Leu Gly Ala Ser Val Lys Leu Thr Cys Thr Leu Ser Ser
145                 150                 155                 160

Gln His Ser Thr Tyr Thr Ile Gly Trp His Gln Gln Gln Pro Glu Lys
                165                 170                 175

Gly Pro Arg Tyr Leu Met Lys Val Asn Ser Asp Gly Ser His Ser Lys
            180                 185                 190

Gly Asp Gly Ile Pro Asp Arg Phe Ser Gly Ser Ser Ser Gly Ala Glu
        195                 200                 205

Arg Tyr Leu Thr Ile Ser Ser Leu Gln Ser Glu Asp Glu Ala Asp Tyr
    210                 215                 220

Tyr Cys Gly Ser Ser Asp Ser Ser Gly Tyr Val Phe Gly Ser Gly Thr
225                 230                 235                 240

Lys Val Thr Val Leu
                245


<210> SEQ ID NO 60
<211> LENGTH: 245
<212> TYPE: PRT
<213> ORGANISM: Artificial Sequence
<220> FEATURE:
<223> OTHER INFORMATION: Synthetic Construct

<400> SEQUENCE: 60

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Thr Thr Gly
            20                  25                  30

Gly Tyr Trp Trp Thr Trp Ile Arg Gln His Pro Gly Lys Gly Leu Glu
        35                  40                  45

Trp Ile Gly Tyr Ile Phe Ser Ser Gly Asn Thr Asn Tyr Asn Pro Ser
    50                  55                  60

Ile Lys Ser Leu Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Tyr Gly Lys Leu Gly Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gln Leu Val Leu Thr Gln Ser Pro Ser Ala
    130                 135                 140

Ser Ala Ser Leu Gly Ala Ser Val Lys Leu Thr Cys Thr Leu Ser Ser
145                 150                 155                 160

Gln His Ser Thr Tyr Thr Ile Gly Trp His Gln Gln Gln Pro Glu Lys
                165                 170                 175

Gly Pro Arg Tyr Leu Met Lys Val Asn Ser Asp Gly Ser His Ser Lys
            180                 185                 190

Gly Asp Gly Ile Pro Asp Arg Phe Ser Gly Ser Ser Ser Gly Ala Glu
        195                 200                 205

Arg Tyr Leu Thr Ile Ser Ser Leu Gln Ser Glu Asp Glu Ala Asp Tyr
    210                 215                 220
```

```
Tyr Cys Gly Ser Ser Asp Ser Ser Gly Tyr Val Phe Gly Ser Gly Thr
225                 230                 235                 240

Lys Val Thr Val Leu
                245
```

<210> SEQ ID NO 61
<211> LENGTH: 245
<212> TYPE: PRT
<213> ORGANISM: Artificial Sequence
<220> FEATURE:
<223> OTHER INFORMATION: Synthetic Construct

<400> SEQUENCE: 61

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Thr Thr Gly
            20                  25                  30

Gly Tyr Trp Trp Thr Trp Ile Arg Gln Pro Pro Gly Lys Gly Leu Glu
        35                  40                  45

Trp Ile Gly Tyr Ile Phe Ser Ser Gly Asn Thr Asn Tyr Asn Pro Ser
    50                  55                  60

Ile Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Tyr Gly Lys Leu Gly Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gln Leu Val Leu Thr Gln Ser Pro Ser Ala
    130                 135                 140

Ser Ala Ser Leu Gly Ala Ser Val Lys Leu Thr Cys Thr Leu Ser Ser
145                 150                 155                 160

Gln His Ser Thr Tyr Thr Ile Gly Trp His Gln Gln Gln Pro Glu Lys
                165                 170                 175

Gly Pro Arg Tyr Leu Met Lys Val Asn Ser Asp Gly Ser His Ser Lys
            180                 185                 190

Gly Asp Gly Ile Pro Asp Arg Phe Ser Gly Ser Ser Ser Gly Ala Glu
        195                 200                 205

Arg Tyr Leu Thr Ile Ser Ser Leu Gln Ser Glu Asp Glu Ala Asp Tyr
    210                 215                 220

Tyr Cys Gly Ser Ser Asp Ser Ser Gly Tyr Val Phe Gly Ser Gly Thr
225                 230                 235                 240

Lys Val Thr Val Leu
                245
```

<210> SEQ ID NO 62
<211> LENGTH: 245
<212> TYPE: PRT
<213> ORGANISM: Artificial Sequence
<220> FEATURE:
<223> OTHER INFORMATION: Synthetic Construct

<400> SEQUENCE: 62

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Thr Thr Gly
```

```
            20                  25                  30

Gly Tyr Trp Trp Thr Trp Ile Arg Gln Pro Pro Gly Lys Gly Leu Glu
        35                  40                  45

Trp Ile Gly Tyr Ile Phe Ser Ser Gly Asn Thr Asn Tyr Asn Pro Ser
    50                  55                  60

Ile Lys Ser Arg Val Thr Ile Ser Arg Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Tyr Gly Lys Leu Gly Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gln Leu Val Leu Thr Gln Ser Pro Ser Ala
    130                 135                 140

Ser Ala Ser Leu Gly Ala Ser Val Lys Leu Thr Cys Thr Leu Ser Ser
145                 150                 155                 160

Gln His Ser Thr Tyr Thr Ile Gly Trp His Gln Gln Gln Pro Glu Lys
                165                 170                 175

Gly Pro Arg Tyr Leu Met Lys Val Asn Ser Asp Gly Ser His Ser Lys
            180                 185                 190

Gly Asp Gly Ile Pro Asp Arg Phe Ser Gly Ser Ser Ser Gly Ala Glu
        195                 200                 205

Arg Tyr Leu Thr Ile Ser Ser Leu Gln Ser Glu Asp Glu Ala Asp Tyr
    210                 215                 220

Tyr Cys Gly Ser Ser Asp Ser Ser Gly Tyr Val Phe Gly Ser Gly Thr
225                 230                 235                 240

Lys Val Thr Val Leu
                245


<210> SEQ ID NO 63
<211> LENGTH: 245
<212> TYPE: PRT
<213> ORGANISM: Artificial Sequence
<220> FEATURE:
<223> OTHER INFORMATION: Synthetic Construct

<400> SEQUENCE: 63

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Thr Thr Gly
            20                  25                  30

Gly Tyr Trp Trp Thr Trp Ile Arg Gln Pro Pro Gly Lys Gly Leu Glu
        35                  40                  45

Trp Ile Gly Tyr Ile Phe Ser Ser Gly Asn Thr Asn Tyr Asn Pro Ser
    50                  55                  60

Ile Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Arg Tyr Tyr
                85                  90                  95

Cys Ala Arg Ala Tyr Gly Lys Leu Gly Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gln Leu Val Leu Thr Gln Ser Pro Ser Ala
```

```
    130                 135                 140

Ser Ala Ser Leu Gly Ala Ser Val Lys Leu Thr Cys Thr Leu Ser Ser
145                 150                 155                 160

Gln His Ser Thr Tyr Thr Ile Gly Trp His Gln Gln Gln Pro Glu Lys
                165                 170                 175

Gly Pro Arg Tyr Leu Met Lys Val Asn Ser Asp Gly Ser His Ser Lys
            180                 185                 190

Gly Asp Gly Ile Pro Asp Arg Phe Ser Gly Ser Ser Ser Gly Ala Glu
        195                 200                 205

Arg Tyr Leu Thr Ile Ser Ser Leu Gln Ser Glu Asp Glu Ala Asp Tyr
    210                 215                 220

Tyr Cys Gly Ser Ser Asp Ser Ser Gly Tyr Val Phe Gly Ser Gly Thr
225                 230                 235                 240

Lys Val Thr Val Leu
                245


<210> SEQ ID NO 64
<211> LENGTH: 246
<212> TYPE: PRT
<213> ORGANISM: Artificial Sequence
<220> FEATURE:
<223> OTHER INFORMATION: Synthetic Construct

<400> SEQUENCE: 64

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Thr Thr Gly
            20                  25                  30

Gly Tyr Trp Trp Thr Trp Ile Arg Gln Pro Pro Gly Lys Gly Leu Glu
        35                  40                  45

Trp Ile Gly Tyr Ile Phe Ser Ser Gly Asn Thr Asn Tyr Asn Pro Ser
    50                  55                  60

Ile Lys Ser Arg Ile Ser Ile Thr Arg Asp Thr Ser Lys Asn Gln Phe
65                  70                  75                  80

Phe Leu Gln Leu Asn Ser Val Thr Thr Glu Gly Asp Thr Ala Arg Tyr
                85                  90                  95

Tyr Cys Ala Arg Ala Tyr Gly Lys Leu Gly Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gln Leu Val Leu Thr Gln Ser Pro Ser
    130                 135                 140

Ala Ser Ala Ser Leu Gly Ala Ser Val Lys Leu Thr Cys Thr Leu Ser
145                 150                 155                 160

Ser Gln His Ser Thr Tyr Thr Ile Gly Trp His Gln Gln Gln Pro Glu
                165                 170                 175

Lys Gly Pro Arg Tyr Leu Met Lys Val Asn Ser Asp Gly Ser His Ser
            180                 185                 190

Lys Gly Asp Gly Ile Pro Asp Arg Phe Ser Gly Ser Ser Ser Gly Ala
        195                 200                 205

Glu Arg Tyr Leu Thr Ile Ser Ser Leu Gln Ser Glu Asp Glu Ala Asp
    210                 215                 220

Tyr Tyr Cys Gly Ser Ser Asp Ser Ser Gly Tyr Val Phe Gly Ser Gly
225                 230                 235                 240

Thr Lys Val Thr Val Leu
```

245

<210> SEQ ID NO 65
<211> LENGTH: 245
<212> TYPE: PRT
<213> ORGANISM: Artificial Sequence
<220> FEATURE:
<223> OTHER INFORMATION: Synthetic Construct

<400> SEQUENCE: 65

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Thr Thr Gly
            20                  25                  30

Gly Tyr Trp Trp Thr Trp Ile Arg Gln Pro Pro Gly Lys Gly Leu Glu
        35                  40                  45

Trp Ile Gly Tyr Ile Phe Ser Ser Gly Asn Thr Asn Tyr Asn Pro Ser
    50                  55                  60

Ile Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Tyr Gly Lys Leu Gly Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Leu Pro Val Leu Thr Gln Pro Pro Ser Ala
    130                 135                 140

Ser Ala Leu Leu Gly Ala Ser Ile Lys Leu Thr Cys Thr Leu Ser Ser
145                 150                 155                 160

Gln His Ser Thr Tyr Thr Ile Gly Trp Tyr Gln Gln Arg Pro Gly Arg
                165                 170                 175

Ser Pro Gln Tyr Ile Met Lys Val Asn Ser Asp Gly Ser His Ser Lys
            180                 185                 190

Gly Asp Gly Ile Pro Asp Arg Phe Met Gly Ser Ser Ser Gly Ala Asp
        195                 200                 205

Arg Tyr Leu Thr Phe Ser Asn Leu Gln Ser Asp Asp Glu Ala Glu Tyr
    210                 215                 220

His Cys Gly Ser Ser Asp Ser Ser Gly Tyr Val Phe Gly Ser Gly Thr
225                 230                 235                 240

Lys Val Thr Val Leu
                245
```

<210> SEQ ID NO 66
<211> LENGTH: 245
<212> TYPE: PRT
<213> ORGANISM: Artificial Sequence
<220> FEATURE:
<223> OTHER INFORMATION: Synthetic Construct

<400> SEQUENCE: 66

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Thr Thr Gly
            20                  25                  30

Gly Tyr Trp Trp Thr Trp Ile Arg Gln His Pro Gly Lys Gly Leu Glu
        35                  40                  45
```

```
Trp Ile Gly Tyr Ile Phe Ser Ser Gly Asn Thr Asn Tyr Asn Pro Ser
    50                  55                  60

Ile Lys Ser Leu Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Tyr Gly Lys Leu Gly Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Leu Pro Val Leu Thr Gln Pro Pro Ser Ala
    130                 135                 140

Ser Ala Leu Leu Gly Ala Ser Ile Lys Leu Thr Cys Thr Leu Ser Ser
145                 150                 155                 160

Gln His Ser Thr Tyr Thr Ile Gly Trp Tyr Gln Gln Arg Pro Gly Arg
                165                 170                 175

Ser Pro Gln Tyr Ile Met Lys Val Asn Ser Asp Gly Ser His Ser Lys
            180                 185                 190

Gly Asp Gly Ile Pro Asp Arg Phe Met Gly Ser Ser Ser Gly Ala Asp
        195                 200                 205

Arg Tyr Leu Thr Phe Ser Asn Leu Gln Ser Asp Asp Glu Ala Glu Tyr
    210                 215                 220

His Cys Gly Ser Ser Asp Ser Ser Gly Tyr Val Phe Gly Ser Gly Thr
225                 230                 235                 240

Lys Val Thr Val Leu
                245


<210> SEQ ID NO 67
<211> LENGTH: 245
<212> TYPE: PRT
<213> ORGANISM: Artificial Sequence
<220> FEATURE:
<223> OTHER INFORMATION: Synthetic Construct

<400> SEQUENCE: 67

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Thr Thr Gly
            20                  25                  30

Gly Tyr Trp Trp Thr Trp Ile Arg Gln Pro Pro Gly Lys Gly Leu Glu
        35                  40                  45

Trp Ile Gly Tyr Ile Phe Ser Ser Gly Asn Thr Asn Tyr Asn Pro Ser
    50                  55                  60

Ile Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Tyr Gly Lys Leu Gly Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Leu Pro Val Leu Thr Gln Pro Pro Ser Ala
    130                 135                 140

Ser Ala Leu Leu Gly Ala Ser Ile Lys Leu Thr Cys Thr Leu Ser Ser
145                 150                 155                 160
```

```
Gln His Ser Thr Tyr Thr Ile Gly Trp Tyr Gln Gln Arg Pro Gly Arg
                165                 170                 175

Ser Pro Gln Tyr Ile Met Lys Val Asn Ser Asp Gly Ser His Ser Lys
            180                 185                 190

Gly Asp Gly Ile Pro Asp Arg Phe Met Gly Ser Ser Ser Gly Ala Asp
        195                 200                 205

Arg Tyr Leu Thr Phe Ser Asn Leu Gln Ser Asp Asp Glu Ala Glu Tyr
    210                 215                 220

His Cys Gly Ser Ser Asp Ser Ser Gly Tyr Val Phe Gly Ser Gly Thr
225                 230                 235                 240

Lys Val Thr Val Leu
                245


<210> SEQ ID NO 68
<211> LENGTH: 245
<212> TYPE: PRT
<213> ORGANISM: Artificial Sequence
<220> FEATURE:
<223> OTHER INFORMATION: Synthetic Construct

<400> SEQUENCE: 68

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Thr Thr Gly
            20                  25                  30

Gly Tyr Trp Trp Thr Trp Ile Arg Gln Pro Pro Gly Lys Gly Leu Glu
        35                  40                  45

Trp Ile Gly Tyr Ile Phe Ser Ser Gly Asn Thr Asn Tyr Asn Pro Ser
    50                  55                  60

Ile Lys Ser Arg Val Thr Ile Ser Arg Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Tyr Gly Lys Leu Gly Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Leu Pro Val Leu Thr Gln Pro Pro Ser Ala
    130                 135                 140

Ser Ala Leu Leu Gly Ala Ser Ile Lys Leu Thr Cys Thr Leu Ser Ser
145                 150                 155                 160

Gln His Ser Thr Tyr Thr Ile Gly Trp Tyr Gln Gln Arg Pro Gly Arg
                165                 170                 175

Ser Pro Gln Tyr Ile Met Lys Val Asn Ser Asp Gly Ser His Ser Lys
            180                 185                 190

Gly Asp Gly Ile Pro Asp Arg Phe Met Gly Ser Ser Ser Gly Ala Asp
        195                 200                 205

Arg Tyr Leu Thr Phe Ser Asn Leu Gln Ser Asp Asp Glu Ala Glu Tyr
    210                 215                 220

His Cys Gly Ser Ser Asp Ser Ser Gly Tyr Val Phe Gly Ser Gly Thr
225                 230                 235                 240

Lys Val Thr Val Leu
                245


<210> SEQ ID NO 69
<211> LENGTH: 245
```

<212> TYPE: PRT
<213> ORGANISM: Artificial Sequence
<220> FEATURE:
<223> OTHER INFORMATION: Synthetic Construct

<400> SEQUENCE: 69

Gln Val Gln Leu Gln Glu Ser Gly Pro Gly Leu Val Lys Pro Ser Glu
1 5 10 15

Thr Leu Ser Leu Thr Cys Thr Val Ser Gly Phe Ser Ile Thr Thr Gly
20 25 30

Gly Tyr Trp Trp Thr Trp Ile Arg Gln Pro Pro Gly Lys Gly Leu Glu
35 40 45

Trp Ile Gly Tyr Ile Phe Ser Ser Gly Asn Thr Asn Tyr Asn Pro Ser
50 55 60

Ile Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Arg Tyr Tyr
85 90 95

Cys Ala Arg Ala Tyr Gly Lys Leu Gly Phe Asp Tyr Trp Gly Gln Gly
100 105 110

Thr Leu Val Thr Val Ser Ser Gly Gly Gly Gly Ser Gly Gly Gly Gly
115 120 125

Ser Gly Gly Gly Gly Ser Leu Pro Val Leu Thr Gln Pro Pro Ser Ala
130 135 140

Ser Ala Leu Leu Gly Ala Ser Ile Lys Leu Thr Cys Thr Leu Ser Ser
145 150 155 160

Gln His Ser Thr Tyr Thr Ile Gly Trp Tyr Gln Gln Arg Pro Gly Arg
165 170 175

Ser Pro Gln Tyr Ile Met Lys Val Asn Ser Asp Gly Ser His Ser Lys
180 185 190

Gly Asp Gly Ile Pro Asp Arg Phe Met Gly Ser Ser Ser Gly Ala Asp
195 200 205

Arg Tyr Leu Thr Phe Ser Asn Leu Gln Ser Asp Asp Glu Ala Glu Tyr
210 215 220

His Cys Gly Ser Ser Asp Ser Ser Gly Tyr Val Phe Gly Ser Gly Thr
225 230 235 240

Lys Val Thr Val Leu
245

<210> SEQ ID NO 70
<211> LENGTH: 246
<212> TYPE: PRT
<213> ORGANISM: Artificial Sequence
<220> FEATURE:
<223> OTHER INFORMATION: Synthetic Construct

<400> SEQUENCE: 70

Gln Val Gln Leu Gln Glu Ser Gly Pro Gly Leu Val Lys Pro Ser Glu
1 5 10 15

Thr Leu Ser Leu Thr Cys Thr Val Ser Gly Phe Ser Ile Thr Thr Gly
20 25 30

Gly Tyr Trp Trp Thr Trp Ile Arg Gln Pro Pro Gly Lys Gly Leu Glu
35 40 45

Trp Ile Gly Tyr Ile Phe Ser Ser Gly Asn Thr Asn Tyr Asn Pro Ser
50 55 60

Ile Lys Ser Arg Ile Ser Ile Thr Arg Asp Thr Ser Lys Asn Gln Phe
65 70 75 80

Phe Leu Gln Leu Asn Ser Val Thr Thr Glu Gly Asp Thr Ala Arg Tyr
85 90 95

Tyr Cys Ala Arg Ala Tyr Gly Lys Leu Gly Phe Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Leu Pro Val Leu Thr Gln Pro Pro Ser
130 135 140

Ala Ser Ala Leu Leu Gly Ala Ser Ile Lys Leu Thr Cys Thr Leu Ser
145 150 155 160

Ser Gln His Ser Thr Tyr Thr Ile Gly Trp Tyr Gln Gln Arg Pro Gly
165 170 175

Arg Ser Pro Gln Tyr Ile Met Lys Val Asn Ser Asp Gly Ser His Ser
180 185 190

Lys Gly Asp Gly Ile Pro Asp Arg Phe Met Gly Ser Ser Ser Gly Ala
195 200 205

Asp Arg Tyr Leu Thr Phe Ser Asn Leu Gln Ser Asp Asp Glu Ala Glu
210 215 220

Tyr His Cys Gly Ser Ser Asp Ser Ser Gly Tyr Val Phe Gly Ser Gly
225 230 235 240

Thr Lys Val Thr Val Leu
245

<210> SEQ ID NO 71
<211> LENGTH: 246
<212> TYPE: PRT
<213> ORGANISM: Artificial Sequence
<220> FEATURE:
<223> OTHER INFORMATION: Synthetic Construct

<400> SEQUENCE: 71

Gln Val Gln Leu Lys Glu Ser Gly Pro Gly Leu Val Lys Pro Ser Gln
1 5 10 15

Ser Leu Ser Leu Thr Cys Ser Val Thr Gly Phe Ser Ile Thr Thr Gly
20 25 30

Gly Tyr Trp Trp Thr Trp Ile Arg Gln Phe Pro Gly Gln Lys Leu Glu
35 40 45

Trp Met Gly Tyr Ile Phe Ser Ser Gly Asn Thr Asn Tyr Asn Pro Ser
50 55 60

Ile Lys Ser Arg Ile Ser Ile Thr Arg Asp Thr Ser Lys Asn Gln Phe
65 70 75 80

Phe Leu Gln Leu Asn Ser Val Thr Thr Glu Gly Asp Thr Ala Arg Tyr
85 90 95

Tyr Cys Ala Arg Ala Tyr Gly Lys Leu Gly Phe Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Gln Pro Val Leu Thr Gln Ser Pro Ser
130 135 140

Ala Ser Ala Ser Leu Gly Asn Ser Val Lys Ile Thr Cys Thr Leu Ser
145 150 155 160

Ser Gln His Ser Thr Tyr Thr Ile Gly Trp Tyr Gln Gln His Pro Asp
165 170 175

Lys Ala Pro Lys Tyr Val Met Tyr Val Asn Ser Asp Gly Ser His Ser
180 185 190

-continued

```
Lys Gly Asp Gly Ile Pro Asp Arg Phe Ser Gly Ser Ser Ser Gly Ala
        195                 200                 205

His Arg Tyr Leu Ser Ile Ser Asn Ile Gln Pro Glu Asp Glu Ala Asp
    210                 215                 220

Tyr Phe Cys Gly Ser Ser Asp Ser Ser Gly Tyr Val Phe Gly Ser Gly
225                 230                 235                 240

Thr Gln Leu Thr Val Leu
                245
```

CD83-BINDING CHIMERIC ANTIGEN RECEPTORS

CROSS-REFERENCE TO RELATED APPLICATIONS

This application is a National Stage of International Application No. PCT/US2019/019065, filed Feb. 22, 2019, which claims benefit of U.S. Provisional Application No. 62/634,435, filed Feb. 23, 2018, and Application Ser. No. 62/677,783, filed May 30, 2018, which are hereby incorporated herein by reference in their entirety.

SEQUENCE LISTING

This application contains a sequence listing filed in electronic form as an ASCII.txt file entitled "320803_2200_Sequence_Listing_ST25" created on Feb. 21, 2019 which is 106,011 bytes in size. The content of the sequence listing is incorporated herein in its entirety.

BACKGROUND

Allogeneic hematopoietic cell transplantation (HCT) is an effective therapy for hematological malignancies but it is limited by acute graft-versus-host disease (GVHD). GVHD arises when donor T cells respond to genetically defined proteins on host cells, and is a key contributor to the high mortality associated with HCT. Dendritic cells (DC) play a major role in the allogeneic T cell stimulation causing GVHD. Donor DCs are the primary antigen presenting cell responsible for indirect presentation of alloantigens following transplantation, and this process commences almost immediately after transplantation. Current immunosuppressive measures to control GVHD target T cells but compromise post-transplant immunity in the patient.

SUMMARY

Chimeric antigen receptor (CAR) polypeptides are disclosed that can be used with adoptive cell transfer to suppress alloreactive cells, such as donor T cells. The disclosed CAR polypeptides contain in an ectodomain an anti-CD83 binding agent that can bind CD83-expressing cells. Also disclosed is an immune effector cell genetically modified to express the disclosed CAR polypeptide.

The anti-CD83 binding agent is in some embodiments an antibody fragment that specifically binds CD83. For example, the antigen binding domain can be a Fab or a single-chain variable fragment (scFv) of an antibody that specifically binds CD83. The anti-CD83 binding agent is in some embodiments an aptamer that specifically binds CD83. For example, the anti-CD83 binding agent can be a peptide aptamer selected from a random sequence pool based on its ability to bind CD83. The anti-CD83 binding agent can also be a natural ligand of CD83, or a variant and/or fragment thereof capable of binding CD83.

In some embodiments, the anti-CD83 scFv can comprise a variable heavy ($V_H$) domain having CDR1, CDR2 and CDR3 sequences and a variable light ($V_L$) domain having CDR1, CDR2 and CDR3 sequences.

For example, in some embodiments, the CDR1 sequence of the $V_H$ domain comprises the amino acid sequence GFSITTGGYWWT (SEQ ID NO:1), SDGIS (SEQ ID NO:7), or SNAMI (SEQ ID NO:13); CDR2 sequence of the $V_H$ domain comprises the amino acid sequence GYIFSSGNTNYNPSIKS (SEQ ID NO:2), IISSGGNTYYASWAKG (SEQ ID NO:8), or AMDSNSRTYYATWAKG (SEQ ID NO:14); CDR3 sequence of the $V_H$ domain comprises the amino acid sequence CARAYGKLGFDY (SEQ ID NO:3), WGGTYSI (SEQ ID NO:9), or GDGGSSDYTEM (SEQ ID NO:15); CDR1 sequence of the $V_L$ comprises the amino acid sequence TLSSQHSTYTIG (SEQ ID NO:4), QSSQSVYNNDFLS (SEQ ID NO:10), or QSSQSVYGNNELS (SEQ ID NO:16); CDR2 sequence of the $V_L$ domain comprises the amino acid sequence VNSDGSHSKGD (SEQ ID NO:5), YASTLAS (SEQ ID NO:11), or QASSLAS (SEQ ID NO:17); and CDR3 sequence of the $V_L$ domain comprises the amino acid sequence GSSDSSGYV (SEQ ID NO:6), TGTYGNSAWYEDA (SEQ ID NO:12), or LGEYSISADNH (SEQ ID NO:18).

For example, in some embodiments, the CDR1 sequence of the $V_H$ domain comprises the amino acid sequence GFSITTGGYWWT (SEQ ID NO:1), CDR2 sequence of the $V_H$ domain comprises the amino acid sequence GYIFSSGNTNYNPSIKS (SEQ ID NO:2), CDR3 sequence of the $V_H$ domain comprises the amino acid sequence CARAYGKLGFDY (SEQ ID NO:3), CDR1 sequence of the $V_L$ comprises the amino acid sequence TLSSQHSTYTIG (SEQ ID NO:4), CDR2 sequence of the $V_L$ domain comprises the amino acid sequence VNSDGSHSKGD (SEQ ID NO:5), and CDR3 sequence of the $V_L$ domain comprises the amino acid sequence GSSDSSGYV (SEQ ID NO:6).

For example, in some embodiments, the CDR1 sequence of the $V_H$ domain comprises the amino acid sequence SDGIS (SEQ ID NO:7), CDR2 sequence of the $V_H$ domain comprises the amino acid sequence IISSGGNTYYASWAKG (SEQ ID NO:8), CDR3 sequence of the $V_H$ domain comprises the amino acid sequence WGGTYSI (SEQ ID NO:9), CDR1 sequence of the $V_L$ comprises the amino acid sequence QSSQS VYNNDFLS (SEQ ID NO:10), CDR2 sequence of the $V_L$ domain comprises the amino acid sequence YASTLAS (SEQ ID NO:11), and CDR3 sequence of the $V_L$ domain comprises the amino acid sequence TGTYGNSAWYEDA (SEQ ID NO:12).

For example, in some embodiments, the CDR1 sequence of the $V_H$ domain comprises the amino acid sequence SNAMI (SEQ ID NO:13), CDR2 sequence of the $V_H$ domain comprises the amino acid sequence AMDSNSRTYYATWAKG (SEQ ID NO:14), CDR3 sequence of the $V_H$ domain comprises the amino acid sequence GDGGSSDYTEM (SEQ ID NO:15), CDR1 sequence of the $V_L$ comprises the amino acid sequence QSSQSVYGNNELS (SEQ ID NO:16), CDR2 sequence of the V domain comprises the amino acid sequence QASSLAS (SEQ ID NO:17), and CDR3 sequence of the $V_L$ domain comprises the amino acid sequence LGEYSISADNH (SEQ ID NO:18).

In some embodiments, the anti-CD83 scFv $V_H$ domain comprises the amino acid sequence:

```
                              (SEQ ID NO: 19, VH-GBM00)
QVQLKESGPGLVKPSQSLSLTCSVTGFSITTGGYWWTWIRQ

FPGQKLEWMGYIFSSGNTNYNPSIKSRISITRDTSKNQFFL

QLNSVTTEGDTARYYCARAYGKLGFDYWGQGTIVIVSS.
```

In some embodiments, the anti-CD83 scFv $V_L$ domain comprises the amino acid sequence:

```
(SEQ ID NO: 20, VL-GBM00)
QPVLTQSPSASASLGNSVKITCTISSQHSTYTIGWYQQHP
DKAPKYVMYVNSDGSHSKGDGIPDRFSGSSSGAHRYLSIS
NIQPEDEADYFCGSSDSSGYVFGSGTQLTVL.
```

In some embodiments, the anti-CD83 scFv $V_H$ domain comprises the amino acid sequence:

```
(SEQ ID NO: 21, 20D04)
METGLRWLLLVAVLKGVQCQSVEESGGRLVTPGTPLTLTC
TVSGFSLSNNAINWVRQAPGKGLEWIGYIWSGGLTYYANW
AEGRFTISKTSTTVDLKMTSPTIEDTATYFCARGINNSAL
WGPGTLVTVSSGQPKAPSVFPLAPCCGDTPSSTVTLGCLV
KGYLPEPVTVTWNSGTLTNGVRTFPSVRQSSGLYSLSSVV
SVTSSSQPVTCNVAHPATNTKVDKTVAPSTCSKPTCPPPE
LLGGPSVFIFPPKPKDTLMISRTPEVTCVVVDVSQDDPEV
QFTWYINNEQVRTARPPLREQQFNSTIRWSTLPIAHQDWL
RGKEFKCKVHNKALPAPIEKTISKARGQPLEPKVYTMGPP
REELSSRSVSLTCMINGFYPSDISVEWEKNGKAEDNYKTT
PAVLDSDGSYFLYNKLSVPTSEWQRGDVFTCSVMHEALHN
HYTQKSISRSPGK.
```

In some embodiments, the anti-CD83 scFv $V_L$ domain comprises the amino acid sequence:

```
(SEQ ID NO: 22, 20D04)
MDMRAPTQLLGLLLLWLPGARCADVVMTQTPASVSAAVGG
TVTINCQASESISNYLSWYQQKPGQPPKLLIYRTSTLASG
VSSRFKGSGSGTEYTLTISGVQCDDVATYYCQCTSGGKFI
SDGAAFGGGTEWVKGDPVAPTVLLFPPSSDEVATGTVTIV
CVANKYFPDVTVTWEVDGTTQTTGIENSKTPQNSADCTYN
LSSTLTLTSTQYNSHKEYTCKVTQGTTSVVQSFSRKNC.
```

In some embodiments, the anti-CD83 scFv $V_H$ domain comprises the amino acid sequence:

```
(SEQ ID NO: 23, 11G05)
METGLRWLLLVAVLKGVQCQSVEESGGRLVTPGTPLTLTC
TVSGFTISDYDLSWVRQAPGEGLKYIGFIAIDGNPYYATW
AKGRFTISKTSTTVDLKITAPTTEDTATYFCARGAGDLWG
PGTLVTVSSGQPKAPSVFPLAPCCGDTPSSTVTLGCLVKG
YLPEPVTVTWNSGTLTNGVRTFPSVRQSSGLYSLSSVVSV
TSSSQPVTCNVAHPATNTKVDKTVAPSTCSKPTCPPPELL
GGPSVFIFPPKPKDTLMISRTPEVTCVVVDVSQDDPEVQF
TWYINNEQVRTARPPLREQQFNSTIRVVSTLPIAHQDWLR
GKEFKCKVHNKALPAPIEKTISKARGQPLEPKVYTMGPPR
```

-continued

```
EELSSRSVSLTCMINGFYPSDISVEWEKNGKAEDNYKTTP
AVLDSDGSYFLYNKLSVPTSEWQRGDVFTCSVMHEALHNH
YTQKSISRSPGK.
```

In some embodiments, the anti-CD83 scFv $V_L$ domain comprises the amino acid sequence:

```
(SEQ ID NO: 24, 11G05)
MDTREPTQLLGLLLLWLPGARCADVVMTQTPASVSAAVGG
TVTINCQSSKNVYNNNWLSWFQQKPGQPPKLLIYYASTLA
SGVPSRFRGSGSGTQFTLTISDVQCDDAATYYCAGDYSSS
SDNGFGGGTEVVVKGDPVAPTVLLFPPSSDEVATGTVTIV
CVANKYFPDVTVTWEVDGTTQTTGIENSKTPQNSADCTYN
LSSTLTLTSTQYNSHKEYTCKVTQGTTSVVQSFSRKNC.
```

In some embodiments, the anti-CD83 scFv $V_H$ domain comprises the amino acid sequence:

```
(SEQ ID NO: 25, 14C12)
METGLRWLLLVAVLKGVHCQSVEESGGRLVTPGTPLTLTC
TASGFSRSSYDMSWVRQAPGKGLEWVGVISTAYNSHYASW
AKGRFTISRTSTTVDLKMTSLTTEDTATYFCARGGSWLDL
WGQGTLVTVSSGQPKAPSVFPLAPCCGDTPSSTVTLGCLV
KGYLPEPVTVTWNSGTLTNGVRTFPSVRQSSGLYSLSSVV
SVTSSSQPVTCNVAHPATNTKVDKTVAPSTCSKPTCPPPE
LLGGPSVFIFPPKPKDTLMISRTPEVTCVWDVSQDDPEVQ
FTWYINNEQVRTARPPLREQQFNSTIRVVSTLPIAHQDWL
RGKEFKCKVHNKALPAPIEKTISKARGQPLEPKVYTMGPP
REELSSRSVSLTCMINGFYPSDISVEWEKNGKAEDNYKTT
PAVLDSDGSYFLYNKLSVPTSEWQRGDVFTCSVMHEALHN
HYTQKSISRSPGK.
```

In some embodiments, the anti-CD83 scFv $V_L$ domain comprises the amino acid sequence:

```
(SEQ ID NO. 26, 14C12)
MDXRAPTQLLGLLLLWLPGARCALVMTQTPASVSAAVGGTVTINCQSSQS
VYDNDELSWYQQKPGQPPKLLIYALASKLASGVPSRFKGSGSGTQFALTI
SGVQCDDAATYYCQATHYSSDWYLTFGGGTEVVVKGFPVAPTVLLFPPSS
DEVATGTVTIVCVANKYFPDVTVTWEVDGTTQTTGTENSKTPQNSADCTY
NLSSTLTLTSTQYNSHKEYTCKVTQGTTSVVQSFSRKNC.
```

In some embodiments, the anti-CD83 scFv $V_H$ domain comprises the amino acid sequence:

```
(SEQ ID NO. 27, 020B08)
METGLRWLLLVAVLKGVQCQSVEESGGRLVTPGTPLTLCTVSGFSLSSYD
MTWVRQAPGKGLEWIGIIYASGTTYYANWAKGRFTISKTSTTVDLKVTSP
TIGDTATYFCAREGAGVSMTLWGPGTLVTVSSGQPKAPSVFPLAPCCGDT
```

-continued

PSSTVTLGCLVKGYLPEPVTVTWNSGTLTNGVRTFPSVRQSSGLYSLSSV
VSVTSSSQPVTCNVAHPATNTKVDKTVAPSTCSKPTCPPPELLGGPSVFI
FPPKPKDTLMISRTPEVTCVVVDVSQDDPEVQFTWYINNEQVRTARPPLR
EQQFNSTIRVVSTLPIAHQDWLRGKEFKCKVHNKALPAPIEKTISKARGQ
PLEPKVYTMGPPREELSSRSVSLTCMINGFYPSDISVEWEKNGKAEDNYK
TTPAVLDSDGSYFLYNKLSVPTSEWQRGDVFTCSVMHEALHNHYTQKSIS
RSPGK.

In some embodiments, the anti-CD83 scFv $V_L$ domain comprises the amino acid sequence:

(SEQ ID NO: 28, 020B08)
MDMRAPTQLLGLLLLWLPGARCAYDMTQTPASVEVAVGGTVTIKCQASQS
ISTYLDWYQQKPGQPPKLLIYDASDLASGVPSRFKGSGSGTQFTLTISDL
ECADAATYYCQQGYTHSNVDNVFGGGTEVVVKGDPVAPTVLLFPPSSDEV
ATGTVTIVCVANKYFPDVTVTWEVDGTTQTTGIENSKTPQNSADCTYNLS
STLTLTSTQYNSHKEYTCKVTQGTTSVVQSFSRKNC

In some embodiments, the anti-CD83 scFv $V_H$ domain comprises the amino acid sequence:

(SEQ ID NO: 29, 006G05)
METGLRWLLLVAVLKGVQCQSVEESGGRLVSPGTPLTLTCTASGFSLSSY
DMSWVRQAPGKGLEYIGIISSSGSTYYASWAKGRFTISKTSTTVDLEVTS
LTTEDTATYFCSREHAGYSGDTGHLWGPGTLVTVSSGQPKAPSVFPLAPC
CGDTPSSTVTLGCLVKGYLPEPVTVTWNSGTLTNGVRTFPSVRQSSGLYS
LSSVVSVTSSSQPVTCNVAHPATNTKVDKTVAPSTCSKPTCPPPELLGGP
SVGIGPPKPKDTLMISRTPEVTCVVVDVSQDDPEVQFTWYINNEQVRTAR
PPLREQQFNSTIRVVSTLPIAHQDWLRGKEFKCKVHNKALPAPIEKTISK
ARGQPLEPKVYTMGPPREELSSRSVSLTCMINGFYPSDISVEWEKNGKAE
DNYKTTPAVLDSDGSYFLYNKLSVPTSEWQRGDVFTCSVMHEALHNHYTQ
KSISRSPGK.

In some embodiments, the anti-CD83 scFv $V_L$ domain comprises the amino acid sequence:

(SEQ ID NO: 30, 006G05)
MDMRAPTQLLGLLLLWLPGARCAYDMTQTPASVEVAVGGTVAIKCQASQS
VSSYLAWYQQKPGQPPKPLIYEASMLAAGVSSRFKGSGSGTDFTLTISDL
ECDDAATYYCQQGYSISDIDNAFGGGTEVVVKGDPVAPTVLLFPPSSDEV
ATGTVTIVCVANKYFPDVTVTWEVDGTTQTTGIENSKTPQNSADCTYNLS
STLTLTSTQYNSHKEYTCKVTQGTTSVVQSFSRKNC

In some embodiments, the anti-CD83 scFv $V_H$ domain comprises the amino acid sequence:

(SEQ ID NO: 31, 96G08)
METGLRWLLLVAVLKGVQCQSVEESGGRLVTPGTPLTLCTVSGIDLSSDG
ISWVRQAPGKGLEWIGIISSGGNTYYASWAKGRFTISRTSTTVDLKMTSL

-continued

TTEDTATYFCARVVGGTYSIWGQGTLVTVSSASTKGPSVYPLAPGSAAQT
NSMVTLGCLVKGYFPEPVTVTWNSGSLSSGVHTFPAVLQSDLYTLSSSVT
VPSSTWPSETVTCNVAHPASSTKVDKKIVPRDCGCKPCICTVPEVSSVFI
FPPKPDVLTITLTPKVTCVVVDISKDDPEVQFSWFVDDVEVHTAQTQPRE
EQFNSTFRSVSELPIMHQDWLNGKEFKCRVNSAAFPAPIEKTISKTKGRP
KAPQVYTIPPPKEQMAKDKVSLTCMITDFFPEDITVEWQWNGQPAENYKN
TQPIMDTDGSYFVYSKLNVQKSNWEAGNTFTCSVLHEGLHNHHTEKSLSH
SPGK.

In some embodiments, the anti-CD83 scFv $V_L$ domain comprises the amino acid sequence:

(SEQ ID NO: 32, 96G08)
MDTRAPTQLLGLLLLWLPGATFAQVLTQTASPVSAPVGGTVTINCOSSQS
VYNNDFLSWYQQKPGQPPKLLIYYASTLASGVPSRFKGSGSGTQFTLTIS
DLECDDAATYYCTGTYGNSAWYEDAFGGGTEVVVKRTPVAPTVLLFPPSS
AELATGTATIVCVANKYFPDGTVTWKVDGITQSSGINNSRTPQNSADCTY
NLSSTLTLSSDEYNSHDEYTCQVAQDSGSPVVQSFSRKSC

In some embodiments, the anti-CD83 scFv $V_H$ domain comprises the amino acid sequence:

(SEQ ID NO: 33, 95F04)
METGLRWLLLVAVLKGVQCQSVEESGGRLVTPGTPLTLTCTVSGIDLSSN
AMIWVRQAPREGLEWIGAMDSNSRTYYATWAKGRFTISRTSSITVDLKIT
SPTTEDTATYFCARGDGGSSDYTEMWGPGTLVTVSSASTKGPSVYPLAPG
SAAQTNSMVTLGCLVKGYFPEPVTVTWNSGSLSSGVHTFPAVLQSDLYIL
SSSVTVPSSTWPSETVTCNVAHPASSTKVDKKIVPRDCGCKPCICTVPEV
SSVFIFFPKPKDVLTITLTPKVTCVVVDISKDDPEVQFSWFVDDVEVHTA
QTQPREEQFNSTFRSVSELPIMHQDWLNGKEFKCIRVNSAAFPAPIEKTI
SKTKGRPKAPQVYTIPPPKEQMAKDKVSLTCMITDFFPEDITVEWQWNGQ
PAENYKNTQPIMDTDGSYFVYSKLNVQKSNWEAGNTFTCSVLHEGLHNHH
TEKSLSHSPGK.

In some embodiments, the anti-CD83 scFv $V_L$ domain comprises the amino acid sequence:

(SEQ ID NO.34 , 95F04)
MDTRAPTQLLGLLLLWLPGATFAQAVVTQTTSPVSAPVGGTVTINCQSSQ
SVYGNNELSWYQQKPGQPPKLLIYQASSLASGVPSRFKGSGSGTQFTLTI
SDLECDDAATYYCLGEYSISADNHFGGGTEVVVKRTPVAPTVLLFPPSSA
ELATGTATIVCVANKYFPDGTVTWKVDGITQSSGINNSRTPQNSADCTYN
LSSTLTLSDEYNHDEYTCQVAQDSGSPVVQSFSRKSC

In some embodiments, the anti-CD83 scFv $V_H$ domain comprises the amino acid sequence:

(SEQ ID NO: 35)
QVQLVQSGGAVVQPGRSLRLSCAASGFTFSTYGMHWVRQAPGKGLEWVAA
VSYDGSNKYYADFVKGRFTISRDNPKNTLYLQMNSLRADDTAVYYCARRG
GLDIWGQGTTVTVSSASTKGPSVFPLAPSSKSTSGGTAALGCLVKDYFPE
PVTVSWNSGALTSGVHTFPAVLQSSGLYSLSSVVTVPSSSLGTQTYICNV
NHKPSNTKVDKKVEPKSCAAA.

In some embodiments, the anti-CD83 scFv $V_L$ domain comprises the amino acid sequence:

(SEQ ID NO: 36)
LTQPPPASGTPGQQRVTISCSGSSSNIGSNTVNWYQQLPGTAPKLLIYYG
NDQRPSGVPDRFSASKSGTSASLAISGLQSEDEAHYYCAAWDGSLNGGVI
FGGGTKVTLG.

In some embodiments, the anti-CD83 scFv $V_L$ domain comprises the amino acid sequence:

(SEQ ID NO: 37)
VTQPPSASGTPGQRVTISCSGSSSNIGTNPVNWYQQLPGTAPKLLIYTTD
QRPSGVPDRFSGSKSGTSASLAISGLQSEDEADYYCAAWDDSLSGLYVFG
TGTKVTVLG.

In some embodiments, the anti-CD83 scFv $V_L$ domain comprises the amino acid sequence:

(SEQ ID NO: 38)
MTHTPLSLSVTPGQPASISCKSSQSLLHSDGKTYLYWYLQRPGQSPQPLI
YEVSNRFSGVPDRFSGSGSGTDFTLKISRVQAEDVGVYYCMQSLQLWFTG
QGTKVEIKR.

In some embodiments, the anti-CD83 scFv $V_L$ domain comprises the amino acid sequence:

(SEQ ID NO: 39)
MTQSPLSLPVTLGQPASISCRSSGSLIHSDGNTYLDWFQQRPGQSPRRLIY
KVSNRDSGVPDRFSGSGSGTDFTLRISRVEAEDIGVYYCMQATHWPRTFGQ
GTKVEIKR.

In some embodiments, the anti-CD83 scFv $V_L$ domain comprises the amino acid sequence:

(SEQ ID NO: 40)
MTQSPLSLPVTLGQPASISCRSSQSLVDSAGNTFLHWFHQRPGQSPRRLIY
KVSNRDSGVPDRFSGSGSGTDFTLKISRVEAEDVGVYYCMQGTHWPRTFGQ
GTKVEIKR.

In some embodiments, the anti-CD83 scFv $V_L$ domain comprises the amino acid sequence:

(SEQ ID NO: 41)
LTQSPLSLPVTLGQPASISCKSSQSLVDSDGNTYLNWFQQRPGQSPRRLIY
KVSNRDSGVPDRFSGSGSGTDFTLKISRVEAEDVGVYYCMQGTHWPRTFGQ
GTKVEIKR.

In some embodiments, the anti-CD83 scFv $V_L$ domain comprises the amino acid sequence:

(SEQ ID NO: 42)
MTQSPLSLPVTLGQPASISCRSSQSLVHSDGNMYLNWFQQRPGQSPRRLIY
KVSNRDSGVPDRFSGSGSGTDFTLKISRVEAEDVGVYYCMQATQPTWTFGQ
GTKLEIKR.

In some embodiments, the anti-CD83 scFv $V_L$ domain comprises the amino acid sequence:

(SEQ ID NO: 43)
MTQSPSSLSASVGDRVTITCQASQDISNYLNWYQQKPGKAPKLLIYDASNL
ETGVPSRFSGSGSGTDFTFTISSATYYCQQTYQGTKLEIKR.

In some embodiments, the anti-CD83 scFv $V_L$ domain comprises the amino acid sequence:

(SEQ ID NO: 44)
MTQSPSSLSASVGHPVTITCRASQSLISYLNWYHQKPGKAFKLLIYAASIL
QSGVPSRFSGSGSGTDFTLTISSLQPENFASYYCQHTDSFPRTFGHGTKVE
IKR.

In some embodiments, the anti-CD83 scFv $V_L$ domain comprises the amino acid sequence:

(SEQ ID NO: 45)
LTQPPSASGTPGQGVTISCRGSTSNIGNNVVNWYQHVPGSAPKLLIWSNIQ
RPSGIPDRFSGSKSGTSASLAISGLQSEDQAVYYCAVWDDGLAGWVFGGGT
TVTVLS.

In some embodiments, the anti-CD83 scFv $V_L$ domain comprises the amino acid sequence:

(SEQ ID NO: 46)
MTQAPVVSVALEQTVRITCQGDSLAIYYDFWYQHKPGQAPVLVIYGKNNRP
SGIPHRFSGSSSNTDSLTITGAQAEDEADYYCNSRDSSGNHWVFGGGTNLT
VLG.

In some embodiments, the anti-CD83 scFv $V_L$ domain comprises the amino acid sequence:

(SEQ ID NO: 47)
LTQSPLSLPVTLGQPASISCKSNQSLVHSDGNTYLNWFQQRPGQSPRRLIY
KVSNRDSGVPDRFSGSGSGTDFTLKINRVEAEDVGVYYCMQGTQWPRTFGG
QGTKLDIKR.

In some embodiments, the anti-CD83 scFv $V_H$ domain has been humanized and comprises the amino acid sequence:

(SEQ ID NO: 48, VH-GBM01)
QVQLQESGPGLVKPSETLSLTCTVSGFSITTGGYWWTWIRQPPGKGLEWIG

YIFSSGNTNYNPSIKSRVTISVDTSKNQFSLKLSSVTAADTAVYYCARAYG

KLGFDYWGQGTLVTVSS.

In some embodiments, the anti-CD83 scFv $V_H$ domain has been humanized and comprises the amino acid sequence:

(SEQ ID NO: 49, VH-GBM02)
QVQLQESGPGLVKPSQTLSLTCTVSGFSITTGGYWWTWIRQHPGKGLEWIG

YIFSSGNTNYNPSIKSLVTISVDTSKNQFSLKLSSVTAADTAVYYCARAYG

KLGFDYWGQGTLVTVSS.

In some embodiments, the anti-CD83 scFv $V_H$ domain as been humanize and comprises the amino acid sequence:

(SEQ ID NO: 50, VH-GBM03)
QVQLQESGPGLVKPSQTLSLTCTVSGFSITTGGYWWTWIRQPPGKGLEWIG

YIFSSGNTNYNPSIKSRVTISVDTSKNQFSLKLSSVTAADTAVYYCARAYG

KLGFDYWGQGTLVTVSS.

In some embodiments, the anti-CD83 scFv $V_H$ domain has been humanized and comprises the amino acid sequence:

(SEQ ID NO: 51, VH-GBM04)
QVQLQESGPGLVKPSETLSLTCTVSGFSITTGGYWWTWIRQPPGKGLEWIG

YIFSSGNTNYNPSIKSRVTISRDTSKNQFSLKLSSVTAADTAVYYCARAYG

KLGFDYWGQGTLVTVSS.

In some embodiments, the anti-CD83 scFv $V_H$ domain has been humanized and comprises the amino acid sequence:

(SEQ ID NO: 52, VH-GBM05)
QVQLQESGPGLVKPSETLSLTCTVSGFSITTGGYWWTWIRQPPGKGLEWIG

YIFSSGNTNYNPSIKSRVTISVDTSKNQFSLKLSSVTAADTARYYCARAYG

KLGFDYWGQGTLVTVSS.

In some embodiments, the anti-CD83 scFv $V_H$ domain has been humanized and comprises the amino acid sequence:

(SEQ ID NO: 53, VH-GBM06)
QVQLQESGPGLVKPSETLSLTCTVSGFSITTGGYWWTWIRQPPGKGLEWIG

YIFSSGNTNYNPSIKSRISITRDTSKNQFFLQLNSVTTEGDTARYYCARAY

GKLGFDYWGQGTLVTVSS.

In some embodiments, the anti-CD83 scFv $V_L$ domain has been humanized and comprises the amino acid sequence:

(SEQ ID NO: 54, VL-GBM01)
QLVLTQSPSASASLGASVKLTCTLSSQHSTYTIGWHQQQPEKGPRYLMKVN

SDGSHSKGDGIPDRFSGSSSGAERYLTISSLQSEDEADYYCGSSDSSGYVF

GSGTKVTVL.

In some embodiments, the anti-CD83 scFv $V_L$ domain has been humanized and comprises the amino acid sequence:

(SEQ ID NO: 55, VL-GBM02)
LPVLTQPPSASALLGASIKLTCTLSSQHSTYTIGWYQQRPGRSPQYIMKVN

SDGSHSKGDGIPDRFMGSSSGADRYLTFSNLQSDDEAEYHCGSSDSSGYVF

GSGTKVTVL.

The heavy and light chains are preferably separated by a linker. Suitable linkers for scFv antibodies are known in the art. In some embodiments, the linker comprises the amino acid sequence GGGGSGGGGSGGGGS (SEQ ID NO:56).

In some embodiments, the anti-CD83 scFv comprises an amino acid sequence:

(SEQ ID NO: 57)
QPVLTQSPSASASLGNSVKITCTLSSQHSTYTIGWYQQHPDKAPKYVMYV

NSDGSHSKGDGIPDRFSGSSSGAHRYLSISNIQPEDEADYFCGSSDSSGY

VFGSGTQLTVLRAAASSGGGGSGGGGSGGGGSQPVLTQSPSASASLGNSV

KITCTLSSQHSTYTIGWYQQHPDKAPKYVMYVNSDGSHSKGDGIPDRFSG

SSSGAHRYLSISNIQPEDEADYFCGSSDSSGYVFGSGTQLTVLRAAA.

In some embodiments, the anti-CD83 scFv comprises an amino acid sequence:

(SEQ ID NO: 58)
QVQLKESGPGLVKPSQSLSLTCSVTGFSITTGGYWWTWIRQFPGQKLEWM

GYIFSSGNTNYNPSIKSRISITRDTSKNQFFLQLNSVTTEGDTARYYCAR

AYGKLGFDYWGQGTLVTVSSGGGGSGGGGSGGGGSQVQLKESGPGINKPS

QSLSLTCSVTGFSITTGGYWWTWIRQFPGQKLEWMGYIFSSGNTNYNPSI

KSRISITRDTSKNQFFLQLNSVTTEGDTARYYCARAYGKLGFDYWGQGTL

VTV.

In some embodiments, the anti-CD83 scFv comprises an amino acid sequence:

(SEQ ID NO: 59)
QVQLQESGPGLVKPSETLSLTCTVSGFSITTGGYWWTWIRQPPGKGLEWI

GYIFSSGNTNYNPSIKSRVTISVDTSKNQFSLKLSSVTAADTAVYYCARA

YGKLGFDYWGQGTLVTVSSGGGGSGGGGSGGGGSQLVLTQSPSASASLGA

SVKLTCTLSSQHSTYTIGWHQQQPEKGPRYLMKVNSDGSHSKGDGIPDRF

SGSSSGAERYLTISSLQSEDEADYYCGSSDSSGYVFGSGTKVTVL.

In some embodiments, the anti-CD83 scFv comprises an amino acid sequence:

(SEQ ID NO: 60
QVQLQESGPGINKPSQTLSLTCTVSGFSITTGGYWWTWIRQHPGKGLEWI
GYIFSSGNTNYNPSIKSLVTISVDTSKNQFSLKLSSVTAADTAVYYCARA
YGKLGFDYWGQGTLVTVSSGGGGSGGGGSGGGGSQLVLTQSPSASASLGA
SVKLTCTLSSQHSTYTIGWHQQQPEKGPRYLMKVNSDGSHSKGDGIPDRF
SGSSSGAERYLTISSLQSEDEADYYCGSSDSSGYVFGSGTKVTVL.

In some embodiments, the anti-CD83 scFv comprises an amino acid sequence:

(SEQ ID NO: 61)
QVQLQESGPGLVKPSQTLSLTCTVSGFSITTGGYWWTWIRQPPGKGLEWI
GYIFSSGNTNYNPSIKSRVTISVDTSKNQFSLKLSSVTAADTAVYYCARA
YGKLGFDYWGQGTLVTVSSGGGGSGGGGSGGGGSQLVLTQSPSASASLGA
SVKLTCTLSSQHSTYTIGWHQQQPEKGPRYLMKVNSDGSHSKGDGIPDRF
SGSSSGAERYLTISSLQSEDEADYYCGSSDSSGYVFGSGTKVTVL.

In some embodiments, the anti-CD83 scFv comprises an amino acid sequence:

(SEQ ID NO: 62)
QVQLQESGPGINKPSETLSLTCTVSGFSITTGGYWWTWIRQPPGKGLEWI
GYIFSSGNTNYNPSIKSRVTISRDTSKNQFSLKLSSVTAADTAVYYCARA
YGKLGFDYWGQGTLVTVSSGGGGSGGGGSGGGGSQLVLTQSPSASASLGA
SVKLTCTLSSQHSTYTIGWHQQQPEKGPRYLMKVNSDGSHSKGDGIPDRF
SGSSSGAERYLTISSLOSEDEADYYCGSSDSSGYVFGSGTKVTVL.

In some embodiments, the anti-CD83 scFv comprises an amino acid sequence:

(SEQ ID NO: 63)
QVQLQESGPGLVKPSETLSLTCTVSGFSITTGGYWWTWIRQPPGKGLEWI
GYIFSSGNTNYNPSIKSRVTISVDTSKNQFSLKLSSVTAADTARYYCARA
YGKLGFDYWGQGTLVTVSSGGGGSGGGGSGGGGSQLVLTQSPSASASLGA
SVKLICTLSSQHSTYTIGWHQQQPEKGPRYLMKVNSDGSHSKGDGIPDRF
SGSSSGAERYLTISSLQSEDEADYYCGSSDSSGYVFGSGTKVTVL.

In some embodiments, the anti-CD83 scFv comprises an amino acid sequence:

(SEQ ID NO: 64)
QVQLQESGPGLVKPSETLSLTCTVSGFSITTGGYWWTWIRQPPGKGLEWI
GYIFSSGNTNYNPSIKSRISITRDTSKNQFFLQLNSVTTEGDTARYYCAR
AYGKLGFDYWGQGTLVTVSSGGGGSGGGGSGGGGSQLVLTQSPSASASLG
ASVKLTCTLSSQHSTYTIGWHQQQPEKGPRYLMKVNSDGSHSKGDGIPDR
FSGSSSGAERYLTISSLQSEDEADYYCGSSDSSGYVFGSGTKVTVL.

In some embodiments, the anti-CD83 scFv comprises an amino acid sequence:

(SEQ ID NO: 65)
QVQLQESGPGLVKPSETLSLTCTVSGFSITTGGYWWTWIRQPPGKGLEWI
GYIFSSGNTNYNPSIKSRVTISVDTSKNQFSLKLSSVTAADTAVYYCARA
YGKLGFDYWGQGTLVTVSSGGGGSGGGGSGGGGSLPVLTQFPSASALLGA
SIKLTCTLSSQHSTYTIGWYQQRPGRSPQYIMKVNSDGSHSKGDGIPDRF
MGSSSGADRYLTFSNLQSDDEAEYHCGSSDSSGYVFGSGTKVTVL.

In some embodiments, the anti-CD83 scFv comprises an amino acid sequence:

(SEQ ID NO: 66)
QVQLQESGPGLVKPSQTLSLTCTVSGFSITTGGYWWTWIRQHPGKGLEWI
GYIFSSGNTNYNPSIKSLVTISVDTSKNQFSLKLSSVTAADTAVYYCARA
YGKLGFDYWGQGTLVTVSSGGGGSGGGGSGGGGSLPVLTQPPSASALLGA
SIKLTCTLSSQHSTYTIGWYQQRPGRSPQYIMKVNSDGSHSKGDGIPDRF
MGSSSGADRYLIFSNLQSDDEAEYHCGSSDSSGYVFGSGTKVTVL.

In some embodiments, the anti-CD83 scFv comprises an amino acid sequence:

(SEQ ID NO: 67)
QVQLQESGPGLVKPSQTLSLTCTVSGFSITTGGYWWTWIRQPPGKGLEWI
GYIFSSGNTNYNPSIKSRVTISVDTSKNQFSLKLSSVTAADTAVYYCARA
YGKLGFDYWGQGTLVTVSSGGGGSGGGGSGGGGSLPVLTQPPSASALLGA
SIKLTCTLSSQHSTYTIGWYQQRPGRSPQYIMKVNSDGSHSKGDGIPDRF
MGSSSGADRYLTFSNLQSDDEAEYHCGSSDSSGYVFGSGTKVTVL.

In some embodiments, the anti-CD83 scFv comprises an amino acid sequence:

(SEQ ID NO: 68)
QVQLQESGPGLVKPSETLSLTCTVSGFSITTGGYVWVTWIRQPPGKGLEW
IGYIFSSGNTNYNPSIKSRVTISRDTSKNQFSLKLSSVTAADTAVYYCAR
AYGKLGFDYWGQGTLVTVSSGGGGSGGGGSGGGGSLPVLTQFPSASALLG
ASIKLTCTLSSQHSTYTIGWYQQRPGRSPQYIMKVNSDGSHSKGDGIPDR
FMGSSSGADRYLTFSNLQSDDEAEYHCGSSDSSGYVFGSGTKVTVL.

In some embodiments, the anti-CD83 scFv comprises an amino acid sequence:

(SEQ ID NO: 69)
QVQLQESGPGLVKPSETLSLTCTVSGFSITTGGYWWTWIRQPPGKGLEWI
GYIFSSGNTNYNPSIKSRVTISVDTSKNQFSLKLSSVTAADTARYYCARA
YGKLGFDYWGQGTLVTVSSGGGGSGGGGSGGGGSLPVLTQPPSASALLGA
SIKLTCTLSSQHSTYTIGWYQQRPGRSPQYIMKVNSDGSHSKGDGIPDRF
MGSSSGADRYLTFSNLQSDDEAEYHCGSSDSSGYVFGSGTKVTVL.

In some embodiments, the anti-CD83 scFv comprises an amino acid sequence:

(SEQ ID NO: 70)

QVQLQESGPGLVKPSETLSLTCTVSGFSITTGGYWWTWIRQPPGKGLEWI

GYIFSSGNTNYNPSIKSRISITRDTSKNQFFLQLNSVTTEGDTARYYCAR

AYGKLGFDYWGQGTLVTVSSGGGGSGGGGSGGGGSLPVLTQPPSASALLG

ASIKLTCTLSSQHSTYTIGWYQQRPGRSPQYIMKVNSDGSHSKGDGIPDR

FMGSSSGADRYLTFSNLQSDDEAEYHCGSSDSSGYVFGSGTKVTVL.

In some embodiments, the anti-CD83 scFv comprises an amino acid sequence:

(SEQ ID NO: 71)

QVQLKESGPGLVKPSQSLSLTCSVTGFSITTGGYWWTWIRQFPGQKLEWM

GYIFSSGNTNYNPSIKSRISITRDTSKNQFFLQLNSVTTEGDTARYYCAR

AYGKLGFDYWGQGTLVTVSSGGGGSGGGGSGGGGSQPVLTQSPSASASLG

NSVKITCTISSQHSTYTIGWYQQHPDKAPKYVMYVNSDGSHSKGDGIPDR

FSGSSSGAHRYLSISNIQPEDEADYFCGSSDSSGYVFGSGTQLTVL.

As with other CARs, the disclosed polypeptides can also contain a transmembrane domain and an endodomain capable of activating an immune effector cell. For example, the endodomain can contain a signaling domain and one or more co-stimulatory signaling regions.

In some embodiments, the intracellular signaling domain is a CD3 zeta (CD3ζ) signaling domain. In some embodiments, the costimulatory signaling region comprises the cytoplasmic domain of CD28, 4-1BB, or a combination thereof. In some cases, the costimulatory signaling region contains 1, 2, 3, or 4 cytoplasmic domains of one or more intracellular signaling and/or costimulatory molecules. In some embodiments, the co-stimulatory signaling region contains one or more mutations in the cytoplasmic domains of CD28 and/or 4-1BB that enhance signaling.

In some embodiments, the CAR polypeptide contains an incomplete endodomain. For example, the CAR polypeptide can contain only an intracellular signaling domain or a co-stimulatory domain, but not both. In these embodiments, the immune effector cell is not activated unless it and a second CAR polypeptide (or endogenous T-cell receptor) that contains the missing domain both bind their respective antigens. Therefore, in some embodiments, the CAR polypeptide contains a CD3 zeta (CD3ζ) signaling domain but does not contain a costimulatory signaling region (CSR). In other embodiments, the CAR polypeptide contains the cytoplasmic domain of CD28, 4-1BB, or a combination thereof, but does not contain a CD3 zeta (CD3ζ) signaling domain (SD).

Also disclosed are isolated nucleic acid sequences encoding the disclosed CAR polypeptides, vectors comprising these isolated nucleic acids, and cells containing these vectors. For example, the cell can be an immune effector cell selected from the group consisting of an alpha-beta T cells, a gamma-delta T cell, a Natural Killer (NK) cells, a Natural Killer T (NKT) cell, a B cell, an innate lymphoid cell (ILC), a cytokine induced killer (CIK) cell, a cytotoxic T lymphocyte (CTL), a lymphokine activated killer (LAK) cell, and a regulatory T cell.

In some embodiments, the cell suppresses alloreactive donor cells, such as T cells, when the antigen binding domain of the CAR binds to CD83.

Also disclosed is a method of preventing GVHD in a subject that involves administering to the subject an effective amount of an immune effector cell genetically modified with a disclosed CD83-specific CAR. In some embodiments, the subject is receiving a tissue transplantation. In some embodiments, the tissue transplantation comprises a bone marrow transplantations. In some embodiments, the tissue transplantation comprises a solid organ transplant, including but not limited to, face transplant, abdominal wall transplant, limb transplant, upper extremity transplant, vascularized composite allograft, or whole tissue graft. In some embodiments, the subject has an autoimmune diseases, sepsis, rheumatological diseases, diabetes, and/or asthma. Also disclosed is a method of treating autoimmunity in a subject that involves administering to the subject an effective amount of an immune effector cell genetically modified with a disclosed CD83-specific CAR. Also disclosed is a method of preventing rejection of solid organ allografts and off-the-shelf CAR-T cells in a subject that involves administering to the subject an effective amount of an immune effector cell genetically modified with a disclosed CD83-specific CAR.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2A is a bar graph showing the amount (mean±SEM) of T cells expressing the eGFP reporter post production among mock transduced (eGFP negative) or the CD83 CAR (eGFP positive) T cells. FIG. 2B is a bar graph demonstrating the relative amount (mean±SEM) of CD4 or CD8 expression among the mock transduced or the CD83 CAR T cells, Sidak's test. FIG. 2C shows the amount of IFNγ released by mock transduced or CD83 CAR T cells after stimulation with CD83+ DCs. FIG. 2D shows cytotoxicity of CD83 CAR T cells or mock transduced T cells co-cultured with CD83+ DCs, measured on a real-time cell analysis system. The data are presented as the average normalized cell index over time for duplicate wells. Normalized cell index is calculated as cell index at a given time point divided by cell index at the normalized time point which is day 1 after addition of T cells. 1 representative experiment of 2 shown, Dunnett's test. FIG. 2E shows absolute number of T cells for CD83 CAR T cells or mock transduced T cells stimulated by CD83+ DCs, calculated weekly over a 14 day period. 1 representative experiment of 2 shown, Sidak's test. P=0.001-0.01, *P=0.0001-0.001, and ****P<0.0001.

Figure 4A:
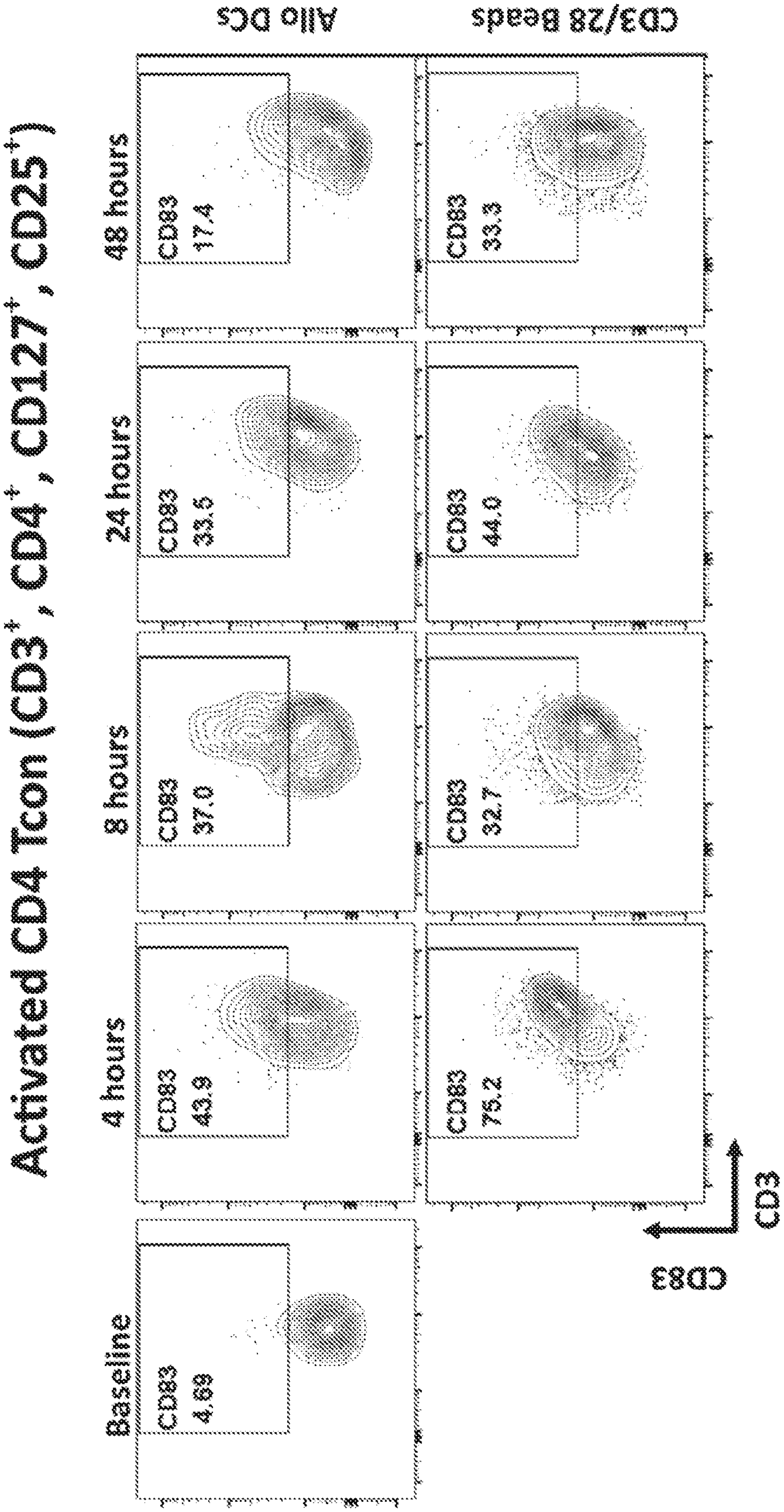
Figure 4B:
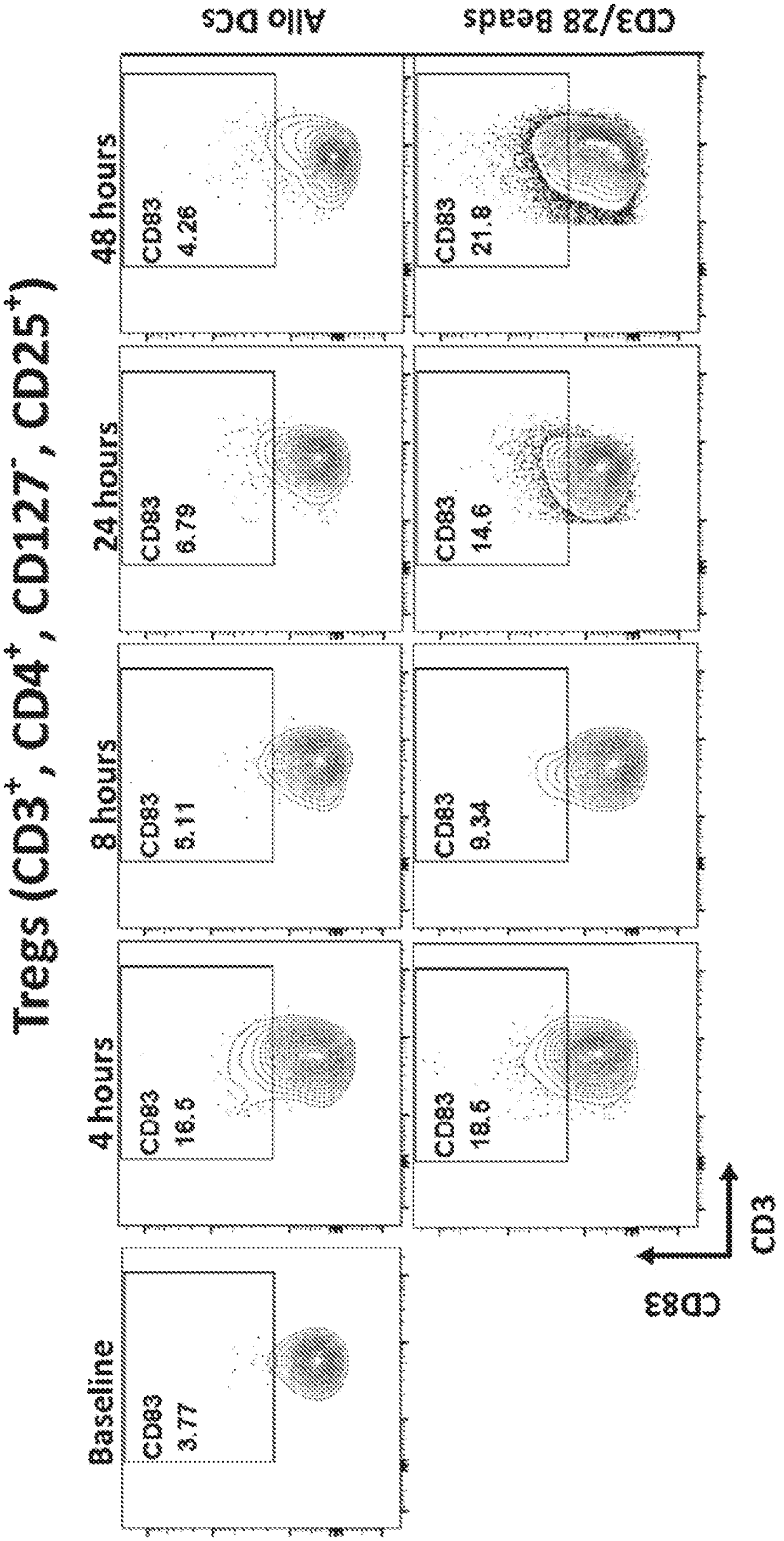
Figure 4D:
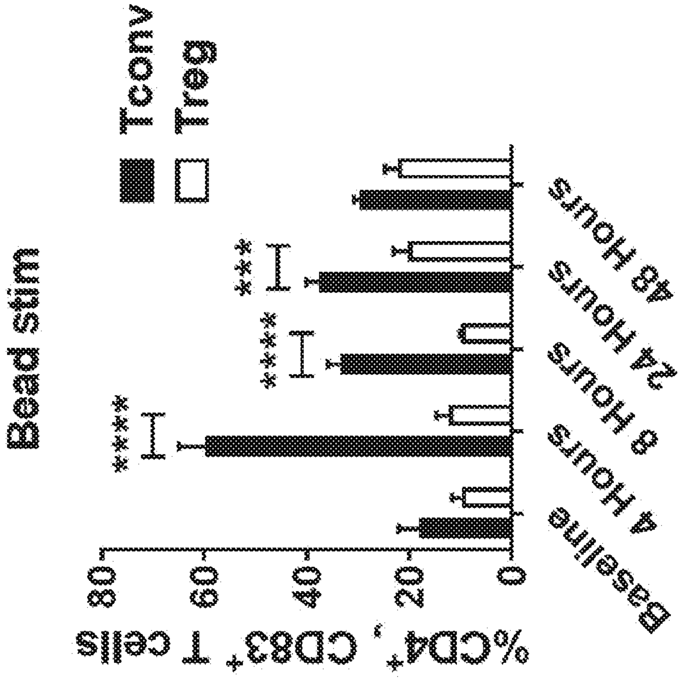
Figure 4C:
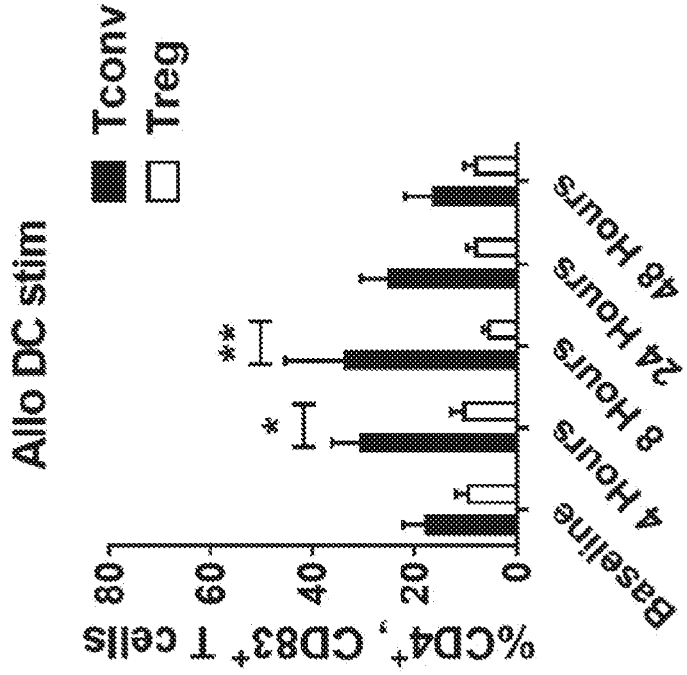

FIGS. 4A to 4D show CD83 is differentially expressed on human activated conventional CD4+ T cells (Tcon) compared to regulatory T cells (Tregs). Human T cells were stimulated by allogeneic moDCs (DC:T cell ration 1:30) or CD3/CD28 beads (Bead:T cell ratio 1:30). CD83 expression on activated Tcon (CD4+, CD127+, CD25+) or Treg (CD4+, CD127−, CD25+, Foxp3+) was measured at baseline, 4 hours, 8 hours, 24 hours, and 48 hours post stimulation. FIGS. 4A and 4B are representative contour plots showing CD83 expression among Tcon (FIG. 4A) and Treg (FIG. 4B) at various time points post stimulation. 1 representative experiment of 3 is shown. FIGS. 4C and 4D are bar graphs showing the amount of CD83+ Tconv or Treg (mean±SEM) after allogeneic DC (FIG. 4C) or CD3/CD28 bead (FIG. 4D) stimulation. n=5 independent experiments, Sidak's test. *P<0.05, P=0.001-0.01, *P=0.0001-0.001, and ****P<0.0001.

Figure 5A:
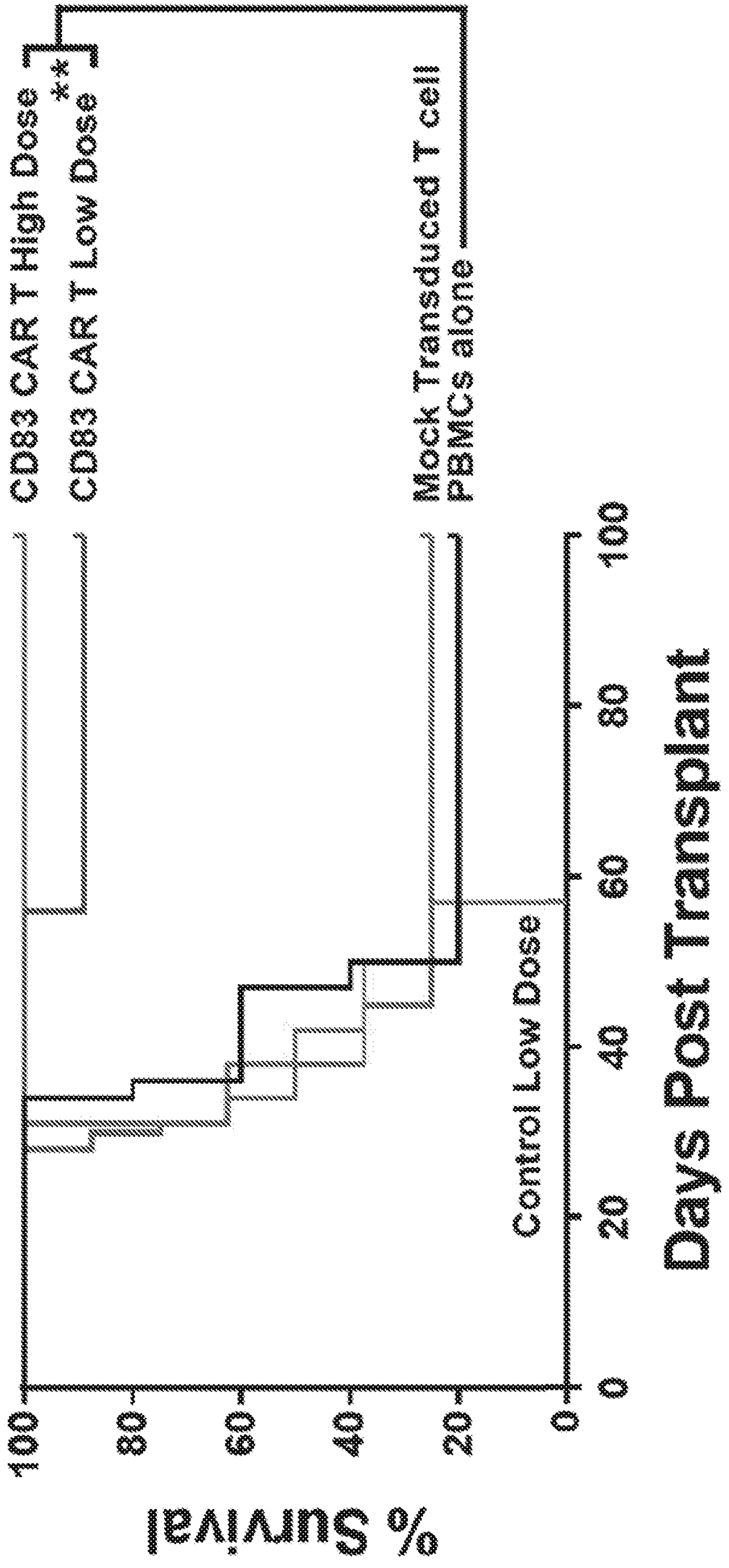
Figure 5B:
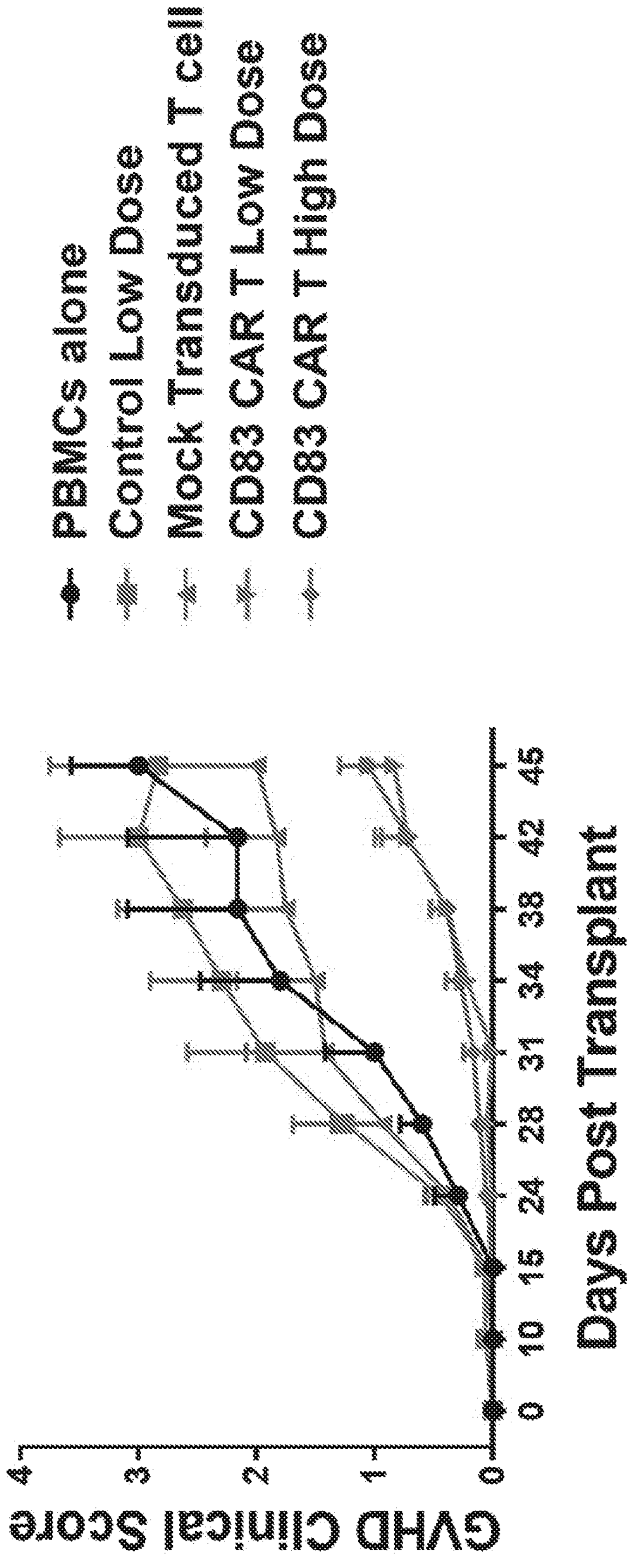

FIGS. 5A and 5B show human CD83 CAR T cells prevents xenogeneic GVHD. NSG mice received $25\times10^6$ human PBMCs and were inoculated with low (1x10) or high dose ($10\times10^8$) CD83 CAR or mock transduced T cells. The CARs were autologous to the PBMC donor. An additional control group of mice received PBMCs alone. FIGS. 5A and 5B show survival (FIGS. 5A) and (B) GVHD clinical scores (FIG. 5B). Clinical scores incorporate an aggregate assessment of activity, fur and skin condition, weight loss, and posture. Pooled data from 3 independent experiments, up to 9 mice per experimental arm. Log-rank test. **P=0.001-0.01.

Figure 6A:
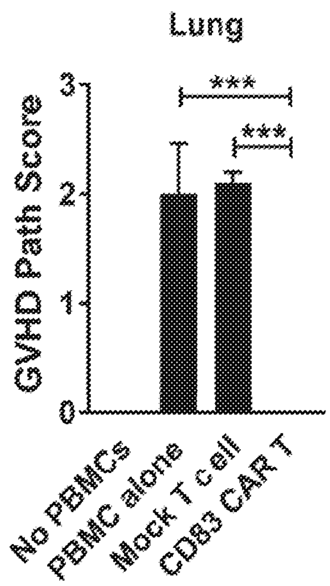
Figure 6B:
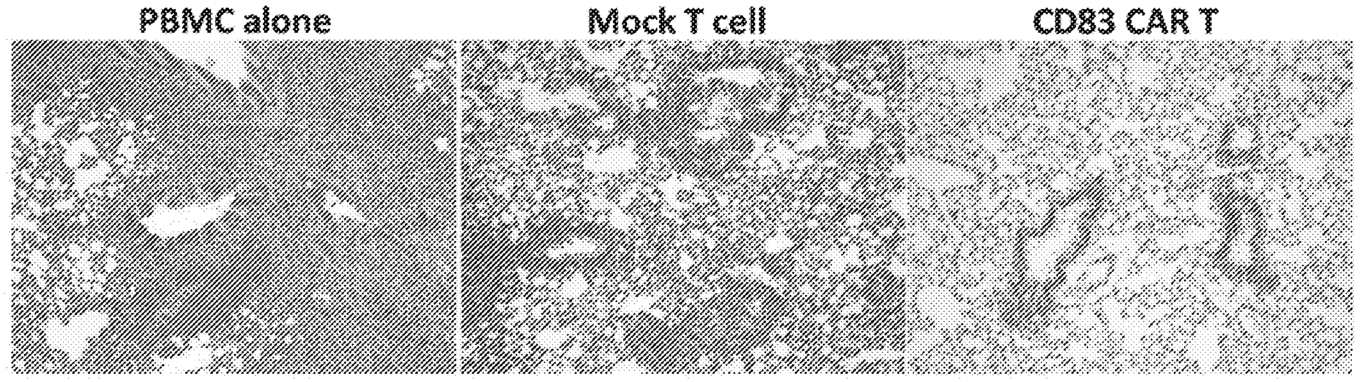
Figure 6D:
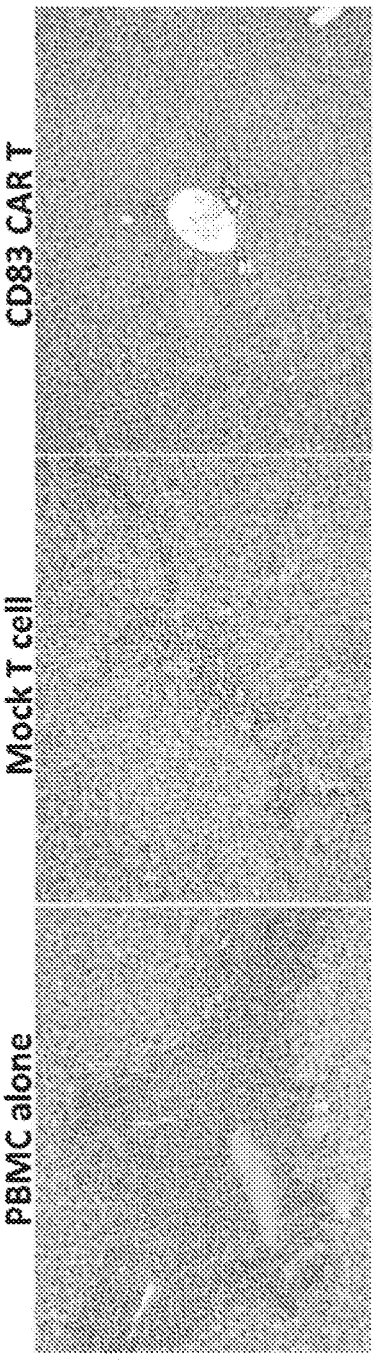
Figure 6C:
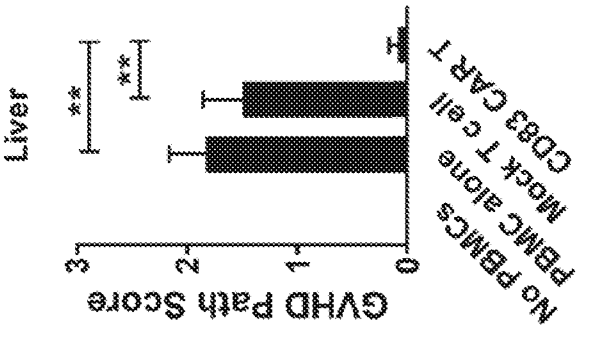

FIGS. 6A to 6D show CD83 CAR T cells significantly reduce GVHD target-organ damage by human T cells. NSG mice were transplanted with $25\times10^8$ human PBMCs plus $1\times10^6$ CD83 CAR or mock transduced T cells. Control groups consisted of mice that received no PBMCs (negative control) and mice that received PBMCs without modified T cells (secondary positive control). Recipient mice were humanely euthanized at day +21 and tissue GVHD severity was evaluated by an expert, blinded pathologist. Xenogeneic GVHD path scores (FIGS. 6A, 6C) and representative H&E images (FIGS. 6B, 6D) are shown for recipient lung (FIGS. 6A, 6B) and liver (FIGS. 6C, 6D). Pooled data from 2 independent experiments, up to 6 mice per experimental arm. Dunnett's test. P=0.001-0.01 and P=0.0001-0.001.

Figure 7:
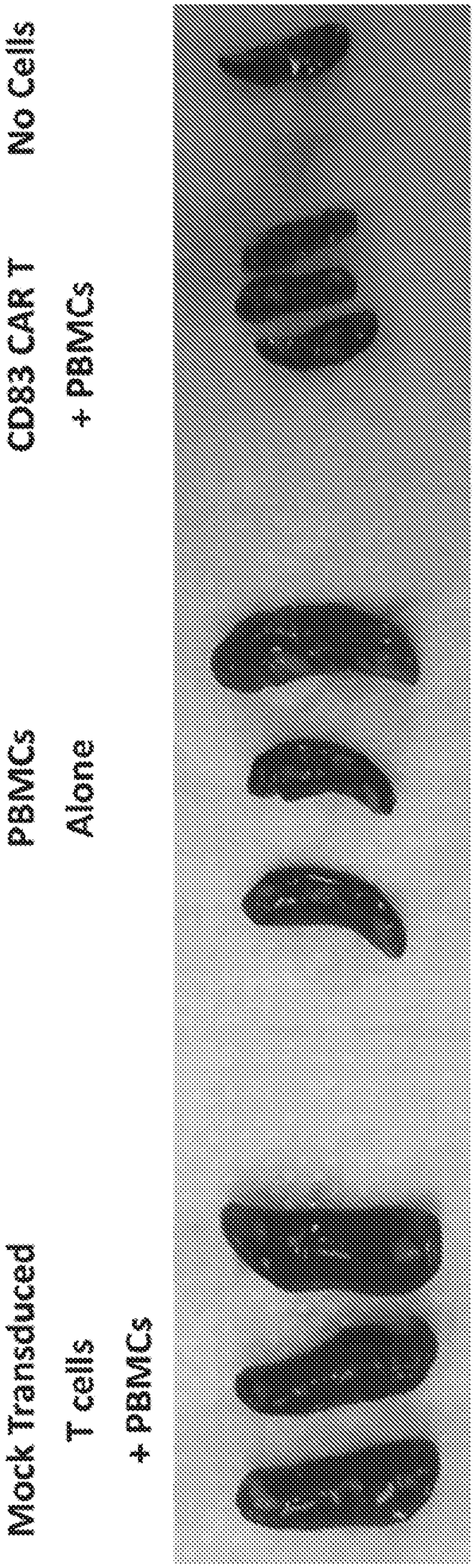

FIG. 7 shows human CD83 CAR T cells reduce the expansion of donor cell expansion in vivo. NSG mice were transplanted with $25\times10^8$ human PBMCs plus $1\times10^6$ CD83 CAR or mock transduced T cells. Control groups consisted of mice that received no PBMCs (negative control) and mice that received PBMCs without modified T cells (secondary positive control). Recipient mice were humanely euthanized at day +21 and their spleens were removed for gross assessment and flow cytometry studies. A representative image shows mice that received PBMCs and CD83 CAR T cells exhibit reduced spleen size, supporting suppression of donor T cell expansion in vivo. 1 representative experiment of 2, up to 6 mice per experimental arm.

Figure 8A:
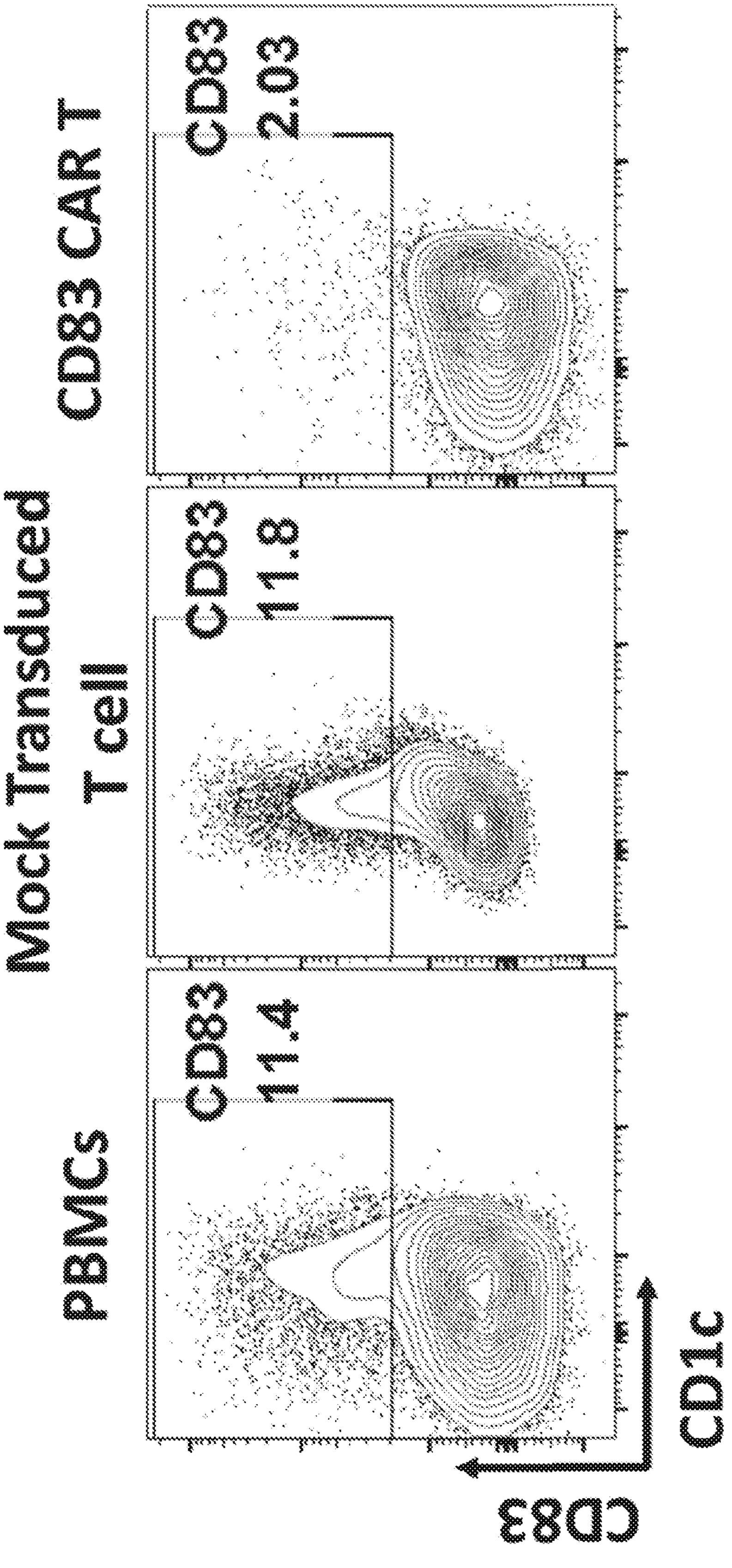
Figure 8D:
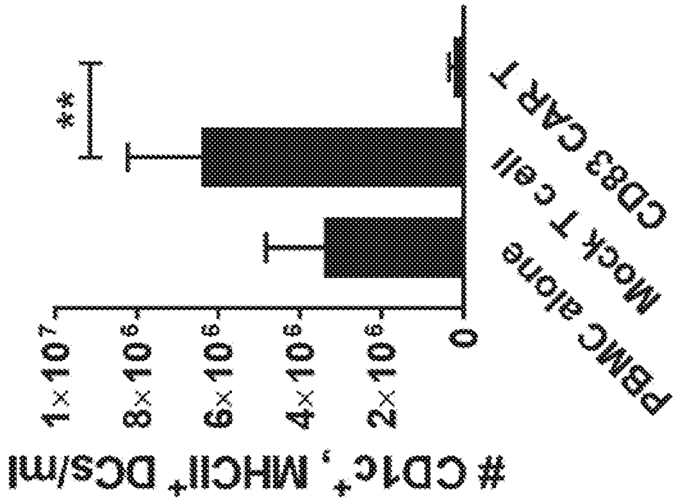
Figure 8B:
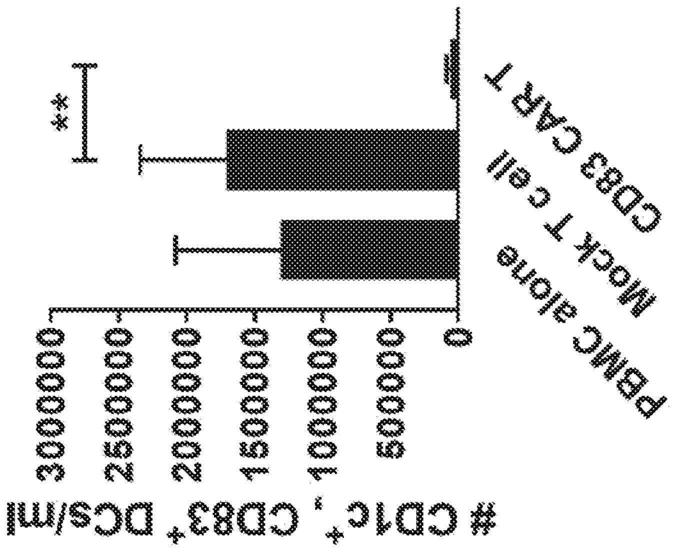
Figure 8C:
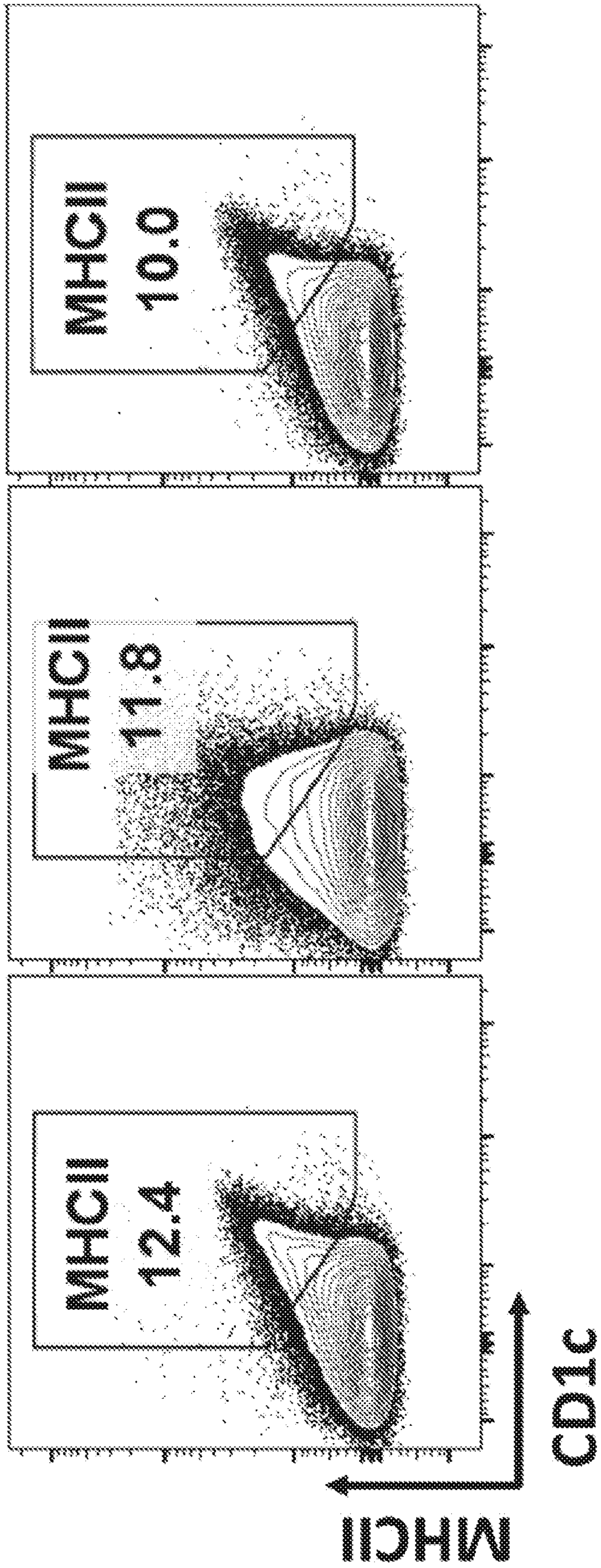
Figure 8E:
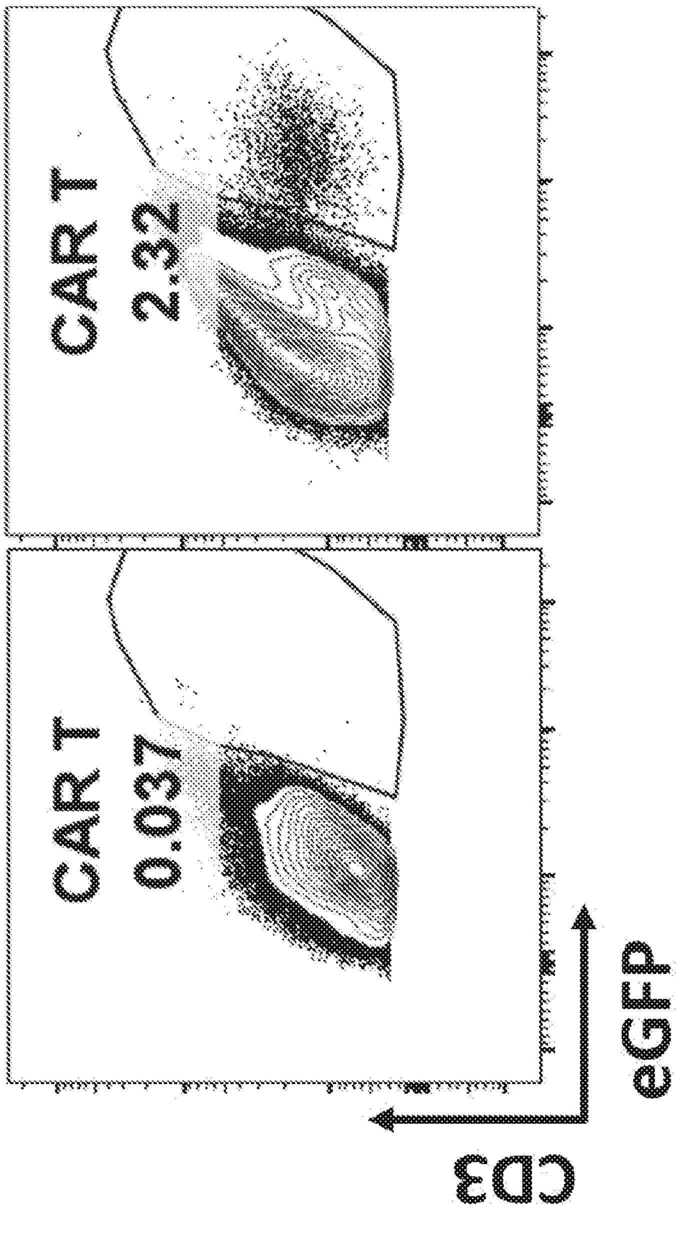

FIGS. 8A to 8E show human CD83 CAR T cell significantly reduces circulating mature, CD83+ DCs in vivo. NSG mice received $25\times10^6$ human PBMCs plus $1\times10^6$ CD83 CAR or mock transduced T cells. FIG. 8A contains representative contour plots showing the frequency of human CD83+, CD1c+ DCs in the mouse spleens at day +21. FIG. 8B\ is a bar graph showing the absolute number (mean±SEM) of human CD83+, CD1c+ DCs in the mouse spleens at day +21, Dunnett's test. FIG. 8C contains representative contour plots showing the percentage of MHC class II+, CD1c+ DCs in the recipient spleens at day +21. FIG. 8D is a bar graph depicting the absolute number (mean±SEM) of these cells, Dunnett's test. FIG. 8E is a representative contour plots showing the amount of eGFP+ CD83 CAR T cells in the inoculated mice at day +21, compared to mice that received mock transduced T cells. Pooled data from 2 independent experiments, up to 6 mice per experimental arm. **P=0.001-0.01.

Figure 9A:
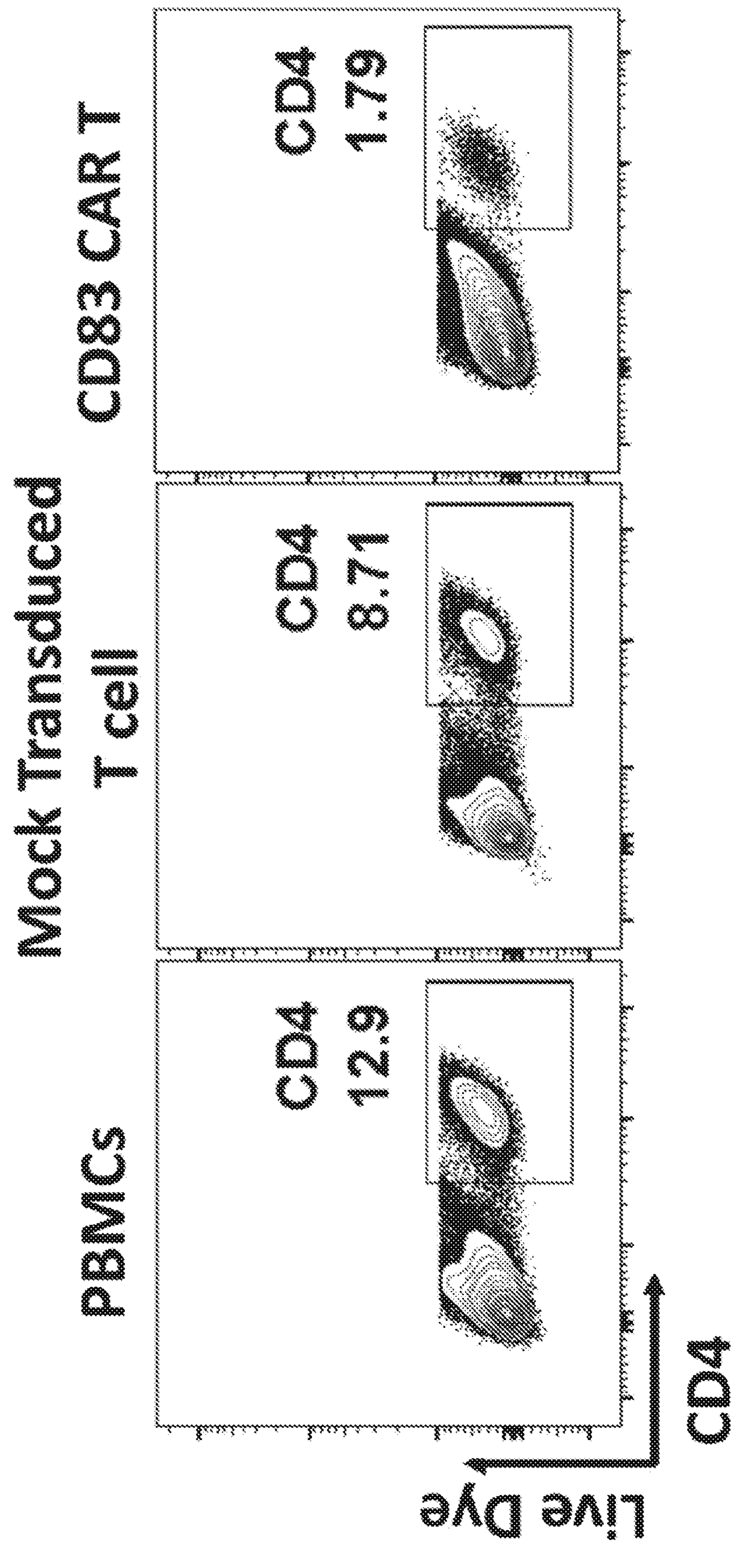
Figure 9B:
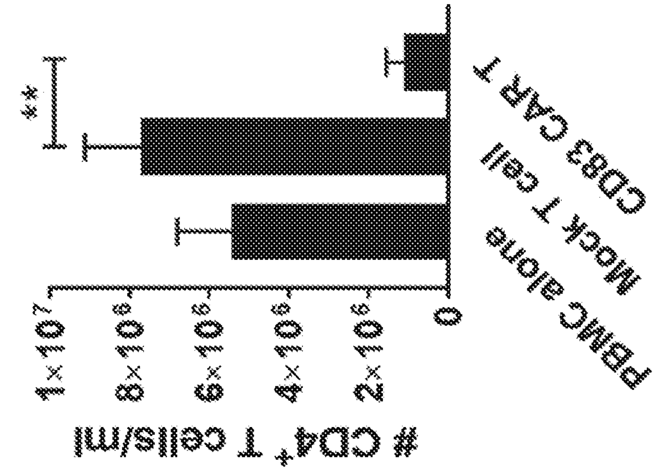
Figure 9C:
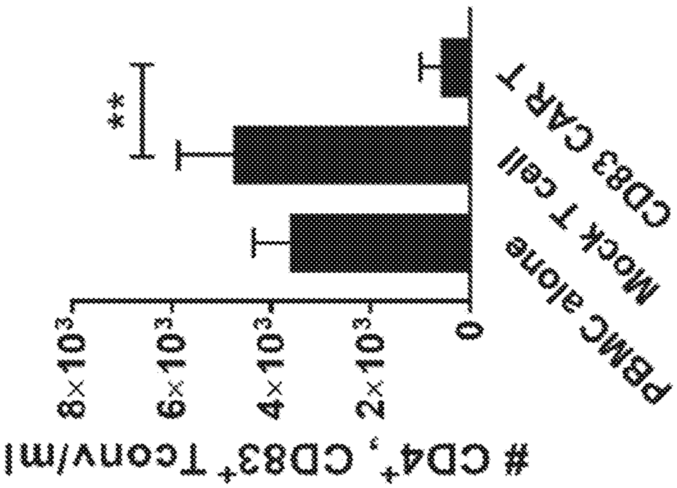
Figure 9D:
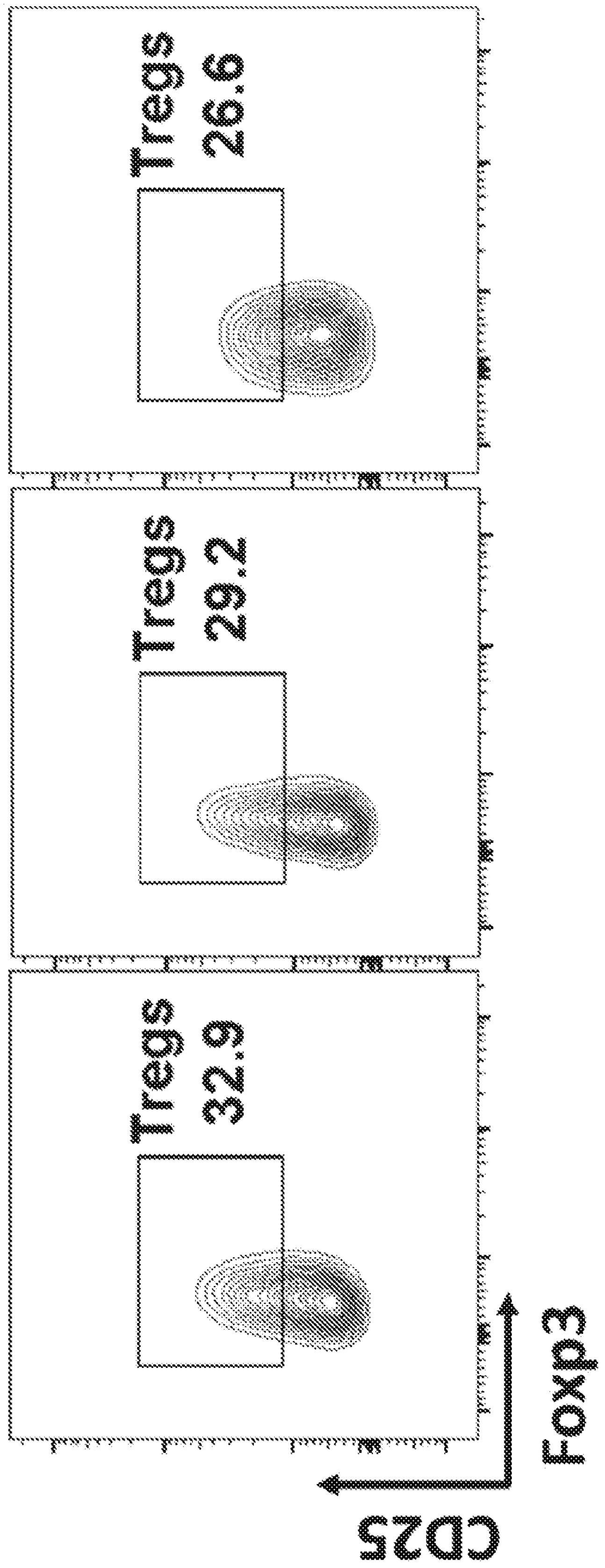
Figure 9F:
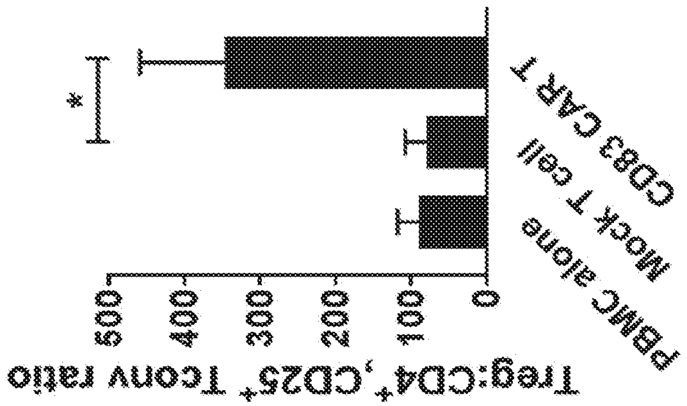
Figure 9E:
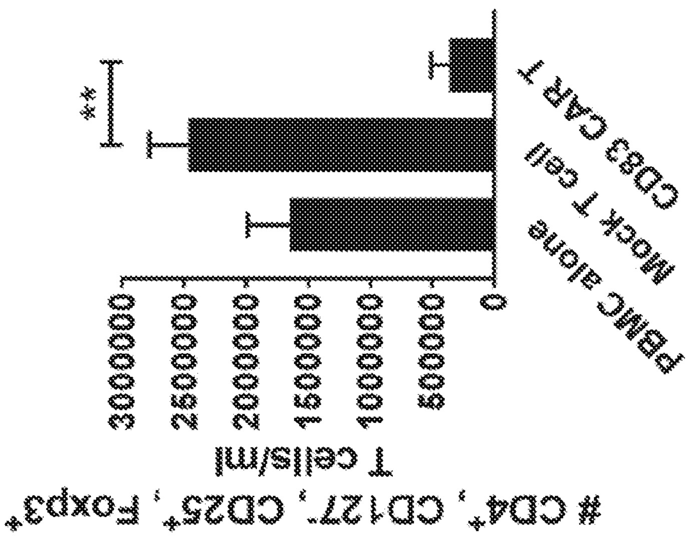
Figure 9G:
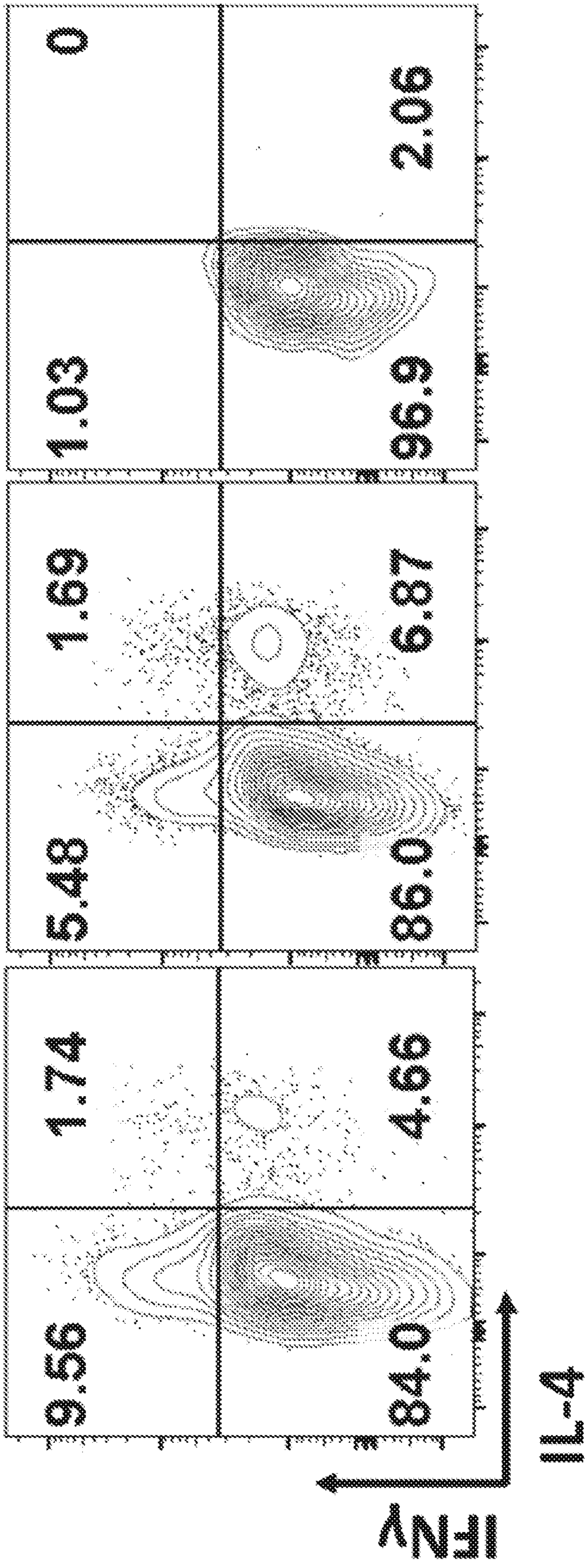
Figure 9I:
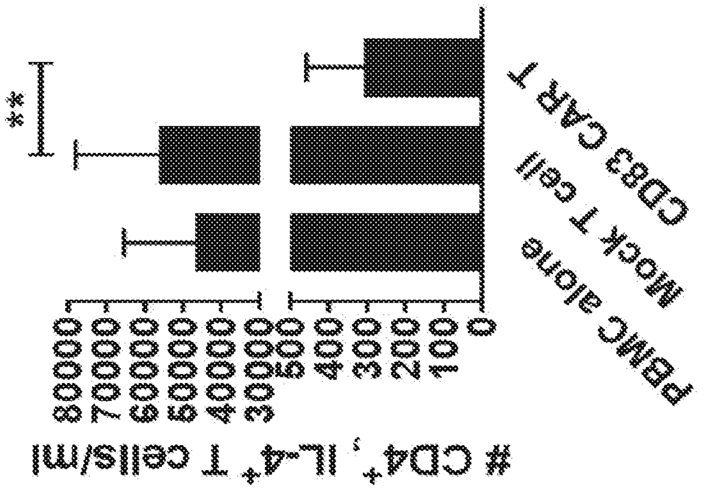
Figure 9H:
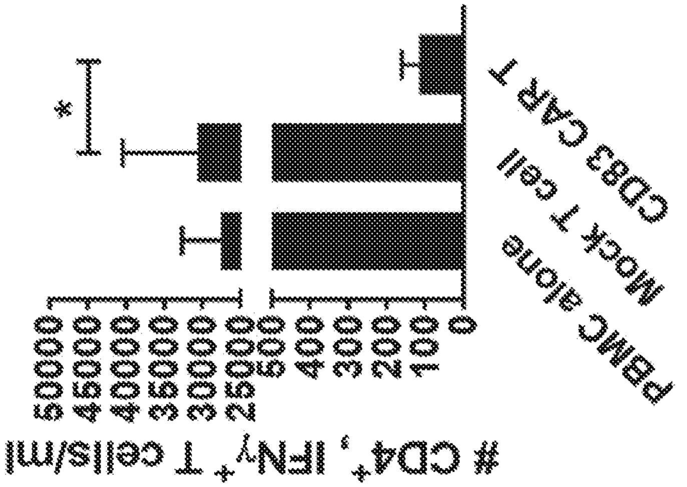

FIGS. 9A to 9I show human CD83 CAR T cells significantly reduce pathogenic Th1 cells, and increase the Treg: Tconv ratio. NSG mice received $25\times10^6$ human PBMCs plus $1\times10^6$ CD83 CAR or mock transduced T cells as described. On day +21, the mice were humanely euthanized and the amount of donor, human T cells were enumerated and characterized. FIG. 9A contains representative contour plots showing the frequency of human CD4+ T cells in the recipient spleens. FIGS. 9B and 9C are bar graphs showing the absolute numbers (mean±SEM) of CD4+(FIG. 9B) and CD8+(FIG. 9C) T cells in the mouse spleens at day +21, Dunnett's test. FIG. 9D contains contour plots depict the percentage of CD4+, CD127−, CD25+, Foxp3+ Tregs in the mouse spleens at day +21. FIGS. 9E and 9F are bar graphs showing the amount (mean±SEM) of Tregs (FIG. 9E) and the Treg:CD4+, CD25+ alloreactive Tconv (FIG. 9F) at day +21 in the recipient mice, Dunnett's test. FIG. 9G contains contour plots depicting the frequency of CD4+, IFNγ+ Th1 cells and CD4+, IL-4+ Th2 cells in the mouse spleens at day +21. FIGS. 9H and 9I are bar graphs demonstrating the absolute numbers (mean±SEM) of Th1 (FIG. 9H) and Th2 (FIG. 9I) cells in the recipient spleens, Dunnett's test. Pooled data from 2 independent experiments, up to 6 mice per experimental arm. *P<0.05, **P=0.001-0.01.

FIG. 10: Human CD83 CAR T cells permit CTL-mediated anti-tumor immunity. NSG mice received $25\times10^6$ human PBMCs plus $1\times10^6$ CD83 CAR or mock transduced T cells as described. A) On day +21, the amount of donor, human CD8+ T cells were enumerated, Dunnett's test. Pooled data from 2 independent experiments, up to 6 mice per experimental arm. B) NSG mice were transplanted with $30\times10^6$ human PBMCs plus $1\times10^6$ CD83 CAR or mock transduced T cells. An inoculum of irradiated K562 cells ($10^7$) was given on days 0 and +7. The mice were humanely euthanized on day +12, and the human CD8 T cells were purified from the recipient spleens. Purified human CD8 T cells were cocultured with fresh K562 cells at an E/T ratio of 10:1 and target cell killing was monitored using the xCELLigence RTCA system, Dunnett's test. 1 representative experiment of 2 is shown. *P<0.05, *P=0.0001-0.001, and **P<0.0001.

Figure 11A:
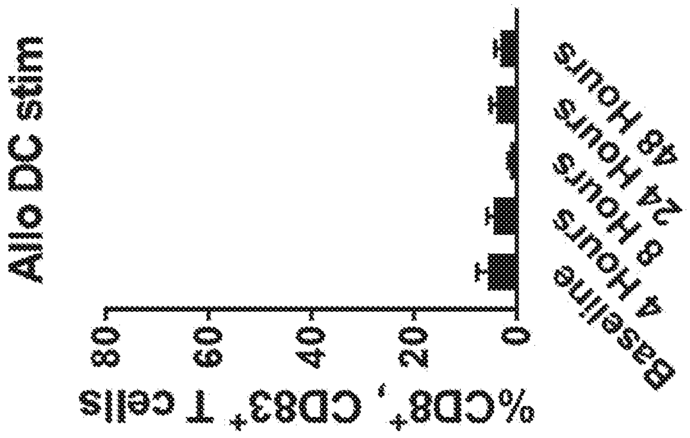
Figure 11B:
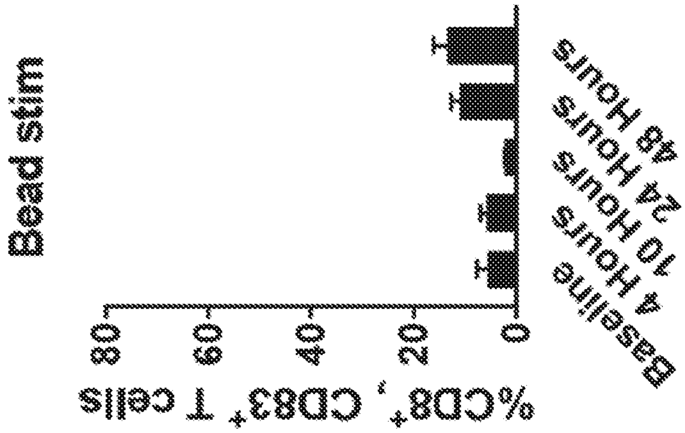

FIGS. 11A and 11B show CD83 expression among human CD8+ T cells after stimulation of allogeneic dendritic cells (FIG. 11A) or CD3/CD28 beads (FIG. 11B).

DETAILED DESCRIPTION

Disclosed herein are chimeric antigen receptors (CAR) that target CD83 on antigen-presenting cells. Also disclosed are immune effector cells, such as T cells or Natural Killer (NK) cells, that are engineered to express these CARs. CAR T cells expressing these CARs can suppress alloreactive donor cells, such as T cells. Therefore, also disclosed are methods for preventing GVHD in a subject that involves adoptive transfer of the disclosed immune effector cells engineered to express the disclosed CD83-specific CARs.

CD83-Specific Chimeric Antigen Receptors (CAR)

CARs generally incorporate an antigen recognition domain from the single-chain variable fragments (scFv) of a monoclonal antibody (mAb) with transmembrane signaling motifs involved in lymphocyte activation (Sadelain M, et al. Nat Rev Cancer 2003 3:35-45). Disclosed herein is a CD83-specific chimeric antigen receptor (CAR) that can be that can be expressed in immune effector cells to suppress alloreactive donor cells.

The disclosed CAR is generally made up of three domains: an ectodomain, a transmembrane domain, and an endodomain. The ectodomain comprises the CD83-binding region and is responsible for antigen recognition. It also optionally contains a signal peptide (SP) so that the CAR can be glycosylated and anchored in the cell membrane of the immune effector cell. The transmembrane domain (TD), is as its name suggests, connects the ectodomain to the endodomain and resides within the cell membrane when expressed by a cell. The endodomain is the business end of the CAR that transmits an activation signal to the immune effector cell after antigen recognition. For example, the endodomain can contain an intracellular signaling domain (ISD) and optionally a co-stimulatory signaling region (CSR).

A "signaling domain (SD)" generally contains immunoreceptortyrosine-based activation motifs (ITAMs) that activate a signaling cascade when the ITAM is phosphorylated. The term "co-stimulatory signaling region (CSR)" refers to intracellular signaling domains from costimulatory protein receptors, such as CD28, 41BB, and ICOS, that are able to enhance T-cell activation by T-cell receptors.

In some embodiments, the endodomain contains an SD or a CSR, but not both. In these embodiments, an immune effector cell containing the disclosed CAR is only activated if another CAR (or a T-cell receptor) containing the missing domain also binds its respective antigen.

In some embodiments, the disclosed CAR is defined by the formula:

SP-CD83-HG-TM-CSR-SD; or

SP-CD83-HG-TM-SD-CSR;

wherein "SP" represents an optional signal peptide,
wherein "CD83" represents a CD83-binding region,
wherein "HG" represents an optional hinge domain,
wherein "TM" represents a transmembrane domain,
wherein "CSR" represents one or more co-stimulatory signaling regions,
wherein "SD" represents a signaling domain, and
wherein "-" represents a peptide bond or linker.

Additional CAR constructs are described, for example, in Fresnak A D, et al. Engineered T cells: the promise and challenges of cancer immunotherapy. Nat Rev Cancer. 2016 Aug. 23; 16(9):566-81, which is incorporated by reference in its entirety for the teaching of these CAR models.

For example, the CAR can be a TRUCK, Universal CAR, Self-driving CAR, Armored CAR, Self-destruct CAR, Conditional CAR, Marked CAR, TenCAR, Dual CAR, or sCAR.

CAR T cells engineered to be resistant to immunosuppression (Armored CARs) may be genetically modified to no longer express various immune checkpoint molecules (for example, cytotoxic T lymphocyte-associated antigen 4 (CTLA4) or programmed cell death protein 1 (PD1)), with an immune checkpoint switch receptor, or may be administered with a monoclonal antibody that blocks immune checkpoint signaling or a checkpoint inhibitor which comprises an anti-PD-1 antibody, anti-PD-L1 antibody, anti-CTLA-4 antibody, or a combination thereof.

A self-destruct CAR may be designed using RNA delivered by electroporation to encode the CAR. Alternatively, inducible apoptosis of the T cell may be achieved based on ganciclovir binding to thymidine kinase in gene-modified lymphocytes or the more recently described system of activation of human caspase 9 by a small-molecule dimerizer.

A conditional CAR T cell is by default unresponsive, or switched 'off', until the addition of a small molecule to complete the circuit, enabling full transduction of both signal 1 and signal 2, thereby activating the CAR T cell. Alternatively, T cells may be engineered to express an adaptor-specific receptor with affinity for subsequently administered secondary antibodies directed at target antigen.

A tandem CAR (TanCAR) T cell expresses a single CAR consisting of two linked single-chain variable fragments (scFvs) that have different affinities fused to intracellular co-stimulatory domain(s) and a CD3ζ domain. TanCAR T cell activation is achieved only when target cells co-express both targets.

A dual CAR T cell expresses two separate CARs with different ligand binding targets; one CAR includes only the CD3ζ domain and the other CAR includes only the co-stimulatory domain(s). Dual CAR T cell activation requires co-expression of both targets.

A safety CAR (sCAR) consists of an extracellular scFv fused to an intracellular inhibitory domain. sCAR T cells co-expressing a standard CAR become activated only when encountering target cells that possess the standard CAR target but lack the sCAR target.

The antigen recognition domain of the disclosed CAR is usually an scFv. There are however many alternatives. An antigen recognition domain from native T-cell receptor (TCR) alpha and beta single chains have been described, as have simple ectodomains (e.g. CD4 ectodomain to recognize HIV infected cells) and more exotic recognition components such as a linked cytokine (which leads to recognition of cells bearing the cytokine receptor). In fact almost anything that binds a given target with high affinity can be used as an antigen recognition region.

The endodomain is the business end of the CAR that after antigen recognition transmits a signal to the immune effector cell, activating at least one of the normal effector functions of the immune effector cell. Effector function of a T cell, for example, may be cytolytic activity or helper activity including the secretion of cytokines. Therefore, the endodomain may comprise the "intracellular signaling domain" of a T cell receptor (TCR) and optional co-receptors. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal.

Cytoplasmic signaling sequences that regulate primary activation of the TCR complex that act in a stimulatory manner may contain signaling motifs which are known as immunoreceptortyrosine-based activation motifs (ITAMs). Examples of ITAM containing cytoplasmic signaling sequences include those derived from CD8, CD3ζ, CD3δ, CD3γ, CD3ε, CD32 (Fc gamma RIIa), DAP10, DAP12, CD79a, CD79b, FcγRIγ, FcγRIIIγ, FcεRIβ (FCERIB), and FcεRIγ (FCERIG).

In particular embodiments, the intracellular signaling domain is derived from CD3 zeta (CD34ζ) (TCR zeta, GenBank accno. BAG36664.1). T-cell surface glycoprotein CD3 zeta (CD3ζ) chain, also known as T-cell receptor T3 zeta chain or CD247 (Cluster of Differentiation 247), is a protein that in humans is encoded by the CD247 gene.

First-generation CARs typically had the intracellular domain from the CD3ζ chain, which is the primary transmitter of signals from endogenous TCRs. Second-generation CARs add intracellular signaling domains from various costimulatory protein receptors (e.g., CD28, 41BB, ICOS) to the endodomain of the CAR to provide additional signals to the T cell. More recent, third-generation CARs combine multiple signaling domains to further augment potency. T cells grafted with these CARs have demonstrated improved expansion, activation, persistence, and tumor-eradicating efficiency independent of costimulatory receptor/ligand interaction (Imai C, et al. Leukemia 2004 18:676-84; Maher J, et al. Nat Biotechnol 2002 20:70-5).

For example, the endodomain of the CAR can be designed to comprise the CD3ζ signaling domain by itself or combined with any other desired cytoplasmic domain(s) useful in the context of the CAR of the invention. For example, the cytoplasmic domain of the CAR can comprise a CD3ζ chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, ICOS, lymphocyte function-associated antigen-1 (LFA-1), CD2, CD7, LIGHT, NKG2C, B7-H3, and a ligand that specifically binds with CD123, CD8, CD4, b2c, CD80, CD86, DAP10, DAP12, MyD88, BTNL3, and NKG2D. Thus, while the CAR is exemplified primarily with CD28 as the co-stimulatory signaling element, other costimulatory elements can be used alone or in combination with other co-stimulatory signaling elements.

In some embodiments, the CAR comprises a hinge sequence. A hinge sequence is a short sequence of amino acids that facilitates antibody flexibility (see, e.g., Woof et al., Nat. Rev. Immunol., 4(2): 89-99 (2004)). The hinge sequence may be positioned between the antigen recognition moiety (e.g., anti-CD83 scFv) and the transmembrane domain. The hinge sequence can be any suitable sequence derived or obtained from any suitable molecule. In some embodiments, for example, the hinge sequence is derived from a CD8a molecule or a CD28 molecule.

The transmembrane domain may be derived either from a natural or from a synthetic source. Where the source is natural, the domain may be derived from any membrane-bound or transmembrane protein. For example, the transmembrane region may be derived from (i.e. comprise at least the transmembrane region(s) of) the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, or CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMFI, CD150, IPO-3), BLAME (SLAMF8), SELPLG (CD162), LTBR, and PAG/Cbp. Alternatively the transmembrane domain may be synthetic, in which case it will comprise predominantly hydrophobic residues such as leucine and valine. In some cases, a triplet of phenylalanine, tryptophan and valine will be found at each end of a synthetic transmembrane domain. A short oligo- or polypeptide linker, such as between 2 and 10 amino acids in length, may form the linkage between the transmembrane domain and the endoplasmic domain of the CAR.

In some embodiments, the CAR has more than one transmembrane domain, which can be a repeat of the same transmembrane domain, or can be different transmembrane domains.

In some embodiments, the CAR is a multi-chain CAR, as described in WO2015/039523, which is incorporated by reference for this teaching. A multi-chain CAR can comprise separate extracellular ligand binding and signaling domains in different transmembrane polypeptides. The signaling domains can be designed to assemble in juxtamembrane position, which forms flexible architecture closer to natural receptors, that confers optimal signal transduction. For example, the multi-chain CAR can comprise a part of an FCERI alpha chain and a part of an FCERI beta chain such that the FCERI chains spontaneously dimerize together to form a CAR.

Tables 1, 2, and 3 below provide some example combinations of CD83-binding region, co-stimulatory signaling regions, and intracellular signaling domain that can occur in the disclosed CARs.

TABLE 1

First Generation CARs

| ScFv | Signal Domain |
|---|---|
| CD83 | CD8 |
| CD83 | CD3ζ |
| CD83 | CD3δ |
| CD83 | CD3γ |
| CD83 | CD3ε |
| CD83 | FcγRI-γ |
| CD83 | FcγRIII-γ |
| CD83 | FcεRIβ |
| CD83 | FcεRIγ |
| CD83 | DAP10 |
| CD83 | DAP12 |
| CD83 | CD32 |
| CD83 | CD79a |

TABLE 2

Second Generation CARs

| ScFv | Co-stimulatory Signal | Signal Domain | ScFv | Co-stimulatory Signal | Signal Domain |
|---|---|---|---|---|---|
| CD83 | CD28 | CD8 | CD83 | CD8C | FcεRIβ |
| CD83 | CD28 | CD3ζ | CD83 | CD8C | FcεRIγ |
| CD83 | CD28 | CD3δ | CD83 | CD8C | DAP10 |
| CD83 | CD28 | CD3γ | CD83 | CD8C | DAP12 |
| CD83 | CD28 | CD3ε | CD83 | CD8C | CD32 |
| CD83 | CD28 | FcγRI-γ | CD83 | CD8C | CD79a |
| CD83 | CD28 | FcyRIII-γ | CD83 | CD8C | CD79b |
| CD83 | CD28 | FcεRIδ | CD83 | CD86 | CD8 |

TABLE 2-continued

| Second Generation CARs | | | | | |
|---|---|---|---|---|---|
| ScFv | Co-stirnulatory Signal | Signal Domain | ScFv | Co-stimulatory Signal | Signal Domain |
| CD83 | CD28 | FcεRIγ | CD83 | CD86 | CD3ζ |
| CD83 | CD28 | DAP10 | CD83 | CD86 | CD3δ |
| CD83 | CD28 | DAP12 | CD83 | CD86 | CD3γ |
| CD83 | CD28 | CD32 | CD83 | CD86 | CD3ε |
| CD83 | CD28 | CD79a | CD83 | CD86 | FcγRI-γ |
| CD83 | CD28 | CD79b | CD83 | CD86 | FcγRIII-γ |
| CD83 | CD8 | CD8 | CD83 | CD86 | FcεRIβ |
| CD83 | CD8 | CD3ζ | CD83 | CD86 | FcεRIγ |
| CD83 | CD8 | CD3δ | CD83 | CD86 | DAP10 |
| CD83 | CD8 | CD3γ | CD83 | CD86 | DAP12 |
| CD83 | CD8 | CD3ε | CD83 | CD86 | CD32 |
| CD83 | CD8 | FcγRI-γ | CD83 | CD86 | CD79a |
| CD83 | CD8 | FcγRIII-γ | CD83 | CD86 | CD79b |
| CD83 | CD8 | FcεRIβ | CD83 | OX4C | CD8 |
| CD83 | CDB | FcεRIγ | CD83 | OX4C | CD3ζ |
| CD83 | CDB | DAP10 | CD83 | OX4C | CD3δ |
| CD83 | CDB | DAP12 | CD83 | OX4C | CD3γ |
| CD83 | CDB | CD32 | CD83 | OX4C | CD3ε |
| CD83 | CD8 | CD79a | CD83 | OX4C | FcγRI-γ |
| CD83 | CD8 | CD79b | CD83 | OX4C | FcγRIII-γ |
| CD83 | CD4 | CD8 | CD83 | OX4C | FcεRIβ |
| CD83 | CD4 | CD3ζ | CD83 | OX4C | FcεRIγ |
| CD83 | CD4 | CD3δ | CD83 | OX4C | DAP10 |
| CD83 | CD4 | CD3γ | CD83 | OX4C | DAP12 |
| CD83 | CD4 | CD3ε | CD83 | OX4C | CD32 |
| CD83 | CD4 | FcγRI-γ | CD83 | OX4C | CD79a |
| CD83 | CD4 | FcγRIII-γ | CD83 | OX4C | CD79b |
| CD83 | CD4 | FcεRIβ | CD83 | DAP10 | CD8 |
| CD83 | CD4 | FcεRIγ | CD83 | DAP10 | CD3ζ |
| CD83 | CD4 | DAP10 | CD83 | DAP10 | CD3δ |
| CD83 | CD4 | DAP12 | CD83 | DAP10 | CD3γ |
| CD83 | CD4 | CD32 | CD83 | DAP10 | CD3ε |
| CD83 | CD4 | CD79a | CD83 | DAP10 | FcγRI-γ |
| CD83 | CD4 | CD79b | CD83 | DAP10 | FcγRIII-γ |
| CD83 | b2c | CD8 | CD83 | DAP10 | FcεRIβ |
| CD83 | b2c | CD3ζ | CD83 | DAP10 | FcεRIγ |
| CD83 | b2c | CD3δ | CD83 | DAP10 | DAP10 |
| CD83 | b2c | CD3γ | CD83 | DAP10 | DAP12 |
| CD83 | b2c | CD3ε | CD83 | DAP10 | CD32 |
| CD83 | b2c | FcγRI-γ | CD83 | DAP10 | CD79a |
| CD83 | b2c | FcγRIII-γ | CD83 | DAP10 | CD79b |
| CD83 | b2c | FcεRI β | CD83 | DAP12 | CD8 |
| CD83 | b2c | FcεRIy | CD83 | DAP12 | CD3ζ |
| CD83 | b2c | DAP10 | CD83 | DAP12 | CD3δ |
| CD83 | b2c | DAP12 | CD83 | DAP12 | CD3γ |
| CD83 | b2c | CD32 | CD83 | DAP12 | CD3ε |
| CD83 | b2c | CD79a | CD83 | DAP12 | FcyRI-γ |
| CD83 | b2c | CD79b | CD83 | DAP12 | FcγRIII-γ |
| CD83 | CD137/41BB | CD8 | CD83 | DAP12 | FcεRIβ |
| CD83 | CD137/41BB | CD3ζ | CD83 | DAP12 | FcεRIγ |
| CD83 | CD137/41BB | CD3δ | CD83 | DAP12 | DAP10 |
| CD83 | CD137/41BB | CD3γ | CD83 | DAP12 | DAP12 |
| CD83 | CD137/41BB | CD3ε | CD83 | DAP12 | CD32 |
| CD83 | CD137/41BB | FcγRI-γ | CD83 | DAP12 | CD79a |
| CD83 | CD137/41BB | FcγRIII-γ | CD83 | DAP12 | CD79b |
| CD83 | CD137/41BB | FcεRIβ | CD83 | MyD88 | CD8 |
| CD83 | CD137/41BB | FcεRIγ | CD83 | MyD88 | CD3ζ |
| CD83 | CD137/41BB | DAP10 | CD83 | MyD88 | CD3δ |
| CD83 | CD137/41BB | DAP12 | CD83 | MyD88 | CD3γ |
| CD83 | CD137/41BB | CD32 | CD83 | MyD88 | CD3ε |
| CD83 | CD137/41BB | CD79a | CD83 | MyD88 | FcγRI-γ |
| CD83 | CD137/41BB | CD79b | CD83 | MyD88 | FcγRIII-γ |
| CD83 | ICOS | CD8 | CD83 | MyD88 | FcεERIβ |
| CD83 | ICOS | CD3ζ | CD83 | MyD88 | FcεRIγ |
| CD83 | ICOS | CD3δ | CD83 | MyD88 | DAP10 |
| CD83 | ICOS | CD3γ | CD83 | MyD88 | DAP12 |
| CD83 | ICOS | CD3ε | CD83 | MyD88 | CD32 |
| CD83 | ICOS | FcγRI-γ | CD83 | MyD88 | CD79a |
| CD83 | ICOS | FcγRIII-γ | CD83 | MyD88 | CD79b |
| CD83 | ICOS | FcεRIβ | CD83 | CD7 | CD8 |
| CD83 | ICOS | FcεRIγ | CD83 | CD7 | CD3ζ |
| CD83 | ICOS | DAP10 | CD83 | CD7 | CD3δ |
| CD83 | ICOS | DAP12 | CD83 | CD7 | CD3γ |
| CD83 | ICOS | CD32 | CD83 | CD7 | CD3ε |
| CD83 | ICOS | CD79a | CD83 | CD7 | FcγRI-γ |

TABLE 2-continued

| Second Generation CARs | | | | | |
|---|---|---|---|---|---|
| ScFv | Co-stirnulatory Signal | Signal Domain | ScFv | Co-stimulatory Signal | Signal Domain |
| CD83 | ICOS | CD79b | CD83 | CD7 | FcγRIII-γ |
| CD83 | CD27 | CDB | CD83 | CD7 | FcεRIβ |
| CD83 | CD27 | CD3ζ | CD83 | CD7 | FcεRIγ |
| CD83 | CD27 | CD3δ | CD83 | CD7 | DAP10 |
| CD83 | CD27 | CD3γ | CD83 | CD7 | DAP12 |
| CD83 | CD27 | CD3ε | CD83 | CD7 | CD32 |
| CD83 | CD27 | FcγRI-γ | CD83 | CD7 | CD79a |
| CD83 | CD27 | FcγRIII-γ | CD83 | CD7 | CD79b |
| CD83 | CD27 | FcεRIβ | CD83 | BTNL3 | CD8 |
| CD83 | CD27 | FcεRIγ | CD83 | BTNL3 | CD3ζ |
| CD83 | CD27 | DAP10 | CD83 | BTNL3 | C D3δ |
| CD83 | CD27 | DAP12 | CD83 | BTNL3 | CD3γ |
| CD83 | CD27 | CD32 | CD83 | BTNL3 | CD3ε |
| CD83 | CD27 | CD79a | CD83 | BTNL3 | FcγRI-γ |
| CD83 | CD27 | CD79b | CD83 | BTNL3 | FcγRIII-γ |
| CD83 | CD28δ | CD8 | CD83 | BTNL3 | FcεRIβ |
| CD83 | CD28δ | CD3ζ | CD83 | BTNL3 | FcεRIγ |
| CD83 | CD28δ | CD3δ | CD83 | BTNL3 | DAP10 |
| CD83 | CD28δ | CD3γ | CD83 | BTNL3 | DAP12 |
| CD83 | CD28δ | CD3ε | CD83 | BTNL3 | CD32 |
| CD83 | CD28δ | FcγRI-γ | CD83 | BTNL3 | CD79a |
| CD83 | CD28δ | FcγRIII-γ | CD83 | BTNL3 | CD79b |
| CD83 | CD28δ | FcεRIβ | CD83 | NKG2D | CD8 |
| CD83 | CD28δ | FcεRIγ | CD83 | NKG2D | CD3ζ |
| CD83 | CD28δ | DAP10 | CD83 | NKG2D | CD3δ |
| CD83 | CD28δ | DAP12 | CD83 | NKG2D | CD3γ |
| CD83 | CD28δ | CD32 | CD83 | NKG2D | CD3ε |
| CD83 | CD28δ | CD79a | CD83 | NKG2D | FcγRI-γ |
| CD83 | CD28δ | CD79b | CD83 | NKG2D | FcγRIII-γ |
| CD83 | CD8C | CD8 | CD83 | NKG2D | FcεRIβ |
| CD83 | CD8C | CD3ζ | CD83 | NKG2D | FcεRIγ |
| CD83 | CD8C | CD3δ | CD83 | NKG2D | DAP10 |
| CD83 | CD8C | CD3γ | CD83 | NKG2D | DAP12 |
| CD83 | CD8C | CD3ε | CD83 | NKG2D | CD32 |
| CD83 | CD8C | FcγRI-γ | CD83 | NKG2D | CD79a |
| CD83 | CD8C | FcγRIII-γ | CD83 | NKG2D | CD79b |

TABLE 3

| Third Generation CARs | | | |
|---|---|---|---|
| Scfu | Co-stimulatory Signal | Co-stimulatory Signal | Signal Domain |
| CD83 | CD28 | CD28 | CD8 |
| CD83 | CD28 | CD28 | CD3ζ |
| CD83 | CD28 | CD28 | CD36 |
| CD83 | CD28 | CD28 | CD3y |
| CD83 | CD28 | CD28 | CD3ε |
| CD83 | CD28 | CD28 | FcγRI-γ |
| CD83 | CD28 | CD28 | FcγRII-γ |
| CD83 | CD28 | CD28 | FcεRIβ |
| CD83 | CD28 | CD28 | FcεRIγ |
| CD83 | CD28 | CD28 | DAP10 |
| CD83 | CD28 | CD28 | DAP12 |
| CD83 | CD28 | CD28 | CD32 |
| CD83 | CD28 | CD28 | CD79a |
| CD83 | CD28 | CD28 | CD79b |
| CD83 | CD28 | CD8 | CD8 |
| CD83 | CD28 | CD8 | CD3ζ |
| CD83 | CD28 | CD8 | CD3δ |
| CD83 | CD28 | CD8 | CD3γ |
| CD83 | CD28 | CD8 | CD3ε |
| CD83 | CD28 | CD8 | FcγRI-γ |
| CD83 | CD28 | CD8 | FcγRII-γ |
| CD83 | CD28 | CD8 | FcεRIβ |
| CD83 | CD28 | CD8 | FcεRIγ |
| CD83 | CD28 | CD8 | DAP10 |
| CD83 | CD28 | CD8 | DAP12 |
| CD83 | CD28 | CD8 | CD32 |
| CD83 | CD28 | CD8 | CD79a |
| CD83 | CD28 | CD8 | CD79b |

TABLE 3-continued

Third Generation CARs

| Scfu | Co-stimulatory Signal | Co-stimulatory Signal | Signal Domain |
|---|---|---|---|
| CD83 | CD28 | CD4 | CD8 |
| CD83 | CD28 | CD4 | CD3ζ |
| CD83 | CD28 | CD4 | CD3δ |
| CD83 | CD28 | CD4 | CD3γ |
| CD83 | CD28 | CD4 | CD3ε |
| CD83 | CD28 | CD4 | FcγRI-γ |
| CD83 | CD28 | CD4 | FcγRII-γ |
| CD83 | CD28 | CD4 | FcεRIβ |
| CD83 | CD28 | CD4 | FcεRIγ |
| CD83 | CD28 | CD4 | DAP10 |
| CD83 | CD28 | CD4 | DAP12 |
| CD83 | CD28 | CD4 | CD32 |
| CD83 | CD28 | CD4 | CD79a |
| CD83 | CD28 | CD4 | CD79b |
| CD83 | CD28 | b2c | CD8 |
| CD83 | CD28 | b2c | CD3ζ |
| CD83 | CD28 | b2c | CD3δ |
| CD83 | CD28 | b2c | CD3γ |
| CD83 | CD28 | b2c | CD3ε |
| CD83 | CD28 | b2c | FcγRI-γ |
| CD83 | CD28 | b2c | FcγRIII-γ |
| CD83 | CD28 | b2c | FcεRIβ |
| CD83 | CD28 | b2c | FcεRIγ |
| CD83 | CD28 | b2c | DAP10 |
| CD83 | CD28 | b2c | DAP12 |
| CD83 | CD28 | b2c | CD32 |
| CD83 | CD28 | b2c | CD79a |
| CD83 | CD28 | b2c | CD79b |
| CD83 | CD28 | CD137/41BB | CD8 |
| CD83 | CD28 | CD137/41BB | CD3ζ |
| CD83 | CD28 | CD137/41BB | CD3δ |
| CD83 | CD28 | CD137/41BB | CD3γ |
| CD83 | CD28 | CD137/41BB | CD3ε |
| CD83 | CD28 | CD137/41BB | FcγRI-γ |
| CD83 | CD28 | CD137/41BB | FcγRIII-γ |
| CD83 | CD28 | CD137/41BB | FcεRIβ |
| CD83 | CD28 | CD137/41BB | FcεRIγ |
| CD83 | CD28 | CD137/41BB | DAP10 |
| CD83 | CD28 | CD137/41BB | DAP12 |
| CD83 | CD28 | CD137/41BB | CD32 |
| CD83 | CD28 | CD137/41BB | CD79a |
| CD83 | CD28 | CD137/41BB | CD79b |
| CD83 | CD28 | ICOS | CD8 |
| CD83 | CD28 | ICOS | CD3ζ |
| CD83 | CD28 | ICOS | CD3δ |
| CD83 | CD28 | ICOS | CD3γ |
| CD83 | CD28 | ICOS | CD3ε |
| CD83 | CD28 | ICOS | FcγRI-γ |
| CD83 | CD28 | ICOS | FcγRIII-γ |
| CD83 | CD28 | ICOS | FcεRIβ |
| CD83 | CD28 | ICOS | FcεRIγ |
| CD83 | CD28 | ICOS | DAP10 |
| CD83 | CD28 | ICOS | DAP12 |
| CD83 | CD28 | ICOS | CD32 |
| CD83 | CD28 | ICOS | CD79a |
| CD83 | CD28 | ICOS | CD79b |
| CD83 | CD28 | CD27 | CD8 |
| CD83 | CD28 | CD27 | CD3ζ |
| CD83 | CD28 | CD27 | CD3δ |
| CD83 | CD28 | CD27 | CD3γ |
| CD83 | CD28 | CD27 | CD3ε |
| CD83 | CD28 | CD27 | FcγRI-γ |
| CD83 | CD28 | CD27 | FcγRIII-γ |
| CD83 | CD28 | CD27 | FcεRIβ |
| CD83 | CD28 | CD27 | FcεRIγ |
| CD83 | CD28 | CD27 | DAP10 |
| CD83 | CD28 | CD27 | DAP12 |
| CD83 | CD28 | CD27 | CD32 |
| CD83 | CD28 | CD27 | CD79a |
| CD83 | CD28 | CD27 | CD79b |
| CD83 | CD28 | CD28δ | CD8 |
| CD83 | CD28 | CD28δ | CD3ζ |
| CD83 | CD28 | CD28δ | CD3δ |
| CD83 | CD28 | CD28δ | CD3γ |
| CD83 | CD28 | CD28δ | CD3ε |

TABLE 3-continued

Third Generation CARs

| Scfu | Co-stimulatory Signal | Co-stimulatory Signal | Signal Domain |
|---|---|---|---|
| CD83 | CD28 | CD28δ | FcγRI-γ |
| CD83 | CD28 | CD28δ | FcγRIII-γ |
| CD83 | CD28 | CD28δ | FcεRIβ |
| CD83 | CD28 | CD28δ | FcεRIγ |
| CD83 | CD28 | CD28δ | DAP10 |
| CD83 | CD28 | CD28δ | DAP12 |
| CD83 | CD28 | CD28δ | CD32 |
| CD83 | CD28 | CD28δ | CD79a |
| CD83 | CD28 | CD28δ | CD79b |
| CD83 | CD28 | CD80 | CD8 |
| CD83 | CD28 | CD80 | CD3ζ |
| CD83 | CD28 | CD80 | CD3δ |
| CD83 | CD28 | CD80 | CD3γ |
| CD83 | CD28 | CD80 | CD3ε |
| CD83 | CD28 | CD80 | FcγRI-γ |
| CD83 | CD28 | CD80 | FcγRIII-γ |
| CD83 | CD28 | CD80 | FcεRIβ |
| CD83 | CD28 | CD80 | FcεRIγ |
| CD83 | CD28 | CD80 | DAP10 |
| CD83 | CD28 | CD80 | DAP12 |
| CD83 | CD28 | CD80 | CD32 |
| CD83 | CD28 | CD80 | CD79a |
| CD83 | CD28 | CD80 | CD79b |
| CD83 | CD28 | CD86 | CD8 |
| CD83 | CD28 | CD86 | CD3ζ |
| CD83 | CD28 | CD86 | CD3δ |
| CD83 | CD28 | CD86 | CD3γ |
| CD83 | CD28 | CD86 | CD3ε |
| CD83 | CD28 | CD86 | FcγRI-γ |
| CD83 | CD28 | CD86 | FcγRIII-γ |
| CD83 | CD28 | CD86 | FcεRIβ |
| CD83 | CD28 | CD86 | FcεRIγ |
| CD83 | CD28 | CD86 | DAP10 |
| CD83 | CD28 | CD86 | DAP12 |
| CD83 | CD28 | CD86 | CD32 |
| CD83 | CD28 | CD86 | CD79a |
| CD83 | CD28 | CD86 | CD79b |
| CD83 | CD28 | OX40 | CD8 |
| CD83 | CD28 | OX40 | CD3ζ |
| CD83 | CD28 | OX40 | CD3δ |
| CD83 | CD28 | OX40 | CD3γ |
| CD83 | CD28 | OX40 | CD3ε |
| CD83 | CD28 | OX40 | FcγRI-γ |
| CD83 | CD28 | OX40 | FcγRIII-γ |
| CD83 | CD28 | OX40 | FcεRIβ |
| CD83 | CD28 | OX40 | FcεRIγ |
| CD83 | CD28 | OX40 | DAP10 |
| CD83 | CD28 | OX40 | DAP12 |
| CD83 | CD28 | OX40 | CD32 |
| CD83 | CD28 | OX40 | CD79a |
| CD83 | CD28 | OX40 | CD79b |
| CD83 | CD28 | DAP10 | CD8 |
| CD83 | CD28 | DAP10 | CD3ζ |
| CD83 | CD28 | DAP10 | CD3δ |
| CD83 | CD28 | DAP10 | CD3γ |
| CD83 | CD28 | DAP10 | CD3ε |
| CD83 | CD28 | DAP10 | FcγRI-γ |
| CD83 | CD28 | DAP10 | FcγRIII-γ |
| CD83 | CD28 | DAP10 | FcεRIβ |
| CD83 | CD28 | DAP10 | FcεRIγ |
| CD83 | CD28 | DAP10 | DAP10 |
| CD83 | CD28 | DAP10 | DAP12 |
| CD83 | CD28 | DAP10 | CD32 |
| CD83 | CD28 | DAP10 | CD79a |
| CD83 | CD28 | DAP10 | CD79b |
| CD83 | CD28 | DAP12 | CD8 |
| CD83 | CD28 | DAP12 | CD3ζ |
| CD83 | CD28 | DAP12 | CD3δ |
| CD83 | CD28 | DAP12 | CD3γ |
| CD83 | CD28 | DAP12 | CD3ε |
| CD83 | CD28 | DAP12 | FcγRI-γ |
| CD83 | CD28 | DAP12 | FcγRIII-γ |
| CD83 | CD28 | DAP12 | FcεRIβ |
| CD83 | CD28 | DAP12 | FcεRIγ |
| CD83 | CD28 | DAP12 | DAP10 |

TABLE 3-continued

| Third Generation CARs | | | |
|---|---|---|---|
| Scfu | Co-stimulatory Signal | Co-stimulatory Signal | Signal Domain |
| CD83 | CD28 | DAP12 | DAP12 |
| CD83 | CD28 | DAP12 | CD32 |
| CD83 | CD28 | DAP12 | CD79a |
| CD83 | CD28 | DAP12 | CD79b |
| CD83 | CD28 | MyD88 | CD8 |
| CD83 | CD28 | MyD88 | CD3ζ |
| CD83 | CD28 | MyD88 | CD3δ |
| CD83 | CD28 | MyD88 | CD3γ |
| CD83 | CD28 | MyD88 | CD3ε |
| CD83 | CD28 | MyD88 | FcγRI-γ |
| CD83 | CD28 | MyD88 | FcγRIII-γ |
| CD83 | CD28 | MyD88 | FcεRIβ |
| CD83 | CD28 | MyD88 | FcεRIγ |
| CD83 | CD28 | MyD88 | DAP10 |
| CD83 | CD28 | MyD88 | DAP12 |
| CD83 | CD28 | MyD88 | CD32 |
| CD83 | CD28 | MyD88 | CD79a |
| CD83 | CD28 | MyD88 | CD79b |
| CD83 | CD28 | CD7 | CD8 |
| CD83 | CD28 | CD7 | CD3ζ |
| CD83 | CD28 | CD7 | CD3δ |
| CD83 | CD28 | CD7 | CD3γ |
| CD83 | CD28 | CD7 | CD3ε |
| CD83 | CD28 | CD7 | FcγRI-γ |
| CD83 | CD28 | CD7 | FcγRIII-γ |
| CD83 | CD28 | CD7 | FcεRIβ |
| CD83 | CD28 | CD7 | FcεRIγ |
| CD83 | CD28 | CD7 | DAP10 |
| CD83 | CD28 | CD7 | DAP12 |
| CD83 | CD28 | CD7 | CD32 |
| CD83 | CD28 | CD7 | CD79a |
| CD83 | CD28 | CD7 | CD79b |
| CD83 | CD28 | BTNL3 | CD8 |
| CD83 | CD28 | BTNL3 | CD3ζ |
| CD83 | CD28 | BTNL3 | CD3δ |
| CD83 | CD28 | BTNL3 | CD3γ |
| CD83 | CD28 | BTNL3 | CD3ε |
| CD83 | CD28 | BTNL3 | FcγRI-γ |
| CD83 | CD28 | BTNL3 | FcγRIII-γ |
| CD83 | CD28 | BTNL3 | FcεRIβ |
| CD83 | CD28 | BTNL3 | FcεRIγ |
| CD83 | CD28 | BTNL3 | DAP10 |
| CD83 | CD28 | BTNL3 | DAP12 |
| CD83 | CD28 | BTNL3 | CD32 |
| CD83 | CD28 | BTNL3 | CD79a |
| CD83 | CD28 | BTNL3 | CD79b |
| CD83 | CD28 | NKG2D | CD8 |
| CD83 | CD28 | NKG2D | CD3ζ |
| CD83 | CD28 | NKG2D | CD3δ |
| CD83 | CD28 | NKG2D | CD3γ |
| CD83 | CD28 | NKG2D | CD3ε |
| CD83 | CD28 | NKG2D | FcγRI-γ |
| CD83 | CD28 | NKG2D | FcγRIII-γ |
| CD83 | CD28 | NKG2D | FcεRIβ |
| CD83 | CD28 | NKG2D | FcεRIγ |
| CD83 | CD28 | NKG2D | DAP10 |
| CD83 | CD28 | NKG2D | DAP12 |
| CD83 | CD28 | NKG2D | CD32 |
| CD83 | CD28 | NKG2D | CD79a |
| CD83 | CD28 | NKG2D | CD79b |
| CD83 | CD8 | CD28 | CD8 |
| CD83 | CD8 | CD28 | CD3ζ |
| CD83 | CD8 | CD28 | CD3δ |
| CD83 | CD8 | CD28 | CD3γ |
| CD83 | CD8 | CD28 | CD3ε |
| CD83 | CD8 | CD28 | FcγRI-γ |
| CD83 | CD8 | CD28 | FcγRIII-γ |
| CD83 | CD8 | CD28 | FcεRIβ |
| CD83 | CD8 | CD28 | FcεRIγ |
| CD83 | CD8 | CD28 | DAP10 |
| CD83 | CD8 | CD28 | DAP12 |
| CD83 | CD8 | CD28 | CD32 |
| CD83 | CD8 | CD28 | CD79a |
| CD83 | CD8 | CD28 | CD79b |
| CD83 | CD8 | CD8 | CD8 |

TABLE 3-continued

| Third Generation CARs | | | |
|---|---|---|---|
| Scfu | Co-stimulatory Signal | Co-stimulatory Signal | Signal Domain |
| CD83 | CD8 | CD8 | CD3ζ |
| CD83 | CD8 | CD8 | CD3δ |
| CD83 | CD8 | CD8 | CD3γ |
| CD83 | CD8 | CD8 | CD3ε |
| CD83 | CD8 | CD8 | FcγRI-γ |
| CD83 | CD8 | CD8 | FcγRIII-γ |
| CD83 | CD8 | CD8 | FcεRIβ |
| CD83 | CD8 | CD8 | FcεRIγ |
| CD83 | CD8 | CD8 | DAP10 |
| CD83 | CD8 | CD8 | DAP12 |
| CD83 | CD8 | CD8 | CD32 |
| CD83 | CD8 | CD8 | CD79a |
| CD83 | CD8 | CD8 | CD79b |
| CD83 | CD8 | CD4 | CD8 |
| CD83 | CD8 | CD4 | CD3ζ |
| CD83 | CD8 | CD4 | CD3δ |
| CD83 | CD8 | CD4 | CD3γ |
| CD83 | CD8 | CD4 | CD3ε |
| CD83 | CD8 | CD4 | FcγRI-γ |
| CD83 | CD8 | CD4 | FcγRIII-γ |
| CD83 | CD8 | CD4 | FcεRIβ |
| CD83 | CD8 | CD4 | FcεRIγ |
| CD83 | CD8 | CD4 | DAP10 |
| CD83 | CD8 | CD4 | DAP12 |
| CD83 | CD8 | CD4 | CD32 |
| CD83 | CD8 | CD4 | CD79a |
| CD83 | CD8 | CD4 | CD79b |
| CD83 | CD8 | b2c | CD8 |
| CD83 | CD8 | b2c | CD3ζ |
| CD83 | CD8 | b2c | CD3δ |
| CD83 | CD8 | b2c | CD3γ |
| CD83 | CD8 | b2c | CD3ε |
| CD83 | CD8 | b2c | FcγRI-γ |
| CD83 | CD8 | b2c | FcγRIII-γ |
| CD83 | CD8 | b2c | FcεRIβ |
| CD83 | CD8 | b2c | FcεRIγ |
| CD83 | CD8 | b2c | DAP10 |
| CD83 | CD8 | b2c | DAP12 |
| CD83 | CD8 | b2c | CD32 |
| CD83 | CD8 | b2c | CD79a |
| CD83 | CD8 | b2c | CD79b |
| CD83 | CD8 | CD137/41BB | CD8 |
| CD83 | CD8 | CD137/41BB | CD3ζ |
| CD83 | CD8 | CD137/41BB | CD3δ |
| CD83 | CD8 | CD137/41BB | CD3γ |
| CD83 | CD8 | CD137/41BB | CD3ε |
| CD83 | CD8 | CD137/41BB | FcγRI-γ |
| CD83 | CD8 | CD137/41BB | FcγRIII-γ |
| CD83 | CD8 | CD137/41BB | FcεRIβ |
| CD83 | CD8 | CD137/41BB | FcεRIγ |
| CD83 | CD8 | CD137/41BB | DAP10 |
| CD83 | CD8 | CD137/41BB | DAP12 |
| CD83 | CD8 | CD137/41BB | CD32 |
| CD83 | CD8 | CD137/41BB | CD79a |
| CD83 | CD8 | CD137/41BB | CD79b |
| CD83 | CD8 | ICOS | CD8 |
| CD83 | CD8 | ICOS | CD3ζ |
| CD83 | CD8 | ICOS | CD3δ |
| CD83 | CD8 | ICOS | CD3γ |
| CD83 | CD8 | ICOS | CD3ε |
| CD83 | CD8 | ICOS | FcγRI-γ |
| CD83 | CD8 | ICOS | FcγRIII-γ |
| CD83 | CD8 | ICOS | FcεRIβ |
| CD83 | CD8 | ICOS | FcεRIγ |
| CD83 | CD8 | ICOS | DAP10 |
| CD83 | CD8 | ICOS | DAP12 |
| CD83 | CD8 | ICOS | CD32 |
| CD83 | CD8 | ICOS | CD79a |
| CD83 | CD8 | ICOS | CD79b |
| CD83 | CD8 | CD27 | CD8 |
| CD83 | CD8 | CD27 | CD3ζ |
| CD83 | CD8 | CD27 | CD3δ |
| CD83 | CD8 | CD27 | CD3γ |
| CD83 | CD8 | CD27 | CD3ε |
| CD83 | CD8 | CD27 | FcγRI-γ |

TABLE 3-continued

| Third Generation CARs | | | |
|---|---|---|---|
| Scfu | Co-stimulatory Signal | Co-stimulatory Signal | Signal Domain |
| CD83 | CD8 | CD27 | FcγRIII-γ |
| CD83 | CD8 | CD27 | FcεRIβ |
| CD83 | CD8 | CD27 | FcεRIγ |
| CD83 | CD8 | CD27 | DAP10 |
| CD83 | CD8 | CD27 | DAP12 |
| CD83 | CD8 | CD27 | CD32 |
| CD83 | CD8 | CD27 | CD79a |
| CD83 | CD8 | CD27 | CD79b |
| CD83 | CD8 | CD28δ | CD8 |
| CD83 | CD8 | CD28δ | CD3ζ |
| CD83 | CD8 | CD28δ | CD3δ |
| CD83 | CD8 | CD28δ | CD3γ |
| CD83 | CD8 | CD28δ | CD3ε |
| CD83 | CD8 | CD28δ | FcγRI-γ |
| CD83 | CD8 | CD28δ | FcγRIII-γ |
| CD83 | CD8 | CD28δ | FcεRIβ |
| CD83 | CD8 | CD28δ | FcεRIγ |
| CD83 | CD8 | CD28δ | DAP10 |
| CD83 | CD8 | CD28δ | DAP12 |
| CD83 | CD8 | CD28δ | CD32 |
| CD83 | CD8 | CD28δ | CD79a |
| CD83 | CD8 | CD28δ | CD79b |
| CD83 | CD8 | CD80 | CD8 |
| CD83 | CD8 | CD80 | CD3ζ |
| CD83 | CD8 | CD80 | CD3δ |
| CD83 | CD8 | CD80 | CD3γ |
| CD83 | CD8 | CD80 | CD3ε |
| CD83 | CD8 | CD80 | FcγRI-γ |
| CD83 | CD8 | CD80 | FcγRIII-γ |
| CD83 | CD8 | CD80 | FcεRIβ |
| CD83 | CD8 | CD80 | FcεRIγ |
| CD83 | CD8 | CD80 | DAP10 |
| CD83 | CD8 | CD80 | DAP12 |
| CD83 | CD8 | CD80 | CD32 |
| CD83 | CD8 | CD80 | CD79a |
| CD83 | CD8 | CD80 | CD79b |
| CD83 | CD8 | CD86 | CD8 |
| CD83 | CD8 | CD86 | CD3ζ |
| CD83 | CD8 | CD86 | CD3δ |
| CD83 | CD8 | CD86 | CD3γ |
| CD83 | CD8 | CD86 | CD3ε |
| CD83 | CD8 | CD86 | FcγRI-γ |
| CD83 | CD8 | CD86 | FcγRIII-γ |
| CD83 | CD8 | CD86 | FcεRIβ |
| CD83 | CD8 | CD86 | FcεRIγ |
| CD83 | CD8 | CD86 | DAP10 |
| CD83 | CD8 | CD86 | DAP12 |
| CD83 | CD8 | CD86 | CD32 |
| CD83 | CD8 | CD86 | CD79a |
| CD83 | CD8 | CD86 | CD79b |
| CD83 | CD8 | OX40 | CD8 |
| CD83 | CD8 | OX40 | CD3ζ |
| CD83 | CD8 | OX40 | CD3δ |
| CD83 | CD8 | OX40 | CD3γ |
| CD83 | CD8 | OX40 | CD3ε |
| CD83 | CD8 | OX40 | FcγRI-γ |
| CD83 | CD8 | OX40 | FcγRIII-γ |
| CD83 | CD8 | OX40 | FcεRIβ |
| CD83 | CD8 | OX40 | FcεRIγ |
| CD83 | CD8 | OX40 | DAP10 |
| CD83 | CD8 | OX40 | DAP12 |
| CD83 | CD8 | OX40 | CD32 |
| CD83 | CD8 | OX40 | CD79a |
| CD83 | CD8 | OX40 | CD79b |
| CD83 | CD8 | DAP10 | CD8 |
| CD83 | CD8 | DAP10 | CD3ζ |
| CD83 | CD8 | DAP10 | CD3δ |
| CD83 | CD8 | DAP10 | CD3γ |
| CD83 | CD8 | DAP10 | CD3ε |
| CD83 | CD8 | DAP10 | FcγRI-γ |
| CD83 | CD8 | DAP10 | FcγRIII-γ |
| CD83 | CD8 | DAP10 | FcεRIβ |
| CD83 | CD8 | DAP10 | FcεRIγ |
| CD83 | CD8 | DAP10 | DAP10 |
| CD83 | CD8 | DAP10 | DAP12 |

TABLE 3-continued

| Third Generation CARs | | | |
|---|---|---|---|
| Scfu | Co-stimulatory Signal | Co-stimulatory Signal | Signal Domain |
| CD83 | CD8 | DAP10 | CD32 |
| CD83 | CD8 | DAP10 | CD79a |
| CD83 | CD8 | DAP10 | CD79b |
| CD83 | CD8 | DAP12 | CD8 |
| CD83 | CD8 | DAP12 | CD3ζ |
| CD83 | CD8 | DAP12 | CD3δ |
| CD83 | CD8 | DAP12 | CD3γ |
| CD83 | CD8 | DAP12 | CD3ε |
| CD83 | CD8 | DAP12 | FcγRI-γ |
| CD83 | CD8 | DAP12 | FcγRIII-γ |
| CD83 | CD8 | DAP12 | FcεRIβ |
| CD83 | CD8 | DAP12 | FcεRIγ |
| CD83 | CD8 | DAP12 | DAP10 |
| CD83 | CD8 | DAP12 | DAP12 |
| CD83 | CD8 | DAP12 | CD32 |
| CD83 | CD8 | DAP12 | CD79a |
| CD83 | CD8 | DAP12 | CD79b |
| CD83 | CD8 | MyD88 | CD8 |
| CD83 | CD8 | MyD88 | CD3ζ |
| CD83 | CD8 | MyD88 | CD3δ |
| CD83 | CD8 | MyD88 | CD3γ |
| CD83 | CD8 | MyD88 | CD3ε |
| CD83 | CD8 | MyD88 | FcγRI-γ |
| CD83 | CD8 | MyD88 | FcγRIII-γ |
| CD83 | CD8 | MyD88 | FcεRIβ |
| CD83 | CD8 | MyD88 | FcεRIγ |
| CD83 | CD8 | MyD88 | DAP10 |
| CD83 | CD8 | MyD88 | DAP12 |
| CD83 | CD8 | MyD88 | CD32 |
| CD83 | CD8 | MyD88 | CD79a |
| CD83 | CD8 | MyD88 | CD79b |
| CD83 | CD8 | CD7 | CD8 |
| CD83 | CD8 | CD7 | CD3ζ |
| CD83 | CD8 | CD7 | CD3δ |
| CD83 | CD8 | CD7 | CD3γ |
| CD83 | CD8 | CD7 | CD3ε |
| CD83 | CD8 | CD7 | FcγRI-γ |
| CD83 | CD8 | CD7 | FcγRIII-γ |
| CD83 | CD8 | CD7 | FcεRIβ |
| CD83 | CD8 | CD7 | FcεRIγ |
| CD83 | CD8 | CD7 | DAP10 |
| CD83 | CD8 | CD7 | DAP12 |
| CD83 | CD8 | CD7 | CD32 |
| CD83 | CD8 | CD7 | CD79a |
| CD83 | CD8 | CD7 | CD79b |
| CD83 | CD8 | BTNL3 | CD8 |
| CD83 | CD8 | BTNL3 | CD3ζ |
| CD83 | CD8 | BTNL3 | CD3δ |
| CD83 | CD8 | BTNL3 | CD3γ |
| CD83 | CD8 | BTNL3 | CD3ε |
| CD83 | CD8 | BTNL3 | FcγRI-γ |
| CD83 | CD8 | BTNL3 | FcγRIII-γ |
| CD83 | CD8 | BTNL3 | FcεRIβ |
| CD83 | CD8 | BTNL3 | FcεRIγ |
| CD83 | CD8 | BTNL3 | DAP10 |
| CD83 | CD8 | BTNL3 | DAP12 |
| CD83 | CD8 | BTNL3 | CD32 |
| CD83 | CD8 | BTNL3 | CD79a |
| CD83 | CD8 | BTNL3 | CD79b |
| CD83 | CD8 | NKG2D | CD8 |
| CD83 | CD8 | NKG2D | CD3ζ |
| CD83 | CD8 | NKG2D | CD3δ |
| CD83 | CD8 | NKG2D | CD3γ |
| CD83 | CD8 | NKG2D | CD3ε |
| CD83 | CD8 | NKG2D | FcγRI-γ |
| CD83 | CD8 | NKG2D | FcγRIII-γ |
| CD83 | CD8 | NKG2D | FcεRIβ |
| CD83 | CD8 | NKG2D | FcεRIγ |
| CD83 | CD8 | NKG2D | DAP10 |
| CD83 | CD8 | NKG2D | DAP12 |
| CD83 | CD8 | NKG2D | CD32 |
| CD83 | CD8 | NKG2D | CD79a |
| CD83 | CD8 | NKG2D | CD79b |
| CD83 | CD4 | CD28 | CD8 |
| CD83 | CD4 | CD28 | CD3ζ |

TABLE 3-continued

| Third Generation CARs | | | |
|---|---|---|---|
| Scfu | Co-stimulatory Signal | Co-stimulatory Signal | Signal Domain |
| CD83 | CD4 | CD28 | CD3δ |
| CD83 | CD4 | CD28 | CD3γ |
| CD83 | CD4 | CD28 | CD3ε |
| CD83 | CD4 | CD28 | FcγRI-γ |
| CD83 | CD4 | CD28 | FcγRIII-γ |
| CD83 | CD4 | CD28 | FcεRIβ |
| CD83 | CD4 | CD28 | FcεRIγ |
| CD83 | CD4 | CD28 | DAP10 |
| CD83 | CD4 | CD28 | DAP12 |
| CD83 | CD4 | CD28 | CD32 |
| CD83 | CD4 | CD28 | CD79a |
| CD83 | CD4 | CD28 | CD79b |
| CD83 | CD4 | CD8 | CD8 |
| CD83 | CD4 | CD8 | CD3ζ |
| CD83 | CD4 | CD8 | CD3δ |
| CD83 | CD4 | CD8 | CD3γ |
| CD83 | CD4 | CD8 | C D3E |
| CD83 | CD4 | CD8 | FcγRI-γ |
| CD83 | CD4 | CD8 | FcγRIII-γ |
| CD83 | CD4 | CD8 | FcεRIβ |
| CD83 | CD4 | CD8 | FcεRIγ |
| CD83 | CD4 | CD8 | DAP10 |
| CD83 | CD4 | CD8 | DAP12 |
| CD83 | CD4 | CD8 | CD32 |
| CD83 | CD4 | CD8 | CD79a |
| CD83 | CD4 | CD8 | CD79b |
| CD83 | CD4 | CD4 | CD8 |
| CD83 | CD4 | CD4 | CD3ζ |
| CD83 | CD4 | CD4 | CD3δ |
| CD83 | CD4 | CD4 | CD3γ |
| CD83 | CD4 | CD4 | CD3ε |
| CD83 | CD4 | CD4 | FcγRI-γ |
| CD83 | CD4 | CD4 | FcγRIII-γ |
| CD83 | CD4 | CD4 | FcεRIβ |
| CD83 | CD4 | CD4 | FcεRIγ |
| CD83 | CD4 | CD4 | DAP10 |
| CD83 | CD4 | CD4 | DAP12 |
| CD83 | CD4 | CD4 | CD32 |
| CD83 | CD4 | CD4 | CD79a |
| CD83 | CD4 | CD4 | CD79b |
| CD83 | CD4 | b2c | CD8 |
| CD83 | CD4 | b2c | CD3ζ |
| CD83 | CD4 | b2c | CD3δ |
| CD83 | CD4 | b2c | CD3γ |
| CD83 | CD4 | b2c | CD3ε |
| CD83 | CD4 | b2c | FcγRI-γ |
| CD83 | CD4 | b2c | FcγRIII-γ |
| CD83 | CD4 | b2c | FcεRIβ |
| CD83 | CD4 | b2c | FcεRIγ |
| CD83 | CD4 | b2c | DAP10 |
| CD83 | CD4 | b2c | DAP12 |
| CD83 | CD4 | b2c | CD32 |
| CD83 | CD4 | b2c | CD79a |
| CD83 | CD4 | b2c | CD79b |
| CD83 | CD4 | CD137/41BB | CD8 |
| CD83 | CD4 | CD137/41BB | CD3ζ |
| CD83 | CD4 | CD137/41BB | CD3δ |
| CD83 | CD4 | CD137/41BB | CD3γ |
| CD83 | CD4 | CD137/41BB | CD3ε |
| CD83 | CD4 | CD137/41BB | FcγRI-γ |
| CD83 | CD4 | CD137/41BB | FcγRIII-γ |
| CD83 | CD4 | CD137/41BB | FcεRIβ |
| CD83 | CD4 | CD137/41BB | FcεRIγ |
| CD83 | CD4 | CD137/41BB | DAP10 |
| CD83 | CD4 | CD137/41BB | DAP12 |
| CD83 | CD4 | CD137/41BB | CD32 |
| CD83 | CD4 | CD137/41BB | CD79a |
| CD83 | CD4 | CD137/41BB | CD79b |
| CD83 | CD4 | ICOS | CD8 |
| CD83 | CD4 | ICOS | CD3ζ |
| CD83 | CD4 | ICOS | CD3δ |
| CD83 | CD4 | ICOS | CD3γ |
| CD83 | CD4 | ICOS | CD3ε |
| CD83 | CD4 | ICOS | FcγRI-γ |
| CD83 | CD4 | ICOS | FcγRIII-γ |

TABLE 3-continued

| Third Generation CARs | | | |
|---|---|---|---|
| Scfu | Co-stimulatory Signal | Co-stimulatory Signal | Signal Domain |
| CD83 | CD4 | ICOS | FcεRIβ |
| CD83 | CD4 | ICOS | FcεRIγ |
| CD83 | CD4 | ICOS | DAP10 |
| CD83 | CD4 | ICOS | DAP12 |
| CD83 | CD4 | ICOS | CD32 |
| CD83 | CD4 | ICOS | CD79a |
| CD83 | CD4 | ICOS | CD79b |
| CD83 | CD4 | CD27 | CD8 |
| CD83 | CD4 | CD27 | CD3ζ |
| CD83 | CD4 | CD27 | CD3δ |
| CD83 | CD4 | CD27 | CD3γ |
| CD83 | CD4 | CD27 | CD3ε |
| CD83 | CD4 | CD27 | FcγRI-γ |
| CD83 | CD4 | CD27 | FcγRIII-γ |
| CD83 | CD4 | CD27 | FcεRIβ |
| CD83 | CD4 | CD27 | FcεRIγ |
| CD83 | CD4 | CD27 | DAP10 |
| CD83 | CD4 | CD27 | DAP12 |
| CD83 | CD4 | CD27 | CD32 |
| CD83 | CD4 | CD27 | CD79a |
| CD83 | CD4 | CD27 | CD79b |
| CD83 | CD4 | CD28δ | CD8 |
| CD83 | CD4 | CD28δ | CD3ζ |
| CD83 | CD4 | CD28δ | CD3δ |
| CD83 | CD4 | CD28δ | CD3γ |
| CD83 | CD4 | CD28δ | CD3ε |
| CD83 | CD4 | CD28δ | FcγRI-γ |
| CD83 | CD4 | CD28δ | FcγRIII-γ |
| CD83 | CD4 | CD28δ | FcεRIβ |
| CD83 | CD4 | CD28δ | FcεRIγ |
| CD83 | CD4 | CD28δ | DAP10 |
| CD83 | CD4 | CD28δ | DAP12 |
| CD83 | CD4 | CD28δ | CD32 |
| CD83 | CD4 | CD28δ | CD79a |
| CD83 | CD4 | CD28δ | CD79b |
| CD83 | CD4 | CD80 | CD8 |
| CD83 | CD4 | CD80 | CD3ζ |
| CD83 | CD4 | CD80 | CD3δ |
| CD83 | CD4 | CD80 | CD3γ |
| CD83 | CD4 | CD80 | CD3ε |
| CD83 | CD4 | CD80 | FcγRI-γ |
| CD83 | CD4 | CD80 | FcγRIII-γ |
| CD83 | CD4 | CD80 | FcεRIβ |
| CD83 | CD4 | CD80 | FcεRIγ |
| CD83 | CD4 | CD80 | DAP10 |
| CD83 | CD4 | CD80 | DAP12 |
| CD83 | CD4 | CD80 | CD32 |
| CD83 | CD4 | CD80 | CD79a |
| CD83 | CD4 | CD80 | CD79b |
| CD83 | CD4 | CD86 | CD8 |
| CD83 | CD4 | CD86 | CD3ζ |
| CD83 | CD4 | CD86 | CD3δ |
| CD83 | CD4 | CD86 | CD3γ |
| CD83 | CD4 | CD86 | CD3ε |
| CD83 | CD4 | CD86 | FcγRI-γ |
| CD83 | CD4 | CD86 | FcγRIII-γ |
| CD83 | CD4 | CD86 | FcεRIβ |
| CD83 | CD4 | CD86 | FcεRIγ |
| CD83 | CD4 | CD86 | DAP10 |
| CD83 | CD4 | CD86 | DAP12 |
| CD83 | CD4 | CD86 | CD32 |
| CD83 | CD4 | CD86 | CD79a |
| CD83 | CD4 | CD86 | CD79b |
| CD83 | CD4 | OX40 | CD8 |
| CD83 | CD4 | OX40 | CD3ζ |
| CD83 | CD4 | OX40 | CD3δ |
| CD83 | CD4 | OX40 | CD3γ |
| CD83 | CD4 | OX40 | CD3ε |
| CD83 | CD4 | OX40 | FcγRI-γ |
| CD83 | CD4 | OX40 | FcγRIII-γ |
| CD83 | CD4 | OX40 | FcεRIβ |
| CD83 | CD4 | OX40 | FcεRIγ |
| CD83 | CD4 | OX40 | DAP10 |
| CD83 | CD4 | OX40 | DAP12 |
| CD83 | CD4 | OX40 | CD32 |

TABLE 3-continued

| Third Generation CARs | | | |
|---|---|---|---|
| Scfu | Co-stimulatory Signal | Co-stimulatory Signal | Signal Domain |
| CD83 | CD4 | OX40 | CD79a |
| CD83 | CD4 | OX40 | CD79b |
| CD83 | CD4 | DAP10 | CD8 |
| CD83 | CD4 | DAP10 | CD3ζ |
| CD83 | CD4 | DAP10 | CD3δ |
| CD83 | CD4 | DAP10 | CD3γ |
| CD83 | CD4 | DAP10 | CD3ε |
| CD83 | CD4 | DAP10 | FcγRI-γ |
| CD83 | CD4 | DAP10 | FcγRIII-γ |
| CD83 | CD4 | DAP10 | FcεRIβ |
| CD83 | CD4 | DAP10 | FcεRIγ |
| CD83 | CD4 | DAP10 | DAP10 |
| CD83 | CD4 | DAP10 | DAP12 |
| CD83 | CD4 | DAP10 | CD32 |
| CD83 | CD4 | DAP10 | CD79a |
| CD83 | CD4 | DAP10 | CD79b |
| CD83 | CD4 | DAP12 | CD8 |
| CD83 | CD4 | DAP12 | CD3ζ |
| CD83 | CD4 | DAP12 | CD3δ |
| CD83 | CD4 | DAP12 | CD3γ |
| CD83 | CD4 | DAP12 | CD3ε |
| CD83 | CD4 | DAP12 | FcγRI-γ |
| CD83 | CD4 | DAP12 | FcγRIII-γ |
| CD83 | CD4 | DAP12 | FcεRIβ |
| CD83 | CD4 | DAP12 | FcεRIγ |
| CD83 | CD4 | DAP12 | DAP10 |
| CD83 | CD4 | DAP12 | DAP12 |
| CD83 | CD4 | DAP12 | CD32 |
| CD83 | CD4 | DAP12 | CD79a |
| CD83 | CD4 | DAP12 | CD79b |
| CD83 | CD4 | MyD88 | CD8 |
| CD83 | CD4 | MyD88 | CD3ζ |
| CD83 | CD4 | MyD88 | CD3δ |
| CD83 | CD4 | MyD88 | CD3γ |
| CD83 | CD4 | MyD88 | CD3ε |
| CD83 | CD4 | MyD88 | FcγRI-γ |
| CD83 | CD4 | MyD88 | FcγRIII-γ |
| CD83 | CD4 | MyD88 | FcεRIβ |
| CD83 | CD4 | MyD88 | FcεRIγ |
| CD83 | CD4 | MyD88 | DAP10 |
| CD83 | CD4 | MyD88 | DAP12 |
| CD83 | CD4 | MyD88 | CD32 |
| CD83 | CD4 | MyD88 | CD79a |
| CD83 | CD4 | MyD88 | CD79b |
| CD83 | CD4 | CD7 | CD8 |
| CD83 | CD4 | CD7 | CD3ζ |
| CD83 | CD4 | CD7 | CD3δ |
| CD83 | CD4 | CD7 | CD3γ |
| CD83 | CD4 | CD7 | CD3ε |
| CD83 | CD4 | CD7 | FcγRI-γ |
| CD83 | CD4 | CD7 | FcγRIII-γ |
| CD83 | CD4 | CD7 | FcεRIβ |
| CD83 | CD4 | CD7 | FcεRIγ |
| CD83 | CD4 | CD7 | DAP10 |
| CD83 | CD4 | CD7 | DAP12 |
| CD83 | CD4 | CD7 | CD32 |
| CD83 | CD4 | CD7 | CD79a |
| CD83 | CD4 | CD7 | CD79b |
| CD83 | CD4 | BTNL3 | CD8 |
| CD83 | CD4 | BTNL3 | CD3ζ |
| CD83 | CD4 | BTNL3 | CD3δ |
| CD83 | CD4 | BTNL3 | CD3γ |
| CD83 | CD4 | BTNL3 | CD3ε |
| CD83 | CD4 | BTNL3 | FcγRI-γ |
| CD83 | CD4 | BTNL3 | FcγRIII-γ |
| CD83 | CD4 | BTNL3 | FcεRIβ |
| CD83 | CD4 | BTNL3 | FcεRIγ |
| CD83 | CD4 | BTNL3 | DAP10 |
| CD83 | CD4 | BTNL3 | DAP12 |
| CD83 | CD4 | BTNL3 | CD32 |
| CD83 | CD4 | BTNL3 | CD79a |
| CD83 | CD4 | BTNL3 | CD79b |
| CD83 | CD4 | NKG2D | CD8 |
| CD83 | CD4 | NKG2D | CD3ζ |
| CD83 | CD4 | NKG2D | CD3δ |

TABLE 3-continued

| Third Generation CARs | | | |
|---|---|---|---|
| Scfu | Co-stimulatory Signal | Co-stimulatory Signal | Signal Domain |
| CD83 | CD4 | NKG2D | CD3γ |
| CD83 | CD4 | NKG2D | CD3ε |
| CD83 | CD4 | NKG2D | FcγRI-γ |
| CD83 | CD4 | NKG2D | FcγRIII-γ |
| CD83 | CD4 | NKG2D | FcεRIβ |
| CD83 | CD4 | NKG2D | FcεRIγ |
| CD83 | CD4 | NKG2D | DAP10 |
| CD83 | CD4 | NKG2D | DAP12 |
| CD83 | CD4 | NKG2D | CD32 |
| CD83 | CD4 | NKG2D | CD79a |
| CD83 | CD4 | NKG2D | CD79b |
| CD83 | b2c | CD28 | CD8 |
| CD83 | b2c | CD28 | CDg |
| CD83 | b2c | CD28 | CD3δ |
| CD83 | b2c | CD28 | CD3γ |
| CD83 | b2c | CD28 | CD3ε |
| CD83 | b2c | CD28 | FcγRI-γ |
| CD83 | b2c | CD28 | FcγRIII-γ |
| CD83 | b2c | CD28 | FcεRIβ |
| CD83 | b2c | CD28 | FcεRIγ |
| CD83 | b2c | CD28 | DAP10 |
| CD83 | b2c | CD28 | DAP12 |
| CD83 | b2c | CD28 | CD32 |
| CD83 | b2c | CD28 | CD79a |
| CD83 | b2c | CD28 | CD79b |
| CD83 | b2c | CD8 | CD8 |
| CD83 | b2c | CD8 | CD3ζ |
| CD83 | b2c | CD8 | CD3δ |
| CD83 | b2c | CD8 | CD3γ |
| CD83 | b2c | CD8 | CD3ε |
| CD83 | b2c | CD8 | FcγRI-γ |
| CD83 | b2c | CD8 | FcγRIII-γ |
| CD83 | b2c | CD8 | FcεRIβ |
| CD83 | b2c | CD8 | FcεRIγ |
| CD83 | b2c | CD8 | DAP10 |
| CD83 | b2c | CD8 | DAP12 |
| CD83 | b2c | CD8 | CD32 |
| CD83 | b2c | CD8 | CD79a |
| CD83 | b2c | CD8 | CD79b |
| CD83 | b2c | CD4 | CD8 |
| CD83 | b2c | CD4 | CD3ζ |
| CD83 | b2c | CD4 | CD3δ |
| CD83 | b2c | CD4 | CD3γ |
| CD83 | b2c | CD4 | CD3ε |
| CD83 | b2c | CD4 | FcγRI-γ |
| CD83 | b2c | CD4 | FcγRIII-γ |
| CD83 | b2c | CD4 | FcεRIβ |
| CD83 | b2c | CD4 | FcεRIγ |
| CD83 | b2c | CD4 | DAP10 |
| CD83 | b2c | CD4 | DAP12 |
| CD83 | b2c | CD4 | CD32 |
| CD83 | b2c | CD4 | CD79a |
| CD83 | b2c | CD4 | CD79b |
| CD83 | b2c | b2c | CD8 |
| CD83 | b2c | b2c | CD3ζ |
| CD83 | b2c | b2c | CD3δ |
| CD83 | b2c | b2c | CD3γ |
| CD83 | b2c | b2c | CD3ε |
| CD83 | b2c | b2c | FcγRI-γ |
| CD83 | b2c | b2c | FcγRIII-γ |
| CD83 | b2c | b2c | FcεRIβ |
| CD83 | b2c | b2c | FcεRIγ |
| CD83 | b2c | b2c | DAP10 |
| CD83 | b2c | b2c | DAP12 |
| CD83 | b2c | b2c | CD32 |
| CD83 | b2c | b2c | CD79a |
| CD83 | b2c | b2c | CD79b |
| CD83 | b2c | CD137/41BB | CD8 |
| CD83 | b2c | CD137/41BB | CDg |
| CD83 | b2c | CD137/41BB | CD3δ |
| CD83 | b2c | CD137/41BB | CD3γ |
| CD83 | b2c | CD137/41BB | CD3ε |
| CD83 | b2c | CD137/41BB | FcγRI-γ |
| CD83 | b2c | CD137/41BB | FcγRIII-γ |
| CD83 | b2c | CD137/41BB | FcεRIβ |

TABLE 3-continued

| Third Generation CARs | | | |
|---|---|---|---|
| Scfu | Co-stimulatory Signal | Co-stimulatory Signal | Signal Domain |
| CD83 | b2c | CD137/41BB | FcεRIγ |
| CD83 | b2c | CD137/41BB | DAP10 |
| CD83 | b2c | CD137/41BB | DAP12 |
| CD83 | b2c | CD137/41BB | CD32 |
| CD83 | b2c | CD137/41BB | CD79a |
| CD83 | b2c | CD137/41BB | CD79b |
| CD83 | b2c | ICOS | CD8 |
| CD83 | b2c | ICOS | CD3ζ |
| CD83 | b2c | ICOS | CD3δ |
| CD83 | b2c | ICOS | CD3γ |
| CD83 | b2c | ICOS | CD3ε |
| CD83 | b2c | ICOS | FcγRI-γ |
| CD83 | b2c | ICOS | FcγRIII-γ |
| CD83 | b2c | ICOS | FcεRIβ |
| CD83 | b2c | ICOS | FcεRIγ |
| CD83 | b2c | ICOS | DAP10 |
| CD83 | b2c | ICOS | DAP12 |
| CD83 | b2c | ICOS | CD32 |
| CD83 | b2c | ICOS | CD79a |
| CD83 | b2c | ICOS | CD79b |
| CD83 | b2c | CD27 | CD8 |
| CD83 | b2c | CD27 | CD3ζ |
| CD83 | b2c | CD27 | CD3δ |
| CD83 | b2c | CD27 | CD3γ |
| CD83 | b2c | CD27 | CD3ε |
| CD83 | b2c | CD27 | FcγRI-γ |
| CD83 | b2c | CD27 | FcγRIII-γ |
| CD83 | b2c | CD27 | FcεRIβ |
| CD83 | b2c | CD27 | FcεRIγ |
| CD83 | b2c | CD27 | DAP10 |
| CD83 | b2c | CD27 | DAP12 |
| CD83 | b2c | CD27 | CD32 |
| CD83 | b2c | CD27 | CD79a |
| CD83 | b2c | CD27 | CD79b |
| CD83 | b2c | CD28δ | CD8 |
| CD83 | b2c | CD28δ | CD3ζ |
| CD83 | b2c | CD28δ | CD3δ |
| CD83 | b2c | CD28δ | CD3γ |
| CD83 | b2c | CD28δ | CD3ε |
| CD83 | b2c | CD28δ | FcγRI-γ |
| CD83 | b2c | CD28δ | FcγRIII-γ |
| CD83 | b2c | CD28δ | FcεRIβ |
| CD83 | b2c | CD28δ | FcεRIγ |
| CD83 | b2c | CD28δ | DAP10 |
| CD83 | b2c | CD28δ | DAP12 |
| CD83 | b2c | CD28δ | CD32 |
| CD83 | b2c | CD28δ | CD79a |
| CD83 | b2c | CD28δ | CD79b |
| CD83 | b2c | CD80 | CD8 |
| CD83 | b2c | CD80 | CD3ζ |
| CD83 | b2c | CD80 | CD3δ |
| CD83 | b2c | CD80 | CD3γ |
| CD83 | b2c | CD80 | CD3ε |
| CD83 | b2c | CD80 | FcγRI-γ |
| CD83 | b2c | CD80 | FcγRIII-γ |
| CD83 | b2c | CD80 | FcεRIβ |
| CD83 | b2c | CD80 | FcεRIγ |
| CD83 | b2c | CD80 | DAP10 |
| CD83 | b2c | CD80 | DAP12 |
| CD83 | b2c | CD80 | CD32 |
| CD83 | b2c | CD80 | CD79a |
| CD83 | b2c | CD80 | CD79b |
| CD83 | b2c | CD86 | CD8 |
| CD83 | b2c | CD86 | CD3ζ |
| CD83 | b2c | CD86 | CD3δ |
| CD83 | b2c | CD86 | CD3γ |
| CD83 | b2c | CD86 | CD3ε |
| CD83 | b2c | CD86 | FcγRI-γ |
| CD83 | b2c | CD86 | FcγRIII-γ |
| CD83 | b2c | CD86 | FcεRIβ |
| CD83 | b2c | CD86 | FcεRIγ |
| CD83 | b2c | CD86 | DAP10 |
| CD83 | b2c | CD86 | DAP12 |
| CD83 | b2c | CD86 | CD32 |
| CD83 | b2c | CD86 | CD79a |

TABLE 3-continued

| Third Generation CARs | | | |
|---|---|---|---|
| Scfu | Co-stimulatory Signal | Co-stimulatory Signal | Signal Domain |
| CD83 | b2c | CD86 | CD79b |
| CD83 | b2c | OX40 | CD8 |
| CD83 | b2c | OX40 | CD3ζ |
| CD83 | b2c | OX40 | CD3δ |
| CD83 | b2c | OX40 | CD3γ |
| CD83 | b2c | OX40 | CD3ε |
| CD83 | b2c | OX40 | FcγRI-γ |
| CD83 | b2c | OX40 | FcγRIII-γ |
| CD83 | b2c | OX40 | FcεRIβ |
| CD83 | b2c | OX40 | FcεRIγ |
| CD83 | b2c | OX40 | DAP10 |
| CD83 | b2c | OX40 | DAP12 |
| CD83 | b2c | OX40 | CD32 |
| CD83 | b2c | OX40 | CD79a |
| CD83 | b2c | OX40 | CD79b |
| CD83 | b2c | DAP10 | CD8 |
| CD83 | b2c | DAP10 | CD3ζ |
| CD83 | b2c | DAP10 | CD3δ |
| CD83 | b2c | DAP10 | CD3γ |
| CD83 | b2c | DAP10 | CD3ε |
| CD83 | b2c | DAP10 | FcγRI-γ |
| CD83 | b2c | DAP10 | FcγRIII-γ |
| CD83 | b2c | DAP10 | FcεRIβ |
| CD83 | b2c | DAP10 | FcεRIγ |
| CD83 | b2c | DAP10 | DAP10 |
| CD83 | b2c | DAP10 | DAP12 |
| CD83 | b2c | DAP10 | CD32 |
| CD83 | b2c | DAP10 | CD79a |
| CD83 | b2c | DAP10 | CD79b |
| CD83 | b2c | DAP12 | CD8 |
| CD83 | b2c | DAP12 | CD3ζ |
| CD83 | b2c | DAP12 | CD3δ |
| CD83 | b2c | DAP12 | CD3γ |
| CD83 | b2c | DAP12 | CD3ε |
| CD83 | b2c | DAP12 | FcγRI-γ |
| CD83 | b2c | DAP12 | FcγRIII-γ |
| CD83 | b2c | DAP12 | FcεRIβ |
| CD83 | b2c | DAP12 | FcεRIγ |
| CD83 | b2c | DAP12 | DAP10 |
| CD83 | b2c | DAP12 | DAP12 |
| CD83 | b2c | DAP12 | CD32 |
| CD83 | b2c | DAP12 | CD79a |
| CD83 | b2c | DAP12 | CD79b |
| CD83 | b2c | MyD88 | CD8 |
| CD83 | b2c | MyD88 | CD3ζ |
| CD83 | b2c | MyD88 | CD3δ |
| CD83 | b2c | MyD88 | CD3γ |
| CD83 | b2c | MyD88 | CD3ε |
| CD83 | b2c | MyD88 | FcγRI-γ |
| CD83 | b2c | MyD88 | FcγRIII-γ |
| CD83 | b2c | MyD88 | FcεRIβ |
| CD83 | b2c | MyD88 | FcεRIγ |
| CD83 | b2c | MyD88 | DAP10 |
| CD83 | b2c | MyD88 | DAP12 |
| CD83 | b2c | MyD88 | CD32 |
| CD83 | b2c | MyD88 | CD79a |
| CD83 | b2c | MyD88 | CD79b |
| CD83 | b2c | CD7 | CD8 |
| CD83 | b2c | CD7 | CD3ζ |
| CD83 | b2c | CD7 | CD3δ |
| CD83 | b2c | CD7 | CD3γ |
| CD83 | b2c | CD7 | CD3ε |
| CD83 | b2c | CD7 | FcγRI-γ |
| CD83 | b2c | CD7 | FcγRIII-γ |
| CD83 | b2c | CD7 | FcεRIβ |
| CD83 | b2c | CD7 | FcεRIγ |
| CD83 | b2c | CD7 | DAP10 |
| CD83 | b2c | CD7 | DAP12 |
| CD83 | b2c | CD7 | CD32 |
| CD83 | b2c | CD7 | CD79a |
| CD83 | b2c | CD7 | CD79b |
| CD83 | b2c | BTNL3 | CD8 |
| CD83 | b2c | BTNL3 | CD3ζ |
| CD83 | b2c | BTNL3 | CD3δ |
| CD83 | b2c | BTNL3 | CD3γ |

TABLE 3-continued

Third Generation CARs

| Scfu | Co-stimulatory Signal | Co-stimulatory Signal | Signal Domain |
|---|---|---|---|
| CD83 | b2c | BTNL3 | CD3ε |
| CD83 | b2c | BTNL3 | FcγRI-γ |
| CD83 | b2c | BTNL3 | FcγRIII-γ |
| CD83 | b2c | BTNL3 | FcεRIβ |
| CD83 | b2c | BTNL3 | FcεRIγ |
| CD83 | b2c | BTNL3 | DAP10 |
| CD83 | b2c | BTNL3 | DAP12 |
| CD83 | b2c | BTNL3 | CD32 |
| CD83 | b2c | BTNL3 | CD79a |
| CD83 | b2c | BTNL3 | CD79b |
| CD83 | b2c | NKG2D | CD8 |
| CD83 | b2c | NKG2D | CD3ζ |
| CD83 | b2c | NKG2D | CD3δ |
| CD83 | b2c | NKG2D | CD3γ |
| CD83 | b2c | NKG2D | CD3ε |
| CD83 | b2c | NKG2D | FcγRI-γ |
| CD83 | b2c | NKG2D | FcγRIII-γ |
| CD83 | b2c | NKG2D | FcεRIβ |
| CD83 | b2c | NKG2D | FcεRIγ |
| CD83 | b2c | NKG2D | DAP10 |
| CD83 | b2c | NKG2D | DAP12 |
| CD83 | b2c | NKG2D | CD32 |
| CD83 | b2c | NKG2D | CD79a |
| CD83 | b2c | NKG2D | CD79b |
| CD83 | CD137/41BB | CD28 | CD8 |
| CD83 | CD137/41BB | CD28 | CD3ζ |
| CD83 | CD137/41BB | CD28 | CD3δ |
| CD83 | CD137/41BB | CD28 | CD3γ |
| CD83 | CD137/41BB | CD28 | CD3ε |
| CD83 | CD137/41BB | CD28 | FcγRI-γ |
| CD83 | CD137/41BB | CD28 | FcγRII-γ |
| CD83 | CD137/41BB | CD28 | FcεRIβ |
| CD83 | CD137/41BB | CD28 | FcεRIγ |
| CD83 | CD137/41BB | CD28 | DAP10 |
| CD83 | CD137/41BB | CD28 | DAP12 |
| CD83 | CD137/41BB | CD28 | CD32 |
| CD83 | CD137/41BB | CD28 | CD79a |
| CD83 | CD137/41BB | CD28 | CD79b |
| CD83 | CD137/41BB | CD8 | CD8 |
| CD83 | CD137/41BB | CD8 | CD3ζ |
| CD83 | CD137/41BB | CD8 | CD3δ |
| CD83 | CD137/41BB | CD8 | CD3γ |
| CD83 | CD137/41BB | CD8 | CD3ε |
| CD83 | CD137/41BB | CD8 | FcγRI-γ |
| CD83 | CD137/41BB | CD8 | FcγRIII-γ |
| CD83 | CD137/41BB | CD8 | FcεRIβ |
| CD83 | CD137/41BB | CD8 | FcεRIγ |
| CD83 | CD137/41BB | CD8 | DAP10 |
| CD83 | CD137/41BB | CD8 | DAP12 |
| CD83 | CD137/41BB | CD8 | CD32 |
| CD83 | CD137/41BB | CD8 | CD79a |
| CD83 | CD137/41BB | CD8 | CD79b |
| CD83 | CD137/41BB | CD4 | CD8 |
| CD83 | CD137/41BB | CD4 | CD3ζ |
| CD83 | CD137/41BB | CD4 | CD3δ |
| CD83 | CD137/41BB | CD4 | CD3γ |
| CD83 | CD137/41BB | CD4 | CD3ε |
| CD83 | CD137/41BB | CD4 | FcγRI-γ |
| CD83 | CD137/41BB | CD4 | FcγRII-γ |
| CD83 | CD137/41BB | CD4 | FcεRIβ |
| CD83 | CD137/41BB | CD4 | FcεRIγ |
| CD83 | CD137/41BB | CD4 | DAP10 |
| CD83 | CD137/41BB | CD4 | DAP12 |
| CD83 | CD137/41BB | CD4 | CD32 |
| CD83 | CD137/41BB | CD4 | CD79a |
| CD83 | CD137/41BB | CD4 | CD79b |
| CD83 | CD137/41BB | b2c | CD8 |
| CD83 | CD137/41BB | b2c | CD3ζ |
| CD83 | CD137/41BB | b2c | CD3δ |
| CD83 | CD137/41BB | b2c | CD3γ |
| CD83 | CD137/41BB | b2c | CD3ε |
| CD83 | CD137/41BB | b2c | FcγRI-γ |
| CD83 | CD137/41BB | b2c | FcγRIII-γ |
| CD83 | CD137/41BB | b2c | FcεRIβ |
| CD83 | CD137/41BB | b2c | FcεRIγ |

TABLE 3-continued

Third Generation CARs

| Scfu | Co-stimulatory Signal | Co-stimulatory Signal | Signal Domain |
|---|---|---|---|
| CD83 | CD137/41BB | b2c | DAP10 |
| CD83 | CD137/41BB | b2c | DAP12 |
| CD83 | CD137/41BB | b2c | CD32 |
| CD83 | CD137/41BB | b2c | CD79a |
| CD83 | CD137/41BB | b2c | CD79b |
| CD83 | CD137/41BB | CD137/41BB | CD8 |
| CD83 | CD137/41BB | CD137/41BB | CD3ζ |
| CD83 | CD137/41BB | CD137/41BB | CD3δ |
| CD83 | CD137/41BB | CD137/41BB | CD3γ |
| CD83 | CD137/41BB | CD137/41BB | CD3ε |
| CD83 | CD137/41BB | CD137/41BB | FcγRI-γ |
| CD83 | CD137/41BB | CD137/41BB | FcγRIII-γ |
| CD83 | CD137/41BB | CD137/41BB | FcεRIβ |
| CD83 | CD137/41BB | CD137/41BB | FcεRIγ |
| CD83 | CD137/41BB | CD137/41BB | DAP10 |
| CD83 | CD137/41BB | CD137/41BB | DAP12 |
| CD83 | CD137/41BB | CD137/41BB | CD32 |
| CD83 | CD137/41BB | CD137/41BB | CD79a |
| CD83 | CD137/41BB | CD137/41BB | CD79b |
| CD83 | CD137/41BB | ICOS | CD8 |
| CD83 | CD137/41BB | ICOS | CD3ζ |
| CD83 | CD137/41BB | ICOS | CD3δ |
| CD83 | CD137/41BB | ICOS | CD3γ |
| CD83 | CD137/41BB | ICOS | CD3ε |
| CD83 | CD137/41BB | ICOS | FcγRI-γ |
| CD83 | CD137/41BB | ICOS | FcγRIII-γ |
| CD83 | CD137/41BB | ICOS | FcεRI-β |
| CD83 | CD137/41BB | ICOS | FcεRIγ |
| CD83 | CD137/41BB | ICOS | DAP10 |
| CD83 | CD137/41BB | ICOS | DAP12 |
| CD83 | CD137/41BB | ICOS | CD32 |
| CD83 | CD137/41BB | ICOS | CD79a |
| CD83 | CD137/41BB | ICOS | CD79b |
| CD83 | CD137/41BB | CD27 | CD8 |
| CD83 | CD137/41BB | CD27 | CD3ζ |
| CD83 | CD137/41BB | CD27 | CD3δ |
| CD83 | CD137/41BB | CD27 | CD3γ |
| CD83 | CD137/41BB | CD27 | CD3ε |
| CD83 | CD137/41BB | CD27 | FcγRI-γ |
| CD83 | CD137/41BB | CD27 | FcγRIII-γ |
| CD83 | CD137/41BB | CD27 | FcεRIβ |
| CD83 | CD137/41BB | CD27 | FcεRIγ |
| CD83 | CD137/41BB | CD27 | DAP10 |
| CD83 | CD137/41BB | CD27 | DAP12 |
| CD83 | CD137/41BB | CD27 | CD32 |
| CD83 | CD137/41BB | CD27 | CD79a |
| CD83 | CD137/41BB | CD27 | CD79b |
| CD83 | CD137/41BB | CD28δ | CD8 |
| CD83 | CD137/41BB | CD28δ | CD3ζ |
| CD83 | CD137/41BB | CD28δ | CD3δ |
| CD83 | CD137/41BB | CD28δ | CD3γ |
| CD83 | CD137/41BB | CD28δ | CD3ε |
| CD83 | CD137/41BB | CD28δ | FcγRI-γ |
| CD83 | CD137/41BB | CD28δ | FcγRIII-γ |
| CD83 | CD137/41BB | CD28δ | FcεRI-β |
| CD83 | CD137/41BB | CD28δ | FcεRIγ |
| CD83 | CD137/41BB | CD28δ | DAP10 |
| CD83 | CD137/41BB | CD28δ | DAP12 |
| CD83 | CD137/41BB | CD28δ | CD32 |
| CD83 | CD137/41BB | CD28δ | CD79a |
| CD83 | CD137/41BB | CD28δ | CD79b |
| CD83 | CD137/41BB | CD80 | CD8 |
| CD83 | CD137/41BB | CD80 | CD3ζ |
| CD83 | CD137/41BB | CD80 | CD3δ |
| CD83 | CD137/41BB | CD80 | CD3γ |
| CD83 | CD137/41BB | CD80 | CD3ε |
| CD83 | CD137/41BB | CD80 | FcγRI-γ |
| CD83 | CD137/41BB | CD80 | FcγRIII-γ |
| CD83 | CD137/41BB | CD80 | FcεRIβ |
| CD83 | CD137/41BB | CD80 | FcεRIγ |
| CD83 | CD137/41BB | CD80 | DAP10 |
| CD83 | CD137/41BB | CD80 | DAP12 |
| CD83 | CD137/41BB | CD80 | CD32 |
| CD83 | CD137/41BB | CD80 | CD79a |
| CD83 | CD137/41BB | CD80 | CD79b |

TABLE 3-continued

| Third Generation CARs | | | |
|---|---|---|---|
| Scfu | Co-stimulatory Signal | Co-stimulatory Signal | Signal Domain |
| CD83 | CD137/41BB | CD86 | CD8 |
| CD83 | CD137/41BB | CD86 | CD3ζ |
| CD83 | CD137/41BB | CD86 | CD3δ |
| CD83 | CD137/41BB | CD86 | CD3γ |
| CD83 | CD137/41BB | CD86 | CD3ε |
| CD83 | CD137/41BB | CD86 | FcγRI-γ |
| CD83 | CD137/41BB | CD86 | FcγRIII-γ |
| CD83 | CD137/41BB | CD86 | FcεRI-β |
| CD83 | CD137/41BB | CD86 | FcεRIγ |
| CD83 | CD137/41BB | CD86 | DAP10 |
| CD83 | CD137/41BB | CD86 | DAP12 |
| CD83 | CD137/41BB | CD86 | CD32 |
| CD83 | CD137/41BB | CD86 | CD79a |
| CD83 | CD137/41BB | CD86 | CD79b |
| CD83 | CD137/41BB | OX40 | CD8 |
| CD83 | CD137/41BB | OX40 | CD3ζ |
| CD83 | CD137/41BB | OX40 | CD3δ |
| CD83 | CD137/41BB | OX40 | CD3γ |
| CD83 | CD137/41BB | OX40 | CD3ε |
| CD83 | CD137/41BB | OX40 | FcγRI-γ |
| CD83 | CD137/41BB | OX40 | FcγRIII-γ |
| CD83 | CD137/41BB | OX40 | FcεRIβ |
| CD83 | CD137/41BB | OX40 | FcεRIγ |
| CD83 | CD137/41BB | OX40 | DAP10 |
| CD83 | CD137/41BB | OX40 | DAP12 |
| CD83 | CD137/41BB | OX40 | CD32 |
| CD83 | CD137/41BB | OX40 | CD79a |
| CD83 | CD137/41BB | OX40 | CD79b |
| CD83 | CD137/41BB | DAP10 | CD8 |
| CD83 | CD137/41BB | DAP10 | CD3ζ |
| CD83 | CD137/41BB | DAP10 | CD3δ |
| CD83 | CD137/41BB | DAP10 | CD3γ |
| CD83 | CD137/41BB | DAP10 | CD3ε |
| CD83 | CD137/41BB | DAP10 | FcγRI-γ |
| CD83 | CD137/41BB | DAP10 | FcγRIII-γ |
| CD83 | CD137/41BB | DAP10 | FcεRIβ |
| CD83 | CD137/41BB | DAP10 | FcεRIγ |
| CD83 | CD137/41BB | DAP10 | DAP10 |
| CD83 | CD137/41BB | DAP10 | DAP12 |
| CD83 | CD137/41BB | DAP10 | CD32 |
| CD83 | CD137/41BB | DAP10 | CD79a |
| CD83 | CD137/41BB | DAP10 | CD79b |
| CD83 | CD137/41BB | DAP12 | CD8 |
| CD83 | CD137/41BB | DAP12 | CD3ζ |
| CD83 | CD137/41BB | DAP12 | CD3δ |
| CD83 | CD137/41BB | DAP12 | CD3γ |
| CD83 | CD137/41BB | DAP12 | CD3ε |
| CD83 | CD137/41BB | DAP12 | FcγRI-γ |
| CD83 | CD137/41BB | DAP12 | FcγRIII-γ |
| CD83 | CD137/41BB | DAP12 | FcεRIβ |
| CD83 | CD137/41BB | DAP12 | FcεRIγ |
| CD83 | CD137/41BB | DAP12 | DAP10 |
| CD83 | CD137/41BB | DAP12 | DAP12 |
| CD83 | CD137/41BB | DAP12 | CD32 |
| CD83 | CD137/41BB | DAP12 | CD79a |
| CD83 | CD137/41BB | DAP12 | CD79b |
| CD83 | CD137/41BB | MyD88 | CD8 |
| CD83 | CD137/41BB | MyD88 | CD3ζ |
| CD83 | CD137/41BB | MyD88 | CD3δ |
| CD83 | CD137/41BB | MyD88 | CD3γ |
| CD83 | CD137/41BB | MyD88 | CD3ε |
| CD83 | CD137/41BB | MyD88 | FcγRI-γ |
| CD83 | CD137/41BB | MyD88 | FcγRIII-γ |
| CD83 | CD137/41BB | MyD88 | FcεRIε |
| CD83 | CD137/41BB | MyD88 | FcεRIγ |
| CD83 | CD137/41BB | MyD88 | DAP10 |
| CD83 | CD137/41BB | MyD88 | DAP12 |
| CD83 | CD137/41BB | MyD88 | CD32 |
| CD83 | CD137/41BB | MyD88 | CD79a |
| CD83 | CD137/41BB | MyD88 | CD79b |
| CD83 | CD137/41BB | CD7 | CD8 |
| CD83 | CD137/41BB | CD7 | CD3ζ |
| CD83 | CD137/41BB | CD7 | CD3δ |
| CD83 | CD137/41BB | CD7 | CD3γ |
| CD83 | CD137/41BB | CD7 | CD3ε |
| CD83 | CD137/41BB | CD7 | FcγRI-γ |
| CD83 | CD137/41BB | CD7 | FcγRIII-γ |
| CD83 | CD137/41BB | CD7 | FcεRIβ |
| CD83 | CD137/41BB | CD7 | FcεRIγ |
| CD83 | CD137/41BB | CD7 | DAP10 |
| CD83 | CD137/41BB | CD7 | DAP12 |
| CD83 | CD137/41BB | CD7 | CD32 |
| CD83 | CD137/41BB | CD7 | CD79a |
| CD83 | CD137/41BB | CD7 | CD79b |
| CD83 | CD137/41BB | BTNL3 | CD8 |
| CD83 | CD137/41BB | BTNL3 | CD3ζ |
| CD83 | CD137/41BB | BTNL3 | CD3δ |
| CD83 | CD137/41BB | BTNL3 | CD3γ |
| CD83 | CD137/41BB | BTNL3 | CD3ε |
| CD83 | CD137/41BB | BTNL3 | FcγRI-γ |
| CD83 | CD137/41BB | BTNL3 | FcγRIII-γ |
| CD83 | CD137/41BB | BTNL3 | FcεRIβ |
| CD83 | CD137/41BB | BTNL3 | FcεRIγ |
| CD83 | CD137/41BB | BTNL3 | DAP10 |
| CD83 | CD137/41BB | BTNL3 | DAP12 |
| CD83 | CD137/41BB | BTNL3 | CD32 |
| CD83 | CD137/41BB | BTNL3 | CD79a |
| CD83 | CD137/41BB | BTNL3 | CD79b |
| CD83 | CD137/41BB | NKG2D | CD8 |
| CD83 | CD137/41BB | NKG2D | CD3ζ |
| CD83 | CD137/41BB | NKG2D | CD3δ |
| CD83 | CD137/41BB | NKG2D | CD3γ |
| CD83 | CD137/41BB | NKG2D | CD3ε |
| CD83 | CD137/41BB | NKG2D | FcγRI-γ |
| CD83 | CD137/41BB | NKG2D | FcγRIII-γ |
| CD83 | CD137/41BB | NKG2D | FcεRIβ |
| CD83 | CD137/41BB | NKG2D | FcεRIγ |
| CD83 | CD137/41BB | NKG2D | DAP10 |
| CD83 | CD137/41BB | NKG2D | DAP12 |
| CD83 | CD137/41BB | NKG2D | CD32 |
| CD83 | CD137/41BB | NKG2D | CD79a |
| CD83 | CD137/41BB | NKG2D | CD79b |
| CD83 | ICOS | CD28 | CD8 |
| CD83 | ICOS | CD28 | CD3ζ |
| CD83 | ICOS | CD28 | CD3δ |
| CD83 | ICOS | CD28 | CD3γ |
| CD83 | ICOS | CD28 | CD3ε |
| CD83 | ICOS | CD28 | FcγRI-y |
| CD83 | ICOS | CD28 | FcγRIII-γ |
| CD83 | ICOS | CD28 | FcεRIβ |
| CD83 | ICOS | CD28 | FcεRIγ |
| CD83 | ICOS | CD28 | DAP10 |
| CD83 | ICOS | CD28 | DAP12 |
| CD83 | ICOS | CD28 | CD32 |
| CD83 | ICOS | CD28 | CD79a |
| CD83 | ICOS | CD28 | CD79b |
| CD83 | ICOS | CD8 | CD8 |
| CD83 | ICOS | CD8 | CD3ζ |
| CD83 | ICOS | CD8 | CD3δ |
| CD83 | ICOS | CD8 | CD3γ |
| CD83 | ICOS | CD8 | CD3ε |
| CD83 | ICOS | CD8 | FcγRI-γ |
| CD83 | ICOS | CD8 | FcγRIII-γ |
| CD83 | ICOS | CD8 | FcεRIβ |
| CD83 | ICOS | CD8 | FcεRIγ |
| CD83 | ICOS | CD8 | DAP10 |
| CD83 | ICOS | CD8 | DAP12 |
| CD83 | ICOS | CD8 | CD32 |
| CD83 | ICOS | CD8 | CD79a |
| CD83 | ICOS | CD8 | CD79b |
| CD83 | ICOS | CD4 | CD8 |
| CD83 | ICOS | CD4 | CD3ζ |
| CD83 | ICOS | CD4 | CD3δ |
| CD83 | ICOS | CD4 | CD3γ |
| CD83 | ICOS | CD4 | CD3ε |
| CD83 | ICOS | CD4 | FcγRI-γ |
| CD83 | ICOS | CD4 | FcγRIII-γ |
| CD83 | ICOS | CD4 | FcεRIβ |
| CD83 | ICOS | CD4 | FcεRIγ |
| CD83 | ICOS | CD4 | DAP10 |

TABLE 3-continued

| Third Generation CARs | | | |
|---|---|---|---|
| Scfu | Co-stimulatory Signal | Co-stimulatory Signal | Signal Domain |
| CD83 | ICOS | CD4 | DAP12 |
| CD83 | ICOS | CD4 | CD32 |
| CD83 | ICOS | CD4 | CD79a |
| CD83 | ICOS | CD4 | CD79b |
| CD83 | ICOS | b2c | CD8 |
| CD83 | ICOS | b2c | CD3ζ |
| CD83 | ICOS | b2c | CD3δ |
| CD83 | ICOS | b2c | CD3γ |
| CD83 | ICOS | b2c | CD3ε |
| CD83 | ICOS | b2c | FcγRI-γ |
| CD83 | ICOS | b2c | FcγRIII-γ |
| CD83 | ICOS | b2c | FcεRIβ |
| CD83 | ICOS | b2c | FcεRIγ |
| CD83 | ICOS | b2c | DAP10 |
| CD83 | ICOS | b2c | DAP12 |
| CD83 | ICOS | b2c | CD32 |
| CD83 | ICOS | b2c | CD79a |
| CD83 | ICOS | b2c | CD79b |
| CD83 | ICOS | CD137/41BB | CD8 |
| CD83 | ICOS | CD137/41BB | CD3ζ |
| CD83 | ICOS | CD137/41BB | CD3δ |
| CD83 | ICOS | CD137/41BB | CD3γ |
| CD83 | ICOS | CD137/41BB | CD3ε |
| CD83 | ICOS | CD137/41BB | FcγRI-γ |
| CD83 | ICOS | CD137/41BB | FcγRIII-γ |
| CD83 | ICOS | CD137/41BB | FcεRIβ |
| CD83 | ICOS | CD137/41BB | FcεRIγ |
| CD83 | ICOS | CD137/41BB | DAP10 |
| CD83 | ICOS | CD137/41BB | DAP12 |
| CD83 | ICOS | CD137/41BB | CD32 |
| CD83 | ICOS | CD137/41BB | CD79a |
| CD83 | ICOS | CD137/41BB | CD79b |
| CD83 | ICOS | ICOS | CD8 |
| CD83 | ICOS | ICOS | CD3ζ |
| CD83 | ICOS | ICOS | CD3δ |
| CD83 | ICOS | ICOS | CD3γ |
| CD83 | ICOS | ICOS | CD3ε |
| CD83 | ICOS | ICOS | FcγRI-γ |
| CD83 | ICOS | ICOS | FcγRIII-γ |
| CD83 | ICOS | ICOS | FcεRIβ |
| CD83 | ICOS | ICOS | FcεRIγ |
| CD83 | ICOS | ICOS | DAP10 |
| CD83 | ICOS | ICOS | DAP12 |
| CD83 | ICOS | ICOS | CD32 |
| CD83 | ICOS | ICOS | CD79a |
| CD83 | ICOS | ICOS | CD79b |
| CD83 | ICOS | CD27 | CD8 |
| CD83 | ICOS | CD27 | CD3ζ |
| CD83 | ICOS | CD27 | CD3δ |
| CD83 | ICOS | CD27 | CD3γ |
| CD83 | ICOS | CD27 | CD3ε |
| CD83 | ICOS | CD27 | FcγRI-γ |
| CD83 | ICOS | CD27 | FcγRIII-γ |
| CD83 | ICOS | CD27 | FcεRIβ |
| CD83 | ICOS | CD27 | FcεRIγ |
| CD83 | ICOS | CD27 | DAP10 |
| CD83 | ICOS | CD27 | DAP12 |
| CD83 | ICOS | CD27 | CD32 |
| CD83 | ICOS | CD27 | CD79a |
| CD83 | ICOS | CD27 | CD79b |
| CD83 | ICOS | CD28δ | CD8 |
| CD83 | ICOS | CD28δ | CD3ζ |
| CD83 | ICOS | CD28δ | CD3δ |
| CD83 | ICOS | CD28δ | CD3γ |
| CD83 | ICOS | CD28δ | CD3ε |
| CD83 | ICOS | CD28δ | FcγRI-γ |
| CD83 | ICOS | CD28δ | FcγRIII-γ |
| CD83 | ICOS | CD28δ | FcεRIβ |
| CD83 | ICOS | CD28δ | FcεRIγ |
| CD83 | ICOS | CD28δ | DAP10 |
| CD83 | ICOS | CD28δ | DAP12 |
| CD83 | ICOS | CD28δ | CD32 |
| CD83 | ICOS | CD28δ | CD79a |
| CD83 | ICOS | CD28δ | CD79b |
| CD83 | ICOS | CD80 | CD8 |

TABLE 3-continued

| Third Generation CARs | | | |
|---|---|---|---|
| Scfu | Co-stimulatory Signal | Co-stimulatory Signal | Signal Domain |
| CD83 | ICOS | CD80 | CD3ζ |
| CD83 | ICOS | CD80 | CD3δ |
| CD83 | ICOS | CD80 | CD3γ |
| CD83 | ICOS | CD80 | CD3ε |
| CD83 | ICOS | CD80 | FcγRI-γ |
| CD83 | ICOS | CD80 | FcγRIII-γ |
| CD83 | ICOS | CD80 | FcεRIβ |
| CD83 | ICOS | CD80 | FcεRIγ |
| CD83 | ICOS | CD80 | DAP10 |
| CD83 | ICOS | CD80 | DAP12 |
| CD83 | ICOS | CD80 | CD32 |
| CD83 | ICOS | CD80 | CD79a |
| CD83 | ICOS | CD80 | CD79b |
| CD83 | ICOS | CD86 | CD8 |
| CD83 | ICOS | CD86 | CD3ζ |
| CD83 | ICOS | CD86 | CD3δ |
| CD83 | ICOS | CD86 | CD3γ |
| CD83 | ICOS | CD86 | CD3ε |
| CD83 | ICOS | CD86 | FcγRI-γ |
| CD83 | ICOS | CD86 | FcγRIII-γ |
| CD83 | ICOS | CD86 | FcεRIβ |
| CD83 | ICOS | CD86 | FcεRIγ |
| CD83 | ICOS | CD86 | DAP10 |
| CD83 | ICOS | CD86 | DAP12 |
| CD83 | ICOS | CD86 | CD32 |
| CD83 | ICOS | CD86 | CD79a |
| CD83 | ICOS | CD86 | CD79b |
| CD83 | ICOS | OX40 | CD8 |
| CD83 | ICOS | OX40 | CD3ζ |
| CD83 | ICOS | OX40 | CD3δ |
| CD83 | ICOS | OX40 | CD3γ |
| CD83 | ICOS | OX40 | CD3ε |
| CD83 | ICOS | OX40 | FcγRI-γ |
| CD83 | ICOS | OX40 | FcγRIII-γ |
| CD83 | ICOS | OX40 | FcεRIβ |
| CD83 | ICOS | OX40 | FcεRIγ |
| CD83 | ICOS | OX40 | DAP10 |
| CD83 | ICOS | OX40 | DAP12 |
| CD83 | ICOS | OX40 | CD32 |
| CD83 | ICOS | OX40 | CD79a |
| CD83 | ICOS | OX40 | CD79b |
| CD83 | ICOS | DAP10 | CD8 |
| CD83 | ICOS | DAP10 | CD3ζ |
| CD83 | ICOS | DAP10 | CD3δ |
| CD83 | ICOS | DAP10 | CD3γ |
| CD83 | ICOS | DAP10 | CD3ε |
| CD83 | ICOS | DAP10 | FcγRI-γ |
| CD83 | ICOS | DAP10 | FcγRIII-γ |
| CD83 | ICOS | DAP10 | FcεRIβ |
| CD83 | ICOS | DAP10 | FcεRIγ |
| CD83 | ICOS | DAP10 | DAP10 |
| CD83 | ICOS | DAP10 | DAP12 |
| CD83 | ICOS | DAP10 | CD32 |
| CD83 | ICOS | DAP10 | CD79a |
| CD83 | ICOS | DAP10 | CD79b |
| CD83 | ICOS | DAP12 | CD8 |
| CD83 | ICOS | DAP12 | CD3ζ |
| CD83 | ICOS | DAP12 | CD3δ |
| CD83 | ICOS | DAP12 | CD3γ |
| CD83 | ICOS | DAP12 | CD3ε |
| CD83 | ICOS | DAP12 | FcγRI-γ |
| CD83 | ICOS | DAP12 | FcγRIII-γ |
| CD83 | ICOS | DAP12 | FcεRIβ |
| CD83 | ICOS | DAP12 | FcεRIγ |
| CD83 | ICOS | DAP12 | DAP10 |
| CD83 | ICOS | DAP12 | DAP12 |
| CD83 | ICOS | DAP12 | CD32 |
| CD83 | ICOS | DAP12 | CD79a |
| CD83 | ICOS | DAP12 | CD79b |
| CD83 | ICOS | MyD88 | CD8 |
| CD83 | ICOS | MyD88 | CD3ζ |
| CD83 | ICOS | MyD88 | CD3δ |
| CD83 | ICOS | MyD88 | CD3γ |
| CD83 | ICOS | MyD88 | CD3ε |
| CD83 | ICOS | MyD88 | FcγRI-γ |

TABLE 3-continued

Third Generation CARs

| Scfu | Co-stimulatory Signal | Co-stimulatory Signal | Signal Domain |
|---|---|---|---|
| CD83 | ICOS | MyD88 | FcγRIII-γ |
| CD83 | ICOS | MyD88 | FcεRIβ |
| CD83 | ICOS | MyD88 | FcεRIγ |
| CD83 | ICOS | MyD88 | DAP10 |
| CD83 | ICOS | MyD88 | DAP12 |
| CD83 | ICOS | MyD88 | CD32 |
| CD83 | ICOS | MyD88 | CD79a |
| CD83 | ICOS | MyD88 | CD79b |
| CD83 | ICOS | CD7 | CD8 |
| CD83 | ICOS | CD7 | CD3ζ |
| CD83 | ICOS | CD7 | CD3δ |
| CD83 | ICOS | CD7 | CD3γ |
| CD83 | ICOS | CD7 | CD3ε |
| CD83 | ICOS | CD7 | FcγRI-γ |
| CD83 | ICOS | CD7 | FcγRIII-γ |
| CD83 | ICOS | CD7 | FcεRIβ |
| CD83 | ICOS | CD7 | FcεRIγ |
| CD83 | ICOS | CD7 | DAP10 |
| CD83 | ICOS | CD7 | DAP12 |
| CD83 | ICOS | CD7 | CD32 |
| CD83 | ICOS | CD7 | CD79a |
| CD83 | ICOS | CD7 | CD79b |
| CD83 | ICOS | BTNL3 | CD8 |
| CD83 | ICOS | BTNL3 | CD3ζ |
| CD83 | ICOS | BTNL3 | CD3δ |
| CD83 | ICOS | BTNL3 | CD3γ |
| CD83 | ICOS | BTNL3 | CD3ε |
| CD83 | ICOS | BTNL3 | FcγRI-γ |
| CD83 | ICOS | BTNL3 | FcγRIII-γ |
| CD83 | ICOS | BTNL3 | FcεRIβ |
| CD83 | ICOS | BTNL3 | FcεRIγ |
| CD83 | ICOS | BTNL3 | DAP10 |
| CD83 | ICOS | BTNL3 | DAP12 |
| CD83 | ICOS | BTNL3 | CD32 |
| CD83 | ICOS | BTNL3 | CD79a |
| CD83 | ICOS | BTNL3 | CD79b |
| CD83 | ICOS | NKG2D | CD8 |
| CD83 | ICOS | NKG2D | CD3ζ |
| CD83 | ICOS | NKG2D | CD3δ |
| CD83 | ICOS | NKG2D | CD3γ |
| CD83 | ICOS | NKG2D | CD3ε |
| CD83 | ICOS | NKG2D | FcγRI-γ |
| CD83 | ICOS | NKG2D | FcγRIII-γ |
| CD83 | ICOS | NKG2D | FcεRIβ |
| CD83 | ICOS | NKG2D | FcεRIγ |
| CD83 | ICOS | NKG2D | DAP10 |
| CD83 | ICOS | NKG2D | DAP12 |
| CD83 | ICOS | NKG2D | CD32 |
| CD83 | ICOS | NKG2D | CD79a |
| CD83 | ICOS | NKG2D | CD79b |
| CD83 | CD27 | CD28 | CD8 |
| CD83 | CD27 | CD28 | CD3ζ |
| CD83 | CD27 | CD28 | CD3δ |
| CD83 | CD27 | CD28 | CD3γ |
| CD83 | CD27 | CD28 | CD3ε |
| CD83 | CD27 | CD28 | FcγRI-γ |
| CD83 | CD27 | CD28 | FcγRIII-γ |
| CD83 | CD27 | CD28 | FcεRIβ |
| CD83 | CD27 | CD28 | FcεRIγ |
| CD83 | CD27 | CD28 | DAP10 |
| CD83 | CD27 | CD28 | DAP12 |
| CD83 | CD27 | CD28 | CD32 |
| CD83 | CD27 | CD28 | CD79a |
| CD83 | CD27 | CD28 | CD79b |
| CD83 | CD27 | CD8 | CD8 |
| CD83 | CD27 | CD8 | CD3ζ |
| CD83 | CD27 | CD8 | CD3δ |
| CD83 | CD27 | CD8 | CD3γ |
| CD83 | CD27 | CD8 | CD3ε |
| CD83 | CD27 | CD8 | FcγRI-γ |
| CD83 | CD27 | CD8 | FcγRIII-γ |
| CD83 | CD27 | CD8 | FcεRIβ |
| CD83 | CD27 | CD8 | FcεRIγ |
| CD83 | CD27 | CD8 | DAP10 |
| CD83 | CD27 | CD8 | DAP12 |

TABLE 3-continued

Third Generation CARs

| Scfu | Co-stimulatory Signal | Co-stimulatory Signal | Signal Domain |
|---|---|---|---|
| CD83 | CD27 | CD8 | CD32 |
| CD83 | CD27 | CD8 | CD79a |
| CD83 | CD27 | CD8 | CD79b |
| CD83 | CD27 | CD4 | CD8 |
| CD83 | CD27 | CD4 | CD3ζ |
| CD83 | CD27 | CD4 | CD3δ |
| CD83 | CD27 | CD4 | CD3γ |
| CD83 | CD27 | CD4 | CD3ε |
| CD83 | CD27 | CD4 | FcγRI-γ |
| CD83 | CD27 | CD4 | FcγRIII-γ |
| CD83 | CD27 | CD4 | FcεRIβ |
| CD83 | CD27 | CD4 | FcεRIγ |
| CD83 | CD27 | CD4 | DAP10 |
| CD83 | CD27 | CD4 | DAP12 |
| CD83 | CD27 | CD4 | CD32 |
| CD83 | CD27 | CD4 | CD79a |
| CD83 | CD27 | CD4 | CD79b |
| CD83 | CD27 | b2c | CD8 |
| CD83 | CD27 | b2c | CD3ζ |
| CD83 | CD27 | b2c | CD3δ |
| CD83 | CD27 | b2c | CD3γ |
| CD83 | CD27 | b2c | CD3ε |
| CD83 | CD27 | b2c | FcγRI-γ |
| CD83 | CD27 | b2c | FcγRIII-γ |
| CD83 | CD27 | b2c | FcεRIβ |
| CD83 | CD27 | b2c | FcεRIγ |
| CD83 | CD27 | b2c | DAP10 |
| CD83 | CD27 | b2c | DAP12 |
| CD83 | CD27 | b2c | CD32 |
| CD83 | CD27 | b2c | CD79a |
| CD83 | CD27 | b2c | CD79b |
| CD83 | CD27 | CD137/41BB | CD8 |
| CD83 | CD27 | CD137/41BB | CD3ζ |
| CD83 | CD27 | CD137/41BB | CD3δ |
| CD83 | CD27 | CD137/41BB | CD3γ |
| CD83 | CD27 | CD137/41BB | CD3ε |
| CD83 | CD27 | CD137/41BB | FcγRI-γ |
| CD83 | CD27 | CD137/41BB | FcγRIII-γ |
| CD83 | CD27 | CD137/41BB | FcεRIβ |
| CD83 | CD27 | CD137/41BB | FcεRIγ |
| CD83 | CD27 | CD137/41BB | DAP10 |
| CD83 | CD27 | CD137/41BB | DAP12 |
| CD83 | CD27 | CD137/41BB | CD32 |
| CD83 | CD27 | CD137/41BB | CD79a |
| CD83 | CD27 | CD137/41BB | CD79b |
| CD83 | CD27 | ICOS | CD8 |
| CD83 | CD27 | ICOS | CD3ζ |
| CD83 | CD27 | ICOS | CD3δ |
| CD83 | CD27 | ICOS | CD3γ |
| CD83 | CD27 | ICOS | CD3ε |
| CD83 | CD27 | ICOS | FcγRI-γ |
| CD83 | CD27 | ICOS | FcγRIII-γ |
| CD83 | CD27 | ICOS | FcεRIβ |
| CD83 | CD27 | ICOS | FcεRIγ |
| CD83 | CD27 | ICOS | DAP10 |
| CD83 | CD27 | ICOS | DAP12 |
| CD83 | CD27 | ICOS | CD32 |
| CD83 | CD27 | ICOS | CD79a |
| CD83 | CD27 | ICOS | CD79b |
| CD83 | CD27 | CD27 | CD8 |
| CD83 | CD27 | CD27 | CD3ζ |
| CD83 | CD27 | CD27 | CD3δ |
| CD83 | CD27 | CD27 | CD3γ |
| CD83 | CD27 | CD27 | CD3ε |
| CD83 | CD27 | CD27 | FcγRI-γ |
| CD83 | CD27 | CD27 | FcγRIII-γ |
| CD83 | CD27 | CD27 | FcεRIβ |
| CD83 | CD27 | CD27 | FcεRIγ |
| CD83 | CD27 | CD27 | DAP10 |
| CD83 | CD27 | CD27 | DAP12 |
| CD83 | CD27 | CD27 | CD32 |
| CD83 | CD27 | CD27 | CD79a |
| CD83 | CD27 | CD27 | CD79b |
| CD83 | CD27 | CD28δ | CD8 |
| CD83 | CD27 | CD28δ | CD3ζ |

TABLE 3-continued

| Third Generation CARs | | | |
|---|---|---|---|
| Scfu | Co-stimulatory Signal | Co-stimulatory Signal | Signal Domain |
| CD83 | CD27 | CD28δ | CD3δ |
| CD83 | CD27 | CD28δ | CD3γ |
| CD83 | CD27 | CD28δ | CD3ε |
| CD83 | CD27 | CD28δ | FcγRI-γ |
| CD83 | CD27 | CD28δ | FcγRIII-γ |
| CD83 | CD27 | CD28δ | FcεRIβ |
| CD83 | CD27 | CD28δ | FcεRIγ |
| CD83 | CD27 | CD28δ | DAP10 |
| CD83 | CD27 | CD28δ | DAP12 |
| CD83 | CD27 | CD28δ | CD32 |
| CD83 | CD27 | CD28δ | CD79a |
| CD83 | CD27 | CD28δ | CD79b |
| CD83 | CD27 | CD80 | CD8 |
| CD83 | CD27 | CD80 | CD3ζ |
| CD83 | CD27 | CD80 | CD3δ |
| CD83 | CD27 | CD80 | CD3γ |
| CD83 | CD27 | CD80 | CD3ε |
| CD83 | CD27 | CD80 | FcγRI-γ |
| CD83 | CD27 | CD80 | FcγRIII-γ |
| CD83 | CD27 | CD80 | FcεRIβ |
| CD83 | CD27 | CD80 | FcεRIγ |
| CD83 | CD27 | CD80 | DAP10 |
| CD83 | CD27 | CD80 | DAP12 |
| CD83 | CD27 | CD80 | CD32 |
| CD83 | CD27 | CD80 | CD79a |
| CD83 | CD27 | CD80 | CD79b |
| CD83 | CD27 | CD86 | CD8 |
| CD83 | CD27 | CD86 | CD3ζ |
| CD83 | CD27 | CD86 | CD3δ |
| CD83 | CD27 | CD86 | CD3γ |
| CD83 | CD27 | CD86 | CD3ε |
| CD83 | CD27 | CD86 | FcγRI-γ |
| CD83 | CD27 | CD86 | FcγRIII-γ |
| CD83 | CD27 | CD86 | FcεRIβ |
| CD83 | CD27 | CD86 | FcεRIγ |
| CD83 | CD27 | CD86 | DAP10 |
| CD83 | CD27 | CD86 | DAP12 |
| CD83 | CD27 | CD86 | CD32 |
| CD83 | CD27 | CD86 | CD79a |
| CD83 | CD27 | CD86 | CD79b |
| CD83 | CD27 | OX40 | CD8 |
| CD83 | CD27 | OX40 | CD3ζ |
| CD83 | CD27 | OX40 | CD3δ |
| CD83 | CD27 | OX40 | CD3γ |
| CD83 | CD27 | OX40 | CD3ε |
| CD83 | CD27 | OX40 | FcγRI-γ |
| CD83 | CD27 | OX40 | FcγRIII-γ |
| CD83 | CD27 | OX40 | FcεRIβ |
| CD83 | CD27 | OX40 | FcεRIγ |
| CD83 | CD27 | OX40 | DAP10 |
| CD83 | CD27 | OX40 | DAP12 |
| CD83 | CD27 | OX40 | CD32 |
| CD83 | CD27 | OX40 | CD79a |
| CD83 | CD27 | OX40 | CD79b |
| CD83 | CD27 | DAP10 | CD8 |
| CD83 | CD27 | DAP10 | CD3ζ |
| CD83 | CD27 | DAP10 | CD3δ |
| CD83 | CD27 | DAP10 | CD3γ |
| CD83 | CD27 | DAP10 | CD3ε |
| CD83 | CD27 | DAP10 | FcγRI-γ |
| CD83 | CD27 | DAP10 | FcγRIII-γ |
| CD83 | CD27 | DAP10 | FcεRIβ |
| CD83 | CD27 | DAP10 | FcεRIγ |
| CD83 | CD27 | DAP10 | DAP10 |
| CD83 | CD27 | DAP10 | DAP12 |
| CD83 | CD27 | DAP10 | CD32 |
| CD83 | CD27 | DAP10 | CD79a |
| CD83 | CD27 | DAP10 | CD79b |
| CD83 | CD27 | DAP12 | CD8 |
| CD83 | CD27 | DAP12 | CD3ζ |
| CD83 | CD27 | DAP12 | CD3δ |
| CD83 | CD27 | DAP12 | CD3γ |
| CD83 | CD27 | DAP12 | CD3ε |
| CD83 | CD27 | DAP12 | FcγRI-γ |
| CD83 | CD27 | DAP12 | FcγRIII-γ |

TABLE 3-continued

| Third Generation CARs | | | |
|---|---|---|---|
| Scfu | Co-stimulatory Signal | Co-stimulatory Signal | Signal Domain |
| CD83 | CD27 | DAP12 | FcεRIβ |
| CD83 | CD27 | DAP12 | FcεRIγ |
| CD83 | CD27 | DAP12 | DAP10 |
| CD83 | CD27 | DAP12 | DAP12 |
| CD83 | CD27 | DAP12 | CD32 |
| CD83 | CD27 | DAP12 | CD79a |
| CD83 | CD27 | DAP12 | CD79b |
| CD83 | CD27 | MyD88 | CD8 |
| CD83 | CD27 | MyD88 | CD3ζ |
| CD83 | CD27 | MyD88 | CD3δ |
| CD83 | CD27 | MyD88 | CD3γ |
| CD83 | CD27 | MyD88 | CD3ε |
| CD83 | CD27 | MyD88 | FcγRI-γ |
| CD83 | CD27 | MyD88 | FcγRIII-γ |
| CD83 | CD27 | MyD88 | FcεRIβ |
| CD83 | CD27 | MyD88 | FcεRIγ |
| CD83 | CD27 | MyD88 | DAP10 |
| CD83 | CD27 | MyD88 | DAP12 |
| CD83 | CD27 | MyD88 | CD32 |
| CD83 | CD27 | MyD88 | CD79a |
| CD83 | CD27 | MyD88 | CD79b |
| CD83 | CD27 | CD7 | CD8 |
| CD83 | CD27 | CD7 | CD3ζ |
| CD83 | CD27 | CD7 | CD3δ |
| CD83 | CD27 | CD7 | CD3γ |
| CD83 | CD27 | CD7 | C D3E |
| CD83 | CD27 | CD7 | FcγRI-γ |
| CD83 | CD27 | CD7 | FcγRIII-γ |
| CD83 | CD27 | CD7 | FcεRIβ |
| CD83 | CD27 | CD7 | FcεRIγ |
| CD83 | CD27 | CD7 | DAP10 |
| CD83 | CD27 | CD7 | DAP12 |
| CD83 | CD27 | CD7 | CD32 |
| CD83 | CD27 | CD7 | CD79a |
| CD83 | CD27 | CD7 | CD79b |
| CD83 | CD27 | BTNL3 | CD8 |
| CD83 | CD27 | BTNL3 | CD3ζ |
| CD83 | CD27 | BTNL3 | CD3δ |
| CD83 | CD27 | BTNL3 | CD3γ |
| CD83 | CD27 | BTNL3 | CD3ε |
| CD83 | CD27 | BTNL3 | FcγRI-γ |
| CD83 | CD27 | BTNL3 | FcγRIII-γ |
| CD83 | CD27 | BTNL3 | FcεRIβ |
| CD83 | CD27 | BTNL3 | FcεRIγ |
| CD83 | CD27 | BTNL3 | DAP10 |
| CD83 | CD27 | BTNL3 | DAP12 |
| CD83 | CD27 | BTNL3 | CD32 |
| CD83 | CD27 | BTNL3 | CD79a |
| CD83 | CD27 | BTNL3 | CD79b |
| CD83 | CD27 | NKG2D | CD8 |
| CD83 | CD27 | NKG2D | CD3ζ |
| CD83 | CD27 | NKG2D | CD3δ |
| CD83 | CD27 | NKG2D | CD3γ |
| CD83 | CD27 | NKG2D | CD3ε |
| CD83 | CD27 | NKG2D | FcγRI-γ |
| CD83 | CD27 | NKG2D | FcγRIII-γ |
| CD83 | CD27 | NKG2D | FcεRIβ |
| CD83 | CD27 | NKG2D | FcεRIγ |
| CD83 | CD27 | NKG2D | DAP10 |
| CD83 | CD27 | NKG2D | DAP12 |
| CD83 | CD27 | NKG2D | CD32 |
| CD83 | CD27 | NKG2D | CD79a |
| CD83 | CD27 | NKG2D | CD79b |
| CD83 | CD28δ | CD28 | CD8 |
| CD83 | CD28δ | CD28 | CD3ζ |
| CD83 | CD28δ | CD28 | CD3δ |
| CD83 | CD28δ | CD28 | CD3γ |
| CD83 | CD28δ | CD28 | CD3ε |
| CD83 | CD28δ | CD28 | FcγRI-γ |
| CD83 | CD28δ | CD28 | FcγRIII-γ |
| CD83 | CD28δ | CD28 | FcεRIβ |
| CD83 | CD28δ | CD28 | FcεRIγ |
| CD83 | CD28δ | CD28 | DAP10 |
| CD83 | CD28δ | CD28 | DAP12 |
| CD83 | CD28δ | CD28 | CD32 |

TABLE 3-continued

Third Generation CARs

| Scfu | Co-stimulatory Signal | Co-stimulatory Signal | Signal Domain |
|---|---|---|---|
| CD83 | CD28δ | CD28 | CD79a |
| CD83 | CD28δ | CD28 | CD79b |
| CD83 | CD28δ | CD8 | CD8 |
| CD83 | CD28δ | CD8 | CD3ζ |
| CD83 | CD28δ | CD8 | CD3δ |
| CD83 | CD28δ | CD8 | CD3γ |
| CD83 | CD28δ | CD8 | CD3ε |
| CD83 | CD28δ | CD8 | FcγRI-γ |
| CD83 | CD28δ | CD8 | FcγRIII-γ |
| CD83 | CD28δ | CD8 | FcεRIβ |
| CD83 | CD28δ | CD8 | FcεRIγ |
| CD83 | CD28δ | CD8 | DAP10 |
| CD83 | CD28δ | CD8 | DAP12 |
| CD83 | CD28δ | CD8 | CD32 |
| CD83 | CD28δ | CD8 | CD79a |
| CD83 | CD28δ | CD8 | CD79b |
| CD83 | CD28δ | CD4 | CD8 |
| CD83 | CD28δ | CD4 | CD3ζ |
| CD83 | CD28δ | CD4 | CD3δ |
| CD83 | CD28δ | CD4 | CD3γ |
| CD83 | CD28δ | CD4 | CD3ε |
| CD83 | CD28δ | CD4 | FcγRI-γ |
| CD83 | CD28δ | CD4 | FcγRIII-γ |
| CD83 | CD28δ | CD4 | FcεRIβ |
| CD83 | CD28δ | CD4 | FcεRIγ |
| CD83 | CD28δ | CD4 | DAP10 |
| CD83 | CD28δ | CD4 | DAP12 |
| CD83 | CD28δ | CD4 | CD32 |
| CD83 | CD28δ | CD4 | CD79a |
| CD83 | CD28δ | CD4 | CD79b |
| CD83 | CD28δ | b2c | CD8 |
| CD83 | CD28δ | b2c | CD3ζ |
| CD83 | CD28δ | b2c | CD3δ |
| CD83 | CD28δ | b2c | CD3γ |
| CD83 | CD28δ | b2c | CD3ε |
| CD83 | CD28δ | b2c | FcγRI-γ |
| CD83 | CD28δ | b2c | FcγRIII-γ |
| CD83 | CD28δ | b2c | FcεRIβ |
| CD83 | CD28δ | b2c | FcεRIγ |
| CD83 | CD28δ | b2c | DAP10 |
| CD83 | CD28δ | b2c | DAP12 |
| CD83 | CD28δ | b2c | CD32 |
| CD83 | CD28δ | b2c | CD79a |
| CD83 | CD28δ | b2c | CD79b |
| CD83 | CD28δ | CD137/41BB | CD8 |
| CD83 | CD28δ | CD137/41BB | CD3ζ |
| CD83 | CD28δ | CD137/41BB | CD3δ |
| CD83 | CD28δ | CD137/41BB | CD3γ |
| CD83 | CD28δ | CD137/41BB | CD3ε |
| CD83 | CD28δ | CD137/41BB | FcγRI-γ |
| CD83 | CD28δ | CD137/41BB | FcγRIII-γ |
| CD83 | CD28δ | CD137/41BB | FcεRIβ |
| CD83 | CD28δ | CD137/41BB | FcεRIγ |
| CD83 | CD28δ | CD137/41BB | DAP10 |
| CD83 | CD28δ | CD137/41BB | DAP12 |
| CD83 | CD28δ | CD137/41BB | CD32 |
| CD83 | CD28δ | CD137/41BB | CD79a |
| CD83 | CD28δ | CD137/41BB | CD79b |
| CD83 | CD28δ | ICOS | CD8 |
| CD83 | CD28δ | ICOS | CD3ζ |
| CD83 | CD28δ | ICOS | CD35 |
| CD83 | CD28δ | ICOS | CD3γ |
| CD83 | CD28δ | ICOS | CD3ε |
| CD83 | CD28δ | ICOS | FcγRI-γ |
| CD83 | CD28δ | ICOS | FcγRIII-γ |
| CD83 | CD28δ | ICOS | FcεRIβ |
| CD83 | CD28δ | ICOS | FcεRIγ |
| CD83 | CD28δ | ICOS | DAP10 |
| CD83 | CD28δ | ICOS | DAP12 |
| CD83 | CD28δ | ICOS | CD32 |
| CD83 | CD28δ | ICOS | CD79a |
| CD83 | CD28δ | ICOS | CD79b |
| CD83 | CD28δ | CD27 | CD8 |
| CD83 | CD28δ | CD27 | CD3ζ |
| CD83 | CD28δ | CD27 | CD3δ |

TABLE 3-continued

Third Generation CARs

| Scfu | Co-stimulatory Signal | Co-stimulatory Signal | Signal Domain |
|---|---|---|---|
| CD83 | CD28δ | CD27 | CD3γ |
| CD83 | CD28δ | CD27 | CD3ε |
| CD83 | CD28δ | CD27 | FcγRI-γ |
| CD83 | CD28δ | CD27 | FcγRIII-γ |
| CD83 | CD28δ | CD27 | FcεRIβ |
| CD83 | CD28δ | CD27 | FcεRIγ |
| CD83 | CD28δ | CD27 | DAP10 |
| CD83 | CD28δ | CD27 | DAP12 |
| CD83 | CD28δ | CD27 | CD32 |
| CD83 | CD28δ | CD27 | CD79a |
| CD83 | CD28δ | CD27 | CD79b |
| CD83 | CD28δ | CD28δ | CD8 |
| CD83 | CD28δ | CD28δ | CD3ζ |
| CD83 | CD28δ | CD28δ | CD3δ |
| CD83 | CD28δ | CD28δ | CD3γ |
| CD83 | CD28δ | CD28δ | CD3ε |
| CD83 | CD28δ | CD28δ | FcγRI-γ |
| CD83 | CD28δ | CD28δ | FcγRIII-γ |
| CD83 | CD28δ | CD28δ | FcεRIβ |
| CD83 | CD28δ | CD28δ | FcεRIγ |
| CD83 | CD28δ | CD28δ | DAP10 |
| CD83 | CD28δ | CD28δ | DAP12 |
| CD83 | CD28δ | CD28δ | CD32 |
| CD83 | CD28δ | CD28δ | CD79a |
| CD83 | CD28δ | CD28δ | CD79b |
| CD83 | CD28δ | CD80 | CD8 |
| CD83 | CD28δ | CD80 | CD3ζ |
| CD83 | CD28δ | CD80 | CD3δ |
| CD83 | CD28δ | CD80 | CD3γ |
| CD83 | CD28δ | CD80 | CD3ε |
| CD83 | CD28δ | CD80 | FcγRI-γ |
| CD83 | CD28δ | CD80 | FcγRIII-γ |
| CD83 | CD28δ | CD80 | FcεRIβ |
| CD83 | CD28δ | CD80 | FcεRIγ |
| CD83 | CD28δ | CD80 | DAP10 |
| CD83 | CD28δ | CD80 | DAP12 |
| CD83 | CD28δ | CD80 | CD32 |
| CD83 | CD28δ | CD80 | CD79a |
| CD83 | CD28δ | CD80 | CD79b |
| CD83 | CD28δ | CD86 | CD8 |
| CD83 | CD28δ | CD86 | CD3ζ |
| CD83 | CD28δ | CD86 | CD3δ |
| CD83 | CD28δ | CD86 | CD3γ |
| CD83 | CD28δ | CD86 | CD3ε |
| CD83 | CD28δ | CD86 | FcγRI-γ |
| CD83 | CD28δ | CD86 | FcγRIII-γ |
| CD83 | CD28δ | CD86 | FcεRIβ |
| CD83 | CD28δ | CD86 | FcεRIγ |
| CD83 | CD28δ | CD86 | DAP10 |
| CD83 | CD28δ | CD86 | DAP12 |
| CD83 | CD28δ | CD86 | CD32 |
| CD83 | CD28δ | CD86 | CD79a |
| CD83 | CD28δ | CD86 | CD79b |
| CD83 | CD28δ | OX40 | CD8 |
| CD83 | CD28δ | OX40 | CD3ζ |
| CD83 | CD28δ | OX40 | CD3δ |
| CD83 | CD28δ | OX40 | CD3γ |
| CD83 | CD28δ | OX40 | CD3ε |
| CD83 | CD28δ | OX40 | FcγRI-γ |
| CD83 | CD28δ | OX40 | FcγRIII-γ |
| CD83 | CD28δ | OX40 | FcεRIβ |
| CD83 | CD28δ | OX40 | FcεRIγ |
| CD83 | CD28δ | OX40 | DAP10 |
| CD83 | CD28δ | OX40 | DAP12 |
| CD83 | CD28δ | OX40 | CD32 |
| CD83 | CD28δ | OX40 | CD79a |
| CD83 | CD28δ | OX40 | CD79b |
| CD83 | CD28δ | DAP10 | CD8 |
| CD83 | CD28δ | DAP10 | CD3ζ |
| CD83 | CD28δ | DAP10 | CD3δ |
| CD83 | CD28δ | DAP10 | CD3γ |
| CD83 | CD28δ | DAP10 | CD3ε |
| CD83 | CD28δ | DAP10 | FcγRI-γ |
| CD83 | CD28δ | DAP10 | FcγRIII-γ |
| CD83 | CD28δ | DAP10 | FcεRIβ |

TABLE 3-continued

Third Generation CARs

| Scfu | Co-stimulatory Signal | Co-stimulatory Signal | Signal Domain |
|---|---|---|---|
| CD83 | CD28δ | DAP10 | FcεRIγ |
| CD83 | CD28δ | DAP10 | DAP10 |
| CD83 | CD28δ | DAP10 | DAP12 |
| CD83 | CD28δ | DAP10 | CD32 |
| CD83 | CD28δ | DAP10 | CD79a |
| CD83 | CD28δ | DAP10 | CD79b |
| CD83 | CD28δ | DAP12 | CD8 |
| CD83 | CD28δ | DAP12 | CD3ζ |
| CD83 | CD28δ | DAP12 | CD3δ |
| CD83 | CD28δ | DAP12 | CD3γ |
| CD83 | CD28δ | DAP12 | CD3ε |
| CD83 | CD28δ | DAP12 | FcγRI-γ |
| CD83 | CD28δ | DAP12 | FcγRIII-γ |
| CD83 | CD28δ | DAP12 | FcεRIβ |
| CD83 | CD28δ | DAP12 | FcεRIγ |
| CD83 | CD28δ | DAP12 | DAP10 |
| CD83 | CD28δ | DAP12 | DAP12 |
| CD83 | CD28δ | DAP12 | CD32 |
| CD83 | CD28δ | DAP12 | CD79a |
| CD83 | CD28δ | DAP12 | CD79b |
| CD83 | CD28δ | MyD88 | CD8 |
| CD83 | CD28δ | MyD88 | CD3ζ |
| CD83 | CD28δ | MyD88 | CD3δ |
| CD83 | CD28δ | MyD88 | CD3γ |
| CD83 | CD28δ | MyD88 | CD3ε |
| CD83 | CD28δ | MyD88 | FcγRI-γ |
| CD83 | CD28δ | MyD88 | FcγRIII-γ |
| CD83 | CD28δ | MyD88 | FcεRIβ |
| CD83 | CD28δ | MyD88 | FcεRIγ |
| CD83 | CD28δ | MyD88 | DAP10 |
| CD83 | CD28δ | MyD88 | DAP12 |
| CD83 | CD28δ | MyD88 | CD32 |
| CD83 | CD28δ | MyD88 | CD79a |
| CD83 | CD28δ | MyD88 | CD79b |
| CD83 | CD28δ | CD7 | CD8 |
| CD83 | CD28δ | CD7 | CD3ζ |
| CD83 | CD28δ | CD7 | CD3δ |
| CD83 | CD28δ | CD7 | CD3γ |
| CD83 | CD28δ | CD7 | CD3ε |
| CD83 | CD28δ | CD7 | FcγRI-γ |
| CD83 | CD28δ | CD7 | FcγRIII-γ |
| CD83 | CD28δ | CD7 | FcεRIβ |
| CD83 | CD28δ | CD7 | FcεRIγ |
| CD83 | CD28δ | CD7 | DAP10 |
| CD83 | CD28δ | CD7 | DAP12 |
| CD83 | CD28δ | CD7 | CD32 |
| CD83 | CD28δ | CD7 | CD79a |
| CD83 | CD28δ | CD7 | CD79b |
| CD83 | CD28δ | BTNL3 | CD8 |
| CD83 | CD28δ | BTNL3 | CD3ζ |
| CD83 | CD28δ | BTNL3 | CD3δ |
| CD83 | CD28δ | BTNL3 | CD3γ |
| CD83 | CD28δ | BTNL3 | CD3ε |
| CD83 | CD28δ | BTNL3 | FcγRI-γ |
| CD83 | CD28δ | BTNL3 | FcγRIII-γ |
| CD83 | CD28δ | BTNL3 | FcεRIβ |
| CD83 | CD28δ | BTNL3 | FcεRIγ |
| CD83 | CD28δ | BTNL3 | DAP10 |
| CD83 | CD28δ | BTNL3 | DAP12 |
| CD83 | CD28δ | BTNL3 | CD32 |
| CD83 | CD28δ | BTNL3 | CD79a |
| CD83 | CD28δ | BTNL3 | CD79b |
| CD83 | CD28δ | NKG2D | CD8 |
| CD83 | CD28δ | NKG2D | CD3ζ |
| CD83 | CD28δ | NKG2D | CD3δ |
| CD83 | CD28δ | NKG2D | CD3γ |
| CD83 | CD28δ | NKG2D | CD3ε |
| CD83 | CD28δ | NKG2D | FcγRI-γ |
| CD83 | CD28δ | NKG2D | FcγRIII-γ |
| CD83 | CD28δ | NKG2D | FcεRIβ |
| CD83 | CD28δ | NKG2D | FcεRIγ |
| CD83 | CD28δ | NKG2D | DAP10 |
| CD83 | CD28δ | NKG2D | DAP12 |
| CD83 | CD28δ | NKG2D | CD32 |
| CD83 | CD28δ | NKG2D | CD79a |

TABLE 3-continued

Third Generation CARs

| Scfu | Co-stimulatory Signal | Co-stimulatory Signal | Signal Domain |
|---|---|---|---|
| CD83 | CD28δ | NKG2D | CD79b |
| CD83 | CD80 | CD28 | CD8 |
| CD83 | CD80 | CD28 | CDζ |
| CD83 | CD80 | CD28 | CD3δ |
| CD83 | CD80 | CD28 | CD3γ |
| CD83 | CD80 | CD28 | CD3ε |
| CD83 | CD80 | CD28 | FcγRI-γ |
| CD83 | CD80 | CD28 | FcγRIII-γ |
| CD83 | CD80 | CD28 | FcεRIβ |
| CD83 | CD80 | CD28 | FcεRIγ |
| CD83 | CD80 | CD28 | DAP10 |
| CD83 | CD80 | CD28 | DAP12 |
| CD83 | CD80 | CD28 | CD32 |
| CD83 | CD80 | CD28 | CD79a |
| CD83 | CD80 | CD28 | CD79b |
| CD83 | CD80 | CD8 | CD8 |
| CD83 | CD80 | CD8 | CD3ζ |
| CD83 | CD80 | CD8 | CD3δ |
| CD83 | CD80 | CD8 | CD3γ |
| CD83 | CD80 | CD8 | CD3ε |
| CD83 | CD80 | CD8 | FcγRI-γ |
| CD83 | CD80 | CD8 | FcγRIII-γ |
| CD83 | CD80 | CD8 | FcεRIβ |
| CD83 | CD80 | CD8 | FcεRIγ |
| CD83 | CD80 | CD8 | DAP10 |
| CD83 | CD80 | CD8 | DAP12 |
| CD83 | CD80 | CD8 | CD32 |
| CD83 | CD80 | CD8 | CD79a |
| CD83 | CD80 | CD8 | CD79b |
| CD83 | CD80 | CD4 | CD8 |
| CD83 | CD80 | CD4 | CD3ζ |
| CD83 | CD80 | CD4 | CD3δ |
| CD83 | CD80 | CD4 | CD3γ |
| CD83 | CD80 | CD4 | CD3ε |
| CD83 | CD80 | CD4 | FcγRI-γ |
| CD83 | CD80 | CD4 | FcγRIII-γ |
| CD83 | CD80 | CD4 | FcεRIβ |
| CD83 | CD80 | CD4 | FcεRIγ |
| CD83 | CD80 | CD4 | DAP10 |
| CD83 | CD80 | CD4 | DAP12 |
| CD83 | CD80 | CD4 | CD32 |
| CD83 | CD80 | CD4 | CD79a |
| CD83 | CD80 | CD4 | CD79b |
| CD83 | CD80 | b2c | CD8 |
| CD83 | CD80 | b2c | CD3ζ |
| CD83 | CD80 | b2c | CD3δ |
| CD83 | CD80 | b2c | CD3γ |
| CD83 | CD80 | b2c | CD3ε |
| CD83 | CD80 | b2c | FcγRI-γ |
| CD83 | CD80 | b2c | FcγRIII-γ |
| CD83 | CD80 | b2c | FcεRIβ |
| CD83 | CD80 | b2c | FcεRIγ |
| CD83 | CD80 | b2c | DAP10 |
| CD83 | CD80 | b2c | DAP12 |
| CD83 | CD80 | b2c | CD32 |
| CD83 | CD80 | b2c | CD79a |
| CD83 | CD80 | b2c | CD79b |
| CD83 | CD80 | CD137/41BB | CD8 |
| CD83 | CD80 | CD137/41BB | CDζ |
| CD83 | CD80 | CD137/41BB | CD3δ |
| CD83 | CD80 | CD137/41BB | CD3γ |
| CD83 | CD80 | CD137/41BB | CD3ε |
| CD83 | CD80 | CD137/41BB | FcγRI-γ |
| CD83 | CD80 | CD137/41BB | FcγRIII-γ |
| CD83 | CD80 | CD137/41BB | FcεRIβ |
| CD83 | CD80 | CD137/41BB | FcεRIγ |
| CD83 | CD80 | CD137/41BB | DAP10 |
| CD83 | CD80 | CD137/41BB | DAP12 |
| CD83 | CD80 | CD137/41BB | CD32 |
| CD83 | CD80 | CD137/41BB | CD79a |
| CD83 | CD80 | CD137/41BB | CD79b |
| CD83 | CD80 | ICOS | CD8 |
| CD83 | CD80 | ICOS | CD3ζ |
| CD83 | CD80 | ICOS | CD3δ |
| CD83 | CD80 | ICOS | CD3γ |

TABLE 3-continued

| Third Generation CARs | | | |
|---|---|---|---|
| Scfu | Co-stimulatory Signal | Co-stimulatory Signal | Signal Domain |
| CD83 | CD80 | ICOS | CD3ε |
| CD83 | CD80 | ICOS | FcγRI-γ |
| CD83 | CD80 | ICOS | FcγRIII-γ |
| CD83 | CD80 | ICOS | FcεRIβ |
| CD83 | CD80 | ICOS | FcεRIγ |
| CD83 | CD80 | ICOS | DAP10 |
| CD83 | CD80 | ICOS | DAP12 |
| CD83 | CD80 | ICOS | CD32 |
| CD83 | CD80 | ICOS | CD79a |
| CD83 | CD80 | ICOS | CD79b |
| CD83 | CD80 | CD27 | CD8 |
| CD83 | CD80 | CD27 | CD3ζ |
| CD83 | CD80 | CD27 | CD3δ |
| CD83 | CD80 | CD27 | CD3γ |
| CD83 | CD80 | CD27 | CD3ε |
| CD83 | CD80 | CD27 | FcγRI-γ |
| CD83 | CD80 | CD27 | FcγRIII-γ |
| CD83 | CD80 | CD27 | FcεRIβ |
| CD83 | CD80 | CD27 | FcεRIγ |
| CD83 | CD80 | CD27 | DAP10 |
| CD83 | CD80 | CD27 | DAP12 |
| CD83 | CD80 | CD27 | CD32 |
| CD83 | CD80 | CD27 | CD79a |
| CD83 | CD80 | CD27 | CD79b |
| CD83 | CD80 | CD28δ | CD8 |
| CD83 | CD80 | CD28δ | CD3ζ |
| CD83 | CD80 | CD28δ | CD3δ |
| CD83 | CD80 | CD28δ | CD3γ |
| CD83 | CD80 | CD28δ | CD3ε |
| CD83 | CD80 | CD28δ | FcγRI-γ |
| CD83 | CD80 | CD28δ | FcγRIII-γ |
| CD83 | CD80 | CD28δ | FcεRIβ |
| CD83 | CD80 | CD28δ | FcεRIγ |
| CD83 | CD80 | CD28δ | DAP10 |
| CD83 | CD80 | CD28δ | DAP12 |
| CD83 | CD80 | CD28δ | CD32 |
| CD83 | CD80 | CD28δ | CD79a |
| CD83 | CD80 | CD28δ | CD79b |
| CD83 | CD80 | CD80 | CD8 |
| CD83 | CD80 | CD80 | CD3ζ |
| CD83 | CD80 | CD80 | CD3δ |
| CD83 | CD80 | CD80 | CD3γ |
| CD83 | CD80 | CD80 | CD3ε |
| CD83 | CD80 | CD80 | FcγRI-γ |
| CD83 | CD80 | CD80 | FcγRIII-γ |
| CD83 | CD80 | CD80 | FcεRIβ |
| CD83 | CD80 | CD80 | FcεRIγ |
| CD83 | CD80 | CD80 | DAP10 |
| CD83 | CD80 | CD80 | DAP12 |
| CD83 | CD80 | CD80 | CD32 |
| CD83 | CD80 | CD80 | CD79a |
| CD83 | CD80 | CD80 | CD79b |
| CD83 | CD80 | CD86 | CD8 |
| CD83 | CD80 | CD86 | CD3ζ |
| CD83 | CD80 | CD86 | CD3δ |
| CD83 | CD80 | CD86 | CD3γ |
| CD83 | CD80 | CD86 | CD3ε |
| CD83 | CD80 | CD86 | FcγRI-γ |
| CD83 | CD80 | CD86 | FcγRIII-γ |
| CD83 | CD80 | CD86 | FcεRIβ |
| CD83 | CD80 | CD86 | FcεRIγ |
| CD83 | CD80 | CD86 | DAP10 |
| CD83 | CD80 | CD86 | DAP12 |
| CD83 | CD80 | CD86 | CD32 |
| CD83 | CD80 | CD86 | CD79a |
| CD83 | CD80 | CD86 | CD79b |
| CD83 | CD80 | OX40 | CD8 |
| CD83 | CD80 | OX40 | CD3ζ |
| CD83 | CD80 | OX40 | CD3δ |
| CD83 | CD80 | OX40 | CD3γ |
| CD83 | CD80 | OX40 | CD3ε |
| CD83 | CD80 | OX40 | FcγRI-γ |
| CD83 | CD80 | OX40 | FcγRIII-γ |
| CD83 | CD80 | OX40 | FcεRIβ |
| CD83 | CD80 | OX40 | FcεRIγ |

TABLE 3-continued

| Third Generation CARs | | | |
|---|---|---|---|
| Scfu | Co-stimulatory Signal | Co-stimulatory Signal | Signal Domain |
| CD83 | CD80 | OX40 | DAP10 |
| CD83 | CD80 | OX40 | DAP12 |
| CD83 | CD80 | OX40 | CD32 |
| CD83 | CD80 | OX40 | CD79a |
| CD83 | CD80 | OX40 | CD79b |
| CD83 | CD80 | DAP10 | CD8 |
| CD83 | CD80 | DAP10 | CD3ζ |
| CD83 | CD80 | DAP10 | CD3δ |
| CD83 | CD80 | DAP10 | CD3γ |
| CD83 | CD80 | DAP10 | CD3ε |
| CD83 | CD80 | DAP10 | FcγRI-γ |
| CD83 | CD80 | DAP10 | FcγRIII-γ |
| CD83 | CD80 | DAP10 | FcεRIβ |
| CD83 | CD80 | DAP10 | FcεRIγ |
| CD83 | CD80 | DAP10 | DAP10 |
| CD83 | CD80 | DAP10 | DAP12 |
| CD83 | CD80 | DAP10 | CD32 |
| CD83 | CD80 | DAP10 | CD79a |
| CD83 | CD80 | DAP10 | CD79b |
| CD83 | CD80 | DAP12 | CD8 |
| CD83 | CD80 | DAP12 | CD3ζ |
| CD83 | CD80 | DAP12 | CD3δ |
| CD83 | CD80 | DAP12 | CD3γ |
| CD83 | CD80 | DAP12 | CD3ε |
| CD83 | CD80 | DAP12 | FcγRI-γ |
| CD83 | CD80 | DAP12 | FcγRIII-γ |
| CD83 | CD80 | DAP12 | FcεRIβ |
| CD83 | CD80 | DAP12 | FcεRIγ |
| CD83 | CD80 | DAP12 | DAP10 |
| CD83 | CD80 | DAP12 | DAP12 |
| CD83 | CD80 | DAP12 | CD32 |
| CD83 | CD80 | DAP12 | CD79a |
| CD83 | CD80 | DAP12 | CD79b |
| CD83 | CD80 | MyD88 | CD8 |
| CD83 | CD80 | MyD88 | CD3ζ |
| CD83 | CD80 | MyD88 | CD3δ |
| CD83 | CD80 | MyD88 | CD3γ |
| CD83 | CD80 | MyD88 | CD3ε |
| CD83 | CD80 | MyD88 | FcγRI-γ |
| CD83 | CD80 | MyD88 | FcγRIII-γ |
| CD83 | CD80 | MyD88 | FcεRIβ |
| CD83 | CD80 | MyD88 | FcεRIγ |
| CD83 | CD80 | MyD88 | DAP10 |
| CD83 | CD80 | MyD88 | DAP12 |
| CD83 | CD80 | MyD88 | CD32 |
| CD83 | CD80 | MyD88 | CD79a |
| CD83 | CD80 | MyD88 | CD79b |
| CD83 | CD80 | CD7 | CD8 |
| CD83 | CD80 | CD7 | CD3ζ |
| CD83 | CD80 | CD7 | CD3δ |
| CD83 | CD80 | CD7 | CD3γ |
| CD83 | CD80 | CD7 | CD3ε |
| CD83 | CD80 | CD7 | FcγRI-γ |
| CD83 | CD80 | CD7 | FcγRIII-γ |
| CD83 | CD80 | CD7 | FcεRIβ |
| CD83 | CD80 | CD7 | FcεRIγ |
| CD83 | CD80 | CD7 | DAP10 |
| CD83 | CD80 | CD7 | DAP12 |
| CD83 | CD80 | CD7 | CD32 |
| CD83 | CD80 | CD7 | CD79a |
| CD83 | CD80 | CD7 | CD79b |
| CD83 | CD80 | BTNL3 | CD8 |
| CD83 | CD80 | BTNL3 | CD3ζ |
| CD83 | CD80 | BTNL3 | CD3δ |
| CD83 | CD80 | BTNL3 | CD3γ |
| CD83 | CD80 | BTNL3 | CD3ε |
| CD83 | CD80 | BTNL3 | FcγRI-γ |
| CD83 | CD80 | BTNL3 | FcγRIII-γ |
| CD83 | CD80 | BTNL3 | FcεRIβ |
| CD83 | CD80 | BTNL3 | FcεRIγ |
| CD83 | CD80 | BTNL3 | DAP10 |
| CD83 | CD80 | BTNL3 | DAP12 |
| CD83 | CD80 | BTNL3 | CD32 |
| CD83 | CD80 | BTNL3 | CD79a |
| CD83 | CD80 | BTNL3 | CD79b |

TABLE 3-continued

| Third Generation CARs | | | |
|---|---|---|---|
| Scfu | Co-stimulatory Signal | Co-stimulatory Signal | Signal Domain |
| CD83 | CD80 | NKG2D | CD8 |
| CD83 | CD80 | NKG2D | CD3ζ |
| CD83 | CD80 | NKG2D | CD3δ |
| CD83 | CD80 | NKG2D | CD3γ |
| CD83 | CD80 | NKG2D | CD3ε |
| CD83 | CD80 | NKG2D | FcγRI-γ |
| CD83 | CD80 | NKG2D | FcγRIII-γ |
| CD83 | CD80 | NKG2D | FcεRIβ |
| CD83 | CD80 | NKG2D | FcεRIγ |
| CD83 | CD80 | NKG2D | DAP10 |
| CD83 | CD80 | NKG2D | DAP12 |
| CD83 | CD80 | NKG2D | CD32 |
| CD83 | CD80 | NKG2D | CD79a |
| CD83 | CD80 | NKG2D | CD79b |
| CD83 | CD86 | CD28 | CD8 |
| CD83 | CD86 | CD28 | CD3ζ |
| CD83 | CD86 | CD28 | CD3δ |
| CD83 | CD86 | CD28 | CD3γ |
| CD83 | CD86 | CD28 | CD3ε |
| CD83 | CD86 | CD28 | FcγRI-γ |
| CD83 | CD86 | CD28 | FcγRIII-γ |
| CD83 | CD86 | CD28 | FcεRIβ |
| CD83 | CD86 | CD28 | FcεRIγ |
| CD83 | CD86 | CD28 | DAP10 |
| CD83 | CD86 | CD28 | DAP12 |
| CD83 | CD86 | CD28 | CD32 |
| CD83 | CD86 | CD28 | CD79a |
| CD83 | CD86 | CD28 | CD79b |
| CD83 | CD86 | CD8 | CD8 |
| CD83 | CD86 | CD8 | CD3ζ |
| CD83 | CD86 | CD8 | CD3δ |
| CD83 | CD86 | CD8 | CD3γ |
| CD83 | CD86 | CD8 | CD3ε |
| CD83 | CD86 | CD8 | FcγRIγ |
| CD83 | CD86 | CD8 | FcγRIII-γ |
| CD83 | CD86 | CD8 | FcεRIβ |
| CD83 | CD86 | CD8 | FcεRIγ |
| CD83 | CD86 | CD8 | DAP10 |
| CD83 | CD86 | CD8 | DAP12 |
| CD83 | CD86 | CD8 | CD32 |
| CD83 | CD86 | CD8 | CD79a |
| CD83 | CD86 | CD8 | CD79b |
| CD83 | CD86 | CD4 | CD8 |
| CD83 | CD86 | CD4 | CD3ζ |
| CD83 | CD86 | CD4 | CD3δ |
| CD83 | CD86 | CD4 | CD3γ |
| CD83 | CD86 | CD4 | CD3ε |
| CD83 | CD86 | CD4 | FcγRI-γ |
| CD83 | CD86 | CD4 | FcγRIII-γ |
| CD83 | CD86 | CD4 | FcεRIβ |
| CD83 | CD86 | CD4 | FcεRIγ |
| CD83 | CD86 | CD4 | DAP10 |
| CD83 | CD86 | CD4 | DAP12 |
| CD83 | CD86 | CD4 | CD32 |
| CD83 | CD86 | CD4 | CD79a |
| CD83 | CD86 | CD4 | CD79b |
| CD83 | CD86 | b2c | CD8 |
| CD83 | CD86 | b2c | CD3ζ |
| CD83 | CD86 | b2c | CD3δ |
| CD83 | CD86 | b2c | CD3γ |
| CD83 | CD86 | b2c | CD3ε |
| CD83 | CD86 | b2c | FcγRI-γ |
| CD83 | CD86 | b2c | FcγRIII-γ |
| CD83 | CD86 | b2c | FcεRIβ |
| CD83 | CD86 | b2c | FcεRIγ |
| CD83 | CD86 | b2c | DAP10 |
| CD83 | CD86 | b2c | DAP12 |
| CD83 | CD86 | b2c | CD32 |
| CD83 | CD86 | b2c | CD79a |
| CD83 | CD86 | b2c | CD79b |
| CD83 | CD86 | CD137/41BB | CD8 |
| CD83 | CD86 | CD137/41BB | CD3ζ |
| CD83 | CD86 | CD137/41BB | CD3δ |
| CD83 | CD86 | CD137/41BB | CD3γ |
| CD83 | CD86 | CD137/41BB | CD3ε |

TABLE 3-continued

| Third Generation CARs | | | |
|---|---|---|---|
| Scfu | Co-stimulatory Signal | Co-stimulatory Signal | Signal Domain |
| CD83 | CD86 | CD137/41BB | FcγRI-γ |
| CD83 | CD86 | CD137/41BB | FcγRIII-γ |
| CD83 | CD86 | CD137/41BB | FcεRIβ |
| CD83 | CD86 | CD137/41BB | FcεRIγ |
| CD83 | CD86 | CD137/41BB | DAP10 |
| CD83 | CD86 | CD137/41BB | DAP12 |
| CD83 | CD86 | CD137/41BB | CD32 |
| CD83 | CD86 | CD137/41BB | CD79a |
| CD83 | CD86 | CD137/41BB | CD79b |
| CD83 | CD86 | ICOS | CD8 |
| CD83 | CD86 | ICOS | CD3ζ |
| CD83 | CD86 | ICOS | CD3δ |
| CD83 | CD86 | ICOS | CD3γ |
| CD83 | CD86 | ICOS | CD3ε |
| CD83 | CD86 | ICOS | FcγRI-γ |
| CD83 | CD86 | ICOS | FcγRIII-γ |
| CD83 | CD86 | ICOS | FcεRIβ |
| CD83 | CD86 | ICOS | FcεRIγ |
| CD83 | CD86 | ICOS | DAP10 |
| CD83 | CD86 | ICOS | DAP12 |
| CD83 | CD86 | ICOS | CD32 |
| CD83 | CD86 | ICOS | CD79a |
| CD83 | CD86 | ICOS | CD79b |
| CD83 | CD86 | CD27 | CD8 |
| CD83 | CD86 | CD27 | CD3ζ |
| CD83 | CD86 | CD27 | CD3δ |
| CD83 | CD86 | CD27 | CD3γ |
| CD83 | CD86 | CD27 | CD3ε |
| CD83 | CD86 | CD27 | FcγRI-γ |
| CD83 | CD86 | CD27 | FcγRIII-γ |
| CD83 | CD86 | CD27 | FcεRIβ |
| CD83 | CD86 | CD27 | FcεRIγ |
| CD83 | CD86 | CD27 | DAP10 |
| CD83 | CD86 | CD27 | DAP12 |
| CD83 | CD86 | CD27 | CD32 |
| CD83 | CD86 | CD27 | CD79a |
| CD83 | CD86 | CD27 | CD79b |
| CD83 | CD86 | CD28δ | CD8 |
| CD83 | CD86 | CD28δ | CD3ζ |
| CD83 | CD86 | CD28δ | CD3δ |
| CD83 | CD86 | CD28δ | CD3γ |
| CD83 | CD86 | CD28δ | CD3ε |
| CD83 | CD86 | CD28δ | FcγRI-γ |
| CD83 | CD86 | CD28δ | FcγRIII-γ |
| CD83 | CD86 | CD28δ | FcεRIβ |
| CD83 | CD86 | CD28δ | FcεRIγ |
| CD83 | CD86 | CD28δ | DAP10 |
| CD83 | CD86 | CD28δ | DAP12 |
| CD83 | CD86 | CD28δ | CD32 |
| CD83 | CD86 | CD28δ | CD79a |
| CD83 | CD86 | CD28δ | CD79b |
| CD83 | CD86 | CD80 | CD8 |
| CD83 | CD86 | CD80 | CD3ζ |
| CD83 | CD86 | CD80 | CD3δ |
| CD83 | CD86 | CD80 | CD3γ |
| CD83 | CD86 | CD80 | CD3ε |
| CD83 | CD86 | CD80 | FcγRI-γ |
| CD83 | CD86 | CD80 | FcγRIII-γ |
| CD83 | CD86 | CD80 | FcεRIβ |
| CD83 | CD86 | CD80 | FcεRIγ |
| CD83 | CD86 | CD80 | DAP10 |
| CD83 | CD86 | CD80 | DAP12 |
| CD83 | CD86 | CD80 | CD32 |
| CD83 | CD86 | CD80 | CD79a |
| CD83 | CD86 | CD80 | CD79b |
| CD83 | CD86 | CD86 | CD8 |
| CD83 | CD86 | CD86 | CD3ζ |
| CD83 | CD86 | CD86 | CD3δ |
| CD83 | CD86 | CD86 | CD3γ |
| CD83 | CD86 | CD86 | CD3ε |
| CD83 | CD86 | CD86 | FcγRI-γ |
| CD83 | CD86 | CD86 | FcγRIII-γ |
| CD83 | CD86 | CD86 | FcεRIβ |
| CD83 | CD86 | CD86 | FcεRIγ |
| CD83 | CD86 | CD86 | DAP10 |

TABLE 3-continued

| Third Generation CARs | | | |
|---|---|---|---|
| Scfu | Co-stimulatory Signal | Co-stimulatory Signal | Signal Domain |
| CD83 | CD86 | CD86 | DAP12 |
| CD83 | CD86 | CD86 | CD32 |
| CD83 | CD86 | CD86 | CD79a |
| CD83 | CD86 | CD86 | CD79b |
| CD83 | CD86 | OX40 | CD8 |
| CD83 | CD86 | OX40 | CD3ζ |
| CD83 | CD86 | OX40 | CD3δ |
| CD83 | CD86 | OX40 | CD3γ |
| CD83 | CD86 | OX40 | CD3ε |
| CD83 | CD86 | OX40 | FcγRI-γ |
| CD83 | CD86 | OX40 | FcγRIII-γ |
| CD83 | CD86 | OX40 | FcεRIβ |
| CD83 | CD86 | OX40 | FcεRIγ |
| CD83 | CD86 | OX40 | DAP10 |
| CD83 | CD86 | OX40 | DAP12 |
| CD83 | CD86 | OX40 | CD32 |
| CD83 | CD86 | OX40 | CD79a |
| CD83 | CD86 | OX40 | CD79b |
| CD83 | CD86 | DAP10 | CD8 |
| CD83 | CD86 | DAP10 | CD3ζ |
| CD83 | CD86 | DAP10 | CD3δ |
| CD83 | CD86 | DAP10 | CD3γ |
| CD83 | CD86 | DAP10 | CD3ε |
| CD83 | CD86 | DAP10 | FcγRI-γ |
| CD83 | CD86 | DAP10 | FcγRIII-γ |
| CD83 | CD86 | DAP10 | FcεRIβ |
| CD83 | CD86 | DAP10 | FcεRIγ |
| CD83 | CD86 | DAP10 | DAP10 |
| CD83 | CD86 | DAP10 | DAP12 |
| CD83 | CD86 | DAP10 | CD32 |
| CD83 | CD86 | DAP10 | CD79a |
| CD83 | CD86 | DAP10 | CD79b |
| CD83 | CD86 | DAP12 | CD8 |
| CD83 | CD86 | DAP12 | CD3ζ |
| CD83 | CD86 | DAP12 | CD3δ |
| CD83 | CD86 | DAP12 | CD3γ |
| CD83 | CD86 | DAP12 | CD3ε |
| CD83 | CD86 | DAP12 | FcγRIγ |
| CD83 | CD86 | DAP12 | FcγRIII-γ |
| CD83 | CD86 | DAP12 | FcεRIβ |
| CD83 | CD86 | DAP12 | FcεRIγ |
| CD83 | CD86 | DAP12 | DAP10 |
| CD83 | CD86 | DAP12 | DAP12 |
| CD83 | CD86 | DAP12 | CD32 |
| CD83 | CD86 | DAP12 | CD79a |
| CD83 | CD86 | DAP12 | CD79b |
| CD83 | CD86 | MyD88 | CD8 |
| CD83 | CD86 | MyD88 | CD3ζ |
| CD83 | CD86 | MyD88 | CD3δ |
| CD83 | CD86 | MyD88 | CD3γ |
| CD83 | CD86 | MyD88 | CD3ε |
| CD83 | CD86 | MyD88 | FcγRI-γ |
| CD83 | CD86 | MyD88 | FcγRIII-γ |
| CD83 | CD86 | MyD88 | FcεRIβ |
| CD83 | CD86 | MyD88 | FcεRIγ |
| CD83 | CD86 | MyD88 | DAP10 |
| CD83 | CD86 | MyD88 | DAP12 |
| CD83 | CD86 | MyD88 | CD32 |
| CD83 | CD86 | MyD88 | CD79a |
| CD83 | CD86 | MyD88 | CD79b |
| CD83 | CD86 | CD7 | CD8 |
| CD83 | CD86 | CD7 | CDζ |
| CD83 | CD86 | CD7 | CD3δ |
| CD83 | CD86 | CD7 | CD3γ |
| CD83 | CD86 | CD7 | CD3ε |
| CD83 | CD86 | CD7 | FcγRI-γ |
| CD83 | CD86 | CD7 | FcγRIII-γ |
| CD83 | CD86 | CD7 | FcεRIβ |
| CD83 | CD86 | CD7 | FcεRIγ |
| CD83 | CD86 | CD7 | DAP10 |
| CD83 | CD86 | CD7 | DAP12 |
| CD83 | CD86 | CD7 | CD32 |
| CD83 | CD86 | CD7 | CD79a |
| CD83 | CD86 | CD7 | CD79b |
| CD83 | CD86 | BTNL3 | CD8 |
| CD83 | CD86 | BTNL3 | CD3ζ |
| CD83 | CD86 | BTNL3 | CD3δ |
| CD83 | CD86 | BTNL3 | CD3γ |
| CD83 | CD86 | BTNL3 | CD3ε |
| CD83 | CD86 | BTNL3 | FcγRI-γ |
| CD83 | CD86 | BTNL3 | FcγRIII-γ |
| CD83 | CD86 | BTNL3 | FcεRIβ |
| CD83 | CD86 | BTNL3 | FcεRIγ |
| CD83 | CD86 | BTNL3 | DAP10 |
| CD83 | CD86 | BTNL3 | DAP12 |
| CD83 | CD86 | BTNL3 | CD32 |
| CD83 | CD86 | BTNL3 | CD79a |
| CD83 | CD86 | BTNL3 | CD79b |
| CD83 | CD86 | NKG2D | CD8 |
| CD83 | CD86 | NKG2D | CD3ζ |
| CD83 | CD86 | NKG2D | CD3δ |
| CD83 | CD86 | NKG2D | CD3γ |
| CD83 | CD86 | NKG2D | CD3ε |
| CD83 | CD86 | NKG2D | FcγRI-γ |
| CD83 | CD86 | NKG2D | FcγRIII-γ |
| CD83 | CD86 | NKG2D | FcεRIβ |
| CD83 | CD86 | NKG2D | FcεRIγ |
| CD83 | CD86 | NKG2D | DAP10 |
| CD83 | CD86 | NKG2D | DAP12 |
| CD83 | CD86 | NKG2D | CD32 |
| CD83 | CD86 | NKG2D | CD79a |
| CD83 | CD86 | NKG2D | CD79b |
| CD83 | OX40 | CD28 | CD8 |
| CD83 | OX40 | CD28 | CD3ζ |
| CD83 | OX40 | CD28 | CD3δ |
| CD83 | OX40 | CD28 | CD3γ |
| CD83 | OX40 | CD28 | CD3ε |
| CD83 | OX40 | CD28 | FcγRI-γ |
| CD83 | OX40 | CD28 | FcγRIII-γ |
| CD83 | OX40 | CD28 | FcεRIβ |
| CD83 | OX40 | CD28 | FcεRIγ |
| CD83 | OX40 | CD28 | DAP10 |
| CD83 | OX40 | CD28 | DAP12 |
| CD83 | OX40 | CD28 | CD32 |
| CD83 | OX40 | CD28 | CD79a |
| CD83 | OX40 | CD28 | CD79b |
| CD83 | OX40 | CD8 | CD8 |
| CD83 | OX40 | CD8 | CD3ζ |
| CD83 | OX40 | CD8 | CD3δ |
| CD83 | OX40 | CD8 | CD3γ |
| CD83 | OX40 | CD8 | CD3ε |
| CD83 | OX40 | CD8 | FcγRI-γ |
| CD83 | OX40 | CD8 | FcγRIII-γ |
| CD83 | OX40 | CD8 | FcεRIβ |
| CD83 | OX40 | CD8 | FcεRIγ |
| CD83 | OX40 | CD8 | DAP10 |
| CD83 | OX40 | CD8 | DAP12 |
| CD83 | OX40 | CD8 | CD32 |
| CD83 | OX40 | CD8 | CD79a |
| CD83 | OX40 | CD8 | CD79b |
| CD83 | OX40 | CD4 | CD8 |
| CD83 | OX40 | CD4 | CD3ζ |
| CD83 | OX40 | CD4 | CD3δ |
| CD83 | OX40 | CD4 | CD3γ |
| CD83 | OX40 | CD4 | CD3ε |
| CD83 | OX40 | CD4 | FcγRI-γ |
| CD83 | OX40 | CD4 | FcγRIII-γ |
| CD83 | OX40 | CD4 | FcεRIβ |
| CD83 | OX40 | CD4 | FcεRIγ |
| CD83 | OX40 | CD4 | DAP10 |
| CD83 | OX40 | CD4 | DAP12 |
| CD83 | OX40 | CD4 | CD32 |
| CD83 | OX40 | CD4 | CD79a |
| CD83 | OX40 | CD4 | CD79b |
| CD83 | OX40 | b2c | CD8 |
| CD83 | OX40 | b2c | CD3ζ |
| CD83 | OX40 | b2c | CD3δ |
| CD83 | OX40 | b2c | CD3γ |
| CD83 | OX40 | b2c | CD3ε |
| CD83 | OX40 | b2c | FcγRI-γ |

TABLE 3-continued

Third Generation CARs

| Scfu | Co-stimulatory Signal | Co-stimulatory Signal | Signal Domain |
|---|---|---|---|
| CD83 | OX40 | b2c | FcγRIII-γ |
| CD83 | OX40 | b2c | FcεRIβ |
| CD83 | OX40 | b2c | FcεRIγ |
| CD83 | OX40 | b2c | DAP10 |
| CD83 | OX40 | b2c | DAP12 |
| CD83 | OX40 | b2c | CD32 |
| CD83 | OX40 | b2c | CD79a |
| CD83 | OX40 | b2c | CD79b |
| CD83 | OX40 | CD137/41BB | CD8 |
| CD83 | OX40 | CD137/41BB | CD3ζ |
| CD83 | OX40 | CD137/41BB | CD3δ |
| CD83 | OX40 | CD137/41BB | CD3γ |
| CD83 | OX40 | CD137/41BB | CD3ε |
| CD83 | OX40 | CD137/41BB | FcγRI-γ |
| CD83 | OX40 | CD137/41BB | FcγRIII-γ |
| CD83 | OX40 | CD137/41BB | FcεRIβ |
| CD83 | OX40 | CD137/41BB | FcεRIγ |
| CD83 | OX40 | CD137/41BB | DAP10 |
| CD83 | OX40 | CD137/41BB | DAP12 |
| CD83 | OX40 | CD137/41BB | CD32 |
| CD83 | OX40 | CD137/41BB | CD79a |
| CD83 | OX40 | CD137/41BB | CD79b |
| CD83 | OX40 | ICOS | CD8 |
| CD83 | OX40 | ICOS | CD3ζ |
| CD83 | OX40 | ICOS | CD3δ |
| CD83 | OX40 | ICOS | CD3γ |
| CD83 | OX40 | ICOS | CD3ε |
| CD83 | OX40 | ICOS | FcγRI-γ |
| CD83 | OX40 | ICOS | FcγRIII-γ |
| CD83 | OX40 | ICOS | FcεRIβ |
| CD83 | OX40 | ICOS | FcεRIγ |
| CD83 | OX40 | ICOS | DAP10 |
| CD83 | OX40 | ICOS | DAP12 |
| CD83 | OX40 | ICOS | CD32 |
| CD83 | OX40 | ICOS | CD79a |
| CD83 | OX40 | ICOS | CD79b |
| CD83 | OX40 | CD27 | CD8 |
| CD83 | OX40 | CD27 | CD3ζ |
| CD83 | OX40 | CD27 | CD3δ |
| CD83 | OX40 | CD27 | CD3γ |
| CD83 | OX40 | CD27 | CD3ε |
| CD83 | OX40 | CD27 | FcγRI-γ |
| CD83 | OX40 | CD27 | FcγRIII-γ |
| CD83 | OX40 | CD27 | FcεRIβ |
| CD83 | OX40 | CD27 | FcεRIγ |
| CD83 | OX40 | CD27 | DAP10 |
| CD83 | OX40 | CD27 | DAP12 |
| CD83 | OX40 | CD27 | CD32 |
| CD83 | OX40 | CD27 | CD79a |
| CD83 | OX40 | CD27 | CD79b |
| CD83 | OX40 | CD28δ | CD8 |
| CD83 | OX40 | CD28δ | CD3ζ |
| CD83 | OX40 | CD28δ | CD3δ |
| CD83 | OX40 | CD28δ | CD3γ |
| CD83 | OX40 | CD28δ | CD3ε |
| CD83 | OX40 | CD28δ | FcγRI-γ |
| CD83 | OX40 | CD28δ | FcγRIII-γ |
| CD83 | OX40 | CD28δ | FcεRIβ |
| CD83 | OX40 | CD28δ | FcεRIγ |
| CD83 | OX40 | CD28δ | DAP10 |
| CD83 | OX40 | CD28δ | DAP12 |
| CD83 | OX40 | CD28δ | CD32 |
| CD83 | OX40 | CD28δ | CD79a |
| CD83 | OX40 | CD28δ | CD79b |
| CD83 | OX40 | CD80 | CD8 |
| CD83 | OX40 | CD80 | CD3ζ |
| CD83 | OX40 | CD80 | CD3δ |
| CD83 | OX40 | CD80 | CD3γ |
| CD83 | OX40 | CD80 | CD3ε |
| CD83 | OX40 | CD80 | FcγRI-γ |
| CD83 | OX40 | CD80 | FcγRIII-γ |
| CD83 | OX40 | CD80 | FcεRIβ |
| CD83 | OX40 | CD80 | FcεRIγ |
| CD83 | OX40 | CD80 | DAP10 |
| CD83 | OX40 | CD80 | DAP12 |

TABLE 3-continued

Third Generation CARs

| Scfu | Co-stimulatory Signal | Co-stimulatory Signal | Signal Domain |
|---|---|---|---|
| CD83 | OX40 | CD80 | CD32 |
| CD83 | OX40 | CD80 | CD79a |
| CD83 | OX40 | CD80 | CD79b |
| CD83 | OX40 | CD86 | CD8 |
| CD83 | OX40 | CD86 | CD3ζ |
| CD83 | OX40 | CD86 | CD3δ |
| CD83 | OX40 | CD86 | CD3γ |
| CD83 | OX40 | CD86 | CD3ε |
| CD83 | OX40 | CD86 | FcγRI-γ |
| CD83 | OX40 | CD86 | FcγRIII-γ |
| CD83 | OX40 | CD86 | FcεRIβ |
| CD83 | OX40 | CD86 | FcεRIγ |
| CD83 | OX40 | CD86 | DAP10 |
| CD83 | OX40 | CD86 | DAP12 |
| CD83 | OX40 | CD86 | CD32 |
| CD83 | OX40 | CD86 | CD79a |
| CD83 | OX40 | CD86 | CD79b |
| CD83 | OX40 | OX40 | CD8 |
| CD83 | OX40 | OX40 | CD3ζ |
| CD83 | OX40 | OX40 | CD3δ |
| CD83 | OX40 | OX40 | CD3γ |
| CD83 | OX40 | OX40 | CD3ε |
| CD83 | OX40 | OX40 | FcγRI-γ |
| CD83 | OX40 | OX40 | FcγRIII-γ |
| CD83 | OX40 | OX40 | FcεRIβ |
| CD83 | OX40 | OX40 | FcεRIγ |
| CD83 | OX40 | OX40 | DAP10 |
| CD83 | OX40 | OX40 | DAP12 |
| CD83 | OX40 | OX40 | CD32 |
| CD83 | OX40 | OX40 | CD79a |
| CD83 | OX40 | OX40 | CD79b |
| CD83 | OX40 | DAP10 | CD8 |
| CD83 | OX40 | DAP10 | CD3ζ |
| CD83 | OX40 | DAP10 | CD3δ |
| CD83 | OX40 | DAP10 | CD3γ |
| CD83 | OX40 | DAP10 | CD3ε |
| CD83 | OX40 | DAP10 | FcγRI-γ |
| CD83 | OX40 | DAP10 | FcγRIII-γ |
| CD83 | OX40 | DAP10 | FcεRIβ |
| CD83 | OX40 | DAP10 | FcεRIγ |
| CD83 | OX40 | DAP10 | DAP10 |
| CD83 | OX40 | DAP10 | DAP12 |
| CD83 | OX40 | DAP10 | CD32 |
| CD83 | OX40 | DAP10 | CD79a |
| CD83 | OX40 | DAP10 | CD79b |
| CD83 | OX40 | DAP12 | CD8 |
| CD83 | OX40 | DAP12 | CD3ζ |
| CD83 | OX40 | DAP12 | CD3δ |
| CD83 | OX40 | DAP12 | CD3γ |
| CD83 | OX40 | DAP12 | CD3ε |
| CD83 | OX40 | DAP12 | FcγRI-γ |
| CD83 | OX40 | DAP12 | FcγRIII-γ |
| CD83 | OX40 | DAP12 | FcεRIβ |
| CD83 | OX40 | DAP12 | FcεRIγ |
| CD83 | OX40 | DAP12 | DAP10 |
| CD83 | OX40 | DAP12 | DAP12 |
| CD83 | OX40 | DAP12 | CD32 |
| CD83 | OX40 | DAP12 | CD79a |
| CD83 | OX40 | DAP12 | CD79b |
| CD83 | OX40 | MyD88 | CD8 |
| CD83 | OX40 | MyD88 | CD3ζ |
| CD83 | OX40 | MyD88 | CD3δ |
| CD83 | OX40 | MyD88 | CD3γ |
| CD83 | OX40 | MyD88 | CD3ε |
| CD83 | OX40 | MyD88 | FcγRI-γ |
| CD83 | OX40 | MyD88 | FcγRIII-γ |
| CD83 | OX40 | MyD88 | FcεRIβ |
| CD83 | OX40 | MyD88 | FcεRIγ |
| CD83 | OX40 | MyD88 | DAP10 |
| CD83 | OX40 | MyD88 | DAP12 |
| CD83 | OX40 | MyD88 | CD32 |
| CD83 | OX40 | MyD88 | CD79a |
| CD83 | OX40 | MyD88 | CD79b |
| CD83 | OX40 | CD7 | CD8 |
| CD83 | OX40 | CD7 | CD3ζ |

TABLE 3-continued

| Third Generation CARs | | | |
|---|---|---|---|
| Scfu | Co-stimulatory Signal | Co-stimulatory Signal | Signal Domain |
| CD83 | OX40 | CD7 | CD3δ |
| CD83 | OX40 | CD7 | CD3γ |
| CD83 | OX40 | CD7 | CD3ε |
| CD83 | OX40 | CD7 | FcγRI-γ |
| CD83 | OX40 | CD7 | FcγRIII-γ |
| CD83 | OX40 | CD7 | FcεRIβ |
| CD83 | OX40 | CD7 | FcεRIγ |
| CD83 | OX40 | CD7 | DAP10 |
| CD83 | OX40 | CD7 | DAP12 |
| CD83 | OX40 | CD7 | CD32 |
| CD83 | OX40 | CD7 | CD79a |
| CD83 | OX40 | CD7 | CD79b |
| CD83 | OX40 | BTNL3 | CD8 |
| CD83 | OX40 | BTNL3 | CD3ζ |
| CD83 | OX40 | BTNL3 | CD3δ |
| CD83 | OX40 | BTNL3 | CD3γ |
| CD83 | OX40 | BTNL3 | CD3ε |
| CD83 | OX40 | BTNL3 | FcγRI-γ |
| CD83 | OX40 | BTNL3 | FcγRIII-γ |
| CD83 | OX40 | BTNL3 | FcεRIβ |
| CD83 | OX40 | BTNL3 | FcεRIγ |
| CD83 | OX40 | BTNL3 | DAP10 |
| CD83 | OX40 | BTNL3 | DAP12 |
| CD83 | OX40 | BTNL3 | CD32 |
| CD83 | OX40 | BTNL3 | CD79a |
| CD83 | OX40 | BTNL3 | CD79b |
| CD83 | OX40 | NKG2D | CD8 |
| CD83 | OX40 | NKG2D | CDζ |
| CD83 | OX40 | NKG2D | CD3δ |
| CD83 | OX40 | NKG2D | CD3γ |
| CD83 | OX40 | NKG2D | CD3ε |
| CD83 | OX40 | NKG2D | FcγRI-γ |
| CD83 | OX40 | NKG2D | FcγRIII-γ |
| CD83 | OX40 | NKG2D | FcεRIβ |
| CD83 | OX40 | NKG2D | FcεRIγ |
| CD83 | OX40 | NKG2D | DAP10 |
| CD83 | OX40 | NKG2D | DAP12 |
| CD83 | OX40 | NKG2D | CD32 |
| CD83 | OX40 | NKG2D | CD79a |
| CD83 | OX40 | NKG2D | CD79b |
| CD83 | DAP10 | CD28 | CD8 |
| CD83 | DAP10 | CD28 | CD3ζ |
| CD83 | DAP10 | CD28 | CD3δ |
| CD83 | DAP10 | CD28 | CD3γ |
| CD83 | DAP10 | CD28 | CD3ε |
| CD83 | DAP10 | CD28 | FcγRI-γ |
| CD83 | DAP10 | CD28 | FcγRIII-γ |
| CD83 | DAP10 | CD28 | FcεRIβ |
| CD83 | DAP10 | CD28 | FcεRIγ |
| CD83 | DAP10 | CD28 | DAP10 |
| CD83 | DAP10 | CD28 | DAP12 |
| CD83 | DAP10 | CD28 | CD32 |
| CD83 | DAP10 | CD28 | CD79a |
| CD83 | DAP10 | CD28 | CD79b |
| CD83 | DAP10 | CD8 | CD8 |
| CD83 | DAP10 | CD8 | CD3ζ |
| CD83 | DAP10 | CD8 | CD3δ |
| CD83 | DAP10 | CD8 | CD3γ |
| CD83 | DAP10 | CD8 | CD3ε |
| CD83 | DAP10 | CD8 | FcγRI-γ |
| CD83 | DAP10 | CD8 | FcγRIII-γ |
| CD83 | DAP10 | CD8 | FcεRIβ |
| CD83 | DAP10 | CD8 | FcεRIγ |
| CD83 | DAP10 | CD8 | DAP10 |
| CD83 | DAP10 | CD8 | DAP12 |
| CD83 | DAP10 | CD8 | CD32 |
| CD83 | DAP10 | CD8 | CD79a |
| CD83 | DAP10 | CD8 | CD79b |
| CD83 | DAP10 | CD4 | CD8 |
| CD83 | DAP10 | CD4 | CD3ζ |
| CD83 | DAP10 | CD4 | CD3δ |
| CD83 | DAP10 | CD4 | CD3γ |
| CD83 | DAP10 | CD4 | CD3ε |
| CD83 | DAP10 | CD4 | FcγRI-γ |
| CD83 | DAP10 | CD4 | FcγRIII-γ |

TABLE 3-continued

| Third Generation CARs | | | |
|---|---|---|---|
| Scfu | Co-stimulatory Signal | Co-stimulatory Signal | Signal Domain |
| CD83 | DAP10 | CD4 | FcεRIβ |
| CD83 | DAP10 | CD4 | FcεRIγ |
| CD83 | DAP10 | CD4 | DAP10 |
| CD83 | DAP10 | CD4 | DAP12 |
| CD83 | DAP10 | CD4 | CD32 |
| CD83 | DAP10 | CD4 | CD79a |
| CD83 | DAP10 | CD4 | CD79b |
| CD83 | DAP10 | b2c | CD8 |
| CD83 | DAP10 | b2c | CD3ζ |
| CD83 | DAP10 | b2c | CD3δ |
| CD83 | DAP10 | b2c | CD3γ |
| CD83 | DAP10 | b2c | CD3ε |
| CD83 | DAP10 | b2c | FcγRI-γ |
| CD83 | DAP10 | b2c | FcγRIII-γ |
| CD83 | DAP10 | b2c | FcεRIβ |
| CD83 | DAP10 | b2c | FcεRIγ |
| CD83 | DAP10 | b2c | DAP10 |
| CD83 | DAP10 | b2c | DAP12 |
| CD83 | DAP10 | b2c | CD32 |
| CD83 | DAP10 | b2c | CD79a |
| CD83 | DAP10 | b2c | CD79b |
| CD83 | DAP10 | CD137/41BB | CD8 |
| CD83 | DAP10 | CD137/41BB | CD3ζ |
| CD83 | DAP10 | CD137/41BB | CD3δ |
| CD83 | DAP10 | CD137/41BB | CD3γ |
| CD83 | DAP10 | CD137/41BB | CD3ε |
| CD83 | DAP10 | CD137/41BB | FcγRI-γ |
| CD83 | DAP10 | CD137/41BB | FcγRIII-γ |
| CD83 | DAP10 | CD137/41BB | FcεRIβ |
| CD83 | DAP10 | CD137/41BB | FcεRIγ |
| CD83 | DAP10 | CD137/41BB | DAP10 |
| CD83 | DAP10 | CD137/41BB | DAP12 |
| CD83 | DAP10 | CD137/41BB | CD32 |
| CD83 | DAP10 | CD137/41BB | CD79a |
| CD83 | DAP10 | CD137/41BB | CD79b |
| CD83 | DAP10 | ICOS | CD8 |
| CD83 | DAP10 | ICOS | CD3ζ |
| CD83 | DAP10 | ICOS | CD3δ |
| CD83 | DAP10 | ICOS | CD3γ |
| CD83 | DAP10 | ICOS | CD3ε |
| CD83 | DAP10 | ICOS | FcγRI-γ |
| CD83 | DAP10 | ICOS | FcγRIII-γ |
| CD83 | DAP10 | ICOS | FcεRIβ |
| CD83 | DAP10 | ICOS | FcεRIγ |
| CD83 | DAP10 | ICOS | DAP10 |
| CD83 | DAP10 | ICOS | DAP12 |
| CD83 | DAP10 | ICOS | CD32 |
| CD83 | DAP10 | ICOS | CD79a |
| CD83 | DAP10 | ICOS | CD79b |
| CD83 | DAP10 | CD27 | CD8 |
| CD83 | DAP10 | CD27 | CD3ζ |
| CD83 | DAP10 | CD27 | CD3δ |
| CD83 | DAP10 | CD27 | CD3γ |
| CD83 | DAP10 | CD27 | CD3ε |
| CD83 | DAP10 | CD27 | FcγRI-γ |
| CD83 | DAP10 | CD27 | FcγRIII-γ |
| CD83 | DAP10 | CD27 | FcεRIβ |
| CD83 | DAP10 | CD27 | FcεRIγ |
| CD83 | DAP10 | CD27 | DAP10 |
| CD83 | DAP10 | CD27 | DAP12 |
| CD83 | DAP10 | CD27 | CD32 |
| CD83 | DAP10 | CD27 | CD79a |
| CD83 | DAP10 | CD27 | CD79b |
| CD83 | DAP10 | CD28δ | CD8 |
| CD83 | DAP10 | CD28δ | CD3ζ |
| CD83 | DAP10 | CD28δ | CD3δ |
| CD83 | DAP10 | CD28δ | CD3γ |
| CD83 | DAP10 | CD28δ | CD3ε |
| CD83 | DAP10 | CD28δ | FcγRI-γ |
| CD83 | DAP10 | CD28δ | FcγRIII-γ |
| CD83 | DAP10 | CD28δ | FcεRIβ |
| CD83 | DAP10 | CD28δ | FcεRIγ |
| CD83 | DAP10 | CD28δ | DAP10 |
| CD83 | DAP10 | CD28δ | DAP12 |
| CD83 | DAP10 | CD28δ | CD32 |

TABLE 3-continued

| Third Generation CARs | | | |
|---|---|---|---|
| Scfu | Co-stimulatory Signal | Co-stimulatory Signal | Signal Domain |
| CD83 | DAP10 | CD28δ | CD79a |
| CD83 | DAP10 | CD28δ | CD79b |
| CD83 | DAP10 | CD80 | CD8 |
| CD83 | DAP10 | CD80 | CD3ζ |
| CD83 | DAP10 | CD80 | CD3δ |
| CD83 | DAP10 | CD80 | CD3γ |
| CD83 | DAP10 | CD80 | CD3ε |
| CD83 | DAP10 | CD80 | FcγRI-γ |
| CD83 | DAP10 | CD80 | FcγRIII-γ |
| CD83 | DAP10 | CD80 | FcεRIβ |
| CD83 | DAP10 | CD80 | FcεRIγ |
| CD83 | DAP10 | CD80 | DAP10 |
| CD83 | DAP10 | CD80 | DAP12 |
| CD83 | DAP10 | CD80 | CD32 |
| CD83 | DAP10 | CD80 | CD79a |
| CD83 | DAP10 | CD80 | CD79b |
| CD83 | DAP10 | CD86 | CD8 |
| CD83 | DAP10 | CD86 | CD3ζ |
| CD83 | DAP10 | CD86 | CD3δ |
| CD83 | DAP10 | CD86 | CD3γ |
| CD83 | DAP10 | CD86 | CD3ε |
| CD83 | DAP10 | CD86 | FcγRI-γ |
| CD83 | DAP10 | CD86 | FcγRIII-γ |
| CD83 | DAP10 | CD86 | FcεRIβ |
| CD83 | DAP10 | CD86 | FcεRIγ |
| CD83 | DAP10 | CD86 | DAP10 |
| CD83 | DAP10 | CD86 | DAP12 |
| CD83 | DAP10 | CD86 | CD32 |
| CD83 | DAP10 | CD86 | CD79a |
| CD83 | DAP10 | CD86 | CD79b |
| CD83 | DAP10 | OX40 | CD8 |
| CD83 | DAP10 | OX40 | CD3ζ |
| CD83 | DAP10 | OX40 | CD3δ |
| CD83 | DAP10 | OX40 | CD3γ |
| CD83 | DAP10 | OX40 | CD3ε |
| CD83 | DAP10 | OX40 | FcγRI-γ |
| CD83 | DAP10 | OX40 | FcγRIII-γ |
| CD83 | DAP10 | OX40 | FcεRIβ |
| CD83 | DAP10 | OX40 | FcεRIγ |
| CD83 | DAP10 | OX40 | DAP10 |
| CD83 | DAP10 | OX40 | DAP12 |
| CD83 | DAP10 | OX40 | CD32 |
| CD83 | DAP10 | OX40 | CD79a |
| CD83 | DAP10 | OX40 | CD79b |
| CD83 | DAP10 | DAP10 | CD8 |
| CD83 | DAP10 | DAP10 | CD3ζ |
| CD83 | DAP10 | DAP10 | CD3δ |
| CD83 | DAP10 | DAP10 | CD3γ |
| CD83 | DAP10 | DAP10 | CD3ε |
| CD83 | DAP10 | DAP10 | FcγRI-γ |
| CD83 | DAP10 | DAP10 | FcγRIII-γ |
| CD83 | DAP10 | DAP10 | FcεRIβ |
| CD83 | DAP10 | DAP10 | FcεRIγ |
| CD83 | DAP10 | DAP10 | DAP10 |
| CD83 | DAP10 | DAP10 | DAP12 |
| CD83 | DAP10 | DAP10 | CD32 |
| CD83 | DAP10 | DAP10 | CD79a |
| CD83 | DAP10 | DAP10 | CD79b |
| CD83 | DAP10 | DAP12 | CD8 |
| CD83 | DAP10 | DAP12 | CD3ζ |
| CD83 | DAP10 | DAP12 | CD3δ |
| CD83 | DAP10 | DAP12 | CD3γ |
| CD83 | DAP10 | DAP12 | CD3ε |
| CD83 | DAP10 | DAP12 | FcγRI-γ |
| CD83 | DAP10 | DAP12 | FcγRIII-γ |
| CD83 | DAP10 | DAP12 | FcεRIβ |
| CD83 | DAP10 | DAP12 | FcεRIγ |
| CD83 | DAP10 | DAP12 | DAP10 |
| CD83 | DAP10 | DAP12 | DAP12 |
| CD83 | DAP10 | DAP12 | CD32 |
| CD83 | DAP10 | DAP12 | CD79a |
| CD83 | DAP10 | DAP12 | CD79b |
| CD83 | DAP10 | MyD88 | CD8 |
| CD83 | DAP10 | MyD88 | CD3ζ |
| CD83 | DAP10 | MyD88 | CD3δ |

TABLE 3-continued

| Third Generation CARs | | | |
|---|---|---|---|
| Scfu | Co-stimulatory Signal | Co-stimulatory Signal | Signal Domain |
| CD83 | DAP10 | MyD88 | CD3γ |
| CD83 | DAP10 | MyD88 | CD3ε |
| CD83 | DAP10 | MyD88 | FcγRI-γ |
| CD83 | DAP10 | MyD88 | FcγRIII-γ |
| CD83 | DAP10 | MyD88 | FcεRIβ |
| CD83 | DAP10 | MyD88 | FcεRIγ |
| CD83 | DAP10 | MyD88 | DAP10 |
| CD83 | DAP10 | MyD88 | DAP12 |
| CD83 | DAP10 | MyD88 | CD32 |
| CD83 | DAP10 | MyD88 | CD79a |
| CD83 | DAP10 | MyD88 | CD79b |
| CD83 | DAP10 | CD7 | CD8 |
| CD83 | DAP10 | CD7 | CD3ζ |
| CD83 | DAP10 | CD7 | CD3δ |
| CD83 | DAP10 | CD7 | CD3γ |
| CD83 | DAP10 | CD7 | CD3ε |
| CD83 | DAP10 | CD7 | FcγRI-γ |
| CD83 | DAP10 | CD7 | FcγRIII-γ |
| CD83 | DAP10 | CD7 | FcεRIβ |
| CD83 | DAP10 | CD7 | FcεRIγ |
| CD83 | DAP10 | CD7 | DAP10 |
| CD83 | DAP10 | CD7 | DAP12 |
| CD83 | DAP10 | CD7 | CD32 |
| CD83 | DAP10 | CD7 | CD79a |
| CD83 | DAP10 | CD7 | CD79b |
| CD83 | DAP10 | BTNL3 | CD8 |
| CD83 | DAP10 | BTNL3 | CD3ζ |
| CD83 | DAP10 | BTNL3 | CD3δ |
| CD83 | DAP10 | BTNL3 | CD3γ |
| CD83 | DAP10 | BTNL3 | CD3ε |
| CD83 | DAP10 | BTNL3 | FcγRI-γ |
| CD83 | DAP10 | BTNL3 | FcγRIII-γ |
| CD83 | DAP10 | BTNL3 | FcεRIβ |
| CD83 | DAP10 | BTNL3 | FcεRIγ |
| CD83 | DAP10 | BTNL3 | DAP10 |
| CD83 | DAP10 | BTNL3 | DAP12 |
| CD83 | DAP10 | BTNL3 | CD32 |
| CD83 | DAP10 | BTNL3 | CD79a |
| CD83 | DAP10 | BTNL3 | CD79b |
| CD83 | DAP10 | NKG2D | CD8 |
| CD83 | DAP10 | NKG2D | CD3ζ |
| CD83 | DAP10 | NKG2D | CD3δ |
| CD83 | DAP10 | NKG2D | CD3γ |
| CD83 | DAP10 | NKG2D | CD3ε |
| CD83 | DAP10 | NKG2D | FcγRI-γ |
| CD83 | DAP10 | NKG2D | FcγRII-γ |
| CD83 | DAP10 | NKG2D | FcεRIβ |
| CD83 | DAP10 | NKG2D | FcεRIγ |
| CD83 | DAP10 | NKG2D | DAP10 |
| CD83 | DAP10 | NKG2D | DAP12 |
| CD83 | DAP10 | NKG2D | CD32 |
| CD83 | DAP10 | NKG2D | CD79a |
| CD83 | DAP10 | NKG2D | CD79b |
| CD83 | DAP12 | CD28 | CD8 |
| CD83 | DAP12 | CD28 | CD3ζ |
| CD83 | DAP12 | CD28 | CD3δ |
| CD83 | DAP12 | CD28 | CD3γ |
| CD83 | DAP12 | CD28 | CD3ε |
| CD83 | DAP12 | CD28 | FcγRI-γ |
| CD83 | DAP12 | CD28 | FcγRIII-γ |
| CD83 | DAP12 | CD28 | FcεRIβ |
| CD83 | DAP12 | CD28 | FcεRIγ |
| CD83 | DAP12 | CD28 | DAP10 |
| CD83 | DAP12 | CD28 | DAP12 |
| CD83 | DAP12 | CD28 | CD32 |
| CD83 | DAP12 | CD28 | CD79a |
| CD83 | DAP12 | CD28 | CD79b |
| CD83 | DAP12 | CD8 | CD8 |
| CD83 | DAP12 | CD8 | CD3ζ |
| CD83 | DAP12 | CD8 | CD3δ |
| CD83 | DAP12 | CD8 | CD3γ |
| CD83 | DAP12 | CD8 | CD3ε |
| CD83 | DAP12 | CD8 | FcγRI-γ |
| CD83 | DAP12 | CD8 | FcγRIII-γ |
| CD83 | DAP12 | CD8 | FcεRIβ |

TABLE 3-continued

| Third Generation CARs | | | |
|---|---|---|---|
| Scfu | Co-stimulatory Signal | Co-stimulatory Signal | Signal Domain |
| CD83 | DAP12 | CD8 | FcεRIγ |
| CD83 | DAP12 | CD8 | DAP10 |
| CD83 | DAP12 | CD8 | DAP12 |
| CD83 | DAP12 | CD8 | CD32 |
| CD83 | DAP12 | CD8 | CD79a |
| CD83 | DAP12 | CD8 | CD79b |
| CD83 | DAP12 | CD4 | CD8 |
| CD83 | DAP12 | CD4 | CD3ζ |
| CD83 | DAP12 | CD4 | CD3δ |
| CD83 | DAP12 | CD4 | CD3γ |
| CD83 | DAP12 | CD4 | CD3ε |
| CD83 | DAP12 | CD4 | FcγRI-γ |
| CD83 | DAP12 | CD4 | FcγRIII-γ |
| CD83 | DAP12 | CD4 | FcεRIβ |
| CD83 | DAP12 | CD4 | FcεRIγ |
| CD83 | DAP12 | CD4 | DAP10 |
| CD83 | DAP12 | CD4 | DAP12 |
| CD83 | DAP12 | CD4 | CD32 |
| CD83 | DAP12 | CD4 | CD79a |
| CD83 | DAP12 | CD4 | CD79b |
| CD83 | DAP12 | b2c | CD8 |
| CD83 | DAP12 | b2c | CD3ζ |
| CD83 | DAP12 | b2c | CD3δ |
| CD83 | DAP12 | b2c | CD3γ |
| CD83 | DAP12 | b2c | CD3ε |
| CD83 | DAP12 | b2c | FcγRI-γ |
| CD83 | DAP12 | b2c | FcγRIII-γ |
| CD83 | DAP12 | b2c | FcεRIβ |
| CD83 | DAP12 | b2c | FcεRIγ |
| CD83 | DAP12 | b2c | DAP10 |
| CD83 | DAP12 | b2c | DAP12 |
| CD83 | DAP12 | b2c | CD32 |
| CD83 | DAP12 | b2c | CD79a |
| CD83 | DAP12 | b2c | CD79b |
| CD83 | DAP12 | CD137/41BB | CD8 |
| CD83 | DAP12 | CD137/41BB | CD3ζ |
| CD83 | DAP12 | CD137/41BB | CD3δ |
| CD83 | DAP12 | CD137/41BB | CD3γ |
| CD83 | DAP12 | CD137/41BB | CD3ε |
| CD83 | DAP12 | CD137/41BB | FcγRI-γ |
| CD83 | DAP12 | CD137/41BB | FcγRIII-γ |
| CD83 | DAP12 | CD137/41BB | FcεRIβ |
| CD83 | DAP12 | CD137/41BB | FcεRIγ |
| CD83 | DAP12 | CD137/41BB | DAP10 |
| CD83 | DAP12 | CD137/41BB | DAP12 |
| CD83 | DAP12 | CD137/41BB | CD32 |
| CD83 | DAP12 | CD137/41BB | CD79a |
| CD83 | DAP12 | CD137/41BB | CD79b |
| CD83 | DAP12 | ICOS | CD8 |
| CD83 | DAP12 | ICOS | CD3ζ |
| CD83 | DAP12 | ICOS | CD3δ |
| CD83 | DAP12 | ICOS | CD3γ |
| CD83 | DAP12 | ICOS | CD3ε |
| CD83 | DAP12 | ICOS | FcγRI-γ |
| CD83 | DAP12 | ICOS | FcγRIII-γ |
| CD83 | DAP12 | ICOS | FcεRIβ |
| CD83 | DAP12 | ICOS | FcεRIγ |
| CD83 | DAP12 | ICOS | DAP10 |
| CD83 | DAP12 | ICOS | DAP12 |
| CD83 | DAP12 | ICOS | CD32 |
| CD83 | DAP12 | ICOS | CD79a |
| CD83 | DAP12 | ICOS | CD79b |
| CD83 | DAP12 | CD27 | CD8 |
| CD83 | DAP12 | CD27 | CD3ζ |
| CD83 | DAP12 | CD27 | CD3δ |
| CD83 | DAP12 | CD27 | CD3γ |
| CD83 | DAP12 | CD27 | CD3ε |
| CD83 | DAP12 | CD27 | FcγRI-γ |
| CD83 | DAP12 | CD27 | FcγRIII-γ |
| CD83 | DAP12 | CD27 | FcεRIβ |
| CD83 | DAP12 | CD27 | FcεRIγ |
| CD83 | DAP12 | CD27 | DAP10 |
| CD83 | DAP12 | CD27 | DAP12 |
| CD83 | DAP12 | CD27 | CD32 |
| CD83 | DAP12 | CD27 | CD79a |

TABLE 3-continued

| Third Generation CARs | | | |
|---|---|---|---|
| Scfu | Co-stimulatory Signal | Co-stimulatory Signal | Signal Domain |
| CD83 | DAP12 | CD27 | CD79b |
| CD83 | DAP12 | CD28δ | CD8 |
| CD83 | DAP12 | CD28δ | CD3ζ |
| CD83 | DAP12 | CD28δ | CD3δ |
| CD83 | DAP12 | CD28δ | CD3γ |
| CD83 | DAP12 | CD28δ | CD3ε |
| CD83 | DAP12 | CD28δ | FcγRI-γ |
| CD83 | DAP12 | CD28δ | FcγRIII-γ |
| CD83 | DAP12 | CD28δ | FcεRIβ |
| CD83 | DAP12 | CD28δ | FcεRIγ |
| CD83 | DAP12 | CD28δ | DAP10 |
| CD83 | DAP12 | CD28δ | DAP12 |
| CD83 | DAP12 | CD28δ | CD32 |
| CD83 | DAP12 | CD28δ | CD79a |
| CD83 | DAP12 | CD28δ | CD79b |
| CD83 | DAP12 | CD80 | CD8 |
| CD83 | DAP12 | CD80 | CD3ζ |
| CD83 | DAP12 | CD80 | CD3δ |
| CD83 | DAP12 | CD80 | CD3γ |
| CD83 | DAP12 | CD80 | CD3c |
| CD83 | DAP12 | CD80 | FcγRI-γ |
| CD83 | DAP12 | CD80 | FcγRIII-γ |
| CD83 | DAP12 | CD80 | FcεRIβ |
| CD83 | DAP12 | CD80 | FcεRIγ |
| CD83 | DAP12 | CD80 | DAP10 |
| CD83 | DAP12 | CD80 | DAP12 |
| CD83 | DAP12 | CD80 | CD32 |
| CD83 | DAP12 | CD80 | CD79a |
| CD83 | DAP12 | CD80 | CD79b |
| CD83 | DAP12 | CD86 | CD8 |
| CD83 | DAP12 | CD86 | CDζ |
| CD83 | DAP12 | CD86 | CD3δ |
| CD83 | DAP12 | CD86 | CD3γ |
| CD83 | DAP12 | CD86 | CD3ε |
| CD83 | DAP12 | CD86 | FcγRI-γ |
| CD83 | DAP12 | CD86 | FcγRIII-γ |
| CD83 | DAP12 | CD86 | FcεRIβ |
| CD83 | DAP12 | CD86 | FcεRIγ |
| CD83 | DAP12 | CD86 | DAP10 |
| CD83 | DAP12 | CD86 | DAP12 |
| CD83 | DAP12 | CD86 | CD32 |
| CD83 | DAP12 | CD86 | CD79a |
| CD83 | DAP12 | CD86 | CD79b |
| CD83 | DAP12 | OX40 | CD8 |
| CD83 | DAP12 | OX40 | CD3ζ |
| CD83 | DAP12 | OX40 | CD3δ |
| CD83 | DAP12 | OX40 | CD3γ |
| CD83 | DAP12 | OX40 | CD3ε |
| CD83 | DAP12 | OX40 | FcγRI-γ |
| CD83 | DAP12 | OX40 | FcγRIII-γ |
| CD83 | DAP12 | OX40 | FcεRIβ |
| CD83 | DAP12 | OX40 | FcεRIγ |
| CD83 | DAP12 | OX40 | DAP10 |
| CD83 | DAP12 | OX40 | DAP12 |
| CD83 | DAP12 | OX40 | CD32 |
| CD83 | DAP12 | OX40 | CD79a |
| CD83 | DAP12 | OX40 | CD79b |
| CD83 | DAP12 | DAP10 | CD8 |
| CD83 | DAP12 | DAP10 | CD3ζ |
| CD83 | DAP12 | DAP10 | CD3δ |
| CD83 | DAP12 | DAP10 | CD3γ |
| CD83 | DAP12 | DAP10 | CD3ε |
| CD83 | DAP12 | DAP10 | FcγRI-γ |
| CD83 | DAP12 | DAP10 | FcγRIII-γ |
| CD83 | DAP12 | DAP10 | FcεRIβ |
| CD83 | DAP12 | DAP10 | FcεRIγ |
| CD83 | DAP12 | DAP10 | DAP10 |
| CD83 | DAP12 | DAP10 | DAP12 |
| CD83 | DAP12 | DAP10 | CD32 |
| CD83 | DAP12 | DAP10 | CD79a |
| CD83 | DAP12 | DAP10 | CD79b |
| CD83 | DAP12 | DAP12 | CD8 |
| CD83 | DAP12 | DAP12 | CD3ζ |
| CD83 | DAP12 | DAP12 | CD3δ |
| CD83 | DAP12 | DAP12 | CD3γ |

TABLE 3-continued

| Third Generation CARs | | | |
|---|---|---|---|
| Scfu | Co-stimulatory Signal | Co-stimulatory Signal | Signal Domain |
| CD83 | DAP12 | DAP12 | CD3ε |
| CD83 | DAP12 | DAP12 | FcγRI-γ |
| CD83 | DAP12 | DAP12 | FcγRIII-γ |
| CD83 | DAP12 | DAP12 | FcεRIβ |
| CD83 | DAP12 | DAP12 | FcεRIγ |
| CD83 | DAP12 | DAP12 | DAP10 |
| CD83 | DAP12 | DAP12 | DAP12 |
| CD83 | DAP12 | DAP12 | CD32 |
| CD83 | DAP12 | DAP12 | CD79a |
| CD83 | DAP12 | DAP12 | CD79b |
| CD83 | DAP12 | MyD88 | CD8 |
| CD83 | DAP12 | MyD88 | CD3ζ |
| CD83 | DAP12 | MyD88 | CD3δ |
| CD83 | DAP12 | MyD88 | CD3γ |
| CD83 | DAP12 | MyD88 | CD3ε |
| CD83 | DAP12 | MyD88 | FcγRI-γ |
| CD83 | DAP12 | MyD88 | FcγRIII-γ |
| CD83 | DAP12 | MyD88 | FcεRI-β |
| CD83 | DAP12 | MyD88 | FcεRIγ |
| CD83 | DAP12 | MyD88 | DAP10 |
| CD83 | DAP12 | MyD88 | DAP12 |
| CD83 | DAP12 | MyD88 | CD32 |
| CD83 | DAP12 | MyD88 | CD79a |
| CD83 | DAP12 | MyD88 | CD79b |
| CD83 | DAP12 | CD7 | CD8 |
| CD83 | DAP12 | CD7 | CD3ζ |
| CD83 | DAP12 | CD7 | CD3δ |
| CD83 | DAP12 | CD7 | CD3γ |
| CD83 | DAP12 | CD7 | CD3ε |
| CD83 | DAP12 | CD7 | FcγRI-γ |
| CD83 | DAP12 | CD7 | FcγRIII-γ |
| CD83 | DAP12 | CD7 | FcεRIβ |
| CD83 | DAP12 | CD7 | FcεRIγ |
| CD83 | DAP12 | CD7 | DAP10 |
| CD83 | DAP12 | CD7 | DAP12 |
| CD83 | DAP12 | CD7 | CD32 |
| CD83 | DAP12 | CD7 | CD79a |
| CD83 | DAP12 | CD7 | CD79b |
| CD83 | DAP12 | BTNL3 | CD8 |
| CD83 | DAP12 | BTNL3 | CD3ζ |
| CD83 | DAP12 | BTNL3 | CD3δ |
| CD83 | DAP12 | BTNL3 | CD3γ |
| CD83 | DAP12 | BTNL3 | CD3ε |
| CD83 | DAP12 | BTNL3 | FcγRI-γ |
| CD83 | DAP12 | BTNL3 | FcγRIII-γ |
| CD83 | DAP12 | BTNL3 | FcεRIβ |
| CD83 | DAP12 | BTNL3 | FcεRIγ |
| CD83 | DAP12 | BTNL3 | DAP10 |
| CD83 | DAP12 | BTNL3 | DAP12 |
| CD83 | DAP12 | BTNL3 | CD32 |
| CD83 | DAP12 | BTNL3 | CD79a |
| CD83 | DAP12 | BTNL3 | CD79b |
| CD83 | DAP12 | NKG2D | CD8 |
| CD83 | DAP12 | NKG2D | CD3ζ |
| CD83 | DAP12 | NKG2D | CD3δ |
| CD83 | DAP12 | NKG2D | CD3γ |
| CD83 | DAP12 | NKG2D | CD3ε |
| CD83 | DAP12 | NKG2D | FcγRI-γ |
| CD83 | DAP12 | NKG2D | FcγRII-γ |
| CD83 | DAP12 | NKG2D | FcεRIβ |
| CD83 | DAP12 | NKG2D | FcεRIγ |
| CD83 | DAP12 | NKG2D | DAP10 |
| CD83 | DAP12 | NKG2D | DAP12 |
| CD83 | DAP12 | NKG2D | CD32 |
| CD83 | DAP12 | NKG2D | CD79a |
| CD83 | DAP12 | NKG2D | CD79b |
| CD83 | MyD88 | CD28 | CD8 |
| CD83 | MyD88 | CD28 | CDζ |
| CD83 | MyD88 | CD28 | CD3δ |
| CD83 | MyD88 | CD28 | CD3γ |
| CD83 | MyD88 | CD28 | CD3ε |
| CD83 | MyD88 | CD28 | FcγRI-γ |
| CD83 | MyD88 | CD28 | FcγRIII-γ |
| CD83 | MyD88 | CD28 | FcεRIβ |
| CD83 | MyD88 | CD28 | FcεRIγ |

TABLE 3-continued

| Third Generation CARs | | | |
|---|---|---|---|
| Scfu | Co-stimulatory Signal | Co-stimulatory Signal | Signal Domain |
| CD83 | MyD88 | CD28 | DAP10 |
| CD83 | MyD88 | CD28 | DAP12 |
| CD83 | MyD88 | CD28 | CD32 |
| CD83 | MyD88 | CD28 | CD79a |
| CD83 | MyD88 | CD28 | CD79b |
| CD83 | MyD88 | CD8 | CD8 |
| CD83 | MyD88 | CD8 | CD3ζ |
| CD83 | MyD88 | CD8 | CD3δ |
| CD83 | MyD88 | CD8 | CD3γ |
| CD83 | MyD88 | CD8 | CD3ε |
| CD83 | MyD88 | CD8 | FcγRI-γ |
| CD83 | MyD88 | CD8 | FcγRIII-γ |
| CD83 | MyD88 | CD8 | FcεRIβ |
| CD83 | MyD88 | CD8 | FcεRIγ |
| CD83 | MyD88 | CD8 | DAP10 |
| CD83 | MyD88 | CD8 | DAP12 |
| CD83 | MyD88 | CD8 | CD32 |
| CD83 | MyD88 | CD8 | CD79a |
| CD83 | MyD88 | CD8 | CD79b |
| CD83 | MyD88 | CD4 | CD8 |
| CD83 | MyD88 | CD4 | CD3ζ |
| CD83 | MyD88 | CD4 | CD3δ |
| CD83 | MyD88 | CD4 | CD3γ |
| CD83 | MyD88 | CD4 | CD3ε |
| CD83 | MyD88 | CD4 | FcγRI-γ |
| CD83 | MyD88 | CD4 | FcγRIII-γ |
| CD83 | MyD88 | CD4 | FcεRIβ |
| CD83 | MyD88 | CD4 | FcεRIγ |
| CD83 | MyD88 | CD4 | DAP10 |
| CD83 | MyD88 | CD4 | DAP12 |
| CD83 | MyD88 | CD4 | CD32 |
| CD83 | MyD88 | CD4 | CD79a |
| CD83 | MyD88 | CD4 | CD79b |
| CD83 | MyD88 | b2c | CD8 |
| CD83 | MyD88 | b2c | CD3ζ |
| CD83 | MyD88 | b2c | CD3δ |
| CD83 | MyD88 | b2c | CD3γ |
| CD83 | MyD88 | b2c | CD3ε |
| CD83 | MyD88 | b2c | FcγRI-γ |
| CD83 | MyD88 | b2c | FcγRIII-γ |
| CD83 | MyD88 | b2c | FcεRIβ |
| CD83 | MyD88 | b2c | FcεRIγ |
| CD83 | MyD88 | b2c | DAP10 |
| CD83 | MyD88 | b2c | DAP12 |
| CD83 | MyD88 | b2c | CD32 |
| CD83 | MyD88 | b2c | CD79a |
| CD83 | MyD88 | b2c | CD79b |
| CD83 | MyD88 | CD137/41BB | CD8 |
| CD83 | MyD88 | CD137/41BB | CD3ζ |
| CD83 | MyD88 | CD137/41BB | CD3δ |
| CD83 | MyD88 | CD137/41BB | CD3γ |
| CD83 | MyD88 | CD137/41BB | CD3ε |
| CD83 | MyD88 | CD137/41BB | FcγRI-γ |
| CD83 | MyD88 | CD137/41BB | FcγRIII-γ |
| CD83 | MyD88 | CD137/41BB | FcεRIβ |
| CD83 | MyD88 | CD137/41BB | FcεRIγ |
| CD83 | MyD88 | CD137/41BB | DAP10 |
| CD83 | MyD88 | CD137/41BB | DAP12 |
| CD83 | MyD88 | CD137/41BB | CD32 |
| CD83 | MyD88 | CD137/41BB | CD79a |
| CD83 | MyD88 | CD137/41BB | CD79b |
| CD83 | MyD88 | ICOS | CD8 |
| CD83 | MyD88 | ICOS | CD3ζ |
| CD83 | MyD88 | ICOS | CD3δ |
| CD83 | MyD88 | ICOS | CD3γ |
| CD83 | MyD88 | ICOS | CD3ε |
| CD83 | MyD88 | ICOS | FcγRI-γ |
| CD83 | MyD88 | ICOS | FcγRIII-γ |
| CD83 | MyD88 | ICOS | FcεRIβ |
| CD83 | MyD88 | ICOS | FcεRIγ |
| CD83 | MyD88 | ICOS | DAP10 |
| CD83 | MyD88 | ICOS | DAP12 |
| CD83 | MyD88 | ICOS | CD32 |
| CD83 | MyD88 | ICOS | CD79a |
| CD83 | MyD88 | ICOS | CD79b |

TABLE 3-continued

Third Generation CARs

| Scfu | Co-stimulatory Signal | Co-stimulatory Signal | Signal Domain |
|---|---|---|---|
| CD83 | MyD88 | CD27 | CD8 |
| CD83 | MyD88 | CD27 | CD3ζ |
| CD83 | MyD88 | CD27 | CD3δ |
| CD83 | MyD88 | CD27 | CD3γ |
| CD83 | MyD88 | CD27 | CD3ε |
| CD83 | MyD88 | CD27 | FcγRI-γ |
| CD83 | MyD88 | CD27 | FcγRIII-γ |
| CD83 | MyD88 | CD27 | FcεRIβ |
| CD83 | MyD88 | CD27 | FcεRIγ |
| CD83 | MyD88 | CD27 | DAP10 |
| CD83 | MyD88 | CD27 | DAP12 |
| CD83 | MyD88 | CD27 | CD32 |
| CD83 | MyD88 | CD27 | CD79a |
| CD83 | MyD88 | CD27 | CD79b |
| CD83 | MyD88 | CD28δ | CD8 |
| CD83 | MyD88 | CD28δ | CD3ζ |
| CD83 | MyD88 | CD28δ | CD3δ |
| CD83 | MyD88 | CD28δ | CD3γ |
| CD83 | MyD88 | CD28δ | CD3ε |
| CD83 | MyD88 | CD28δ | FcγRI-γ |
| CD83 | MyD88 | CD28δ | FcγRIII-γ |
| CD83 | MyD88 | CD28δ | FcεRIβ |
| CD83 | MyD88 | CD28δ | FcεRIγ |
| CD83 | MyD88 | CD28δ | DAP10 |
| CD83 | MyD88 | CD28δ | DAP12 |
| CD83 | MyD88 | CD28δ | CD32 |
| CD83 | MyD88 | CD28δ | CD79a |
| CD83 | MyD88 | CD28δ | CD79b |
| CD83 | MyD88 | CD80 | CD8 |
| CD83 | MyD88 | CD80 | CD3ζ |
| CD83 | MyD88 | CD80 | CD3δ |
| CD83 | MyD88 | CD80 | CD3γ |
| CD83 | MyD88 | CD80 | CD3ε |
| CD83 | MyD88 | CD80 | FcγRI-γ |
| CD83 | MyD88 | CD80 | FcγRIII-γ |
| CD83 | MyD88 | CD80 | FcεRIβ |
| CD83 | MyD88 | CD80 | FcεRIγ |
| CD83 | MyD88 | CD80 | DAP10 |
| CD83 | MyD88 | CD80 | DAP12 |
| CD83 | MyD88 | CD80 | CD32 |
| CD83 | MyD88 | CD80 | CD79a |
| CD83 | MyD88 | CD80 | CD79b |
| CD83 | MyD88 | CD86 | CD8 |
| CD83 | MyD88 | CD86 | CD3ζ |
| CD83 | MyD88 | CD86 | CD3δ |
| CD83 | MyD88 | CD86 | CD3γ |
| CD83 | MyD88 | CD86 | CD3ε |
| CD83 | MyD88 | CD86 | FcγRI-γ |
| CD83 | MyD88 | CD86 | FcγRIII-γ |
| CD83 | MyD88 | CD86 | FcεRIβ |
| CD83 | MyD88 | CD86 | FcεRIγ |
| CD83 | MyD88 | CD86 | DAP10 |
| CD83 | MyD88 | CD86 | DAP12 |
| CD83 | MyD88 | CD86 | CD32 |
| CD83 | MyD88 | CD86 | CD79a |
| CD83 | MyD88 | CD86 | CD79b |
| CD83 | MyD88 | OX40 | CD8 |
| CD83 | MyD88 | OX40 | CD3ζ |
| CD83 | MyD88 | OX40 | CD3δ |
| CD83 | MyD88 | OX40 | CD3γ |
| CD83 | MyD88 | OX40 | CD3ε |
| CD83 | MyD88 | OX40 | FcγRI-γ |
| CD83 | MyD88 | OX40 | FcγRIII-γ |
| CD83 | MyD88 | OX40 | FcεRIβ |
| CD83 | MyD88 | OX40 | FcεRIγ |
| CD83 | MyD88 | OX40 | DAP10 |
| CD83 | MyD88 | OX40 | DAP12 |
| CD83 | MyD88 | OX40 | CD32 |
| CD83 | MyD88 | OX40 | CD79a |
| CD83 | MyD88 | OX40 | CD79b |
| CD83 | MyD88 | DAP10 | CD8 |
| CD83 | MyD88 | DAP10 | CD3ζ |
| CD83 | MyD88 | DAP10 | CD3δ |
| CD83 | MyD88 | DAP10 | CD3γ |
| CD83 | MyD88 | DAP10 | CD3ε |

TABLE 3-continued

Third Generation CARs

| Scfu | Co-stimulatory Signal | Co-stimulatory Signal | Signal Domain |
|---|---|---|---|
| CD83 | MyD88 | DAP10 | FcγRI-γ |
| CD83 | MyD88 | DAP10 | FcγRIII-γ |
| CD83 | MyD88 | DAP10 | FcεRIβ |
| CD83 | MyD88 | DAP10 | FcεRIγ |
| CD83 | MyD88 | DAP10 | DAP10 |
| CD83 | MyD88 | DAP10 | DAP12 |
| CD83 | MyD88 | DAP10 | CD32 |
| CD83 | MyD88 | DAP10 | CD79a |
| CD83 | MyD88 | DAP10 | CD79b |
| CD83 | MyD88 | DAP12 | CD8 |
| CD83 | MyD88 | DAP12 | CD3ζ |
| CD83 | MyD88 | DAP12 | CD3δ |
| CD83 | MyD88 | DAP12 | CD3γ |
| CD83 | MyD88 | DAP12 | CD3ε |
| CD83 | MyD88 | DAP12 | FcγRI-γ |
| CD83 | MyD88 | DAP12 | FcγRIII-γ |
| CD83 | MyD88 | DAP12 | FcεRIβ |
| CD83 | MyD88 | DAP12 | FcεRIγ |
| CD83 | MyD88 | DAP12 | DAP10 |
| CD83 | MyD88 | DAP12 | DAP12 |
| CD83 | MyD88 | DAP12 | CD32 |
| CD83 | MyD88 | DAP12 | CD79a |
| CD83 | MyD88 | DAP12 | CD79b |
| CD83 | MyD88 | MyD88 | CD8 |
| CD83 | MyD88 | MyD88 | CD3ζ |
| CD83 | MyD88 | MyD88 | CD3δ |
| CD83 | MyD88 | MyD88 | CD3γ |
| CD83 | MyD88 | MyD88 | CD3ε |
| CD83 | MyD88 | MyD88 | FcγRI-γ |
| CD83 | MyD88 | MyD88 | FcγRIII-γ |
| CD83 | MyD88 | MyD88 | FcεRIβ |
| CD83 | MyD88 | MyD88 | FcεRIγ |
| CD83 | MyD88 | MyD88 | DAP10 |
| CD83 | MyD88 | MyD88 | DAP12 |
| CD83 | MyD88 | MyD88 | CD32 |
| CD83 | MyD88 | MyD88 | CD79a |
| CD83 | MyD88 | MyD88 | CD79b |
| CD83 | MyD88 | CD7 | CD8 |
| CD83 | MyD88 | CD7 | CD3ζ |
| CD83 | MyD88 | CD7 | CD3δ |
| CD83 | MyD88 | CD7 | CD3γ |
| CD83 | MyD88 | CD7 | CD3ε |
| CD83 | MyD88 | CD7 | FcγRI-γ |
| CD83 | MyD88 | CD7 | FcγRIII-γ |
| CD83 | MyD88 | CD7 | FcεRIβ |
| CD83 | MyD88 | CD7 | FcεRIγ |
| CD83 | MyD88 | CD7 | DAP10 |
| CD83 | MyD88 | CD7 | DAP12 |
| CD83 | MyD88 | CD7 | CD32 |
| CD83 | MyD88 | CD7 | CD79a |
| CD83 | MyD88 | CD7 | CD79b |
| CD83 | MyD88 | BTNL3 | CD8 |
| CD83 | MyD88 | BTNL3 | CD3ζ |
| CD83 | MyD88 | BTNL3 | CD3δ |
| CD83 | MyD88 | BTNL3 | CD3γ |
| CD83 | MyD88 | BTNL3 | CD3ε |
| CD83 | MyD88 | BTNL3 | FcγRI-γ |
| CD83 | MyD88 | BTNL3 | FcγRIII-γ |
| CD83 | MyD88 | BTNL3 | FcεRIβ |
| CD83 | MyD88 | BTNL3 | FcεRIγ |
| CD83 | MyD88 | BTNL3 | DAP10 |
| CD83 | MyD88 | BTNL3 | DAP12 |
| CD83 | MyD88 | BTNL3 | CD32 |
| CD83 | MyD88 | BTNL3 | CD79a |
| CD83 | MyD88 | BTNL3 | CD79b |
| CD83 | MyD88 | NKG2D | CD8 |
| CD83 | MyD88 | NKG2D | CD3ζ |
| CD83 | MyD88 | NKG2D | CD3δ |
| CD83 | MyD88 | NKG2D | CD3γ |
| CD83 | MyD88 | NKG2D | CD3ε |
| CD83 | MyD88 | NKG2D | FcγRI-γ |
| CD83 | MyD88 | NKG2D | FcγRIII-γ |
| CD83 | MyD88 | NKG2D | FcεRIβ |
| CD83 | MyD88 | NKG2D | FcεRIγ |
| CD83 | MyD88 | NKG2D | DAP10 |

TABLE 3-continued

Third Generation CARs

| Scfu | Co-stimulatory Signal | Co-stimulatory Signal | Signal Domain |
|---|---|---|---|
| CD83 | MyD88 | NKG2D | DAP12 |
| CD83 | MyD88 | NKG2D | CD32 |
| CD83 | MyD88 | NKG2D | CD79a |
| CD83 | MyD88 | NKG2D | CD79b |
| CD83 | CD7 | CD28 | CD8 |
| CD83 | CD7 | CD28 | CD3ζ |
| CD83 | CD7 | CD28 | CD3δ |
| CD83 | CD7 | CD28 | CD3γ |
| CD83 | CD7 | CD28 | CD3ε |
| CD83 | CD7 | CD28 | FcγRI-γ |
| CD83 | CD7 | CD28 | FcγRIII-γ |
| CD83 | CD7 | CD28 | FcεRIβ |
| CD83 | CD7 | CD28 | FcεRIγ |
| CD83 | CD7 | CD28 | DAP10 |
| CD83 | CD7 | CD28 | DAP12 |
| CD83 | CD7 | CD28 | CD32 |
| CD83 | CD7 | CD28 | CD79a |
| CD83 | CD7 | CD28 | CD79b |
| CD83 | CD7 | CD8 | CD8 |
| CD83 | CD7 | CD8 | CD3ζ |
| CD83 | CD7 | CD8 | CD3δ |
| CD83 | CD7 | CD8 | CD3γ |
| CD83 | CD7 | CD8 | CD3ε |
| CD83 | CD7 | CD8 | FcγRI-γ |
| CD83 | CD7 | CD8 | FcγRIII-γ |
| CD83 | CD7 | CD8 | FcεRIβ |
| CD83 | CD7 | CD8 | FcεRIγ |
| CD83 | CD7 | CD8 | DAP10 |
| CD83 | CD7 | CD8 | DAP12 |
| CD83 | CD7 | CD8 | CD32 |
| CD83 | CD7 | CD8 | CD79a |
| CD83 | CD7 | CD8 | CD79b |
| CD83 | CD7 | CD4 | CD8 |
| CD83 | CD7 | CD4 | CDζ |
| CD83 | CD7 | CD4 | CD3δ |
| CD83 | CD7 | CD4 | CD3γ |
| CD83 | CD7 | CD4 | CD3ε |
| CD83 | CD7 | CD4 | FcγRI-γ |
| CD83 | CD7 | CD4 | FcγRIII-γ |
| CD83 | CD7 | CD4 | FcεRIβ |
| CD83 | CD7 | CD4 | FcεRIγ |
| CD83 | CD7 | CD4 | DAP10 |
| CD83 | CD7 | CD4 | DAP12 |
| CD83 | CD7 | CD4 | CD32 |
| CD83 | CD7 | CD4 | CD79a |
| CD83 | CD7 | CD4 | CD79b |
| CD83 | CD7 | b2c | CD8 |
| CD83 | CD7 | b2c | CD3ζ |
| CD83 | CD7 | b2c | CD3δ |
| CD83 | CD7 | b2c | CD3γ |
| CD83 | CD7 | b2c | CD3ε |
| CD83 | CD7 | b2c | FcγRI-γ |
| CD83 | CD7 | b2c | FcγRIII-γ |
| CD83 | CD7 | b2c | FcεRIβ |
| CD83 | CD7 | b2c | FcεRIγ |
| CD83 | CD7 | b2c | DAP10 |
| CD83 | CD7 | b2c | DAP12 |
| CD83 | CD7 | b2c | CD32 |
| CD83 | CD7 | b2c | CD79a |
| CD83 | CD7 | b2c | CD79b |
| CD83 | CD7 | CD137/41BB | CD8 |
| CD83 | CD7 | CD137/41BB | CD3ζ |
| CD83 | CD7 | CD137/41BB | CD3δ |
| CD83 | CD7 | CD137/41BB | CD3γ |
| CD83 | CD7 | CD137/41BB | CD3ε |
| CD83 | CD7 | CD137/41BB | FcγRI-γ |
| CD83 | CD7 | CD137/41BB | FcγRIII-γ |
| CD83 | CD7 | CD137/41BB | FcεRIβ |
| CD83 | CD7 | CD137/41BB | FcεRIγ |
| CD83 | CD7 | CD137/41BB | DAP10 |
| CD83 | CD7 | CD137/41BB | DAP12 |
| CD83 | CD7 | CD137/41BB | CD32 |
| CD83 | CD7 | CD137/41BB | CD79a |
| CD83 | CD7 | CD1374/1BB | CD79b |
| CD83 | CD7 | ICOS | CD8 |

TABLE 3-continued

Third Generation CARs

| Scfu | Co-stimulatory Signal | Co-stimulatory Signal | Signal Domain |
|---|---|---|---|
| CD83 | CD7 | ICOS | CD3ζ |
| CD83 | CD7 | ICOS | CD3δ |
| CD83 | CD7 | ICOS | CD3γ |
| CD83 | CD7 | ICOS | CD3ε |
| CD83 | CD7 | ICOS | FcγRI-γ |
| CD83 | CD7 | ICOS | FcγRIII-γ |
| CD83 | CD7 | ICOS | FcεRIβ |
| CD83 | CD7 | ICOS | FcεRIγ |
| CD83 | CD7 | ICOS | DAP10 |
| CD83 | CD7 | ICOS | DAP12 |
| CD83 | CD7 | ICOS | CD32 |
| CD83 | CD7 | ICOS | CD79a |
| CD83 | CD7 | ICOS | CD79b |
| CD83 | CD7 | CD27 | CD8 |
| CD83 | CD7 | CD27 | CDζ |
| CD83 | CD7 | CD27 | CD3δ |
| CD83 | CD7 | CD27 | CD3γ |
| CD83 | CD7 | CD27 | CD3ε |
| CD83 | CD7 | CD27 | FcγRI-γ |
| CD83 | CD7 | CD27 | FcγRIII-γ |
| CD83 | CD7 | CD27 | FcεRIβ |
| CD83 | CD7 | CD27 | FcεRIγ |
| CD83 | CD7 | CD27 | DAP10 |
| CD83 | CD7 | CD27 | DAP12 |
| CD83 | CD7 | CD27 | CD32 |
| CD83 | CD7 | CD27 | CD79a |
| CD83 | CD7 | CD27 | CD79b |
| CD83 | CD7 | CD28δ | CD8 |
| CD83 | CD7 | CD28δ | CD3ζ |
| CD83 | CD7 | CD28δ | CD3δ |
| CD83 | CD7 | CD28δ | CD3γ |
| CD83 | CD7 | CD28δ | CD3ε |
| CD83 | CD7 | CD28δ | FcγRI-γ |
| CD83 | CD7 | CD28δ | FcγRIII-γ |
| CD83 | CD7 | CD28δ | FcεRIβ |
| CD83 | CD7 | CD28δ | FcεRIγ |
| CD83 | CD7 | CD28δ | DAP10 |
| CD83 | CD7 | CD28δ | DAP12 |
| CD83 | CD7 | CD28δ | CD32 |
| CD83 | CD7 | CD28δ | CD79a |
| CD83 | CD7 | CD28δ | CD79b |
| CD83 | CD7 | CD80 | CD8 |
| CD83 | CD7 | CD80 | CD3ζ |
| CD83 | CD7 | CD80 | CD3δ |
| CD83 | CD7 | CD80 | CD3γ |
| CD83 | CD7 | CD80 | CD3ε |
| CD83 | CD7 | CD80 | FcγRI-γ |
| CD83 | CD7 | CD80 | FcγRIII-γ |
| CD83 | CD7 | CD80 | FcεRIβ |
| CD83 | CD7 | CD80 | FcεRIγ |
| CD83 | CD7 | CD80 | DAP10 |
| CD83 | CD7 | CD80 | DAP12 |
| CD83 | CD7 | CD80 | CD32 |
| CD83 | CD7 | CD80 | CD79a |
| CD83 | CD7 | CD80 | CD79b |
| CD83 | CD7 | CD86 | CD8 |
| CD83 | CD7 | CD86 | CD3ζ |
| CD83 | CD7 | CD86 | CD3δ |
| CD83 | CD7 | CD86 | CD3γ |
| CD83 | CD7 | CD86 | CD3ε |
| CD83 | CD7 | CD86 | FcγRI-γ |
| CD83 | CD7 | CD86 | FcγRIII-γ |
| CD83 | CD7 | CD86 | FcεRIβ |
| CD83 | CD7 | CD86 | FcεRIγ |
| CD83 | CD7 | CD86 | DAP10 |
| CD83 | CD7 | CD86 | DAP12 |
| CD83 | CD7 | CD86 | CD32 |
| CD83 | CD7 | CD86 | CD79a |
| CD83 | CD7 | CD86 | CD79b |
| CD83 | CD7 | OX40 | CD8 |
| CD83 | CD7 | OX40 | CDζ |
| CD83 | CD7 | OX40 | CD3δ |
| CD83 | CD7 | OX40 | CD3γ |
| CD83 | CD7 | OX40 | CD3ε |
| CD83 | CD7 | OX40 | FcγRI-γ |

TABLE 3-continued

| Third Generation CARs | | | |
|---|---|---|---|
| Scfu | Co-stimulatory Signal | Co-stimulatory Signal | Signal Domain |
| CD83 | CD7 | OX40 | FcγRIII-γ |
| CD83 | CD7 | OX40 | FcεRIβ |
| CD83 | CD7 | OX40 | FcεRIγ |
| CD83 | CD7 | OX40 | DAP10 |
| CD83 | CD7 | OX40 | DAP12 |
| CD83 | CD7 | OX40 | CD32 |
| CD83 | CD7 | OX40 | CD79a |
| CD83 | CD7 | OX40 | CD79b |
| CD83 | CD7 | DAP10 | CD8 |
| CD83 | CD7 | DAP10 | CD3ζ |
| CD83 | CD7 | DAP10 | CD3δ |
| CD83 | CD7 | DAP10 | CD3γ |
| CD83 | CD7 | DAP10 | CD3ε |
| CD83 | CD7 | DAP10 | FcγRI-γ |
| CD83 | CD7 | DAP10 | FcγRIII-γ |
| CD83 | CD7 | DAP10 | FcεRIβ |
| CD83 | CD7 | DAP10 | FcεRIγ |
| CD83 | CD7 | DAP10 | DAP10 |
| CD83 | CD7 | DAP10 | DAP12 |
| CD83 | CD7 | DAP10 | CD32 |
| CD83 | CD7 | DAP10 | CD79a |
| CD83 | CD7 | DAP10 | CD79b |
| CD83 | CD7 | DAP12 | CD8 |
| CD83 | CD7 | DAP12 | CD3ζ |
| CD83 | CD7 | DAP12 | CD3δ |
| CD83 | CD7 | DAP12 | CD3γ |
| CD83 | CD7 | DAP12 | CD3ε |
| CD83 | CD7 | DAP12 | FcγRI-γ |
| CD83 | CD7 | DAP12 | FcγRIII-γ |
| CD83 | CD7 | DAP12 | FcεRIβ |
| CD83 | CD7 | DAP12 | FcεRIγ |
| CD83 | CD7 | DAP12 | DAP10 |
| CD83 | CD7 | DAP12 | DAP12 |
| CD83 | CD7 | DAP12 | CD32 |
| CD83 | CD7 | DAP12 | CD79a |
| CD83 | CD7 | DAP12 | CD79b |
| CD83 | CD7 | MyD88 | CD8 |
| CD83 | CD7 | MyD88 | CD3ζ |
| CD83 | CD7 | MyD88 | CD3δ |
| CD83 | CD7 | MyD88 | CD3γ |
| CD83 | CD7 | MyD88 | CD3ε |
| CD83 | CD7 | MyD88 | FcγRI-γ |
| CD83 | CD7 | MyD88 | FcγRIII-γ |
| CD83 | CD7 | MyD88 | FcεRIβ |
| CD83 | CD7 | MyD88 | FcεRIγ |
| CD83 | CD7 | MyD88 | DAP10 |
| CD83 | CD7 | MyD88 | DAP12 |
| CD83 | CD7 | MyD88 | CD32 |
| CD83 | CD7 | MyD88 | CD79a |
| CD83 | CD7 | MyD88 | CD79b |
| CD83 | CD7 | CD7 | CD8 |
| CD83 | CD7 | CD7 | CD3ζ |
| CD83 | CD7 | CD7 | CD3δ |
| CD83 | CD7 | CD7 | CD3γ |
| CD83 | CD7 | CD7 | CD3ε |
| CD83 | CD7 | CD7 | FcγRI-γ |
| CD83 | CD7 | CD7 | FcγRIII-γ |
| CD83 | CD7 | CD7 | FcεRIβ |
| CD83 | CD7 | CD7 | FcεRIγ |
| CD83 | CD7 | CD7 | DAP10 |
| CD83 | CD7 | CD7 | DAP12 |
| CD83 | CD7 | CD7 | CD32 |
| CD83 | CD7 | CD7 | CD79a |
| CD83 | CD7 | CD7 | CD79b |
| CD83 | CD7 | BTNL3 | CD8 |
| CD83 | CD7 | BTNL3 | CD3ζ |
| CD83 | CD7 | BTNL3 | CD3δ |
| CD83 | CD7 | BTNL3 | CD3γ |
| CD83 | CD7 | BTNL3 | CD3ε |
| CD83 | CD7 | BTNL3 | FcγRI-γ |
| CD83 | CD7 | BTNL3 | FcγRIII-γ |
| CD83 | CD7 | BTNL3 | FcεRIβ |
| CD83 | CD7 | BTNL3 | FcεRIγ |
| CD83 | CD7 | BTNL3 | DAP10 |
| CD83 | CD7 | BTNL3 | DAP12 |

TABLE 3-continued

| Third Generation CARs | | | |
|---|---|---|---|
| Scfu | Co-stimulatory Signal | Co-stimulatory Signal | Signal Domain |
| CD83 | CD7 | BTNL3 | CD32 |
| CD83 | CD7 | BTNL3 | CD79a |
| CD83 | CD7 | BTNL3 | CD79b |
| CD83 | CD7 | NKG2D | CD8 |
| CD83 | CD7 | NKG2D | CD3ζ |
| CD83 | CD7 | NKG2D | CD3δ |
| CD83 | CD7 | NKG2D | CD3γ |
| CD83 | CD7 | NKG2D | CD3ε |
| CD83 | CD7 | NKG2D | FcγRI-γ |
| CD83 | CD7 | NKG2D | FcγRIII-γ |
| CD83 | CD7 | NKG2D | FcεRIβ |
| CD83 | CD7 | NKG2D | FcεRIγ |
| CD83 | CD7 | NKG2D | DAP10 |
| CD83 | CD7 | NKG2D | DAP12 |
| CD83 | CD7 | NKG2D | CD32 |
| CD83 | CD7 | NKG2D | CD79a |
| CD83 | CD7 | NKG2D | CD79b |
| CD83 | BTNL3 | CD28 | CD8 |
| CD83 | BTNL3 | CD28 | CD3ζ |
| CD83 | BTNL3 | CD28 | CD3δ |
| CD83 | BTNL3 | CD28 | CD3γ |
| CD83 | BTNL3 | CD28 | CD3ε |
| CD83 | BTNL3 | CD28 | FcγRI-γ |
| CD83 | BTNL3 | CD28 | FcγRIII-γ |
| CD83 | BTNL3 | CD28 | FcεRIβ |
| CD83 | BTNL3 | CD28 | FcεRIγ |
| CD83 | BTNL3 | CD28 | DAP10 |
| CD83 | BTNL3 | CD28 | DAP12 |
| CD83 | BTNL3 | CD28 | CD32 |
| CD83 | BTNL3 | CD28 | CD79a |
| CD83 | BTNL3 | CD28 | CD79b |
| CD83 | BTNL3 | CD8 | CD8 |
| CD83 | BTNL3 | CD8 | CD3ζ |
| CD83 | BTNL3 | CD8 | CD3δ |
| CD83 | BTNL3 | CD8 | CD3γ |
| CD83 | BTNL3 | CD8 | CD3ε |
| CD83 | BTNL3 | CD8 | FcγRI-γ |
| CD83 | BTNL3 | CD8 | FcγRIII-γ |
| CD83 | BTNL3 | CD8 | FcεRIβ |
| CD83 | BTNL3 | CD8 | FcεRIγ |
| CD83 | BTNL3 | CD8 | DAP10 |
| CD83 | BTNL3 | CD8 | DAP12 |
| CD83 | BTNL3 | CD8 | CD32 |
| CD83 | BTNL3 | CD8 | CD79a |
| CD83 | BTNL3 | CD8 | CD79b |
| CD83 | BTNL3 | CD4 | CD8 |
| CD83 | BTNL3 | CD4 | CD3ζ |
| CD83 | BTNL3 | CD4 | CD3δ |
| CD83 | BTNL3 | CD4 | CD3γ |
| CD83 | BTNL3 | CD4 | CD3ε |
| CD83 | BTNL3 | CD4 | FcγRI-γ |
| CD83 | BTNL3 | CD4 | FcγRIII-γ |
| CD83 | BTNL3 | CD4 | FcεRIβ |
| CD83 | BTNL3 | CD4 | FcεRIγ |
| CD83 | BTNL3 | CD4 | DAP10 |
| CD83 | BTNL3 | CD4 | DAP12 |
| CD83 | BTNL3 | CD4 | CD32 |
| CD83 | BTNL3 | CD4 | CD79a |
| CD83 | BTNL3 | CD4 | CD79b |
| CD83 | BTNL3 | b2c | CD8 |
| CD83 | BTNL3 | b2c | CD3ζ |
| CD83 | BTNL3 | b2c | CD3δ |
| CD83 | BTNL3 | b2c | CD3γ |
| CD83 | BTNL3 | b2c | CD3ε |
| CD83 | BTNL3 | b2c | FcγRI-γ |
| CD83 | BTNL3 | b2c | FcγRIII-γ |
| CD83 | BTNL3 | b2c | FcεRIβ |
| CD83 | BTNL3 | b2c | FcεRIγ |
| CD83 | BTNL3 | b2c | DAP10 |
| CD83 | BTNL3 | b2c | DAP12 |
| CD83 | BTNL3 | b2c | CD32 |
| CD83 | BTNL3 | b2c | CD79a |
| CD83 | BTNL3 | b2c | CD79b |
| CD83 | BTNL3 | CD137/41BB | CD8 |
| CD83 | BTNL3 | CD137/41BB | CD3ζ |

TABLE 3-continued

| Third Generation CARs | | | |
|---|---|---|---|
| Scfu | Co-stimulatory Signal | Co-stimulatory Signal | Signal Domain |
| CD83 | BTNL3 | CD137/41BB | CD3δ |
| CD83 | BTNL3 | CD137/41BB | CD3γ |
| CD83 | BTNL3 | CD137/41BB | CD3ε |
| CD83 | BTNL3 | CD137/41BB | FcγRI-γ |
| CD83 | BTNL3 | CD137/41BB | FcγRIII-γ |
| CD83 | BTNL3 | CD137/41BB | FcεRIβ |
| CD83 | BTNL3 | CD137/41BB | FcεRIγ |
| CD83 | BTNL3 | CD137/41BB | DAP10 |
| CD83 | BTNL3 | CD137/41BB | DAP12 |
| CD83 | BTNL3 | CD137/41BB | CD32 |
| CD83 | BTNL3 | CD137/41BB | CD79a |
| CD83 | BTNL3 | CD137/41BB | CD79b |
| CD83 | BTNL3 | ICOS | CD8 |
| CD83 | BTNL3 | ICOS | CD3ζ |
| CD83 | BTNL3 | ICOS | CD3δ |
| CD83 | BTNL3 | ICOS | CD3γ |
| CD83 | BTNL3 | ICOS | CD3ε |
| CD83 | BTNL3 | ICOS | FcγRI-γ |
| CD83 | BTNL3 | ICOS | FcγRIII-γ |
| CD83 | BTNL3 | ICOS | FcεRIβ |
| CD83 | BTNL3 | ICOS | FcεRIγ |
| CD83 | BTNL3 | ICOS | DAP10 |
| CD83 | BTNL3 | ICOS | DAP12 |
| CD83 | BTNL3 | ICOS | CD32 |
| CD83 | BTNL3 | ICOS | CD79a |
| CD83 | BTNL3 | ICOS | CD79b |
| CD83 | BTNL3 | CD27 | CD8 |
| CD83 | BTNL3 | CD27 | CD3ζ |
| CD83 | BTNL3 | CD27 | CD3δ |
| CD83 | BTNL3 | CD27 | CD3γ |
| CD83 | BTNL3 | CD27 | CD3ε |
| CD83 | BTNL3 | CD27 | FcγRI-γ |
| CD83 | BTNL3 | CD27 | FcγRIII-γ |
| CD83 | BTNL3 | CD27 | FcεRIβ |
| CD83 | BTNL3 | CD27 | FcεRIγ |
| CD83 | BTNL3 | CD27 | DAP10 |
| CD83 | BTNL3 | CD27 | DAP12 |
| CD83 | BTNL3 | CD27 | CD32 |
| CD83 | BTNL3 | CD27 | CD79a |
| CD83 | BTNL3 | CD27 | CD79b |
| CD83 | BTNL3 | CD28δ | CD8 |
| CD83 | BTNL3 | CD28δ | CD3ζ |
| CD83 | BTNL3 | CD28δ | CD3δ |
| CD83 | BTNL3 | CD28δ | CD3γ |
| CD83 | BTNL3 | CD28δ | CD3ε |
| CD83 | BTNL3 | CD28δ | FcγRIγ |
| CD83 | BTNL3 | CD28δ | FcγRIII-γ |
| CD83 | BTNL3 | CD28δ | FcεRIβ |
| CD83 | BTNL3 | CD28δ | FcεRIγ |
| CD83 | BTNL3 | CD28δ | DAP10 |
| CD83 | BTNL3 | CD28δ | DAP12 |
| CD83 | BTNL3 | CD28δ | CD32 |
| CD83 | BTNL3 | CD28δ | CD79a |
| CD83 | BTNL3 | CD28δ | CD79b |
| CD83 | BTNL3 | CD80 | CD8 |
| CD83 | BTNL3 | CD80 | CD3ζ |
| CD83 | BTNL3 | CD80 | CD3δ |
| CD83 | BTNL3 | CD80 | CD3γ |
| CD83 | BTNL3 | CD80 | CD3ε |
| CD83 | BTNL3 | CD80 | FcγRI-γ |
| CD83 | BTNL3 | CD80 | FcγRIII-γ |
| CD83 | BTNL3 | CD80 | FcεRIβ |
| CD83 | BTNL3 | CD80 | FcεRIγ |
| CD83 | BTNL3 | CD80 | DAP10 |
| CD83 | BTNL3 | CD80 | DAP12 |
| CD83 | BTNL3 | CD80 | CD32 |
| CD83 | BTNL3 | CD80 | CD79a |
| CD83 | BTNL3 | CD80 | CD79b |
| CD83 | BTNL3 | CD86 | CD8 |
| CD83 | BTNL3 | CD86 | CD3ζ |
| CD83 | BTNL3 | CD86 | CD3δ |
| CD83 | BTNL3 | CD86 | CD3γ |
| CD83 | BTNL3 | CD86 | CD3ε |
| CD83 | BTNL3 | CD86 | FcγRIγ |
| CD83 | BTNL3 | CD86 | FcγRIII-γ |

TABLE 3-continued

| Third Generation CARs | | | |
|---|---|---|---|
| Scfu | Co-stimulatory Signal | Co-stimulatory Signal | Signal Domain |
| CD83 | BTNL3 | CD86 | FcεRIγ |
| CD83 | BTNL3 | CD86 | FcεRIγ |
| CD83 | BTNL3 | CD86 | DAP10 |
| CD83 | BTNL3 | CD86 | DAP12 |
| CD83 | BTNL3 | CD86 | CD32 |
| CD83 | BTNL3 | CD86 | CD79a |
| CD83 | BTNL3 | CD86 | CD79b |
| CD83 | BTNL3 | OX40 | CD8 |
| CD83 | BTNL3 | OX40 | CD3ζ |
| CD83 | BTNL3 | OX40 | CD3δ |
| CD83 | BTNL3 | OX40 | CD3γ |
| CD83 | BTNL3 | OX40 | CD3ε |
| CD83 | BTNL3 | OX40 | FcγRI-γ |
| CD83 | BTNL3 | OX40 | FcγRIII-γ |
| CD83 | BTNL3 | OX40 | FcER ip |
| CD83 | BTNL3 | OX40 | FcεRIγ |
| CD83 | BTNL3 | OX40 | DAP10 |
| CD83 | BTNL3 | OX40 | DAP12 |
| CD83 | BTNL3 | OX40 | CD32 |
| CD83 | BTNL3 | OX40 | CD79a |
| CD83 | BTNL3 | OX40 | CD79b |
| CD83 | BTNL3 | DAP10 | CD8 |
| CD83 | BTNL3 | DAP10 | CD3ζ |
| CD83 | BTNL3 | DAP10 | CD3δ |
| CD83 | BTNL3 | DAP10 | CD3γ |
| CD83 | BTNL3 | DAP10 | CD3ε |
| CD83 | BTNL3 | DAP10 | FcγRI-γ |
| CD83 | BTNL3 | DAP10 | FcγRIII-γ |
| CD83 | BTNL3 | DAP10 | FcεRIβ |
| CD83 | BTNL3 | DAP10 | FcεRIγ |
| CD83 | BTNL3 | DAP10 | DAP10 |
| CD83 | BTNL3 | DAP10 | DAP12 |
| CD83 | BTNL3 | DAP10 | CD32 |
| CD83 | BTNL3 | DAP10 | CD79a |
| CD83 | BTNL3 | DAP10 | CD79b |
| CD83 | BTNL3 | DAP12 | CD8 |
| CD83 | BTNL3 | DAP12 | CDζ |
| CD83 | BTNL3 | DAP12 | CD3δ |
| CD83 | BTNL3 | DAP12 | CD3γ |
| CD83 | BTNL3 | DAP12 | CD3ε |
| CD83 | BTNL3 | DAP12 | FcγRI-γ |
| CD83 | BTNL3 | DAP12 | FcγRIII-γ |
| CD83 | BTNL3 | DAP12 | FcεRIβ |
| CD83 | BTNL3 | DAP12 | FcεRIγ |
| CD83 | BTNL3 | DAP12 | DAP10 |
| CD83 | BTNL3 | DAP12 | DAP12 |
| CD83 | BTNL3 | DAP12 | CD32 |
| CD83 | BTNL3 | DAP12 | CD79a |
| CD83 | BTNL3 | DAP12 | CD79b |
| CD83 | BTNL3 | MyD88 | CD8 |
| CD83 | BTNL3 | MyD88 | CD3ζ |
| CD83 | BTNL3 | MyD88 | CD3δ |
| CD83 | BTNL3 | MyD88 | CD3γ |
| CD83 | BTNL3 | MyD88 | CD3ε |
| CD83 | BTNL3 | MyD88 | FcγRI-γ |
| CD83 | BTNL3 | MyD88 | FcγRIII-γ |
| CD83 | BTNL3 | MyD88 | FcεRIβ |
| CD83 | BTNL3 | MyD88 | FcεRIγ |
| CD83 | BTNL3 | MyD88 | DAP10 |
| CD83 | BTNL3 | MyD88 | DAP12 |
| CD83 | BTNL3 | MyD88 | CD32 |
| CD83 | BTNL3 | MyD88 | CD79a |
| CD83 | BTNL3 | MyD88 | CD79b |
| CD83 | BTNL3 | CD7 | CD8 |
| CD83 | BTNL3 | CD7 | CD3ζ |
| CD83 | BTNL3 | CD7 | CD3δ |
| CD83 | BTNL3 | CD7 | CD3γ |
| CD83 | BTNL3 | CD7 | CD3ε |
| CD83 | BTNL3 | CD7 | FcγRI-γ |
| CD83 | BTNL3 | CD7 | FcγRIII-γ |
| CD83 | BTNL3 | CD7 | FcεRIβ |
| CD83 | BTNL3 | CD7 | FcεRIγ |
| CD83 | BTNL3 | CD7 | DAP10 |
| CD83 | BTNL3 | CD7 | DAP12 |
| CD83 | BTNL3 | CD7 | CD32 |

TABLE 3-continued

| Third Generation CARs | | | |
|---|---|---|---|
| Scfu | Co-stimulatory Signal | Co-stimulatory Signal | Signal Domain |
| CD83 | BTNL3 | CD7 | CD79a |
| CD83 | BTNL3 | CD7 | CD79b |
| CD83 | BTNL3 | BTNL3 | CD8 |
| CD83 | BTNL3 | BTNL3 | CD3ζ |
| CD83 | BTNL3 | BTNL3 | CD3δ |
| CD83 | BTNL3 | BTNL3 | CD3γ |
| CD83 | BTNL3 | BTNL3 | CD3ε |
| CD83 | BTNL3 | BTNL3 | FcγRI-γ |
| CD83 | BTNL3 | BTNL3 | FcγRIII-γ |
| CD83 | BTNL3 | BTNL3 | FcεRI-β |
| CD83 | BTNL3 | BTNL3 | FcεRIγ |
| CD83 | BTNL3 | BTNL3 | DAP10 |
| CD83 | BTNL3 | BTNL3 | DAP12 |
| CD83 | BTNL3 | BTNL3 | CD32 |
| CD83 | BTNL3 | BTNL3 | CD79a |
| CD83 | BTNL3 | BTNL3 | CD79b |
| CD83 | BTNL3 | NKG2D | CD8 |
| CD83 | BTNL3 | NKG2D | CD3ζ |
| CD83 | BTNL3 | NKG2D | CD3δ |
| CD83 | BTNL3 | NKG2D | CD3γ |
| CD83 | BTNL3 | NKG2D | CD3ε |
| CD83 | BTNL3 | NKG2D | FcγRI-γ |
| CD83 | BTNL3 | NKG2D | FcγRIII-γ |
| CD83 | BTNL3 | NKG2D | FcεRIβ |
| CD83 | BTNL3 | NKG2D | FcεRIγ |
| CD83 | BTNL3 | NKG2D | DAP10 |
| CD83 | BTNL3 | NKG2D | DAP12 |
| CD83 | BTNL3 | NKG2D | CD32 |
| CD83 | BTNL3 | NKG2D | CD79a |
| CD83 | BTNL3 | NKG2D | CD79b |
| CD83 | NKG2D | CD28 | CD8 |
| CD83 | NKG2D | CD28 | CD3ζ |
| CD83 | NKG2D | CD28 | CD3δ |
| CD83 | NKG2D | CD28 | CD3γ |
| CD83 | NKG2D | CD28 | CD3ε |
| CD83 | NKG2D | CD28 | FcγRI-γ |
| CD83 | NKG2D | CD28 | FcγRIII-γ |
| CD83 | NKG2D | CD28 | FcεRIβ |
| CD83 | NKG2D | CD28 | FcεRIγ |
| CD83 | NKG2D | CD28 | DAP10 |
| CD83 | NKG2D | CD28 | DAP12 |
| CD83 | NKG2D | CD28 | CD32 |
| CD83 | NKG2D | CD28 | CD79a |
| CD83 | NKG2D | CD28 | CD79b |
| CD83 | NKG2D | CD8 | CD8 |
| CD83 | NKG2D | CD8 | CD3ζ |
| CD83 | NKG2D | CD8 | CD3δ |
| CD83 | NKG2D | CD8 | CD3γ |
| CD83 | NKG2D | CD8 | CD3ε |
| CD83 | NKG2D | CD8 | FcγRI-γ |
| CD83 | NKG2D | CD8 | FcγRIII-γ |
| CD83 | NKG2D | CD8 | FcεRIβ |
| CD83 | NKG2D | CD8 | FcεRIγ |
| CD83 | NKG2D | CD8 | DAP10 |
| CD83 | NKG2D | CD8 | DAP12 |
| CD83 | NKG2D | CD8 | CD32 |
| CD83 | NKG2D | CD8 | CD79a |
| CD83 | NKG2D | CD8 | CD79b |
| CD83 | NKG2D | CD4 | CD8 |
| CD83 | NKG2D | CD4 | CD3ζ |
| CD83 | NKG2D | CD4 | CD3δ |
| CD83 | NKG2D | CD4 | CD3γ |
| CD83 | NKG2D | CD4 | CD3ε |
| CD83 | NKG2D | CD4 | FcγRI-γ |
| CD83 | NKG2D | CD4 | FcγRIII-γ |
| CD83 | NKG2D | CD4 | FcεRIβ |
| CD83 | NKG2D | CD4 | FcεRIγ |
| CD83 | NKG2D | CD4 | DAP10 |
| CD83 | NKG2D | CD4 | DAP12 |
| CD83 | NKG2D | CD4 | CD32 |
| CD83 | NKG2D | CD4 | CD79a |
| CD83 | NKG2D | CD4 | CD79b |
| CD83 | NKG2D | b2c | CD8 |
| CD83 | NKG2D | b2c | CD3ζ |
| CD83 | NKG2D | b2c | CD3δ |

TABLE 3-continued

| Third Generation CARs | | | |
|---|---|---|---|
| Scfu | Co-stimulatory Signal | Co-stimulatory Signal | Signal Domain |
| CD83 | NKG2D | b2c | CD3γ |
| CD83 | NKG2D | b2c | CD3ε |
| CD83 | NKG2D | b2c | FcγRI-γ |
| CD83 | NKG2D | b2c | FcγRIII-γ |
| CD83 | NKG2D | b2c | FcεRIβ |
| CD83 | NKG2D | b2c | FcεRIγ |
| CD83 | NKG2D | b2c | DAP10 |
| CD83 | NKG2D | b2c | DAP12 |
| CD83 | NKG2D | b2c | CD32 |
| CD83 | NKG2D | b2c | CD79a |
| CD83 | NKG2D | b2c | CD79b |
| CD83 | NKG2D | CD137/41BB | CD8 |
| CD83 | NKG2D | CD137/41BB | CD3ζ |
| CD83 | NKG2D | CD137/41BB | CD3δ |
| CD83 | NKG2D | CD137/41BB | CD3γ |
| CD83 | NKG2D | CD137/41BB | CD3ε |
| CD83 | NKG2D | CD137/41BB | FcγRI-γ |
| CD83 | NKG2D | CD137/41BB | FcγRIII-γ |
| CD83 | NKG2D | CD137/41BB | FcεRIβ |
| CD83 | NKG2D | CD137/41BB | FcεRIγ |
| CD83 | NKG2D | CD137/41BB | DAP10 |
| CD83 | NKG2D | CD137/41BB | DAP12 |
| CD83 | NKG2D | CD137/41BB | CD32 |
| CD83 | NKG2D | CD137/41BB | CD79a |
| CD83 | NKG2D | CD137/41BB | CD79b |
| CD83 | NKG2D | ICOS | CD8 |
| CD83 | NKG2D | ICOS | CD3ζ |
| CD83 | NKG2D | ICOS | CD3δ |
| CD83 | NKG2D | ICOS | CD3γ |
| CD83 | NKG2D | ICOS | CD3ε |
| CD83 | NKG2D | ICOS | FcγRI-γ |
| CD83 | NKG2D | ICOS | FcγRIII-γ |
| CD83 | NKG2D | ICOS | FcεRIβ |
| CD83 | NKG2D | ICOS | FcεRIγ |
| CD83 | NKG2D | ICOS | DAP10 |
| CD83 | NKG2D | ICOS | DAP12 |
| CD83 | NKG2D | ICOS | CD32 |
| CD83 | NKG2D | ICOS | CD79a |
| CD83 | NKG2D | ICOS | CD79b |
| CD83 | NKG2D | CD27 | CD8 |
| CD83 | NKG2D | CD27 | CD3ζ |
| CD83 | NKG2D | CD27 | CD3δ |
| CD83 | NKG2D | CD27 | CD3γ |
| CD83 | NKG2D | CD27 | CD3ε |
| CD83 | NKG2D | CD27 | FcγRI-γ |
| CD83 | NKG2D | CD27 | FcγRIII-γ |
| CD83 | NKG2D | CD27 | FcεRIβ |
| CD83 | NKG2D | CD27 | FcεRIγ |
| CD83 | NKG2D | CD27 | DAP10 |
| CD83 | NKG2D | CD27 | DAP12 |
| CD83 | NKG2D | CD27 | CD32 |
| CD83 | NKG2D | CD27 | CD79a |
| CD83 | NKG2D | CD27 | CD79b |
| CD83 | NKG2D | CD28δ | CD8 |
| CD83 | NKG2D | CD28δ | CD3ζ |
| CD83 | NKG2D | CD28δ | CD3δ |
| CD83 | NKG2D | CD28δ | CD3γ |
| CD83 | NKG2D | CD28δ | CD3ε |
| CD83 | NKG2D | CD28δ | FcγRI-γ |
| CD83 | NKG2D | CD28δ | FcγRIII-γ |
| CD83 | NKG2D | CD28δ | FcεRIβ |
| CD83 | NKG2D | CD28δ | FcεRIγ |
| CD83 | NKG2D | CD28δ | DAP10 |
| CD83 | NKG2D | CD28δ | DAP12 |
| CD83 | NKG2D | CD28δ | CD32 |
| CD83 | NKG2D | CD28δ | CD79a |
| CD83 | NKG2D | CD28δ | CD79b |
| CD83 | NKG2D | CD80 | CD8 |
| CD83 | NKG2D | CD80 | CD3ζ |
| CD83 | NKG2D | CD80 | CD3δ |
| CD83 | NKG2D | CD80 | CD3γ |
| CD83 | NKG2D | CD80 | CD3ε |
| CD83 | NKG2D | CD80 | FcγRI-γ |
| CD83 | NKG2D | CD80 | FcγRIII-γ |
| CD83 | NKG2D | CD80 | FcεRIβ |

TABLE 3-continued

| Third Generation CARs | | | |
|---|---|---|---|
| Scfu | Co-stimulatory Signal | Co-stimulatory Signal | Signal Domain |
| CD83 | NKG2D | CD80 | FcεRIγ |
| CD83 | NKG2D | CD80 | DAP10 |
| CD83 | NKG2D | CD80 | DAP12 |
| CD83 | NKG2D | CD80 | CD32 |
| CD83 | NKG2D | CD80 | CD79a |
| CD83 | NKG2D | CD80 | CD79b |
| CD83 | NKG2D | CD86 | CD8 |
| CD83 | NKG2D | CD86 | CD3ζ |
| CD83 | NKG2D | CD86 | CD3δ |
| CD83 | NKG2D | CD86 | CD3γ |
| CD83 | NKG2D | CD86 | CD3ε |
| CD83 | NKG2D | CD86 | FcγRI-γ |
| CD83 | NKG2D | CD86 | FcγRIII-γ |
| CD83 | NKG2D | CD86 | FcεRIβ |
| CD83 | NKG2D | CD86 | FcεRIγ |
| CD83 | NKG2D | CD86 | DAP10 |
| CD83 | NKG2D | CD86 | DAP12 |
| CD83 | NKG2D | CD86 | CD32 |
| CD83 | NKG2D | CD86 | CD79a |
| CD83 | NKG2D | CD86 | CD79b |
| CD83 | NKG2D | OX40 | CD8 |
| CD83 | NKG2D | OX40 | CD3ζ |
| CD83 | NKG2D | OX40 | CD3δ |
| CD83 | NKG2D | OX40 | CD3γ |
| CD83 | NKG2D | OX40 | CD3ε |
| CD83 | NKG2D | OX40 | FcγRI-γ |
| CD83 | NKG2D | OX40 | FcγRIII-γ |
| CD83 | NKG2D | OX40 | FcεRIβ |
| CD83 | NKG2D | OX40 | FcεRIγ |
| CD83 | NKG2D | OX40 | DAP10 |
| CD83 | NKG2D | OX40 | DAP12 |
| CD83 | NKG2D | OX40 | CD32 |
| CD83 | NKG2D | OX40 | CD79a |
| CD83 | NKG2D | OX40 | CD79b |
| CD83 | NKG2D | DAP10 | CD8 |
| CD83 | NKG2D | DAP10 | CD3ζ |
| CD83 | NKG2D | DAP10 | CD3δ |
| CD83 | NKG2D | DAP10 | CD3γ |
| CD83 | NKG2D | DAP10 | CD3ε |
| CD83 | NKG2D | DAP10 | FcγRI-γ |
| CD83 | NKG2D | DAP10 | FcγRIII-γ |
| CD83 | NKG2D | DAP10 | FcεRIβ |
| CD83 | NKG2D | DAP10 | FcεRIγ |
| CD83 | NKG2D | DAP10 | DAP10 |
| CD83 | NKG2D | DAP10 | DAP12 |
| CD83 | NKG2D | DAP10 | CD32 |
| CD83 | NKG2D | DAP10 | CD79a |
| CD83 | NKG2D | DAP10 | CD79b |
| CD83 | NKG2D | DAP12 | CD8 |
| CD83 | NKG2D | DAP12 | CD3ζ |
| CD83 | NKG2D | DAP12 | CD3δ |
| CD83 | NKG2D | DAP12 | CD3γ |
| CD83 | NKG2D | DAP12 | CD3ε |
| CD83 | NKG2D | DAP12 | FcγRI-γ |
| CD83 | NKG2D | DAP12 | FcγRIII-γ |
| CD83 | NKG2D | DAP12 | FcεRIβ |
| CD83 | NKG2D | DAP12 | FcεRIγ |
| CD83 | NKG2D | DAP12 | DAP10 |
| CD83 | NKG2D | DAP12 | DAP12 |
| CD83 | NKG2D | DAP12 | CD32 |
| CD83 | NKG2D | DAP12 | CD79a |
| CD83 | NKG2D | DAP12 | CD79b |
| CD83 | NKG2D | MyD88 | CD8 |
| CD83 | NKG2D | MyD88 | CD3ζ |
| CD83 | NKG2D | MyD88 | CD3δ |
| CD83 | NKG2D | MyD88 | CD3γ |
| CD83 | NKG2D | MyD88 | CD3ε |
| CD83 | NKG2D | MyD88 | FcγRI-γ |
| CD83 | NKG2D | MyD88 | FcγRIII-γ |
| CD83 | NKG2D | MyD88 | FcεRIβ |
| CD83 | NKG2D | MyD88 | FcεRIγ |
| CD83 | NKG2D | MyD88 | DAP10 |
| CD83 | NKG2D | MyD88 | DAP12 |
| CD83 | NKG2D | MyD88 | CD32 |
| CD83 | NKG2D | MyD88 | CD79a |

TABLE 3-continued

| Third Generation CARs | | | |
|---|---|---|---|
| Scfu | Co-stimulatory Signal | Co-stimulatory Signal | Signal Domain |
| CD83 | NKG2D | MyD88 | CD79b |
| CD83 | NKG2D | CD7 | CD8 |
| CD83 | NKG2D | CD7 | CD3ζ |
| CD83 | NKG2D | CD7 | CD3δ |
| CD83 | NKG2D | CD7 | CD3γ |
| CD83 | NKG2D | CD7 | CD3ε |
| CD83 | NKG2D | CD7 | FcγRI-γ |
| CD83 | NKG2D | CD7 | FcγRIII-γ |
| CD83 | NKG2D | CD7 | FcεRIβ |
| CD83 | NKG2D | CD7 | FcεRIγ |
| CD83 | NKG2D | CD7 | DAP10 |
| CD83 | NKG2D | CD7 | DAP12 |
| CD83 | NKG2D | CD7 | CD32 |
| CD83 | NKG2D | CD7 | CD79a |
| CD83 | NKG2D | CD7 | CD79b |
| CD83 | NKG2D | BTNL3 | CD8 |
| CD83 | NKG2D | BTNL3 | CD3ζ |
| CD83 | NKG2D | BTNL3 | CD3δ |
| CD83 | NKG2D | BTNL3 | CD3γ |
| CD83 | NKG2D | BTNL3 | CD3ε |
| CD83 | NKG2D | BTNL3 | FcγRI-γ |
| CD83 | NKG2D | BTNL3 | FcγRIII-γ |
| CD83 | NKG2D | BTNL3 | FcεRIβ |
| CD83 | NKG2D | BTNL3 | FcεRIγ |
| CD83 | NKG2D | BTNL3 | DAP10 |
| CD83 | NKG2D | BTNL3 | DAP12 |
| CD83 | NKG2D | BTNL3 | CD32 |
| CD83 | NKG2D | BTNL3 | CD79a |
| CD83 | NKG2D | BTNL3 | CD79b |
| CD83 | NKG2D | NKG2D | CD8 |
| CD83 | NKG2D | NKG2D | CD3ζ |
| CD83 | NKG2D | NKG2D | CD3δ |
| CD83 | NKG2D | NKG2D | CD3γ |
| CD83 | NKG2D | NKG2D | CD3ε |
| CD83 | NKG2D | NKG2D | FcγRI-γ |
| CD83 | NKG2D | NKG2D | FcγRIII-γ |
| CD83 | NKG2D | NKG2D | FcεRIβ |
| CD83 | NKG2D | NKG2D | FcεRIγ |
| CD83 | NKG2D | NKG2D | DAP10 |
| CD83 | NKG2D | NKG2D | DAP12 |
| CD83 | NKG2D | NKG2D | CD32 |
| CD83 | NKG2D | NKG2D | CD79a |
| CD83 | NKG2D | NKG2D | CD79b |

TABLE 4

| CARs lacking Co-Simulatory Signal (for dual CAR approach) | | |
|---|---|---|
| ScFv | Co-stimulatory Signal | Signal Domain |
| CD83 | none | CD8 |
| CD83 | none | CD3ζ |
| CD83 | none | CD3δ |
| CD83 | none | CD3γ |
| CD83 | none | CD3ε |
| CD83 | none | FcγRI-γ |
| CD83 | none | FcγRIII-γ |
| CD83 | none | FcεRIβ |
| CD83 | none | FcεRIγ |
| CD83 | none | DAP10 |
| CD83 | none | DAP12 |
| CD83 | none | CD32 |
| CD83 | none | CD79a |
| CD83 | none | CD8 |
| CD83 | none | CD3ζ |
| CD83 | none | CD3δ |
| CD83 | none | CD3γ |
| CD83 | none | CD3ε |
| CD83 | none | FcγRI-γ |

TABLE 5

| CARs lacking Signal Domain (for dual CAR approach) | | |
|---|---|---|
| ScFv | Co-stimulatory Signal | Signal Domain |
| CD83 | CD28 | none |
| CD83 | CD8 | none |
| CD83 | CD4 | none |
| CD83 | b2c | none |
| CD83 | CD137/41BB | none |
| CD83 | ICOS | none |
| CD83 | CD27 | none |
| CD83 | CD28δ | none |
| CD83 | CD80 | none |
| CD83 | CD86 | none |
| CD83 | OX40 | none |
| CD83 | DAP10 | none |
| CD83 | MyD88 | none |
| CD83 | CD7 | none |
| CD83 | DAP12 | none |
| CD83 | MyD88 | none |
| CD83 | CD7 | none |
| CD83 | BTNL3 | none |
| CD83 | NKG2D | none |

TABLE 6

| Third Generation CARs lacking Signal Domain (for dual CAR approach) | | | |
|---|---|---|---|
| ScFv | Co-stimulatory Signal | Co-stimulatory Signal | Signal Domain |
| CD83 | CD28 | CD28 | none |
| CD83 | CD28 | CD8 | none |
| CD83 | CD28 | CD4 | none |
| CD83 | CD28 | b2c | none |
| CD83 | CD28 | CD137/41BB | none |
| CD83 | CD28 | ICOS | none |
| CD83 | CD28 | CD27 | none |
| CD83 | CD28 | CD28δ | none |
| CD83 | CD28 | CD80 | none |
| CD83 | CD28 | CD86 | none |
| CD83 | CD28 | OX40 | none |
| CD83 | CD28 | DAP10 | none |
| CD83 | CD28 | MyD88 | none |
| CD83 | CD28 | CD7 | none |
| CD83 | CD28 | DAP12 | none |
| CD83 | CD28 | MyD88 | none |
| CD83 | CD28 | CD7 | none |
| CD83 | CD8 | CD28 | none |
| CD83 | CD8 | CD8 | none |
| CD83 | CD8 | CD4 | none |
| CD83 | CD8 | b2c | none |
| CD83 | CD8 | CD137/41BB | none |
| CD83 | CD8 | ICOS | none |
| CD83 | CD8 | CD27 | none |
| CD83 | CD8 | CD28δ | none |
| CD83 | CD8 | CD80 | none |
| CD83 | CD8 | CD86 | none |
| CD83 | CD8 | OX40 | none |
| CD83 | CD8 | DAP10 | none |
| CD83 | CD8 | MyD88 | none |
| CD83 | CD8 | CD7 | none |
| CD83 | CD8 | DAP12 | none |
| CD83 | CD8 | MyD88 | none |
| CD83 | CD8 | CD7 | none |
| CD83 | CD4 | CD28 | none |
| CD83 | CD4 | CD8 | none |
| CD83 | CD4 | CD4 | none |
| CD83 | CD4 | b2c | none |
| CD83 | CD4 | CD137/41BB | none |
| CD83 | CD4 | ICOS | none |
| CD83 | CD4 | CD27 | none |
| CD83 | CD4 | CD28δ | none |
| CD83 | CD4 | CD80 | none |

TABLE 6-continued

| Third Generation CARs lacking Signal Domain (for dual CAR approach) | | | |
|---|---|---|---|
| ScFv | Co-stimulatory Signal | Co-stimulatory Signal | Signal Domain |
| CD83 | CD4 | CD86 | none |
| CD83 | CD4 | OX40 | none |
| CD83 | CD4 | DAP10 | none |
| CD83 | CD4 | MyD88 | none |
| CD83 | CD4 | CD7 | none |
| CD83 | CD4 | DAP12 | none |
| CD83 | CD4 | MyD88 | none |
| CD83 | CD4 | CD7 | none |
| CD83 | b2c | CD28 | none |
| CD83 | b2c | CD8 | none |
| CD83 | b2c | CD4 | none |
| CD83 | b2c | b2c | none |
| CD83 | b2c | CD137/41BB | none |
| CD83 | b2c | ICOS | none |
| CD83 | b2c | CD27 | none |
| CD83 | b2c | CD28δ | none |
| CD83 | b2c | CD80 | none |
| CD83 | b2c | CD86 | none |
| CD83 | b2c | OX40 | none |
| CD83 | b2c | DAP10 | none |
| CD83 | b2c | MyD88 | none |
| CD83 | b2c | CD7 | none |
| CD83 | b2c | DAP12 | none |
| CD83 | b2c | MyD88 | none |
| CD83 | b2c | CD7 | none |
| CD83 | CD137/41BB | CD28 | none |
| CD83 | CD137/41BB | CD8 | none |
| CD83 | CD137/41BB | CD4 | none |
| CD83 | CD137/41BB | b2c | none |
| CD83 | CD137/41BB | CD137/41BB | none |
| CD83 | CD137/41BB | ICOS | none |
| CD83 | CD137/41BB | CD27 | none |
| CD83 | CD137/41BB | CD28δ | none |
| CD83 | CD137/41BB | CD80 | none |
| CD83 | CD137/41BB | CD86 | none |
| CD83 | CD137/41BB | OX40 | none |
| CD83 | CD137/41BB | DAP10 | none |
| CD83 | CD137/41BB | MyD88 | none |
| CD83 | CD137/41BB | CD7 | none |
| CD83 | CD137/41BB | DAP12 | none |
| CD83 | CD137/41BB | MyD88 | none |
| CD83 | CD137/41BB | CD7 | none |
| CD83 | ICOS | CD28 | none |
| CD83 | ICOS | CD8 | none |
| CD83 | ICOS | CD4 | none |
| CD83 | ICOS | b2c | none |
| CD83 | ICOS | CD137/41BB | none |
| CD83 | ICOS | ICOS | none |
| CD83 | ICOS | CD27 | none |
| CD83 | ICOS | CD28δ | none |
| CD83 | ICOS | CD80 | none |
| CD83 | ICOS | CD86 | none |
| CD83 | ICOS | OX40 | none |
| CD83 | ICOS | DAP10 | none |
| CD83 | ICOS | MyD88 | none |
| CD83 | ICOS | CD7 | none |
| CD83 | ICOS | DAP12 | none |
| CD83 | ICOS | MyD88 | none |
| CD83 | ICOS | CD7 | none |
| CD83 | ICOS | CD28 | none |
| CD83 | ICOS | CD8 | none |
| CD83 | ICOS | CD4 | none |
| CD83 | ICOS | b2c | none |
| CD83 | ICOS | CD137/41BB | none |
| CD83 | ICOS | ICOS | none |
| CD83 | ICOS | CD27 | none |
| CD83 | ICOS | CD28δ | none |
| CD83 | ICOS | CD80 | none |
| CD83 | ICOS | CD86 | none |
| CD83 | ICOS | OX40 | none |
| CD83 | ICOS | DAP10 | none |
| CD83 | ICOS | MyD88 | none |
| CD83 | ICOS | CD7 | none |
| CD83 | ICOS | DAP12 | none |

TABLE 6-continued

| Third Generation CARs lacking Signal Domain (for dual CAR approach) | | | |
|---|---|---|---|
| ScFv | Co-stimulatory Signal | Co-stimulatory Signal | Signal Domain |
| CD83 | ICOS | MyD88 | none |
| CD83 | ICOS | CD7 | none |
| CD83 | CD27 | CD28 | none |
| CD83 | CD27 | CD8 | none |
| CD83 | CD27 | CD4 | none |
| CD83 | CD27 | b2c | none |
| CD83 | CD27 | CD137/41BB | none |
| CD83 | CD27 | ICOS | none |
| CD83 | CD27 | CD27 | none |
| CD83 | CD27 | CD28δ | none |
| CD83 | CD27 | CD80 | none |
| CD83 | CD27 | CD86 | none |
| CD83 | CD27 | OX40 | none |
| CD83 | CD27 | DAP10 | none |
| CD83 | CD27 | MyD88 | none |
| CD83 | CD27 | CD7 | none |
| CD83 | CD27 | DAP12 | none |
| CD83 | CD27 | MyD88 | none |
| CD83 | CD27 | CD7 | none |
| CD83 | CD28δ | CD28 | none |
| CD83 | CD28δ | CD8 | none |
| CD83 | CD28δ | CD4 | none |
| CD83 | CD28δ | b2c | none |
| CD83 | CD28δ | CD137/41BB | none |
| CD83 | CD28δ | ICOS | none |
| CD83 | CD28δ | CD27 | none |
| CD83 | CD28δ | CD28δ | none |
| CD83 | CD28δ | CD80 | none |
| CD83 | CD28δ | CD86 | none |
| CD83 | CD28δ | OX40 | none |
| CD83 | CD28δ | DAP10 | none |
| CD83 | CD28δ | MyD88 | none |
| CD83 | CD28δ | CD7 | none |
| CD83 | CD28δ | DAP12 | none |
| CD83 | CD28δ | MyD88 | none |
| CD83 | CD28δ | CD7 | none |
| CD83 | CD80 | CD28 | none |
| CD83 | CD80 | CD8 | none |
| CD83 | CD80 | CD4 | none |
| CD83 | CD80 | b2c | none |
| CD83 | CD80 | CD137/41BB | none |
| CD83 | CD80 | ICOS | none |
| CD83 | CD80 | CD27 | none |
| CD83 | CD80 | CD28δ | none |
| CD83 | CD80 | CD80 | none |
| CD83 | CD80 | CD86 | none |
| CD83 | CD80 | OX40 | none |
| CD83 | CD80 | DAP10 | none |
| CD83 | CD80 | MyD88 | none |
| CD83 | CD80 | CD7 | none |
| CD83 | CD80 | DAP12 | none |
| CD83 | CD80 | MyD88 | none |
| CD83 | CD80 | CD7 | none |
| CD83 | CD86 | CD28 | none |
| CD83 | CD86 | CD8 | none |
| CD83 | CD86 | CD4 | none |
| CD83 | CD86 | b2c | none |
| CD83 | CD86 | CD137/41BB | none |
| CD83 | CD86 | ICOS | none |
| CD83 | CD86 | CD27 | none |
| CD83 | CD86 | CD28δ | none |
| CD83 | CD86 | CD80 | none |
| CD83 | CD86 | CD86 | none |
| CD83 | CD86 | OX40 | none |
| CD83 | CD86 | DAP10 | none |
| CD83 | CD86 | MyD88 | none |
| CD83 | CD86 | CD7 | none |
| CD83 | CD86 | DAP12 | none |
| CD83 | CD86 | MyD88 | none |
| CD83 | CD86 | CD7 | none |
| CD83 | OX40 | CD28 | none |
| CD83 | OX40 | CD8 | none |
| CD83 | OX40 | CD4 | none |
| CD83 | OX40 | b2c | none |

TABLE 6-continued

| Third Generation CARs lacking Signal Domain (for dual CAR approach) | | | |
|---|---|---|---|
| ScFv | Co-stimulatory Signal | Co-stimulatory Signal | Signal Domain |
| CD83 | OX40 | CD137/41BB | none |
| CD83 | OX40 | ICOS | none |
| CD83 | OX40 | CD27 | none |
| CD83 | OX40 | CD28δ | none |
| CD83 | OX40 | CD80 | none |
| CD83 | OX40 | CD86 | none |
| CD83 | OX40 | OX40 | none |
| CD83 | OX40 | DAP10 | none |
| CD83 | OX40 | MyD88 | none |
| CD83 | OX40 | CD7 | none |
| CD83 | OX40 | DAP12 | none |
| CD83 | OX40 | MyD88 | none |
| CD83 | OX40 | CD7 | none |
| CD83 | DAP10 | CD28 | none |
| CD83 | DAP10 | CD8 | none |
| CD83 | DAP10 | CD4 | none |
| CD83 | DAP10 | b2c | none |
| CD83 | DAP10 | CD137/41BB | none |
| CD83 | DAP10 | ICOS | none |
| CD83 | DAP10 | CD27 | none |
| CD83 | DAP10 | CD28δ | none |
| CD83 | DAP10 | CD80 | none |
| CD83 | DAP10 | CD86 | none |
| CD83 | DAP10 | OX40 | none |
| CD83 | DAP10 | DAP10 | none |
| CD83 | DAP10 | MyD88 | none |
| CD83 | DAP10 | CD7 | none |
| CD83 | DAP10 | DAP12 | none |
| CD83 | DAP10 | MyD88 | none |
| CD83 | DAP10 | CD7 | none |
| CD83 | DAP12 | CD28 | none |
| CD83 | DAP12 | CD8 | none |
| CD83 | DAP12 | CD4 | none |
| CD83 | DAP12 | b2c | none |
| CD83 | DAP12 | CD137/41BB | none |
| CD83 | DAP12 | ICOS | none |
| CD83 | DAP12 | CD27 | none |
| CD83 | DAP12 | CD28δ | none |
| CD83 | DAP12 | CD80 | none |
| CD83 | DAP12 | CD86 | none |
| CD83 | DAP12 | OX40 | none |
| CD83 | DAP12 | DAP10 | none |
| CD83 | DAP12 | MyD88 | none |
| CD83 | DAP12 | CD7 | none |
| CD83 | DAP12 | DAP12 | none |
| CD83 | DAP12 | MyD88 | none |
| CD83 | DAP12 | CD7 | none |
| CD83 | MyD88 | CD28 | none |
| CD83 | MyD88 | CD8 | none |
| CD83 | MyD88 | CD4 | none |
| CD83 | MyD88 | b2c | none |
| CD83 | MyD88 | CD137/41BB | none |
| CD83 | MyD88 | ICOS | none |
| CD83 | MyD88 | CD27 | none |
| CD83 | MyD88 | CD28δ | none |
| CD83 | MyD88 | CD80 | none |
| CD83 | MyD88 | CD86 | none |
| CD83 | MyD88 | OX40 | none |
| CD83 | MyD88 | DAP10 | none |
| CD83 | MyD88 | MyD88 | none |
| CD83 | MyD88 | CD7 | none |
| CD83 | MyD88 | DAP12 | none |
| CD83 | MyD88 | MyD88 | none |
| CD83 | MyD88 | CD7 | none |
| CD83 | CD7 | CD28 | none |
| CD83 | CD7 | CD8 | none |
| CD83 | CD7 | CD4 | none |
| CD83 | CD7 | b2c | none |
| CD83 | CD7 | CD137/41BB | none |
| CD83 | CD7 | ICOS | none |
| CD83 | CD7 | CD27 | none |
| CD83 | CD7 | CD28δ | none |
| CD83 | CD7 | CD80 | none |
| CD83 | CD7 | CD86 | none |

TABLE 6-continued

Third Generation CARs lacking Signal Domain (for dual CAR approach)

| ScFv | Co-stimulatory Signal | Co-stimulatory Signal | Signal Domain |
|---|---|---|---|
| CD83 | CD7 | OX40 | none |
| CD83 | CD7 | DAP10 | none |
| CD83 | CD7 | MyD88 | none |
| CD83 | CD7 | CD7 | none |
| CD83 | CD7 | DAP12 | none |
| CD83 | CD7 | MyD88 | none |
| CD83 | CD7 | CD7 | none |
| CD83 | BTNL3 | CD28 | none |
| CD83 | BTNL3 | CD8 | none |
| CD83 | BTNL3 | CD4 | none |
| CD83 | BTNL3 | b2c | none |
| CD83 | BTNL3 | CD137/41BB | none |
| CD83 | BTNL3 | ICOS | none |
| CD83 | BTNL3 | CD27 | none |
| CD83 | BTNL3 | CD28δ | none |
| CD83 | BTNL3 | CD80 | none |
| CD83 | BTNL3 | CD86 | none |
| CD83 | BTNL3 | OX40 | none |
| CD83 | BTNL3 | DAP10 | none |
| CD83 | BTNL3 | MyD88 | none |
| CD83 | BTNL3 | CD7 | none |
| CD83 | BTNL3 | DAP12 | none |
| CD83 | BTNL3 | MyD88 | none |
| CD83 | BTNL3 | CD7 | none |
| CD83 | NKG2D | CD28 | none |
| CD83 | NKG2D | CD8 | none |
| CD83 | NKG2D | CD4 | none |
| CD83 | NKG2D | b2c | none |
| CD83 | NKG2D | CD137/41BB | none |
| CD83 | NKG2D | ICOS | none |
| CD83 | NKG2D | CD27 | none |
| CD83 | NKG2D | CD28δ | none |
| CD83 | NKG2D | CD80 | none |
| CD83 | NKG2D | CD86 | none |
| CD83 | NKG2D | OX40 | none |
| CD83 | NKG2D | DAP10 | none |
| CD83 | NKG2D | MyD88 | none |
| CD83 | NKG2D | CD7 | none |
| CD83 | NKG2D | DAP12 | none |
| CD83 | NKG2D | MyD88 | none |
| CD83 | NKG2D | CD7 | none |

In some embodiments, the anti-CD83 binding agent is single chain variable fragment (scFv) antibody. The affinity/specificity of an anti-CD83 scFv is driven in large part by specific sequences within complementarity determining regions (CDRs) in the heavy ($V_H$) and light ($V_L$) chain. Each $V_H$ and $V_L$ sequence will have three CDRs (CDR1, CDR2, CDR3).

In some embodiments, the anti-CD83 binding agent is derived from natural antibodies, such as monoclonal antibodies. In some cases, the antibody is human. In some cases, the antibody has undergone an alteration to render it less immunogenic when administered to humans. For example, the alteration comprises one or more techniques selected from the group consisting of chimerization, humanization, CDR-grafting, deimmunization, and mutation of framework amino acids to correspond to the closest human germline sequence.

Also disclosed are bi-specific CARs that target CD83 and at least one additional antigen. Also disclosed are CARs designed to work only in conjunction with another CAR that binds a different antigen. For example, in these embodiments, the endodomain of the disclosed CAR can contain only a signaling domain (SD) or a co-stimulatory signaling region (CSR), but not both. The second CAR (or endogenous T-cell) provides the missing signal if it is activated. For example, if the disclosed CAR contains an SD but not a CSR, then the immune effector cell containing this CAR is only activated if another CAR (or T-cell) containing a CSR binds its respective antigen. Likewise, if the disclosed CAR contains a CSR but not a SD, then the immune effector cell containing this CAR is only activated if another CAR (or T-cell) containing an SD binds its respective antigen.

Nucleic Acids and Vectors

Also disclosed are polynucleotides and polynucleotide vectors encoding the disclosed CD83-specific CARs that allow expression of the CD83-specific CARs in the disclosed immune effector cells.

Nucleic acid sequences encoding the disclosed CARs, and regions thereof, can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Expression of nucleic acids encoding CARs is typically achieved by operably linking a nucleic acid encoding the CAR polypeptide to a promoter, and incorporating the construct into an expression vector. Typical cloning vectors contain transcription and translation terminators, initiation sequences, and promoters useful for regulation of the expression of the desired nucleic acid sequence.

The disclosed nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. In some embodiments, the polynucleotide vectors are lentiviral or retroviral vectors.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, MND (myeloproliferative sarcoma virus) promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. The promoter can alternatively be an inducible promoter. Examples of inducible promoters include, but are not limited to a metallothionine promoter, a glucocorticoid promoter, a progesterone promoter, and a tetracycline promoter.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene. Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

Biological methods for introducing a polynucleotide of interest into a host cell include the use of DNA and RNA vectors. Viral vectors, and especially retroviral vectors, have become the most widely used method for inserting genes into mammalian, e.g., human cells.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes. Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc, (Birmingham, Ala.).

Immune Effector Cells

Also disclosed are immune effector cells that are engineered to express the disclosed CARs (also referred to herein as "CAR-T cells." These cells are preferably obtained from the subject to be treated (i.e. are autologous). However, in some embodiments, immune effector cell lines or donor effector cells (allogeneic) are used. Immune effector cells can be obtained from a number of sources, including peripheral blood mononuclear cells, bone marrow, lymph node tissue, cord blood, thymus tissue, tissue from a site of infection, ascites, pleural effusion, spleen tissue, and tumors. Immune effector cells can be obtained from blood collected from a subject using any number of techniques known to the skilled artisan, such as Ficoll™ separation. For example, cells from the circulating blood of an individual may be obtained by apheresis. In some embodiments, immune effector cells are isolated from peripheral blood lymphocytes by lysing the red blood cells and depleting the monocytes, for example, by centrifugation through a PERCOLL™ gradient or by counterflow centrifugal elutriation. A specific subpopulation of immune effector cells can be further isolated by positive or negative selection techniques. For example, immune effector cells can be isolated using a combination of antibodies directed to surface markers unique to the positively selected cells, e.g., by incubation with antibody-conjugated beads for a time period sufficient for positive selection of the desired immune effector cells. Alternatively, enrichment of immune effector cells population can be accomplished by negative selection using a combination of antibodies directed to surface markers unique to the negatively selected cells.

In some embodiments, the immune effector cells comprise any leukocyte involved in defending the body against infectious disease and foreign materials. For example, the immune effector cells can comprise lymphocytes, monocytes, macrophages, dentritic cells, mast cells, neutrophils, basophils, eosinophils, or any combinations thereof. For example, the immune effector cells can comprise T lymphocytes.

T cells or T lymphocytes can be distinguished from other lymphocytes, such as B cells and natural killer cells (NK cells), by the presence of a T-cell receptor (TCR) on the cell surface. They are called T cells because they mature in the thymus (although some also mature in the tonsils). There are several subsets of T cells, each with a distinct function.

T helper cells ($T_H$ cells) assist other white blood cells in immunologic processes, including maturation of B cells into plasma cells and memory B cells, and activation of cytotoxic T cells and macrophages. These cells are also known as CD4+ T cells because they express the CD4 glycoprotein on their surface. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H7$, $T_H9$, or $T_{FH}$, which secrete different cytokines to facilitate a different type of immune response.

Cytotoxic T cells (Tc cells, or CTLs) destroy virally infected cells and tumor cells, and are also implicated in transplant rejection. These cells are also known as $CD8^+$ T cells since they express the CD8 glycoprotein at their surface. These cells recognize their targets by binding to antigen associated with MHC class I molecules, which are present on the surface of all nucleated cells. Through IL-10, adenosine and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory cells may be either $CD4^+$ or $CD8^+$. Memory T cells typically express the cell surface protein CD45RO.

Regulatory T cells ($T_{reg}$ cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus. Two major classes of $CD4^+$ $T_{reg}$ cells have been described—naturally occurring $T_{reg}$ cells and adaptive $T_{reg}$ cells.

Natural killer T (NKT) cells (not to be confused with natural killer (NK) cells) bridge the adaptive immune system with the innate immune system. Unlike conventional T cells that recognize peptide antigens presented by major histocompatibility complex (MHC) molecules, NKT cells recognize glycolipid antigen presented by a molecule called CD1d.

In some embodiments, the T cells comprise a mixture of CD4+ cells. In other embodiments, the T cells are enriched for one or more subsets based on cell surface expression. For example, in some cases, the T comprise are cytotoxic $CD8^+$ T lymphocytes. In some embodiments, the T cells comprise γδ T cells, which possess a distinct T-cell receptor (TCR) having one γ chain and one δ chain instead of a and β chains.

Natural-killer (NK) cells are $CD56^+CD3^-$ large granular lymphocytes that can kill virally infected and transformed cells, and constitute a critical cellular subset of the innate immune system (Godfrey J, et al. Leuk Lymphoma 2012 53:1666-1676). Unlike cytotoxic $CD8^+$ T lymphocytes, NK cells launch cytotoxicity against tumor cells without the requirement for prior sensitization, and can also eradicate MHC-I-negative cells (Nami-Mancinelli E, et al. Int Immunol 201123:427-431). NK cells are safer effector cells, as they may avoid the potentially lethal complications of cytokine storms (Morgan R A, et al. Mol Ther 2010 18:843-851), tumor lysis syndrome (Porter D L, et al. N Engl J Med 2011 365:725-733), and on-target, off-tumor effects.

Therapeutic Methods

Immune effector cells expressing the disclosed CARs suppress alloreactive donor cells, such as T-cells, and prevent GVHD. Therefore, the disclosed CARs can be administered to any subject at risk for GVHD. In some embodiments, the subject receives a bone marrow transplant and the disclosed CAR-modified immune effector cells suppress alloreactivity of donor T-cells or dendritic cells.

The disclosed CAR-modified immune effector cells may be administered either alone, or as a pharmaceutical composition in combination with diluents and/or with other components such as IL-2, IL-15, or other cytokines or cell populations.

In some embodiments, the disclosed CAR-modified immune effector cells are administered in combination with ER stress blockade (compounds to target the IRE-1/XBP-1 pathway (e.g., B-I09). In some embodiments, the disclosed CAR-modified immune effector cells are administered in combination with a JAK2 inhibitor, a STAT3 inhibitor, an Aurora kinase inhibitor, an mTOR inhibitor, or any combination thereof.

Briefly, pharmaceutical compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions for use in the disclosed methods are in some embodiments formulated for intravenous administration. Pharmaceutical compositions may be administered in any manner appropriate treat MM. The quantity and frequency of administration will be determined by such factors as the condition of the patient, and the severity of the patient's disease, although appropriate dosages may be determined by clinical trials.

When a "therapeutic amount" is indicated, the precise amount of the compositions of the present invention to be administered can be determined by a physician with consideration of individual differences in age, weight, extent of transplantation, and condition of the patient (subject). It can generally be stated that a pharmaceutical composition comprising the T cells described herein may be administered at a dosage of $10^4$ to $10^9$ cells/kg body weight, such as $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently re-draw blood (or have an apheresis performed), activate T cells therefrom according to the disclosed methods, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Using this multiple blood draw/multiple reinfusion protocol may serve to select out certain populations of T cells.

The administration of the disclosed compositions may be carried out in any convenient manner, including by injection, transfusion, or implantation. The compositions described herein may be administered to a patient subcutaneously, intradermally, intranodally, intramedullary, intramuscularly, by intravenous (i.v.) injection, or intraperitoneally. In some embodiments, the disclosed compositions are administered to a patient by intradermal or subcutaneous injection. In some embodiments, the disclosed compositions are administered by i.v. injection. The compositions may also be injected directly into a site of transplantation.

In certain embodiments, the disclosed CAR-modified immune effector cells are administered to a patient in conjunction with (e.g., before, simultaneously or following) any number of relevant treatment modalities, including but not limited to thalidomide, dexamethasone, bortezomib, and lenalidomide. In further embodiments, the CAR-modified immune effector cells may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. In some embodiments, the CAR-modified immune effector cells are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

One primary concern with CAR-T cells as a form of "living therapeutic" is their manipulability in vivo and their potential immune-stimulating side effects. To better control CAR-T therapy and prevent against unwanted side effects, a variety of features have been engineered including off-switches, safety mechanisms, and conditional control mechanisms. Both self-destruct and marked/tagged CAR-T cells for example, are engineered to have an "off-switch" that promotes clearance of the CAR-expressing T-cell. A self-destruct CAR-T contains a CAR, but is also engineered to express a pro-apoptotic suicide gene or "elimination gene" inducible upon administration of an exogenous molecule. A variety of suicide genes may be employed for this purpose, including HSV-TK (herpes simplex virus thymidine kinase), Fas, iCasp9 (inducible caspase 9), CD20, MYC TAG, and truncated EGFR (endothelial growth factor receptor). HSK for example, will convert the prodrug ganciclovir (GCV) into GCV-triphosphate that incorporates itself into replicating DNA, ultimately leading to cell death. iCasp9 is a chimeric protein containing components of FK506-binding protein that binds the small molecule API903, leading to caspase 9 dimerization and apoptosis. A marked/tagged CAR-T cell however, is one that possesses a CAR but also is engineered to express a selection marker. Administration of a mAb against this selection marker will promote clearance of the CAR-T cell. Truncated EGFR is one such targetable antigen by the anti-EGFR mAb, and administration of cetuximab works to promotes elimination of the CAR-T cell. CARs created to have these features are also referred to as sCARs for 'switchable CARs', and RCARs for 'regulatable CARs'. A "safety CAR", also known as an "inhibitory CAR" (iCAR), is engineered to express two antigen binding domains. One of these extracellular domains is directed against a firstantigen and bound to an intracellular costimulatory and stimulatory domain. The second extracellular antigen binding domain however is specific for normal tissue and bound to an intracellular checkpoint domain such as CTLA4, PD1, or CD45. Incorporation of multiple intracellular inhibitory domains to the iCAR is also possible. Some inhibitory molecules that may provide these inhibitory domains include B7-H1, B7-1, CD160, PIH, 2B4, CEACAM (CEACAM-1. CEACAM-3, and/or CEACAM-5), LAG-3, TIGIT, BTLA, LAIR1, and TGFβ-R. In the presence of normal tissue, stimulation of this second antigen binding domain will work to inhibit the CAR. It should be noted that due to this dual antigen specificity, iCARs are also a form of bi-specific CAR-T cells. The safety CAR-T engineering enhances specificity of the CAR-T cell for tissue, and is advantageous in situations where certain normal tissues may express very low levels of a antigen that would lead to off target effects with a standard CAR (Morgan 2010). A conditional CAR-T cell expresses an extracellular antigen binding domain connected to an intracellular costimulatory domain and a separate, intracellular costimulator. The costimulatory and stimulatory domain sequences are engineered in such a way that upon administration of an exogenous molecule the resultant proteins will come together intracellularly to complete the CAR circuit. In this way, CAR-T activation can be modulated, and possibly even 'fine-tuned' or personalized to a specific patient. Similar to a dual CAR design, the stimulatory and costimulatory domains are physically separated when inactive in the conditional CAR; for this reason these too are also referred to as a "split CAR".

Typically, CAR-T cells are created using α-β T cells, however γ-δ T cells may also be used. In some embodiments, the described CAR constructs, domains, and engineered features used to generate CAR-T cells could similarly be employed in the generation of other types of CAR-expressing immune cells including NK (natural killer) cells, B cells, mast cells, myeloid-derived phagocytes, and NKT cells. Alternatively, a CAR-expressing cell may be created to have properties of both T-cell and NK cells. In an additional embodiment, the transduced with CARs may be autologous or allogeneic.

Several different methods for CAR expression may be used including retroviral transduction (including γ-retroviral), lentiviral transduction, transposon/transposases (Sleeping Beauty and PiggyBac systems), and messenger RNA transfer-mediated gene expression. Gene editing (gene insertion or gene deletion/disruption) has become of increasing importance with respect to the possibility for engineering CAR-T cells as well. CRISPR-Cas9, ZFN (zinc finger nuclease), and TALEN (transcription activator like effector nuclease) systems are three potential methods through which CAR-T cells may be generated.

Definitions

The term "amino acid sequence" refers to a list of abbreviations, letters, characters or words representing amino acid residues. The amino acid abbreviations used herein are conventional one letter codes for the amino acids and are expressed as follows: A, alanine: B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class. In addition to intact immunoglobulin molecules, also included in the term "antibodies" are fragments or polymers of those immunoglobulin molecules, and human or humanized versions of immunoglobulin molecules that selectively bind the target antigen.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')2, scFv, Fv, dsFv diabody, Fc, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "antigen binding site" refers to a region of an antibody that specifically binds an epitope on an antigen.

The term "aptamer" refers to oligonucleic acid or peptide molecules that bind to a specific target molecule. These molecules are generally selected from a random sequence pool. The selected aptamers are capable of adapting unique tertiary structures and recognizing target molecules with high affinity and specificity. A "nucleic acid aptamer" is a DNA or RNA oligonucleic acid that binds to a target molecule via its conformation, and thereby inhibits or suppresses functions of such molecule. A nucleic acid aptamer may be constituted by DNA, RNA, or a combination thereof. A "peptide aptamer" is a combinatorial protein molecule with a variable peptide sequence inserted within a constant scaffold protein. Identification of peptide aptamers is typically performed under stringent yeast dihybrid conditions, which enhances the probability for the selected peptide aptamers to be stably expressed and correctly folded in an intracellular context.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "chimeric molecule" refers to a single molecule created by joining two or more molecules that exist separately in their native state. The single, chimeric molecule has the desired functionality of all of its constituent molecules. One type of chimeric molecules is a fusion protein.

The term "engineered antibody" refers to a recombinant molecule that comprises at least an antibody fragment comprising an antigen binding site derived from the variable domain of the heavy chain and/or light chain of an antibody and may optionally comprise the entire or part of the variable and/or constant domains of an antibody from any of the Ig classes (for example IgA, IgD, IgE, IgG, IgM and IgY).

The term "epitope" refers to the region of an antigen to which an antibody binds preferentially and specifically. A monoclonal antibody binds preferentially to a single specific epitope of a molecule that can be molecularly defined. In the present invention, multiple epitopes can be recognized by a multispecific antibody.

The term "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "Fab fragment" refers to a fragment of an antibody comprising an antigen-binding site generated by cleavage of the antibody with the enzyme papain, which cuts at the hinge region N-terminally to the inter-H-chain disulfide bond and generates two Fab fragments from one antibody molecule.

The term "F(ab')2 fragment" refers to a fragment of an antibody containing two antigen-binding sites, generated by cleavage of the antibody molecule with the enzyme pepsin which cuts at the hinge region C-terminally to the inter-H-chain disulfide bond.

The term "Fc fragment" refers to the fragment of an antibody comprising the constant domain of its heavy chain.

The term "Fv fragment" refers to the fragment of an antibody comprising the variable domains of its heavy chain and light chain.

"Gene construct" refers to a nucleic acid, such as a vector, plasmid, viral genome or the like which includes a "coding sequence" for a polypeptide or which is otherwise transcribable to a biologically active RNA (e.g., antisense, decoy, ribozyme, etc), may be transfected into cells, e.g. in certain embodiments mammalian cells, and may cause expression of the coding sequence in cells transfected with the construct. The gene construct may include one or more regulatory elements operably linked to the coding sequence, as well as intronic sequences, polyadenylation sites, origins of replication, marker genes, etc.

The term "identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

The term "linker" is art-recognized and refers to a molecule or group of molecules connecting two compounds, such as two polypeptides. The linker may be comprised of a single linking molecule or may comprise a linking molecule and a spacer molecule, intended to separate the linking molecule and a compound by a specific distance.

The term "multivalent antibody" refers to an antibody or engineered antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "peptide," "protein," and "polypeptide" are used interchangeably to refer to a natural or synthetic molecule comprising two or more amino acids linked by the carboxyl group of one amino acid to the alpha amino group of another.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The terms"polypeptide fragment" or "fragment", when used in reference to a particular polypeptide, refers to a polypeptide in which amino acid residues are deleted as compared to the reference polypeptide itself, but where the remaining amino acid sequence is usually identical to that of the reference polypeptide. Such deletions may occur at the amino-terminus or carboxy-terminus of the reference polypeptide, or alternatively both. Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. A fragment can retain one or more of the biological activities of the reference polypeptide. In various embodiments, a fragment may comprise an enzymatic activity and/or an interaction site of the reference polypeptide. In another embodiment, a fragment may have immunogenic properties.

The term "protein domain" refers to a portion of a protein, portions of a protein, or an entire protein showing structural integrity; this determination may be based on amino acid composition of a portion of a protein, portions of a protein, or the entire protein.

The term "single chain variable fragment or scFv" refers to an Fv fragment in which the heavy chain domain and the light chain domain are linked. One or more scFv fragments may be linked to other antibody fragments (such as the constant domain of a heavy chain or a light chain) to form antibody constructs having one or more antigen recognition sites.

A "spacer" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}M^{-1}$, and $10^{12}$ $M^{-1}$ or more) with that second molecule.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The terms "transformation" and "transfection" mean the introduction of a nucleic acid, e.g., an expression vector, into a recipient cell including introduction of a nucleic acid to the chromosomal DNA of said cell.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder, and supportive treatment, that is, treatment employed to supplement another specific therapy directed toward the improvement of the associated disease, pathological condition, or disorder.

The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, 95%, 96%, 97%, 98%, 99% sequence identity to a reference sequence.

The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element).

A number of embodiments of the invention have been described. Nevertheless, it will be understood that various modifications may be made without departing from the spirit and scope of the invention. Accordingly, other embodiments are within the scope of the following claims.

EXAMPLES

Example 1: A Novel Human CD83 Chimeric Antigen Receptor T Cell Prevents GVHD while Maintaining Donor Anti-Tumor Immunity

Introduction

Allo-HCT is a procedure performed with curative intent for high risk hematologic malignancies and bone marrow failure syndromes. Annually, 30,000 patients receive an allo-HCT worldwide, and 34-89% will develop acute GVHD despite standard pharmacologic immune suppression (Cutler C., et al., Blood 2014 124:1372-1377; Pidala J., et al., Haematologica 2012 97:1882-1889). The current practice is to use broadly suppressive calcineurin-inhibitors combined with methotrexate, sirolimus, or mycophenolate mofetil to prevent GVHD. Despite known off-target impairment of beneficial GVL and limited tolerance induction (Zeiser R., et al., Blood 2006 108:390-399), calcineurin-inhibitors have been included in GVHD prophylaxis and treatment for over 3 decades (Powles R. L., et al., Lancet 1978 2:1327-1331; Storb R., et al., Blood 1986 68:119-125; Storb R., et al., N Engl J Med 1986 314:729-735). While advancements in donor and graft source selection (Pidala J., et al., Blood 2014 124:2596-2606; Anasetti C., et al., N Engl J Med 2012 367:1487-1496), recipient comorbidity assessment (Sorror M. L., et al., Blood 2004 104:961-968; Thakar M., et al., Blood. 2019 133(7):754-762), and conditioning regimens have improved allo-HCT outcomes (Solh M. M., et al., Biol Blood Marrow Transplant. 2018 Sep. 19; Scott B. L., et al., J Clin Oncol 2017 35:1154-1161), it is striking that calcineurin-inhibitors remain the prevalent immune suppressive backbone of GVHD prevention today (Cutler C., et al., Blood 2014 124:1372-1377).

Beyond calcineurin-inhibitors, cell-based immune suppression is increasingly being studied in GVHD prevention. In part, cell-based strategies, such as Tregs, offer potent and potentially antigen-specific inhibition of alloreactive T cells (Veerapathran A., et al. Blood 2011 118:5671-5680; Veerapathran A., et al., Blood 2013 122:2251-2261). Past clinical trials incorporating Tregs in GVHD prophylaxis, have proven that cell-mediated immune suppression delivers safe and effective control over donor T cells without impairing GVL (Brunstein C. G. et al., Blood 2011 117:1061-1070; Brunstein C. G., et al., Blood 2016 127:1044-1051; Kellner J. N., et al., Oncotarget 2018 9:35611-35622). Preclinical and clinical evidence also supports the translational potential of novel cell products, including natural killer (NK) cells, invariant NKT cells, myeloid derived suppressor cells, and type 2 innate lymphoid cells to reduce GVHD and preserve GVL (Ruggeri L., et al., Science 2002 295:2097-2100; Olson J. A., et al., Blood 2010 115:4293-4301: Asai O., et al., J Clin Invest 1998 101:1835-1842; Du J., et al., Blood. 2017 129(23):3121-3125; Highfill S. L., et al., Blood 2010 116:5738-5747; Bruce D. W., et al., J Clin Invest 2017 127:1813-1825). Currently, these cell products remain largely investigational, though Tregs and NK cells have been widely studied in the clinical setting. More recently, CAR T cells have demonstrated unparalleled activity in refractory acute lymphoblastic leukemia and diffuse large B cell lymphoma (Neelapu S. S., et al., N Engl J Med 2017 377:2531-2544; Schuster S. J., et al., N Engl J Med 2019 380:45-56; Maude S. L., et al., N Engl J Med 2018 378:439-448). Thus, FDA indications were awarded to CD19 CAR T cells in these high risk hematologic malignancies. While these CAR T cells are indeed cytolytic and by no means immune suppressive, they do highlight the potential role for CAR T cells in targeting mediators of GVHD pathogenesis. Moreover, CAR T cells are unique in that they carry a reduced capacity to elicit GVHD when administered post allo-HCT as a donor-derived product (Ghosh A., et al., Nat Med 2017 23:242-249).

CD83 represents a clinically relevant target to eliminate inflammatory dendritic cells as well as alloreactive donor T cells. CD83 is a protein member of the immunoglobulin superfamily and is expressed on the surface of activated human dendritic cells (Ju X., et al., J Immunol 2016 197:4613-4625). CD83 is also expressed on human T cells following stimulation by allo-antigen and is present on circulating T cells in patients with GVHD (Ju X., et al., J Immunol 2016 197:4613-4625). Targeting CD83 with monoclonal antibody reduces xenogeneic GVHD in mice without impairing GVL or T cell responses against pathogenic viruses (Wilson J., et al., J Exp Med 2009 206:387-398). However, the immune suppressive effect by the antibody is temporary and dependent upon NK-cell mediated antibody-dependent cellular cytotoxicity (ADCC) (Wilson J., et al., J Exp Med 2009 206:387-398; Seldon T. A., et al., Leukemia 2016 30:692-700).

To overcome the limitations of antibody-targeting of CD83, a CD83 CAR T cell was designed. This Example describes the production and preclinical efficacy of the human CD83 CAR T cell in GVHD prevention. Unlike monoconal antibody, the CD83 CAR T cell does not require ADCC to kill its target. Moreover, the CD83 CAR T cell provides lasting GVHD prophylaxis in a human T cell mediated xenogeneic GVHD model; even after a single infusion of cells. In part, the disclosed CAR takes advantage of the differential expression of CD83 on activated Tconv versus Tregs. Thus, the CD83 CAR T cell eliminates pathogenic Th1 cells, and significantly increases the ratio of Treg to Tconv in vivo. Moreover, the CD83 CAR T cell permits potent anti-tumor immunity by donor T cells. The CD83 CAR T cell represents a new cell-based approach to GVHD prevention, and delivers durable and selective immune suppression without the need for broadly acting calcineurin-inhibitors.

Materials and Methods

Study Design.

This is a preclinical study of the design, production, and efficacy of a new human CD83 CAR T cell for GVHD prophylaxis. The first part of the study describes the CAR construct as well as the in vitro activity of the CD83 CAR T cell with regard to phenotype, cytokine production, on-target killing, and proliferation in response to CD83+ targets. Next demonstrated is the immune suppressive effect of the CD83 CAR T cell in vitro using standard alloMLRs. Additionally, CD83 expression was measure among human T cells showing differential expression of CD83 on Tconv versus Treg cells. In a human T cell mediated xenogeneic GVHD model (Betts B. C., et al., Proc Natl Acad Sci USA 2018 115:1582-1587; Betts B. C., et al., Sci Transl Med. 2017 9(372); Betts B. C., et al., Front Immunol. 2018 9:2887), the preclinical efficacy of the CD83 CAR in GVHD prophylaxis is demonstrate. This includes a thorough evaluation of in vivo target killing of CD83+ dendritic cells and Tconv. Also shown is the effects of the CD83 CAR T cell on various T cell subsets in vivo. Last, CD83 CAR T cells are shown to spare donor anti-tumor immunity using an established xenogeneic model (Betts B. C., et al., Proc Natl Acad Sci USA 2018 115:1582-1587; Betts B. C., et al., Sci Transl Med. 2017 9(372); Betts B. C., et al., Front Immunol. 2018 9:2887) to generate human, tumor-specific CD8 CTL in vivo and killing by the CTL was tested in vitro using the xCELLigence RTCA (real-time cell analysis) system (Li G., et al., JCI Insight. 2018 3(18)).

CD83 CAR T Cell Construct and Production.

Monoclonal Antibodies and Flow Cytometry.

Fluorochrome-conjugated mouse anti-human monoclonal antibodies included anti-CD3, CD4, CD25, CD83, CD127, MHCII, Foxp3, Ki-67, IFNγ, IL-17A, and IL-4 (BD Biosciences, San Jose, CA USA; eBioscience San Jose, CA USA; Cell Signaling Technology, Boston, MA USA). LIVE/DEAD Fixable Yellow or Aqua Dead Cell Stain (Life Technologies, Grand Island, NY) was used to determine viability. Live events were acquired on a BD FACSCanto II flow cytometer (FlowJo software, ver. 7.6.4; TreeStar, Ashland, OR, USA).

Cytokine Immunoassays.

CD83 CAR and mock transduced T cells ($1\times10^6$) were cocultured with CD83+ moDCs ($1\times10^5$) for 24 hours. Supernatants were harvested and analyzed using a Simple Plex Assay Kit (R&D Systems) on an Ella machine (ProteinSimple). Manufacturers' instructions were followed (47).

Human CD83 CAR T Cell In Vitro Proliferation.

Normalized numbers (1 or $2\times10^6$) of human CD83 CAR T cells were cocultured with $2\times10^5$ CD83+ moDCs per well in non-tissue-culture-treated 6-well plates in triplicate. Cells were grown in human T cell complete medium supplemented with 60 IU/ml IL-2 and split every 2 to 3 days or whenever the medium turned yellow. Cell viability and total cell numbers in each well were measured daily or every 2 to 4 days (T isolation as day 0) on a cell counter (Bio-Rad) with trypan blue staining.

In Vitro alloMLRs.

Human monocyte-derived dendritic cells (moDC) were cytokine-generated, differentiated, and matured as described (Betts B. C., et al., Sci Transl Med. 2017 9(372)). T cells purified (105) purified from leukocyte concentrates (OneBlood or Memorial Blood Center) were cultured with allogeneic moDCs (T cell:DC ratio 30:1) in 100 ul complete RPMI supplemented with 10% heat-inactivated, pooled human serum. CD83 CAR, CD19 CAR, or mock transduced T cells (autologous to the T cell donor) were added to the alloMLR at a range of CAR to DC ratios. T cell proliferation was measured after 5 days by Ki-67 expression.

CD83 Expression Time Course.

Purified human T cells were stimulated with either allogeneic moDCs (T cell:DC ratio 30:1) or CD3/CD28 beads (T cell:bead ratio 30:1). T cells were harvested from triplicate wells in a 96-well plate at 4, 8, 24, and 48 hours of culture. The T cells were stained for CD3, CD4, CD127, CD25, and CD83, then fixed. CD83 expression was evaluated in activated Tconv ($CD3^+$, $CD4^+$, $CD127^+$, $CD25^+$) (38), Tregs ($CD3^+$, $CD4^+$, $CD127^-$, $CD25^+$)(38), and CD8 T cells ($CD3^+$, $CD4^-$).

Xenogeneic GVHD Model.

NOD scid gamma (NSG) mice (male or female, 6-24 weeks old) were raised within an IACUC-approved colony maintained at the Moffitt/USF vivarium. Recipient mice received $25\times10^6$ fresh, human PBMCs (OneBlood) once on day 0 of the transplant. As indicated, mice either received PBMCs alone, PBMCs plus CD83 CAR T cells (low dose: $1\times10^6$ or high dose: $10\times10^6$), or PBMCs plus mock transduced T cells ($10\times10^6$). Each independent experiment was performed with a different human PBMC donor, where the CAR T cells and mock transduced T cells were derived from the PBMC donor. Mice were monitored for GVHD clinical scores and premoribund status. Where indicated, short term experiments were completed on day +21 via humane euthanasia to evaluate GVHD target organ pathology (Betts B. C., et al., Proc Natl Acad Sci USA 2018 115:1582-1587; Betts B. C., et al., Sci Transl Med. 2017 9(372); Betts B. C., et al., Front Immunol. 2018 9:2887), tissue-resident lymphocytes, and the content of human DCs and T cell subsets within the murine spleens. These mice were transplanted with PBMCs ($25\times10^6$) with or without CD83 CAR ($1\times10^6$) or mock transduced T cells ($1\times10^6$). All vertebrate animal work was performed under an AICUC-approved protocol.

In Vivo Generation of Human Anti-Tumor CTL.

NSG mice were transplanted with human PBMCs ($25\times10^6$) with or without CD83 CAR T cells ($1\times10^6$) or mock transduced T cells ($1\times10^6$). Additionally, recipient mice received an inoculum of irradiated K562 cells ($10^7$/mouse) on days 0 and +7 (Betts B. C., et al., Proc Natl Acad Sci USA 2018 115:1582-1587; Betts B. C., et al., Sci Transl Med. 2017 9(372); Betts B. C., et al., Front Immunol. 2018 9:2887). Mice were humanely euthanized on day +12, spleens were harvested, and human $CD8^+$ T cells were isolated by magnetic bead separation. Purified human CD8 T cells were cocultured with fresh K562 cells at an E/T ratio of 10:1 and target cell killing was monitored using the xCELLigence RTCA system (Li G., et al., JCI Insight. 2018 3(18)).

Statistical Analysis.

Data are reported as mean values ±SEM. ANOVA was used for group comparisons, including a Dunnett's or Sidak's post-test with correction for multiple-comparisons. For comparison of survival curves, a Log-rank test was used. The statistical analysis was conducted using Prism software version 5.04 (GraphPad). Statistical significance was defined by $P<0.05$ (two-tailed).

Results

Schema of the Human CD83 CAR Construct.

Figure 1:
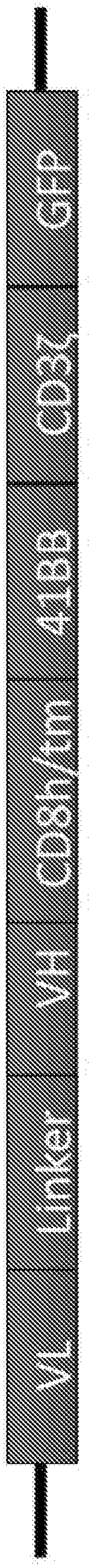
FIG. 1 is a schema of a human CD83 CAR construct according to one embodiment disclosed herein. An anti-CD83 single chain variable fragment is followed by a CD8 hinge and transmembrane domain, as well as a 41BB co-stimulatory domain and CD3ζ activation domain. The CAR is tagged with a fluorescent reporter at the 3' end. The CAR Reporter gene is cloned into a SFG retroviral vector.

The CD83 CAR T cell was designed based on the single chain variable fragment of an anti-human CD83 antibody, C312 (Wilson J., et al., J Exp Med 2009 206:387-398). The CD83 CAR T cell construct uses a 41BB co-stimulatory domain and a CD3ζ activation domain. To facilitate tracking of the CAR T cell, the construct contains an eGFP tag, which can be used to identify the CAR T cell among normal non-CAR T cells. CD83-targeted CAR T cells were retrovirally transduced and generated exactly as published (FIG. 1) (Li G., et al. Methods Mol Biol 2017 1514:111-118).

Characterization of the Human CD83 CAR T Cell.

Figure 2A:
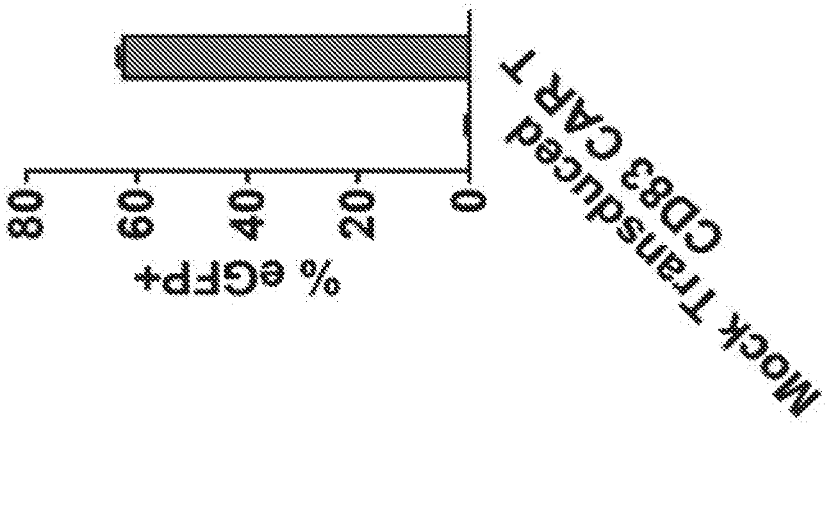
FIGS. 2A to 2E show characterization of the human CD83 CAR T cell.
Figure 2B:
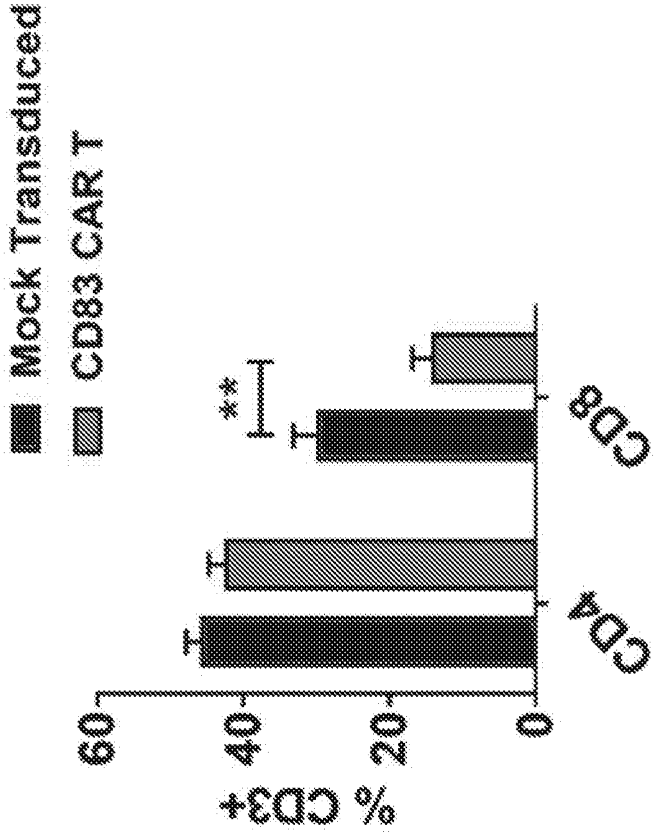
Figure 2C:
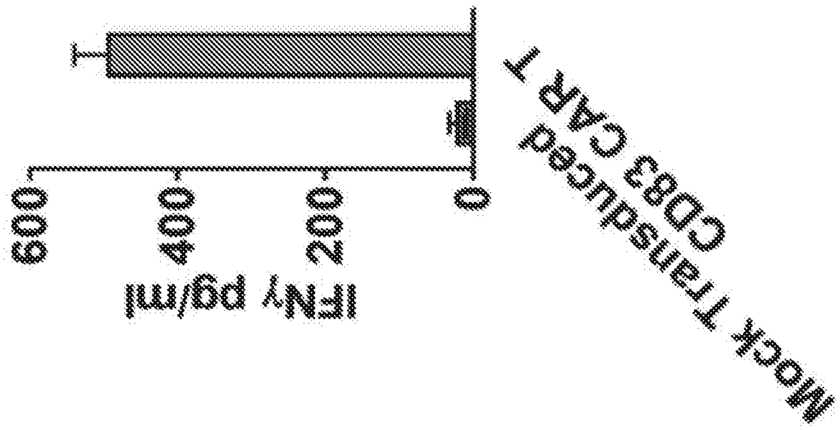
Figure 2D:
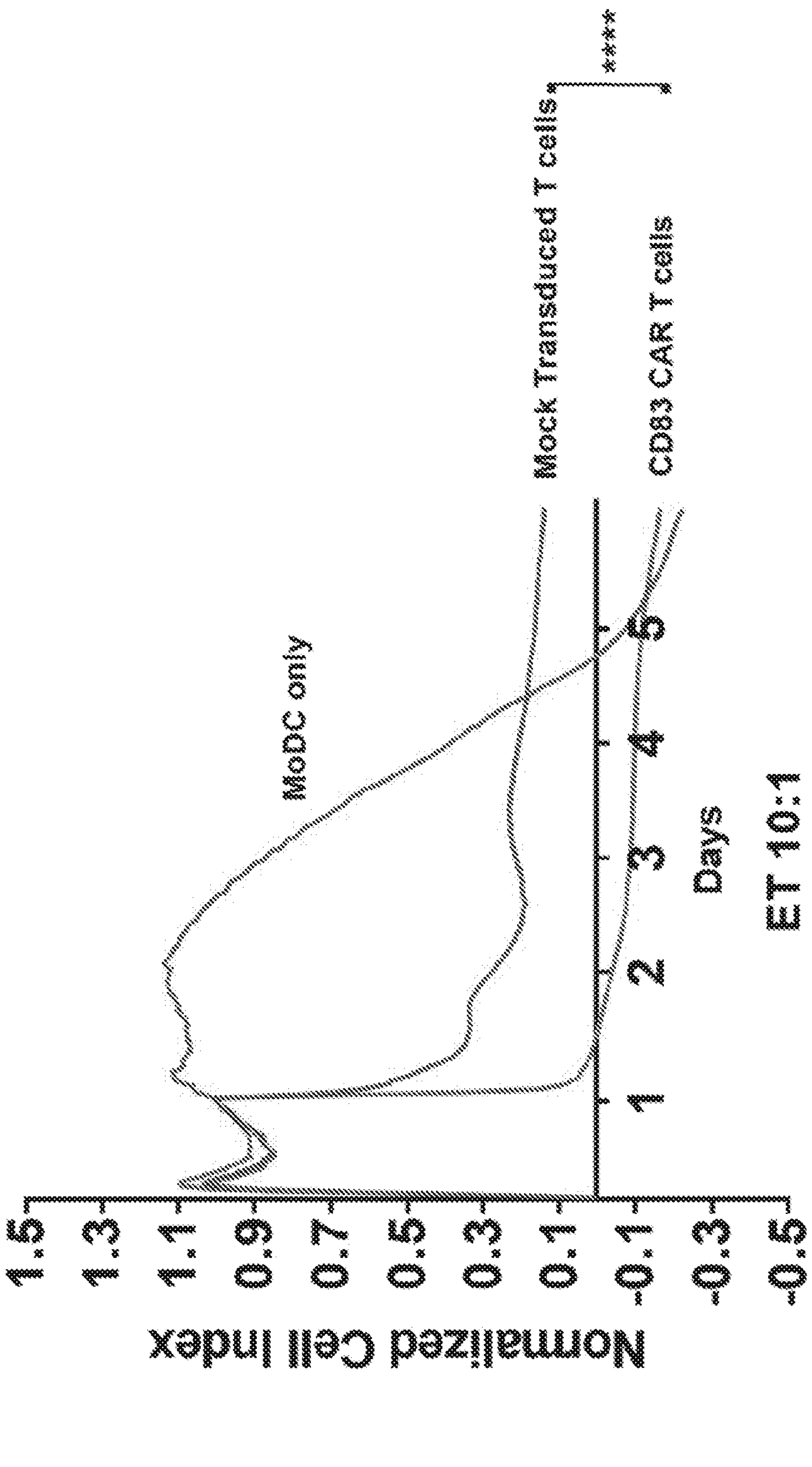
Figure 2E:
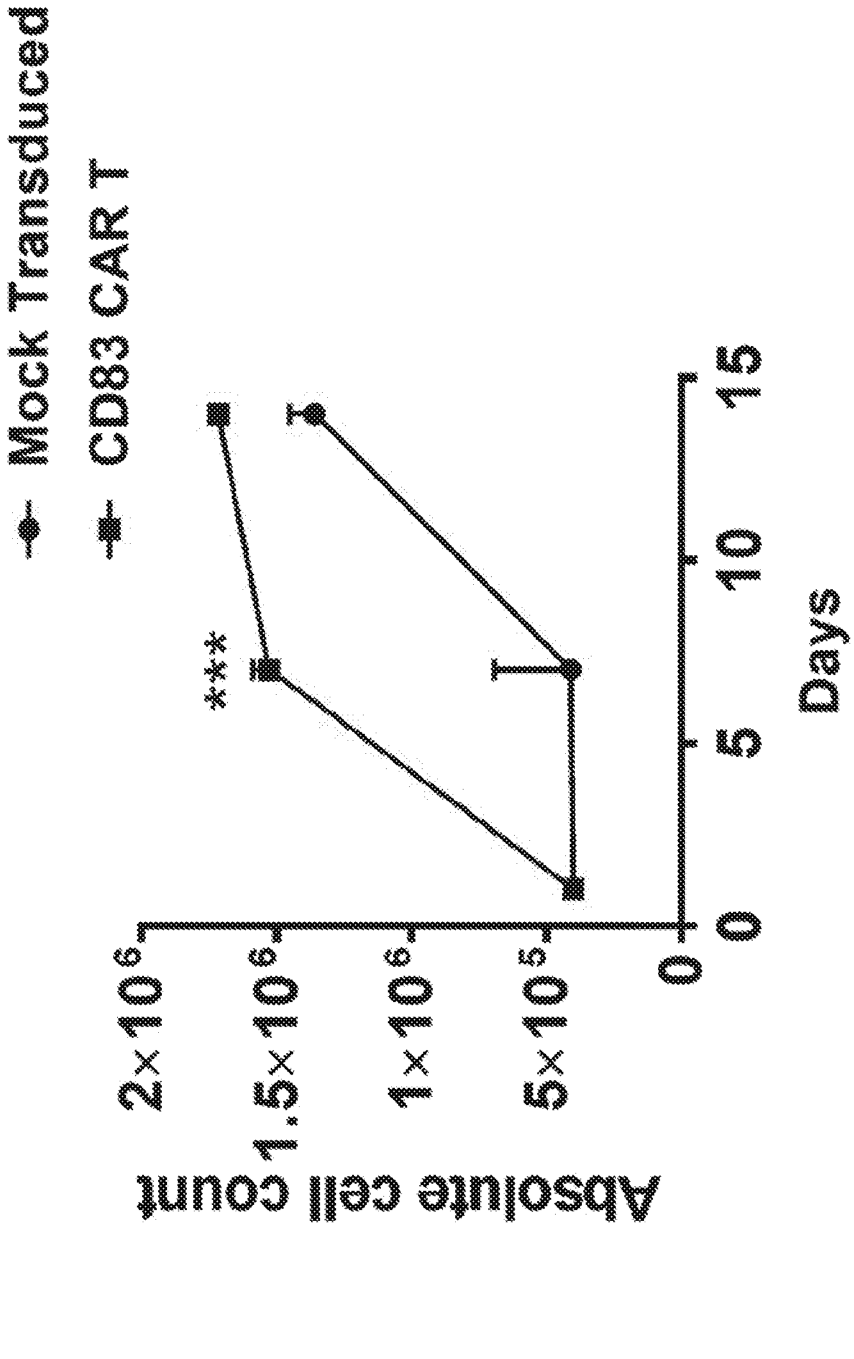

The CD83 CAR construct exhibited a high degree of transduction efficiency, with over 60% of T cells expressing eGFP post production (FIG. 2A). While CD4 expression was similar among both groups, a significant reduction in CD8 expression was observed among the CD83 CAR T cells compared to mock transduced T cells (FIG. 2B). However, the CD83 CAR T cells demonstrated robust IFNγ production when cultured with cytokine-matured, $CD83^+$ human moDCs (FIG. 2C). Additionally, the CD83 CAR T cells demonstrated potent killing of and proliferation against $CD83^+$ moDCs, compared to mock transduced T cells (FIG. 2D,2E). The target moDCs in these experiments were allogeneic to the T cells, therefore the baseline lysis and proliferation by the mock transduced T cells represent baseline alloreactivity (FIG. 2D,2E).

Human CD83 CAR T Cells Reduce Alloreactivity.

Figure 3:
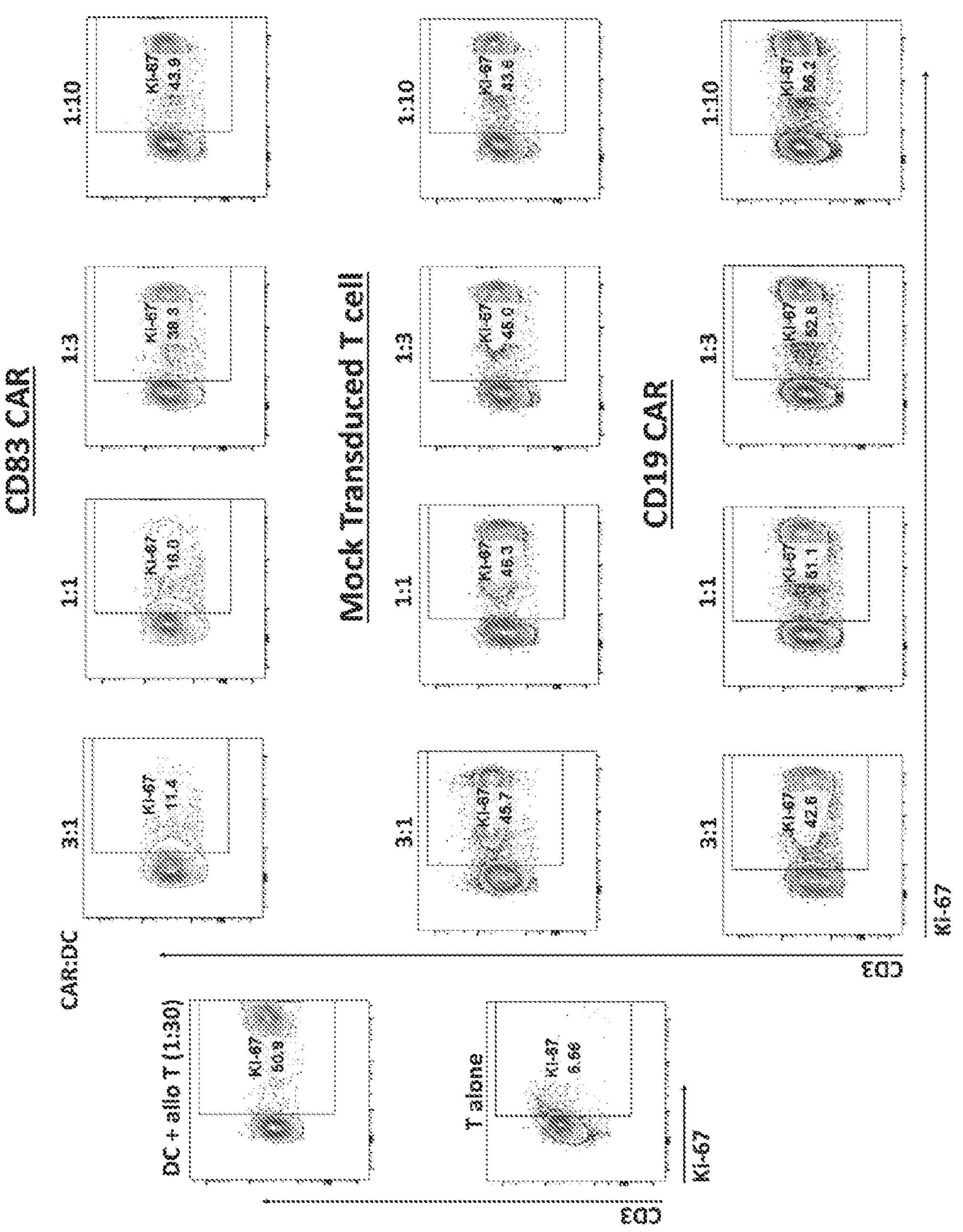
FIG. 3 shows human CD83 chimeric antigen receptor T cells reduce alloreactivity. Human T cells were cultured with allogeneic, cytokine matured, monocyte-derived dendritic cells (moDC) at a DC:T cell ratio of 1:30 (ie 100,000 T cells and 3333 moDCs). CD83 CAR T (autologous to the cultured T cells) were added at specific ratios to the moDCs (3:1 to 1:10, where the lowest amount of CAR T added was 333 cells). T cell proliferation was measured by Ki-67 expression at day +5. CAR T were gated out by their expression of GFP. Controls included T cells alone (ie no proliferation), mock transduced T cells, and CD19 CAR T cells. These mock transduced T cell did not express a chimeric antigen receptor but were treated in an identical fashion as the transduced CD83 cells. The CD19 CAR T cell used a 41BB co-stimulation domain, and targeted an irrelevant antigen in this system. 1 of 2 representative experiments is shown.

To test whether the human CD83 CAR T could reduce alloreactivity in vitro, their suppressive function in allogeneic mixed leukocyte reactions (alloMLR) was investigated. CD83 and mock transduced CAR T cells were generated from healthy donor, human T cells. CD19 CAR T cells target B cells, thus an irrelevant cell type in the alloMLR, were also tested as an additional control. The CD19 and CD83 CAR T cells were similar in that they both receive costimulation via 41BB. CAR T cells were added to 5-day alloMLRs consisting of autologous, untransduced T cells ($1\times10^5$) and allogeneic, cytokine-matured, $CD83^+$ moDCs ($3.33\times10^3$). The CAR T cell: moDC ratio ranged from 3:1 to 1:10. The CD83 CAR T potently reduced alloreactive proliferation at the 3:1 to 1:3 target ratios (FIG. 3, upper panel). The mock transduced and CD19 CAR T cells had no suppressive effect against the alloreactive T cells (FIG. 3, middle and lower panels). Moreover, the CD19 CAR T cell control group shows that the suppression of alloreactive T cells by the CD83 CAR T cells was not related to fratricide (FIG. 3, upper and lower panels).

CD83 is Differentially Expressed on Activated Human Tcon Compared to Treg.

CD83 is an established marker of human dendritic cell maturation and is also expressed on activated human B cells. Using a CD83 reporter mouse system, it was previously shown that murine B cell expression of CD83 is primarily restricted to late pre-B cells (Lechmann M., et al. Proc Natl Acad Sci USA 2008 105:11887-11892). Moreover, CD83 was also found on T cells from the reporter mice (Lechmann M., et al. Proc Natl Acad Sci USA 2008 105:11887-11892). It is known that CD83 is expressed on human T cells after stimulation, and is detectable on circulating T cells after allo-HCT (Ju X., et al., J Immunol 2016 197:4613-4625). However, the precise expression of CD83 on Tregs versus T conv was unclear. As disclosed herein, human T cell expression of CD83 occurs with stimulation, including allogeneic dendritic cells or CD3/CD28 beads (FIG. 3A-3D). Importantly, CD83 is differentially expressed on human $CD4^+$ Tconv compared to immune suppressive $CD4^+$ Tregs in response to DC-alloactivation (FIG. 3C). $CD4^+$ Tconv expression of CD83 peaks at 4-8 hours of DC-allostimulation and declines to baseline levels by 48 hours, with minimal amounts observed on Tregs (FIG. 3C). The expression of CD83 is more abundant with supraphysiologic CD3/CD28 bead stimulation, which also causes a late increase in CD83 expression on Tregs by 48 hours of activation (FIG. 3D). Though reportedly expressed on murine CD8+ T cells (Ju X., et al., J Immunol 2016 197:4613-4625), no significant amounts of CD83 were detected on human CD8' T cells in vitro after DC-allostimulation or CD3/CD28 bead activation (FIG. 11A,11B).

The Human CD83 CAR T Cell Prevents Xenogeneic GVHD.

A xenogeneic GVHD model was used to evaluate the efficacy of the human CD83 CAR T cell in vivo. A well-established NSG mouse model was used, where the recipients were inoculated with $25\times10^6$ human PBMCs plus either $1\text{-}10\times10^6$ autologous CD83 or mock transduced CAR T cells all on day 0. The transplanted mice were monitored daily for clinical signs of xenogeneic GVHD up to day +100. The CD83 and mock transduced CAR T cells were safe in the NSG mice, without any evidence of early GVHD or toxicity compared to PBMCs alone (FIG. 5A,5B). The CD83 CAR T cells significantly improved xenogeneic GVHD survival after transplant, compared to PBMCs alone or mock transduced CAR T cells (FIG. 5A). Additionally, xenogeneic GVHD clinical severity was reduced by the CD83 CAR T cells (FIG. 5B). Remarkably, mice in both dose cohorts of CD83 CAR T cells demonstrated 3-month survival of 90% or better (FIG. 5A). In separate experiments, transplanted NSG mice received PBMCs alone or with mock transduced T cells ($1\times10^6$) or CD83 CAR T cells ($1\times10^6$) and were humanely euthanized at day +21 to evaluate target organ GVHD severity. GVHD scores were determined by a blinded expert pathologist. The CD83 CAR T cells essentially eliminated target organ tissue damage by human T cells in the recipient lung (FIG. 6A,6B) and liver (FIG. 6C,6D), compared to PBMCs alone or mock transduced T cells.

The Human CD83 CAR T Cell Significantly Reduces Circulating Mature, $CD83^+$ DCs In Vivo.

Mature, $CD83^+$ dendritic cells are implicated in the sensitization of alloreactive donor T cells. As such, we determined the effect of the CD83 CAR T cells on the immune recovery of human $CD1c^+$ DCs in the transplanted mice. NSG mice transplanted with human PBMCs plus CD83 CAR or mock transduced T cells were euthanized on day +21. Upon harvesting the recipient spleens, it was clear that the CD83 CAR T cells reduced the expansion of donor cells in vivo as indicted by much smaller spleens in this treatment group (FIG. 7). The CD83 CAR T cells significantly reduced the amount of human $CD1c^+$, $CD83^+$ DCs in the recipient mice (FIG. 8A,8B). While the proportion of $CD1c^+$ DCs expressing MHC class II was similar among the experimental groups, mice transplanted with CD83 CAR T cells exhibited significantly fewer DCs altogether (FIG. 8C,8D). Using the eGFP tag, it was confirmed that infused human CD83 CAR T cells were detectable in the murine spleens at day +21 (FIG. 8E).

Human CD83 CAR T Cells Significantly Reduce Pathogenic Th1 Cells and Increase the Treg:Tconv Ratio.

At day +21, there was a significant reduction in the total amount of human $CD4^+$ in the spleens of mice treated with CD83 CAR T cells (FIG. 9A,9B). As there were significant amounts of $CD83^+$, $CD4^+$ Tconv after DC-allostimulation in vitro, it was confirmed that $CD83^+$ Tconv were increased at day +21 among mice treated with PBMCs alone or with mock transduced T cells (FIG. 9C). Moreover, the amount of $CD83^+$ Tconv was significantly decreased in recipients of CD83 CAR T cells in vivo (FIG. 9C). In separate experiments, NSG mice were transplanted with human T cells alone or T cells plus dendritic cells. While the lack of dendritic cells slightly delayed GVHD onset, the median GVHD survival was similar among both groups. Thus, it was surmise the CD83 CAR T protects recipients from GVHD primarily by eliminating the alloreactive Tconv implicated in GVHD (FIG. 9C). The frequency of human Tregs in murine spleens was similar among al experimental groups at day +21 (FIG. 9D). Similar to the reduction in total $CD4^+$ T cells, the absolute number of Tregs was significantly decreased in the mice treated with the CD83 CAR T cells (FIG. 9D,9E). However, the ratio of Treg to alloreactive Tconv was significantly increased in the mice that receive the CD83 CAR T cells (FIG. 9F). Th1 cells contribute toward GVHD pathogenesis. Importantly, mice treated with CD83 CAR T cells exhibited a profound reduction in human Th1 cells (FIG. 9G,9H). Additionally, the amount of spleen-resident, human Th2 cells were also significantly decreased in the mice injected with CD83 CAR T cells (FIG. 9G,9I). Conversely, the CD83 CAR T cells did not suppress the amount of human Th17 cells in the murine spleens, compared to PBMCs alone or the mock transduced CAR.

Human CD83 CAR T Cells Spare the Anti-Tumor Activity of CD8+ Cytotoxic T Lymphocytes (CTL).

Figure 10A:
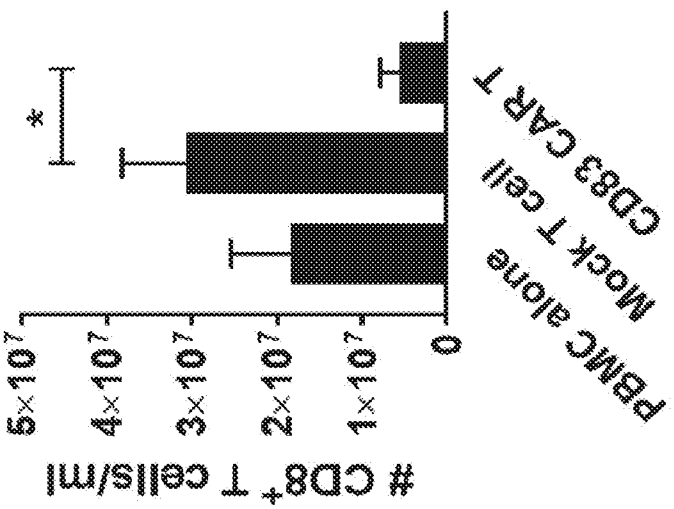
Figure 10B:
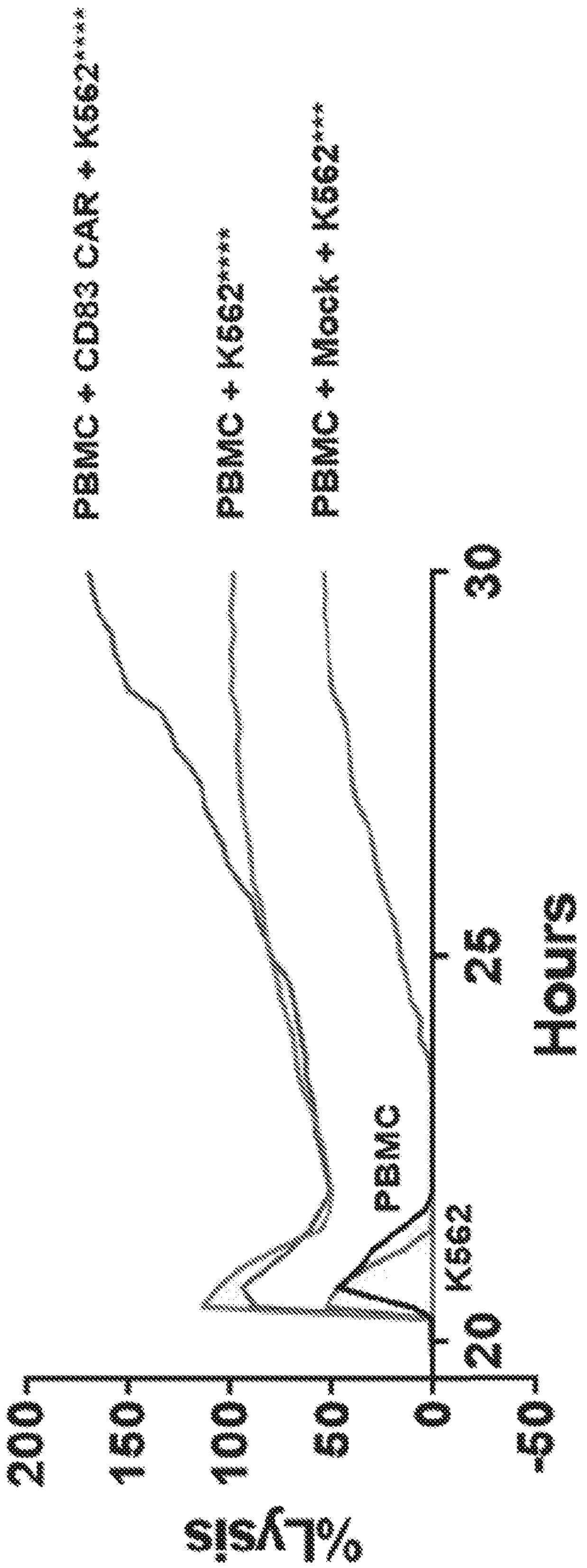

Like $CD4^+$ T cells, the total amount of human $CD8^+$ T cells at day +21 were also significantly reduced in mice treated with PBMCs and CD83 CAR T cells, compared to mice injected with PBMCs and mock transduced T cells (FIG. 10A). To test how the CD83 CAR T cells influenced donor anti-tumor immunity, human CD8 CTLs specific to K562 were generated in vivo by injecting mice with PBMCs followed by mock transduced T cells or CD83 CAR T cells. Mice also received an inoculum of irradiated K562 on days 0 and +10. Controls received PBMCs alone. Mice were humanely euthanized on day +12, and the $CD8^+$ T cells were purified from the recipient spleens. Specific tumor lysis against fresh K562 cells was evaluated in vitro using the xCELLigence platform. All mice injected with human PBMCs and irradiated K562 cells demonstrated intact killing by CD8 CTL purified from their spleens, compared to control mice transplanted with PBMCs alone (FIG. 10B). Interestingly, mice treated with human CD83 CART cells exhibited superior CD8 CTL-mediated anti-tumor activity, compared to mice treated with PBMCs alone or mock T cells (FIG. 10B).

Discussion

The use of CAR T cells as cellular immunotherapy to prevent GVHD is an innovative strategy, distinct from pharmacologic immune suppression or adoptive transfer of donor Tregs. Targeting cells that express CD83 efficiently depletes transplant recipients of inflammatory, mature DCs as well as alloreactive $CD4^+$ T cells. Mechanistically, the in vivo elimination of alloreactive Tconv may drive the efficacy of these CAR T cells, as donor dendritic cell-depletion does not reduce GVHD in separate xenogeneic experiments. Moreover, the CD83 CAR T cells do not impair the anti-tumor activity of human cytolytic $CD8^+$ T cells. Though CD8 T cells were reduced in mice treated with CD83 CAR T cells, CTLs from these mice demonstrated enhanced tumor killing. The in vivo depletion of alloreactive T effectors by the CD83 CAR T cells also mediates a significant rise in the Treg:activated Tconv ratio.

The CD83 CAR T cells significantly reduce pathogenic, human Th1 and Th2 cells in vivo. Experiments using STAT4 and STAT6 knock out donor T cells have shown that Th1 and Th2 cells independently mediate lethal GVHD in mice (Nikolic B., et al. J Clin Invest 2000 105:1289-1298). Additionally, the combination of Th1 and Th2 cells in vivo cooperatively worsen murine GVHD (Nikolic B., et al. J Clin Invest 2000 105:1289-1298). In part, Th1 and Th2 cells cause tissue-specific damage to the intestine and lungs respectively (Yi T., et al., Blood 2009 114:3101-3112). Novel strategies to target donor Th1 responses currently exist, and are largely driven by p40 cytokine neutralization or inhibition of relevant downstream receptor signal transduction (Pidala J., et al., Haematologica 2018 103:531-539; Fu J., et al., J Immunol 2016 196:3168-3179; Betts B. C., et al., Proc Natl Acad Sci USA 2018 115:1582-1587; Betts B. C., et al., Sci Transl Med. 2017 9(372); Betts B. C., et al., Front Immunol. 2018 9:2887). However, few approaches concurrently target pathogenic responses by donor Th1 and Th2 cells. Conversely, in the context of JAK2, a relevant signaling molecule for Th1 and Th2 differentiation; its neutralization or inhibition yields suppression of Th1 cells while significantly increasing Th2 cells (Betts B. C., et al., Proc Natl Acad Sci USA 2018 115:1582-1587). Thus, human CD83 CAR T cells represent a novel cell product to simultaneously suppress donor Th1/Th2 responses after alloHCT.

The disclosed data support that human CD83 CAR T cells provide durable protection from activated Tconv and GVHD mortality. Though CD83 is not significantly expressed on human Tregs, mice treated with the human CD83 CAR T cells exhibited reduced amounts of Tregs. This may be due to limited availability of $CD4^+$ T cell precursors for iTreg differentiation or diminished IL-2 concentrations by the overall reduction in circulating donor T cells. In rodents, CD83 participates in Treg stability in vivo and mice bearing CD83-deficient Tregs are susceptible to autoimmune syndromes (Doebbeler M., et al. JCI Insight. 2018 3(11)). However, in the xenotransplantation experiments the ratio of human Treg to activated Tconv was significantly increased in mice treated with CD83 CAR T cells compared to controls. The increased ratio of Treg to Tconv is a clinically relevant immune indicator, and even correlates with response to Treg-directed GVHD therapy such as low-dose IL-2 (Koreth J., et al., Blood 2016 128:130-137). Moreover, the human CD83 CAR T cells were well tolerated and eliminated immune-mediated organ damage in vivo. Thus, the role of CD83 may differ among murine and human Tregs.

Interestingly, recipients of CD83 CAR T cells had similar amounts of human Th17 cells in their spleens compared to controls. The role of Th17 cells in GVHD pathogenesis is less clear compared to Th1 cells. In mice, allogeneic Th17 cells can induce lethal GVHD. Deficiency of donor T cell RORγt, a critical transcription factor for Th17 cells, augments but does not eliminate GVHD (Yu Y., et al., Blood 2011 118:5011-5020). However, IL-17A can also be protective in GVHD when produced by mucosal-associated invariant T (MAIT) cells, in part due to reductions in semaphorin 6d and 4b which regulate T cell activation (Varelias A., et al., J Clin Invest 2018 128:1919-1936). Moreover, IL-17 has also been shown to suppress Th1 responses in murine models of inflammatory colitis (O'Connor, Jr. W. et al., Nat Immunol 2009 10:603-609). Therefore, the preservation of human Th17 cells by the CD83 CAR T cells could participate in the overall reduction in GVHD mortality.

CD83 is a unique immune regulatory molecule. In mice, soluble CD83 mediates immune suppressive effects by enhancing Treg responses through indoleamine 2,3-dioxygenase- and TGFβ-mechanisms (Bock F., et al., J Immunol 2013 191:1965-1975). The extracellular domain of human CD83 was also shown to impair alloreactive T cell proliferation in vitro (Lechmann M., et al., J Exp Med 2001 194:1813-1821). Conversely, direct neutralization of CD83 with monoclonal antibody, 3C12C, significantly reduces xenogeneic GVHD mediated by human T cells in vivo (Wilson J., et al., J Exp Med 2009 206:387-398). The CD83 antibody also preserved Treg and antiviral responses by donor, human CD8+ T cells (Seldon T. A., et al., Leukemia 2016 30:692-700). This suggests that while soluble CD83 may have immune suppressive properties, targeting the cell surface expression of CD83 can prevent GVHD while retaining key effector and Treg function. The disclosed CD83 CAR T cell is distinct from the monoclonal antibody, 3C12C. The greatest functional difference between the two approaches is that the CD83 CAR T cell kills its target without the need for NK-cell mediated antibody-dependent cellular cytotoxicity (Seldon T. A., et al., Leukemia 2016 30:692-700). This is an advantage when rapid, efficient elimination of alloreactive T cells and mature DCs is needed to prevent GVHD. Moreover, the protective effect by the CD83 CAR T cells delivered over 90% survival 3 months post-transplant, whereas published data with the CD83 monoclonal antibody limits the protective effect to 30 days with approximately 50% survival.

In conclusion, the CD83 CAR T cell represents the first programmed cytoytic effector cell designed to prevent GVHD. The translational potential of the CD83 CAR T cell in GVHD prophylaxis, though it is expected to have merit in preventing solid organ and vascularized composite allograft rejection too. The CD83 CAR T cell may overcome the barriers of HLA disparity in hematopoietic cell and solid organ donor selection, and greatly extend the application of curative transplantation procedures to patients in need. Importantly, the CD83 CAR T cell provides a platform to eliminate alloreactive T cells without the need for broadly suppressive, nonselective calcineurin-inhibitors or glucocorticoids. Thus, the CD83 CAR T cell carries high likelihood to reduce transplant-related mortality and improve outcomes after allo-HCT.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A chimeric antigen receptor (CAR) polypeptide, comprising a CD83 antigen binding domain, a transmembrane domain, an intracellular signaling domain, and a co-stimulatory signaling region, wherein the anti-CD83 scFv comprises a variable heavy ($V_H$) domain and a variable light ($V_L$) domain, wherein the anti-CD83 scFv $V_H$ domain comprises the amino acid sequence SEQ ID NO: 48, SEQ ID NO:49, SEQ ID NO:50, SEQ ID NO:51, SEQ ID NO:52, or SEQ ID NO:53, and wherein the anti-CD83 scFv $V_L$ domain comprises the amino acid sequence SEQ ID NO: 54 or SEQ ID NO:55.

2. The polypeptide of claim 1, wherein the anti-CD83 scFv comprises the amino acid sequence SEQ ID NO:59, SEQ ID NO:60, SEQ ID NO: 61, SEQ ID NO: 62, SEQ ID NO: 63, SEQ ID NO: 64, SEQ ID NO:65, SEQ ID NO:66, SEQ ID NO: 67, SEQ ID NO:68, SEQ ID NO: 69, or SEQ ID NO: 70.

3. The polypeptide of claim 1, wherein the costimulatory signaling region comprises the cytoplasmic domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.

4. The polypeptide of claim 1, wherein the CAR polypeptide is defined by the formula:

SP-CD83-HG-TM-CSR-SD; or

SP-CD83-HG-TM-SD-CSR;

wherein "SP" represents an optional signal peptide,
wherein "CD83" represents a CD83-binding region,
wherein "HG" represents an optional hinge domain,
wherein "TM" represents a transmembrane domain,
wherein "CSR" represents one or more co-stimulatory signaling regions,
wherein "SD" represents a signaling domain, and
wherein "-" represents a peptide bond or linker.

5. The polypeptide of claim 1, wherein the intracellular signaling domain comprises a CD3 zeta (CD32) signaling domain.

6. An isolated nucleic acid sequence encoding the recombinant polypeptide of claim 1.

7. A vector comprising the isolated nucleic acid sequence of claim 6.

8. A cell comprising the vector of claim 7.

9. The cell of claim 8, wherein the cell is selected from the group consisting of an αβT cell, γδT cell, a Natural Killer (NK) cells, a Natural Killer T (NKT) cell, a B cell, an innate lymphoid cell (ILC), a cytokine induced killer (CIK) cell, a cytotoxic T lymphocyte (CTL), a lymphokine activated killer (LAK) cell, a regulatory T cell, or any combination thereof.

10. The cell of claim 9, wherein the cell suppresses alloreactive donor cells when the antigen binding domain of the CAR binds to CD83.

11. A method of suppressing alloreactive donor cells in a subject receiving transplant donor cells, the method comprising administering to the subject an effective amount of an immune effector cell genetically modified to express the CAR polypeptide of claim 1, thereby suppressing alloreactive donor cells in the subject.

12. The method of claim 11, wherein the immune effector cell is selected from the group consisting of a T cell, a Natural Killer (NK) cell, a cytotoxic T lymphocyte (CTL), and a regulatory T cell.

13. The method of claim 11, wherein the donor cells are bone marrow cells comprising alloreactive T-cells, dendritic cells, or a combination thereof.

14. The method of claim 13, further comprising administering to the subject a checkpoint inhibitor, wherein the checkpoint inhibitor comprises an anti-PD-1 antibody, anti-PD-L1 antibody, anti-CTLA-4 antibody, or a combination thereof.

15. The method of claim 11, further comprising administering to the subject a monoclonal antibody that blocks immune checkpoint signaling.

* * * * *